(12) United States Patent
Schultheiss et al.

(10) Patent No.: US 9,944,946 B2
(45) Date of Patent: Apr. 17, 2018

(54) FUNGAL RESISTANT PLANTS EXPRESSING HCP4

(71) Applicant: BASF Plant Science Company GmbH, Ludwigshafen (DE)

(72) Inventors: Holger Schultheiss, Boehl-Iggelheim (DE); Ralf Flachmann, Limburgerhof (DE)

(73) Assignee: BASF PLANT SCIENCE COMPANY GMBH, Ludwigshafen (DE)

( * ) Notice: Subject to any disclaimer, the term of this patent is extended or adjusted under 35 U.S.C. 154(b) by 0 days.

(21) Appl. No.: 14/417,836

(22) PCT Filed: Aug. 1, 2013

(86) PCT No.: PCT/IB2013/056316
§ 371 (c)(1),
(2) Date: Jan. 28, 2015

(87) PCT Pub. No.: WO2014/041444
PCT Pub. Date: Mar. 20, 2014

(65) Prior Publication Data
US 2015/0252381 A1 Sep. 10, 2015

Related U.S. Application Data

(60) Provisional application No. 61/681,155, filed on Aug. 9, 2012.

(30) Foreign Application Priority Data

Aug. 9, 2012 (EP) .................................. 12179842

(51) Int. Cl.
C12N 15/82 (2006.01)
C07K 14/415 (2006.01)

(52) U.S. Cl.
CPC ........ *C12N 15/8282* (2013.01); *C07K 14/415* (2013.01)

(58) Field of Classification Search
None
See application file for complete search history.

(56) References Cited

FOREIGN PATENT DOCUMENTS

| CN | 101874115 A | | 10/2010 |
|---|---|---|---|
| CN | 102257144 A | | 11/2011 |
| WO | WO 2008/017706 | * | 2/2008 |
| WO | WO-2010/037714 A1 | | 4/2010 |
| WO | WO-2012/023099 A1 | | 2/2012 |
| WO | WO-2012/023111 A1 | | 2/2012 |
| WO | WO-2012/172498 A1 | | 12/2012 |
| WO | WO-2013/001435 A1 | | 1/2013 |
| WO | WO-2013/092275 A2 | | 6/2013 |
| WO | WO-2013/093738 A1 | | 6/2013 |
| WO | WO-2013/149801 A1 | | 10/2013 |
| WO | WO-2013/149804 A1 | | 10/2013 |

OTHER PUBLICATIONS

Parker et al (1999, Plant Cell 11:2099-2112).*
GenBank Accession No. CP002687 bases 10625787 to 10630137.*
Guo et al, 2004, Proc. Natl. Acad. Sci. USA 101.*
European Search Report in EP 12 17 9842, dated Dec. 12, 2012.
Frederick et al., "Polymerase chain reaction assays for the detection and discrimination of the soybean rust pathogens *Phakopsora pachyrhizi* and *P. meibomiae*", Phytopathology, 92(2):217-227 (2002).
GenBank Accession No. AK229329.1, "*Arabidopsis thaliana* mRNA for resistence protein-like, complete cds, clone: RAFL16-58-J06" dated Jul. 27, 2006.
GenBank Accession No. NM_001203843.1, "*Arabidopsis thaliana* nucleoside-triphosphatase/transmembrane receptor/nucleotide binding/ATP binding mRNA, complete cds" dated Jan. 22, 2014.
Grover et al., "Strategies for development of fungus-resistant transgenic plants", Current Science, 84(3):330-340 (2003).
Gururani et al., "Plant disease resistance genes: current status and future directions", Physiological and Molecular Plant Pathology, 78:51-65 (2012).
Heath, "Cellular interactions between biotrophic fungal pathogens and host or nonhost plants", Can. J. Plant Pathol. 24:259-264 (2002).
International Search Report and Written Opinion for Application No. PCT/IB2013/056316 dated Jan. 2, 2014.
Meyers et al., "Genome-wide analysis of NBS-LRR-encoding genes in *Arabidopsis*", 15:809-834 (2003).
Neu et al., "Cytological and molecular analysis of the *Hordeum vulgare-Puccinia triticina* nonhost interaction", MPMI, 16(7):626-633 (2003).
Rytter et al., "Additional alternative hosts of *Phakopsora pachyrhizi*, causal agent of soybean rust", Plant Disease, 68(9):818-819 (1984).
Sinclair et al., (eds.) Proceedings of the Soybean Rust Workshop, Aug. 9-11, 1995. Urbana, IL: National Soybean Research Laboratory, (1995).
Uniprot Accession No. F4JT79, Nucleoside-triphosphatase/transmembrane receptor/nucleotide binding/ATP binding dated Jun. 28, 2011.
Uniprot Accession No. Q0WNV7, Resistance protein-like dated Sep. 5, 2006.

(Continued)

*Primary Examiner* — Anne Kubelik
(74) *Attorney, Agent, or Firm* — Marshall, Gerstein & Borun LLP

(57) ABSTRACT

The present invention relates to a method of increasing resistance against fungal pathogens of the order Pucciniales, preferably the family Phacopsoraceae, in plants and/or plant cells. This is achieved by increasing the expression of an HCP4 protein or fragment thereof in a plant, plant part and/or plant cell in comparison to wild type plants, wild type plant parts and/or wild type plant cells. Furthermore, the invention relates to transgenic plants, plant parts, and/or plant cells having

(56) References Cited

OTHER PUBLICATIONS

Figure 1:
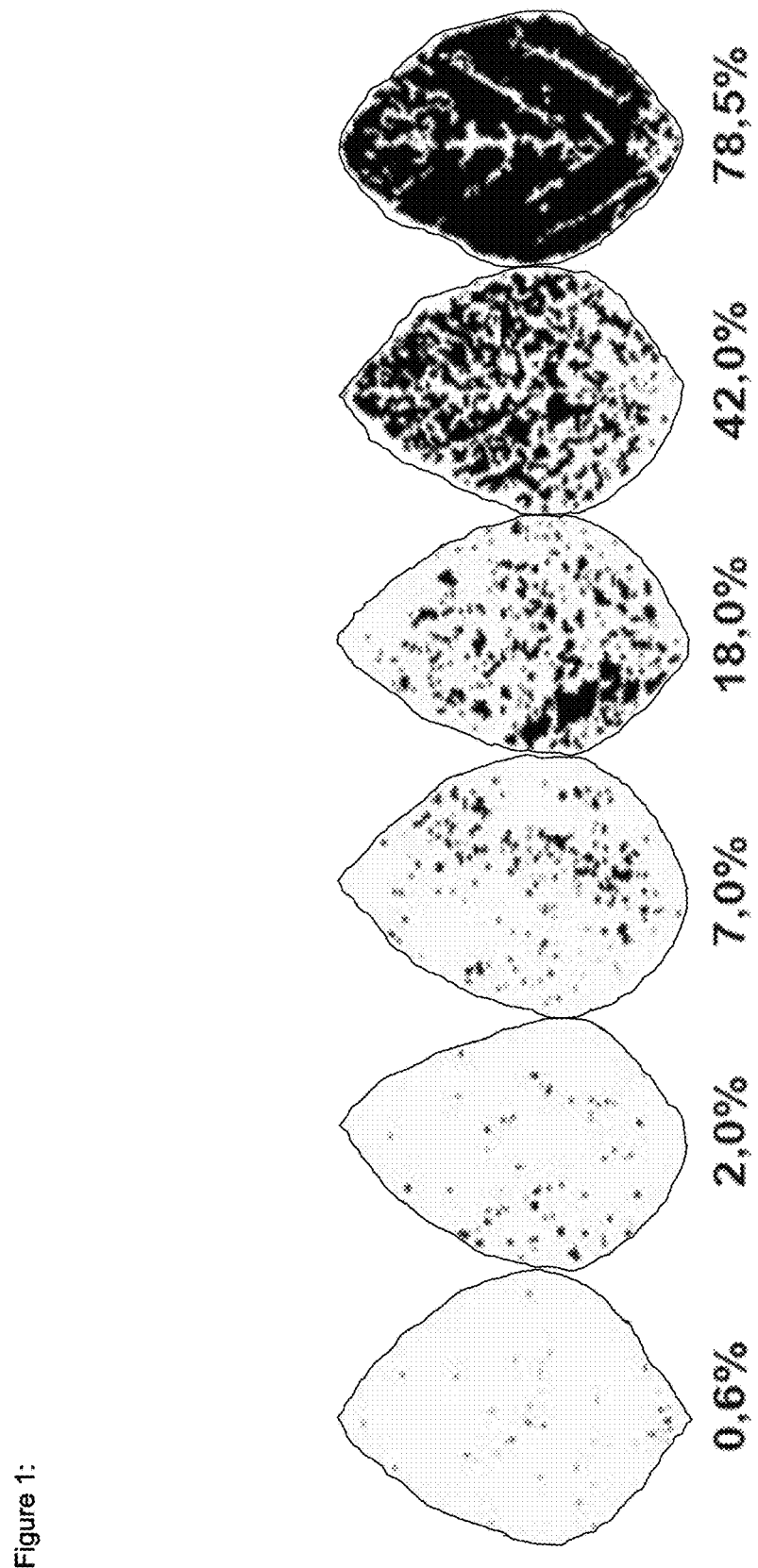

Van der Biezen et al., "The NB-ARC domain: a novel signalling motif shared by plant resistance gene products and regulartor of cell death in animals", *Current Biology*, 8(7):R226-R227 (1998).

Van Ooijen et al., "Structure-function analysis of the NB-ARC domain of plant disease resistance proteins", *Journal of Experimental Botany*, 59(6):1383-1397 (2008).

* cited by examiner

Figure 3:

```
   1 ATGGCAGCTT CTTTTTGCGG CAGCCGGAGA TACGATGTTT TCCCGAGCTT
  51 CAGTAAGGTA GATGTCCGCA GGTCATTCCT CGCGCATCTT CTCAAGGAGC
 101 TCGACCGCAG ATTAATCAAT ACGTTCACAG ATCATGGTAT GGAGAGAAAC
 151 CTCCCAATCG ACGCTGAACT TTTATCGGCG ATAGCAGAAT CGAGGATCTC
 201 AATAGTCATC TTCTCTAAAA ACTATGCTTC TTCCACGTGG TGCTTAGATG
 251 AATTGGTTGA GATCCACACG TGTTATAAGG AATTGGCTCA AATAGTGGTT
 301 CCGGTTTTCT TTAACGTACA TCCTTCGCAA GTTAAAAAAC AGACCGGAGA
 351 ATTTGGTAAG GTTTTTGGAA AGACATGCAA AGGTAAACCA GAGAATCGGA
 401 AACTAAGATG GATGCAAGCT CTAGCAGCGG TAGCAAATAT TGCTGGATAT
 451 GATCTTCAGA ACTGGTATTT TCTTTTCCAT TCCAACCCTA ATATATATAT
 501 GTGCCTGTGT TCAATTTTGG GGTGCCTCTT TAATGACAAA ATTGACTATT
 551 GTTATTAGGC CTGATGAAGC TGTCATGATT GAGATGGTAG CTGACGATGT
 601 TTCGAAAAAA CTTTTTAAAT CATCGAATGA TTTCAGTGAT ATCGTCGGGA
 651 TTGAAGCTCA TTTAGAGGCA ATGAGTTCAA TATTGCGCTT GAAATCTGAG
 701 AAAGCTAGAA TGGTCGGGAT TTCGGGGCCT TCAGGGATTG GTAAGACTAC
 751 CATCGCAAAA GCTCTTTTCA GTAAACTCTC TCCCCAATTC CACCTTCGTG
 801 CTTTCGTTAC TTATAAAAGA ACCAACCAGG ACGACTATGA CATGAAGTTG
 851 TGTTGGATAG AAAAATTTCT GTCAGAAATT CTTGGTCAAA AGGACTTGAA
 901 GGTTTTGGAT TTAGGTGCGG TGGAACAAAG TCTAATGCAC AAGAAAGTTC
 951 TTATCATTCT TGACGATGTA GATGATCTTG AGCTATTAAA GACCTTGGTG
1001 GGACAAACTG GATGGTTCGG GTTTGGAAGC AGAATTGTTG TGATCACTCA
1051 GGATAGGCAG CTTCTCAAGG CTCATGATAT TAACCTCATA TATGAGGTGG
1101 CCTTCCCATC TGCCCATCTT GCTCTTGAGA TTTTCTGCCA ATCTGCTTTT
1151 GGGAAAATAT ATCCACCATC TGATTTTAGA GAACTCTCTG TTGAATTTGC
1201 ATATCTTGCC GGCAATCTTC CTTTGGATCT TAGGGTCTTG GGTTTGGCCA
1251 TGAAAGGAAA GCACAGGGAG GAGTGGATAG AGATGCTGCC TAGGCTCCGA
1301 AATGATTTGG ACGGAAATT TAAGAAAACA TTGAGAAATT ACCTGCCTGT
1351 GATACGGAAG CGCGTTTCCA ATGAAGAAGG GGGCCGTGAG AAATTGAAAA
1401 AGGGAAATAA AAAGTTGGAT TTGGATGAGG AGTTTCCTGG TGGAGAAATT
1451 TACAGTGATG AGATACCTTC GCCAACATCT AACTGGAAAG ATACAGATGA
1501 CTTTGATTCA GGGGACATCA TTCCAATCAT TGCAGACAAA TCTACTACTA
1551 TAATTCCCAA CAGGAGGCAC TCGAACGATG ACTGGTGTTC TTTCTGTGAG
1601 TTCCTCAGAA ACCGTATACC CCCGTTGAAT CCCTTTAAAT GTAGTGCCAA
1651 TGATGTCATT GATTTTCTTC GCACACGGCA GGTTTTAGGC AGCACTGAGG
1701 CTCTCGTTGA CCGCCTCATT TTCAGTAGTG AGGCATTTGG CATAAAACCT
1751 GAGGAAAACC CTTTTCGCAG CCAAGCTGTA ACATCGTACT TGAAGGCGGC
1801 CAGGGATATG ACACGAGAAA AAGAATGCAT ACTTGTGTTT TCGTGCCACG
1851 ACAACCTTGA TGTAGATGAA ACATCTTTCA TTGAAGCCAT CTCAAAAGAA
1901 TTGCACAAGC AGGGGTTCAT CCCTTTGACA TATAATCTTT GGGCAGAGA
1951 GAACCTCGAT GAGGAGATGT TATACGGATC TAGAGTCGGT ATCATGATAC
2001 TTTCAAGTAG TTATGTTTCT TCTAGACAGT CCCTGGATCA CCTGGTTGCA
2051 GTTATGGAGC ATTGGAAAAC AACAGACCTT GTAATTATTC CTATATATTT
2101 TAAAGTAAGA CTTTCAGACA TTTGTGGGTT GAAAGGCAGG TTTGAAGCAG
2151 CGTTTCTGCA GCTTCATATG TCTCTCCAGG AAGACAGAGT TCAGAAATGG
2201 AAGGCGGCTA TGTCTGAAAT AGTGTCCATC GGTGGACATG AATGGACCAA
2251 GGGAAGTCAG TTTATTCTTG CCGAGGAAGT TGTAAGAAAT GCATCCTTAA
2301 GGCTATATCT GAAAAGTAGC AAGAATCTGC TTGGAATCTT AGCGTTGTTA
2351 AATCACTCCC AGTCTACAGA CGTGGAAATT ATGGGAATCT GGGGTATAGC
2401 AGGAATAGGT AAGACATCGA TTGCAAGAGA AATATTTGAA TTACATGCTC
2451 CACATTATGA TTTCTGTTAC TTCCTGCAAG ACTTTCATCT AATGTGTCAG
2501 ATGAAAAGGC CGAGGCAATT GCGTGAAGAT TTTATCTCAA AATTGTTTGG
2551 GGAAGAAAAA GGTCTAGGTG CTAGTGATGT AAAGCCAAGT TCATGAGGG
2601 ACTGGTTCCA TAAAAAAACG ATTCTTCTCG TTCTTGATGA CGTGAGTAAT
2651 GCCAGAGATG CAGAAGCTGT AATCGGAGGG TTTGGCTGGT TTTCTCATGG
2701 ACACAGAATC ATCTTAACCT CTAGGAGTAA ACAAGTTCTT GTACAGTGTA
```

Figure 3 - continued:

```
2751 AGGTTAAAAA GCCATACGAG ATCCAAAAAT TAAGCGATTT TGAATCGTTT
2801 CGTCTCTGCA AACAATATTT GGATGGCGAA AATCCGGTCA TCTCTGAGCT
2851 TATCAGCTGC AGTAGTGGTA TTCCATTGGC TCTCAAACTT TTAGTTTCCT
2901 CTGTATCAAA GCAGTATATA ACGAATATGA AAGACCATCT CCAAAGCTTG
2951 AGGAAAGATC CTCCTACTCA GATTCAAGAA GCATTTCGGA GAAGTTTTGA
3001 TGGACTAGAT GAAAACGAGA AAAACATATT TTTGGATCTT GCATGTTTTT
3051 TCAGGGGGCA GAGCAAAGAT TATGCGGTGC TATTACTTGA TGCTTGTGGT
3101 TTTTTTACAT ATATGGGAAT CTGTGAGCTC ATTGACGAGT CACTCATTAG
3151 CCTTGTAGAC AACAAGATAG AGATGCCTAT TCCTTTTCAA GACATGGGCC
3201 GAATTATTGT TCATGAAGAA GATGAGGATC CATGTGAACG TAGCAGATTG
3251 TGGGACTCGA AGGACATCGT TGATGTTTTG ACAAACAATT CAGGAACAGA
3301 AGCAATTGAG GGCATCTTCC TGGATGCGTC TGACTTGACC TGCGAGCTTA
3351 GTCCTACTGT GTTTGGTAAG ATGTATAATC TTAGATTGCT GAAGTTCTAT
3401 TGTTCAACCT CTGGGAACCA GTGCAAGCTT ACTCTACCTC ACGGCCTAGA
3451 CACTTTGCCT GATGAGCTAA GTCTACTTCA CTGGGAGAAT TACCCTCTGG
3501 TTTACTTGCC TCAGAAATTT AATCCTGTGA ACCTTGTAGA GTTAAACATG
3551 CCTTATAGCA ACATGGAGAA GTTGTGGGAA GGAAAGAAAA ATCTCGAGAA
3601 GCTAAAGAAC ATCAAACTGA GTCACTCCAG AGAATTAACT GATATCCTGA
3651 TGTTATCAGA AGCCCTGAAC CTGAACACA TTGATCTCGA AGGGTGTACG
3701 AGTCTGATTG ATGTTAGCAT GTCTATTCCT TGTTGTGGGA AGCTTGTTTC
3751 CTTGAATATG AAAGACTGTT CTCGTTTGCG AAGTCTGCCT TCTATGGTTG
3801 ATTTAACAAC TCTCAAGCTT CTTAATTTGT CTGGCTGCTC AGAATTTGAG
3851 GATATTCAGG ATTTTGCACC AAACCTGGAA GAGATATATC TAGCTGGGAC
3901 ATCCATTAGA GAGCTTCCGT TGTCAATCAG GAATCTCACT GAACTTGTTA
3951 CGCTAGATCT GGAGAACTGC GAAAGACTTC AGGAAATGCC GAGTCTTCCG
4001 GTGGAAATAA TCAGGAGAAC CTGA
```

```
MIFRTGIFFSIPTLIYICACVQFWGASLMTKLTIVIRPDEAVMIEMVADD   50
VSKKLFKSSNDFSDIVGIEAHLEAMSSILRLKSEKARMVGISGPSGIGKT  100
TIAKALFSKLSPQFHLRAFVTYKRTNQDDYDMKLCWIEKFLSEILGQKDL  150
KVLDLGAVEQSLMHKKVLIILDDVDDLELLKTLVGQTGWFGFGSRIVVIT  200
QDRQLLKAHDINLIYEVAFPSAHLALEIFCQSAFGKIYPPSDFRELSVEF  250
AYLAGNLPLDLRVLGLAMKGKHREEWIEMLPRLRNDLDGKFKKTLRNYLP  300
VIRKRVSNEEGGREKLKKGNKKLDLDEEFPGGEIYSDEIPSPTSNWKDTD  350
DFDSGDIIPIIADKSTTIIPNRRHSNDDWCSFCEFLRNRIPPLNPFKCSA  400
NDVIDFLRTRQVLGSTEALVDRLIFSSEAFGIKPEENPFRSQAVTSYLKA  450
ARDMTREKECILVFSCHDNLDVDETSFIEAISKELHKQGFIPLTYNLLGR  500
ENLDEEMLYGSRVGIMILSSSYVSSRQSLDHLVAVMEHWKTTDLVIIPIY  550
FKVRLSDICGLKGRFEAAFLQLHMSLQEDRVQKWKAAMSEIVSIGGHEWT  600
KGSQFILAEEVVRNASLRLYLKSSKNLLGILALLNHSQSTDVEIMGIWGI  650
AGIGKTSIAREIFELHAPHYDFCYFLQDFHLMCQMKRPRQLREDFISKLF  700
GEEKGLGASDVKPSFMRDWFHKKTILLVLDDVSNARDAEAVIGGFGWFSH  750
GHRIILTSRSKQVLVQCKVKKPYEIQKLSDFESFRLCKQYLDGENPVISE  800
LISCSSGIPLALKLLVSSVSKQYITNMKDHLQSLRKDPPTQIQEAFRRSF  850
DGLDENEKNIFLDLACFFRGQSKDYAVLLLDACGFFTYMGICELIDESLI  900
SLVDNKIEMPIPFQDMGRIIVHEEDEDPCERSRLWDSKDIVDVLTNNSGT  950
EAIEGIFLDASDLTCELSPTVFGKMYNLRLLKFYCSTSGNQCKLTLPHGL 1000
DTLPDELSLLHWENYPLVYLPQKFNPVNLVELNMPYSNMEKLWEGKKNLE 1050
KLKNIKLSHSRELTDILMLSEALNLEHIDLEGCTSLIDVSMSIPCCGKLV 1100
SLNMKDCSRLRSLPSMVDLTTLKLLNLSGCSEFEDIQDFAPNLEEIYLAG 1150
TSIRELPLSIRNLTELVTLDLENCERLQEMPSLPVEIIRRT*
```

Figure 6:

```
   1 ATGGCAGCTT CTTTTTGCGG CAGCCGGAGA TACGATGTTT TCCCGAGCTT
  51 CAGTAAGGTA GATGTCCGCA GGTCATTCCT CGCGCATCTT CTCAAGGAGC
 101 TCGACCGCAG ATTAATCAAT ACGTTCACAG ATCATGGTAT GGAGAGAAAC
 151 CTCCCAATCG ACGCTGAACT TTTATCGGCG ATAGCAGAAT CGAGGATCTC
 201 AATAGTCATC TTCTCTAAAA ACTATGCTTC TTCCACGTGG TGCTTAGATG
 251 AATTGGTTGA GATCCACACG TGTTATAAGG AATTGGCTCA AATAGTGGTT
 301 CCGGTTTTCT TTAACGTACA TCCTTCGCAA GTTAAAAAAC AGACCGGAGA
 351 ATTTGGTAAG GTTTTTGGAA AGACATGCAA AGGTAAACCA GAGAATCGGA
 401 AACTAAGATG GATGCAAGCT CTAGCAGCGG TAGCAAATAT TGCTGGATAT
 451 GATCTTCAGA ACTGGCCTGA TGAAGCTGTC ATGATTGAGA TGGTAGCTGA
 501 CGATGTTTCG AAAAAACTTT TTAAATCATC GAATGATTTC AGTGATATCG
 551 TCGGGATTGA AGCTCATTTA GAGGCAATGA GTTCAATATT GCGCTTGAAA
 601 TCTGAGAAAG CTAGAATGGT CGGGATTTCG GGGCCTTCAG GGATTGGTAA
 651 GACTACCATC GCAAAAGCTC TTTTCAGTAA ACTCTCTCCC CAATTCCACC
 701 TTCGTGCTTT CGTTACTTAT AAAAGAACCA ACCAGGACGA CTATGACATG
 751 AAGTTGTGTT GGATAGAAAA ATTTCTGTCA GAAATTCTTG GTCAAAAGGA
 801 CTTGAAGGTT TTGGATTTAG GTGCGGTGGA ACAAAGTCTA ATGCACAAGA
 851 AAGTTCTTAT CATTCTTGAC GATGTAGATG ATCTTGAGCT ATTAAAGACC
 901 TTGGTGGGAC AAACTGGATG GTTCGGGTTT GGAAGCAGAA TTGTTGTGAT
 951 CACTCAGGAT AGGCAGCTTC TCAAGGCTCA TGATATTAAC CTCATATATG
1001 AGGTGGCCTT CCCATCTGCC CATCTTGCTC TTGAGATTTT CTGCCAATCT
1051 GCTTTTGGGA AAATATATCC ACCATCTGAT TTTAGAGAAC TCTCTGTTGA
1101 ATTTGCATAT CTTGCCGGCA ATCTTCCTTT GGATCTTAGG GTCTTGGGTT
1151 TGGCCATGAA AGGAAAGCAC AGGGAGGAGT GGATAGAGAT GCTGCCTAGG
1201 CTCCGAAATG ATTTGGACGG GAAATTTAAG AAAACATTGA GAAATTACCT
1251 GCCTGTGATA CGGAAGCGCG TTTCCAATGA AGAAGGGGGC CGTGAGAAAT
1301 TGAAAAAGGG AAATAAAAAG TTGGATTTGG ATGAGGAGTT TCCTGGTGGA
1351 GAAATTTACA GTGATGAGAT ACCTTCGCCA ACATCTAACT GGAAAGATAC
1401 AGATGACTTT GATTCAGGGG ACATCATTCC AATCATTGCA GACAAATCTA
1451 CTACTATAAT TCCCAACAGG AGGCACTCGA ACGATGACTG GTGTTCTTTC
1501 TGTGAGTTCC TCAGAAACCG TATACCCCCG TTGAATCCCT TTAAATGTAG
1551 TGCCAATGAT GTCATTGATT TTCTTCGCAC ACGGCAGGTT TTAGGCAGCA
1601 CTGAGGCTCT CGTTGACCGC CTCATTTTCA GTAGTGAGGC ATTTGGCATA
1651 AAACCTGAGG AAAACCCTTT TCGCAGCCAA GCTGTAACAT CGTACTTGAA
1701 GGCGGCCAGG GATATGACAC GAGAAAAAGA ATGCATACTT GTGTTTTCGT
1751 GCCACGACAA CCTTGATGTA GATGAAACAT CTTTCATTGA AGCCATCTCA
1801 AAAGAATTGC ACAAGCAGGG GTTCATCCCT TTGACATATA ATCTTTTGGG
1851 CAGAGAGAAC CTCGATGAGG AGATGTTATA CGGATCTAGA GTCGGTATCA
1901 TGATACTTTC AAGTAGTTAT GTTTCTTCTA GACAGTCCCT GGATCACCTG
1951 GTTGCAGTTA TGGAGCATTG GAAAACAACA GACCTTGTAA TTATTCCTAT
2001 ATATTTTAAA GTAAGACTTT CAGACATTTG TGGGTTGAAA GGCAGGTTTG
2051 AAGCAGCGTT TCTGCAGCTT CATATGTCTC TCCAGGAAGA CAGAGTTCAG
2101 AAATGGAAGG CGGCTATGTC TGAAATAGTG TCCATCGGTG GACATGAATG
2151 GACCAAGGGA AGTCAGTTTA TTCTTGCCGA GGAAGTTGTA AGAAATGCAT
2201 CCTTAAGGCT ATATCTGAAA AGTAGCAAGA ATCTGCTTGG AATCTTAGCG
2251 TTGTTAAATC ACTCCCAGTC TACAGACGTG GAAATTATGG GAATCTGGGG
2301 TATAGCAGGA ATAGGTAAGA CATCGATTGC AAGAGAAATA TTTGAATTAC
2351 ATGCTCCACA TTATGATTTC TGTTACTTCC TGCAAGACTT TCATCTAATG
2401 TGTCAGATGA AAAGGCCGAG GCAATTGCGT GAAGATTTTA TCTCAAAATT
2451 GTTTGGGGAA GAAAAAGGTC TAGGTGCTAG TGATGTAAAG CCAAGTTTCA
2501 TGAGGGACTG GTTCCATAAA AAAACGATTC TTCTCGTTCT TGATGACGTG
2551 AGTAATGCCA GAGATGCAGA AGCTGTAATC GGAGGGTTTG GCTGGTTTTC
2601 TCATGGACAC AGAATCATCT TAACCTCTAG GAGTAAACAA GTTCTTGTAC
2651 AGTGTAAGGT TAAAAAGCCA TACGAGATCC AAAAATTAAG CGATTTTGAA
2701 TCGTTTCGTC TCTGCAAACA ATATTTGGAT GGCGAAAATC CGGTCATCTC
2751 TGAGCTTATC AGCTGCAGTA GTGGTATTCC ATTGGCTCTC AAACTTTTAG
2801 TTTCCTCTGT ATCAAAGCAG TATATAACGA ATATGAAAGA CCATCTCCAA
2851 AGCTTGAGGA AAGATCCTCC TACTCAGATT CAAGAAGCAT TTCGGAGAAG
```

Figure 6 - continued:

```
2901 TTTTGATGGA CTAGATGAAA ACGAGAAAAA CATATTTTTG GATCTTGCAT
2951 GTTTTTTCAG GGGGCAGAGC AAAGATTATG CGGTGCTATT ACTTGATGCT
3001 TGTGGTTTTT TTACATATAT GGGAATCTGT GAGCTCATTG ACGAGTCACT
3051 CATTAGCCTT GTAGACAACA AGATAGAGAT GCCTATTCCT TTTCAAGACA
3101 TGGGCCGAAT TATTGTTCAT GAAGAAGATG AGGATCCATG TGAACGTAGC
3151 AGATTGTGGG ACTCGAAGGA CATCGTTGAT GTTTTGACAA ACAATTCAGG
3201 AACAGAAGCA ATTGAGGGCA TCTTCCTGGA TGCGTCTGAC TTGACCTGCG
3251 AGCTTAGTCC TACTGTGTTT GGTAAGATGT ATAATCTTAG ATTGCTGAAG
3301 TTCTATTGTT CAACCTCTGG GAACCAGTGC AAGCTTACTC TACCTCACGG
3351 CCTAGACACT TTGCCTGATG AGCTAAGTCT ACTTCACTGG GAGAATTACC
3401 CTCTGGTTTA CTTGCCTCAG AAATTTAATC CTGTGAACCT TGTAGAGTTA
3451 AACATGCCTT ATAGCAACAT GGAGAAGTTG TGGGAAGGAA AGAAAAATCT
3501 CGAGAAGCTA AAGAACATCA AACTGAGTCA CTCCAGAGAA TTAACTGATA
3551 TCCTGATGTT ATCAGAAGCC CTGAACCTGG AACACATTGA TCTCGAAGGG
3601 TGTACGAGTC TGATTGATGT TAGCATGTCT ATTCCTTGTT GTGGGAAGCT
3651 TGTTTCCTTG AATATGAAAG ACTGTTCTCG TTTGCGAAGT CTGCCTTCTA
3701 TGGTTGATTT AACAACTCTC AAGCTTCTTA ATTTGTCTGG CTGCTCAGAA
3751 TTTGAGGATA TTCAGGATTT TGCACCAAAC CTGGAAGAGA TATATCTAGC
3801 TGGGACATCC ATTAGAGAGC TTCCGTTGTC AATCAGGAAT CTCACTGAAC
3851 TTGTTACGCT AGATCTGGAG AACTGCGAAA GACTTCAGGA AATGCCGAGT
3901 CTTCCGGTGG AAATAATCAG GAGAACCTGA
```

Figure 7:

```
MAASFCGSRRYDVFPSFSKVDVRRSFLAHLLKELDRRLINTFTDHGMERN  50
LPIDAELLSAIAESRISIVIFSKNYASSTWCLDELVEIHTCYKELAQIVV  100
PVFFNVHPSQVKKQTGEFGKVFGKTCKGKPENRKLRWMQALAAVANIAGY  150
DLQNWPDEAVMIEMVADDVSKKLFKSSNDFSDIVGIEAHLEAMSSILRLK  200
SEKARMVGISGPSGIGKTTIAKALFSKLSPQFHLRAFVTYKRTNQDDYDM  250
KLCWIEKFLSEILGQKDLKVLDLGAVEQSLMHKKVLIILDDVDDLELLKT  300
LVGQTGWFGFGSRIVVITQDRQLLKAHDINLIYEVAFPSAHLALEIFCQS  350
AFGKIYPPSDFRELSVEFAYLAGNLPLDLRVLGLAMKGKHREEWIEMLPR  400
LRNDLDGKFKKTLRNYLPVIRKRVSNEEGGREKLKKGNKKLDLDEEFPGG  450
EIYSDEIPSPTSNWKDTDDFDSGDIIPIIADKSTTIIPNRRHSNDDWCSF  500
CEFLRNRIPPLNPFKCSANDVIDFLRTRQVLGSTEALVDRLIFSSEAFGI  550
KPEENPFRSQAVTSYLKAARDMTREKECILVFSCHDNLDVDETSFIEAIS  600
KELHKQGFIPLTYNLLGRENLDEEMLYGSRVGIMILSSSYVSSRQSLDHL  650
VAVMEHWKTTDLVIIPIYFKVRLSDICGLKGRFEAAFLQLHMSLQEDRVQ  700
KWKAAMSEIVSIGGHEWTKGSQFILAEEVVRNASLRLYLKSSKNLLGILA  750
LLNHSQSTDVEIMGIWGIAGIGKTSIAREIFELHAPHYDFCYFLQDFHLM  800
CQMKRPRQLREDFISKLFGEEKGLGASDVKPSFMRDWFHKKTILLVLDDV  850
SNARDAEAVIGGFGWFSHGHRIILTSRSKQVLVQCKVKKPYEIQKLSDFE  900
SFRLCKQYLDGENPVISELISCSSGIPLALKLLVSSVSKQYITNMKDHLQ  950
SLRKDPPTQIQEAFRRSFDGLDENEKNIFLDLACFFRGQSKDYAVLLLDA  1000
CGFFTYMGICELIDESLISLVDNKIEMPIPFQDMGRIIVHEEDEDPCERS  1050
RLWDSKDIVDVLTNNSGTEAIEGIFLDASDLTCELSPTVFGKMYNLRLLK  1100
FYCSTSGNQCKLTLPHGLDTLPDELSLLHWENYPLVYLPQKFNPVNLVEL  1150
NMPYSNMEKLWEGKKNLEKLKNIKLSHSRELTDILMLSEALNLEHIDLEG  1200
CTSLIDVSMSIPCCGKLVSLNMKDCSRLRSLPSMVDLTTLKLLNLSGCSE  1250
FEDIQDFAPNLEEIYLAGTSIRELPLSIRNLTELVTLDLENCERLQEMPS  1300
LPVEIIRRT*
```

Figure 8:

```
   1 ACTGGATAGG CCTTTATCTT TCATTCTTGG GGTTTCGCAT CTCTTCCACT
  51 AATTTATTTG AGATGGAATT CCATTGAGAA TATTCGTCTC TTCTTTCTTT
 101 CGTTCTCAAT TCCCATCCCA TATTCCCCAT GGCAGCTTCT TTTTGCGGCA
 151 GCCGGAGATA CGATGTTTTC CCGAGCTTCA GTAAGGTAGA TGTCCGCAGG
 201 TCATTCCTCG CGCATCTTCT CAAGGAGCTC GACCGCAGAT TAATCAATAC
 251 GTTCACAGAT CATGGTATGG AGAGAAACCT CCCAATCGAC GCTGAACTTT
 301 TATCGGCGAT AGCAGAATCG AGGATCTCAA TAGTCATCTT CTCTAAAAAC
 351 TATGCTTCTT CCACGTGGTG CTTAGATGAA TTGGTTGAGA TCCACACGTG
 401 TTATAAGGAA TTGGCTCAAA TAGTGGTTCC GGTTTTCTTT AACGTACATC
 451 CTTCGCAAGT TAAAAACAG ACCGGAGAAT TTGGTAAGGT TTTTGGAAAG
 501 ACATGCAAAG GTAAACCAGA GAATCGGAAA CTAAGATGGA TGCAAGCTCT
 551 AGCAGCGGTA GCAAATATTG CTGGATATGA TCTTCAGAAC TGGCCTGATG
 601 AAGCTGTCAT GATTGAGATG GTAGCTGACG ATGTTTCGAA AAAACTTTTT
 651 AAATCATCGA ATGATTTCAG TGATATCGTC GGGATTGAAG CTCATTTAGA
 701 GGCAATGAGT TCAATATTGC GCTTGAAATC TGAGAAAGCT AGAATGGTCG
 751 GGATTTCGGG GCCTTCAGGG ATTGGTAAGA CTACCATCGC AAAAGCTCTT
 801 TTCAGTAAAC TCTCTCCCCA ATTCCACCTT CGTGCTTTCG TTACTTATAA
 851 AAGAACCAAC CAGGACGACT ATGACATGAA GTTGTGTTGG ATAGAAAAAT
 901 TTCTGTCAGA AATTCTTGGT CAAAAGGACT TGAAGGTTTT GGATTTAGGT
 951 GCGGTGGAAC AAAGTCTAAT GCACAAGAAA GTTCTTATCA TTCTTGACGA
1001 TGTAGATGAT CTTGAGCTAT TAAAGACCTT GGTGGGACAA ACTGGATGGT
1051 TCGGGTTTGG AAGCAGAATT GTTGTGATCA CTCAGGATAG GCAGCTTCTC
1101 AAGGCTCATG ATATTAACCT CATATATGAG GTGGCTTCC CATCTGCCCA
1151 TCTTGCTCTT GAGATTTTCT GCCAATCTGC TTTTGGGAAA ATATATCCAC
1201 CATCTGATTT TAGAGAACTC TCTGTTGAAT TTGCATATCT TGCCGGCAAT
1251 CTTCCTTTGG ATCTTAGGGT CTTGGGTTTG GCCATGAAAG GAAAGCACAG
1301 GGAGGAGTGG ATAGAGATGC TGCCTAGGCT CCGAAATGAT TTGGACGGGA
1351 AATTTAAGAA AACATTGAGA AATTACCTGC CTGTGATACG GAAGCGCGTT
1401 TCCAATGAAG AAGGGGGCCG TGAGAAATTG AAAAAGGGAA ATAAAAAGTT
1451 GGATTTGGAT GAGGAGTTTC CTGGTGGAGA AATTTACAGT GATGAGATAC
1501 CTTCGCCAAC ATCTAACTGG AAAGATACAG ATGACTTTGA TTCAGGGGAC
1551 ATCATTCCAA TCATTGCAGA CAAATCTACT ACTATAATTC CCAACAGGAG
1601 GCACTCGAAC GATGACTGGT GTTCTTTCTG TGAGTTCCTC AGAAACCGTA
1651 TACCCCCGTT GAATCCCTTT AAATGTAGTG CCAATGATGT CATTGATTTT
1701 CTTCGCACAC GGCAGGTTTT AGGCAGCACT GAGGCTCTCG TTGACCGCCT
1751 CATTTTCAGT AGTGAGGCAT TTGGCATAAA ACCTGAGGAA AACCCTTTTC
1801 GCAGCCAAGC TGTAACATCG TACTTGAAGG CGGCCAGGGA TATGACACGA
1851 GAAAAGAAT GCATACTTGT GTTTTCGTGC CACGACAACC TTGATGTAGA
1901 TGAAACATCT TTCATTGAAG CCATCTCAAA AGAATTGCAC AAGCAGGGGT
1951 TCATCCCTTT GACATATAAT CTTTTGGGCA GAGAGAACCT CGATGAGGAG
2001 ATGTTATACG GATCTAGAGT CGGTATCATG ATACTTTCAA GTAGTTATGT
2051 TTCTTCTAGA CAGTCCCTGG ATCACCTGGT TGCAGTTATG GAGCATTGGA
2101 AAACAACAGA CCTTGTAATT ATTCCTATAT ATTTTAAAGT AAGACTTTCA
2151 GACATTTGTG GGTTGAAAGG CAGGTTTGAA GCAGCGTTTC TGCAGCTTCA
2201 TATGTCTCTC CAGGAAGACA GAGTTCAGAA ATGGAAGGCG GCTATGTCTG
2251 AAATAGTGTC CATCGGTGGA CATGAATGGA CCAAGGGAAG TCAGTTTATT
2301 CTTGCCGAGG AAGTTGTAAG AAATGCATCC TTAAGGCTAT ATCTGAAAAG
2351 TAGCAAGAAT CTGCTTGGAA TCTTAGCGTT GTTAAATCAC TCCCAGTCTA
2401 CAGACGTGGA AATTATGGGA ATCTGGGGTA TAGCAGGAAT AGGTAAGACA
2451 TCGATTGCAA GAGAAATATT TGAATTACAT GCTCCACATT ATGATTTCTG
2501 TTACTTCCTG CAAGACTTTC ATCTAATGTG TCAGATGAAA AGGCCGAGGC
2551 AATTGCGTGA AGATTTATC TCAAATTGT TTGGGGAAGA AAAAGGTCTA
2601 GGTGCTAGTG ATGTAAAGCC AAGTTTCATG AGGGACTGGT TCCATAAAAA
2651 AACGATTCTT CTCGTTCTTG ATGACGTGAG TAATGCCAGA GATGCAGAAG
2701 CTGTAATCGG AGGGTTTGGC TGGTTTTCTC ATGGACACAG AATCATCTTA
```

Figure 8 - continued:

```
2751 ACCTCTAGGA GTAAACAAGT TCTTGTACAG TGTAAGGTTA AAAAGCCATA
2801 CGAGATCCAA AAATTAAGCG ATTTTGAATC GTTTCGTCTC TGCAAACAAT
2851 ATTTGGATGG CGAAAATCCG GTCATCTCTG AGCTTATCAG CTGCAGTAGT
2901 GGTATTCCAT TGGCTCTCAA ACTTTTAGTT TCCTCTGTAT CAAAGCAGTA
2951 TATAACGAAT ATGAAAGACC ATCTCCAAAG CTTGAGGAAA GATCCTCCTA
3001 CTCAGATTCA AGAAGCATTT CGGAGAAGTT TTGATGGACT AGATGAAAAC
3051 GAGAAAAACA TATTTTTGGA TCTTGCATGT TTTTTCAGGG GGCAGAGCAA
3101 AGATTATGCG GTGCTATTAC TTGATGCTTG TGGTTTTTTT ACATATATGG
3151 GAATCTGTGA GCTCATTGAC GAGTCACTCA TTAGCCTTGT AGACAACAAG
3201 ATAGAGATGC CTATTCCTTT TCAAGACATG GGCCGAATTA TTGTTCATGA
3251 AGAAGATGAG GATCCATGTG AACGTAGCAG ATTGTGGGAC TCGAAGGACA
3301 TCGTTGATGT TTTGACAAAC AATTCAGGAA CAGAAGCAAT TGAGGGCATC
3351 TTCCTGGATG CGTCTGACTT GACCTGCGAG CTTAGTCCTA CTGTGTTTGG
3401 TAAGATGTAT AATCTTAGAT TGCTGAAGTT CTATTGTTCA ACCTCTGGGA
3451 ACCAGTGCAA GCTTACTCTA CCTCACGGCC TAGACACTTT GCCTGATGAG
3501 CTAAGTCTAC TTCACTGGGA GAATTACCCT CTGGTTTACT TGCCTCAGAA
3551 ATTTAATCCT GTGAACCTTG TAGAGTTAAA CATGCCTTAT AGCAACATGG
3601 AGAAGTTGTG GGAAGGAAAG AAAAATCTCG AGAAGCTAAA GAACATCAAA
3651 CTGAGTCACT CCAGAGAATT AACTGATATC CTGATGTTAT CAGAAGCCCT
3701 GAACCTGGAA CACATTGATC TCGAAGGGTG TACGAGTCTG ATTGATGTTA
3751 GCATGTCTAT TCCTTGTTGT GGGAAGCTTG TTTCCTTGAA TATGAAAGAC
3801 TGTTCTCGTT TGCGAAGTCT GCCTTCTATG GTTGATTTAA CAACTCTCAA
3851 GCTTCTTAAT TTGTCTGGCT GCTCAGAATT TGAGGATATT CAGGATTTTG
3901 CACCAAACCT GGAAGAGATA TATCTAGCTG GGACATCCAT TAGAGAGCTT
3951 CCGTTGTCAA TCAGGAATCT CACTGAACTT GTTACGCTAG ATCTGGAGAA
4001 CTGCGAAAGG CTTCAGGAAA TGCCGAGTCT TCCGGTGGAA ATAATCAGGA
4051 GAACCTGAAA AAACGCAGAA ATCACCTCTC AATCCCTGTT CTACCAAGGG
4101 ATTGTGATGT AATTGTGGTA TATTCTCGGA CCGTGTATTC TCTATCTTAT
4151 TTCCCAAACG TTTTTGTAGA TTAGGCAAGG AAAGGAAAAA TCCTAATTGA
4201 CACAGATTTG TTAATAGATT TAGATGATCA TTGTGTTTTA ATAATATTAT
4251 TGTTATTTGT TGTATTTTAA CAGTTCTATA ATGATAATTG TGATCTCAAA
4301 ATCTCGTTTA TTA
```

Figure 9:

```
MAASFCGSRRYDVFPSFSKVDVRRSFLAHLLKELDRRLINTFTDHGMERN   50
LPIDAELLSAIAESRISIVIFSKNYASSTWCLDELVEIHTCYKELAQIVV  100
PVFFNVHPSQVKKQTGEFGKVFGKTCKGKPENRKLRWMQALAAVANIAGY  150
DLQNWPDEAVMIEMVADDVSKKLFKSSNDFSDIVGIEAHLEAMSSILRLK  200
SEKARMVGISGPSGIGKTTIAKALFSKLSPQFHLRAFVTYKRTNQDDYDM  250
KLCWIEKFLSEILGQKDLKVLDLGAVEQSLMHKKVLIILDDVDDLELLKT  300
LVGQTGWFGFGSRIVVITQDRQLLKAHDINLIYEVAFPSAHLALEIFCQS  350
AFGKIYPPSDFRELSVEFAYLAGNLPLDLRVLGLAMKGKHREEWIEMLPR  400
LRNDLDGKFKKTLRNYLPVIRKRVSNEEGGREKLKKGNKKLDLDEEFPGG  450
EIYSDEIPSPTSNWKDTDDFDSGDIIPIIADKSTTIIPNRRHSNDDWCSF  500
CEFLRNRIPPLNPFKCSANDVIDFLRTRQVLGSTEALVDRLIFSSEAFGI  550
KPEENPFRSQAVTSYLKAARDMTREKECILVFSCHDNLDVDETSFIEAIS  600
KELHKQGFIPLTYNLLGRENLDEEMLYGSRVGIMILSSSYVSSRQSLDHL  650
VAVMEHWKTTDLVIIPIYFKVRLSDICGLKGRFEAAFLQLHMSLQEDRVQ  700
KWKAAMSEIVSIGGHEWTKGSQFILAEEVVRNASLRLYLKSSKNLLGILA  750
LLNHSQSTDVEIMGIWGIAGIGKTSIAREIFELHAPHYDFCYFLQDFHLM  800
CQMKRPRQLREDFISKLFGEEKGLGASDVKPSFMRDWFHKKTILLVLDDV  850
SNARDAEAVIGGFGWFSHGHRIILTSRSKQVLVQCKVKKPYEIQKLSDFE  900
SFRLCKQYLDGENPVISELISCSSGIPLALKLLVSSVSKQYITNMKDHLQ  950
SLRKDPPTQIQEAFRRSFDGLDENEKNIFLDLACFFRGQSKDYAVLLLDA 1000
CGFFTYMGICELIDESLISLVDNKIEMPIPFQDMGRIIVHEEDEDPCERS 1050
RLWDSKDIVDVLTNNSGTEAIEGIFLDASDLTCELSPTVFGKMYNLRLLK 1100
FYCSTSGNQCKLTLPHGLDTLPDELSLLHWENYPLVYLPQKFNPVNLVEL 1150
NMPYSNMEKLWEGKKNLEKLKNIKLSHSRELTDILMLSEALNLEHIDLEG 1200
CTSLIDVSMSIPCCGKLVSLNMKDCSRLRSLPSMVDLTTLKLLNLSGCSE 1250
FEDIQDFAPNLEEIYLAGTSIRELPLSIRNLTELVTLDLENCERLQEMPS 1300
LPVEIIRRT*
```

Figure 10:

```
   1 ACTGGATAGG CCTTTATCTT TCATTCTTGG GGTTTCGCAT CTCTTCCACT
  51 AATTTATTTG AGATGGAATT CCATTGAGAA TATTCGTCTC TTCTTTCTTT
 101 CGTTCTCAAT TCCCATCCCA TATTCCCCAT GGCAGCTTCT TTTTGCGGCA
 151 GCCGGAGATA CGATGTTTTC CCGAGCTTCA GTAAGGTAGA TGTCCGCAGG
 201 TCATTCCTCG CGCATCTTCT CAAGGAGCTC GACCGCAGAT TAATCAATAC
 251 GTTCACAGAT CATGGTATGG AGAGAAACCT CCCAATCGAC GCTGAACTTT
 301 TATCGGCGAT AGCAGAATCG AGGATCTCAA TAGTCATCTT CTCTAAAAAC
 351 TATGCTTCTT CCACGTGGTG CTTAGATGAA TTGGTTGAGA TCCACACGTG
 401 TTATAAGGAA TTGGCTCAAA TAGTGGTTCC GGTTTTCTTT AACGTACATC
 451 CTTCGCAAGT TAAAAAACAG ACCGGAGAAT TTGGTAAGGT TTTTGGAAAG
 501 ACATGCAAAG GTAAACCAGA GAATCGGAAA CTAAGATGGA TGCAAGCTCT
 551 AGCAGCGGTA GCAAATATTG CTGGATATGA TCTTCAGAAC TGGCCTGATG
 601 AAGCTGTCAT GATTGAGATG GTAGCTGACG ATGTTTCGAA AAAACTTTTT
 651 AAATCATCGA ATGATTTCAG TGATATCGTC GGGATTGAAG CTCATTTAGA
 701 GGCAATGAGT TCAATATTGC GCTTGAAATC TGAGAAAGCT AGAATGGTCG
 751 GGATTTCGGG GCCTTCAGGG ATTGGTAAGA CTACCATCGC AAAAGCTCTT
 801 TTCAGTAAAC TCTCTCCCCA ATTCCACCTT CGTGCTTTCG TTACTTATAA
 851 AAGAACCAAC CAGGACGACT ATGACATGAA GTTGTGTTGG ATAGAAAAAT
 901 TTCTGTCAGA AATTCTTGGT CAAAAGGACT TGAAGGTTTT GGATTTAGAG
 951 AACTCTCTGT TGAATTTGCA TATCTTGCCG GCAATCTTCC TTTGGATCTT
1001 AGGGTCTTGG GTTTGGCCAT GAAAGGAAAG CACAGGGAGG AGTGGATAGA
1051 GATGCTGCCT AGGCTCCGAA ATGATTTGGA CGGGAAATTT AAGAAAACAT
1101 TGAGAAATTA CCTGCCTGTG ATACGGAAGC GCGTTTCCAA TGAAGAAGGG
1151 GGCCGTGAGA AATTGAAAAA GGGAAATAAA AAGTTGGATT TGGATGAGGA
1201 GTTTCCTGGT GGAGAAATTT ACAGTGATGA GATACCTTCG CCAACATCTA
1251 ACTGGAAAGA TACAGATGAC TTTGATTCAG GGGACATCAT TCCAATCATT
1301 GCAGACAAAT CTACTACTAT AATTCCCAAC AGGAGGCACT CGAACGATGA
1351 CTGGTGTTCT TTCTGTTTTA GGCAGCACTG AGGCTCTCGT TGACCGCCTC
1401 ATTTTCAGTA GTGAGGCATT TGGCATAAAA CCTGAGGAAA ACCCTTTTCG
1451 CAGCCAAGCT GTAACATCGT ACTTGAAGGC GGCCAGGGAT ATGACACGAG
1501 AAAAAGAATG CATACTTGTG TTTTCGTGCC ACGACAACCT TGATGTAGAT
1551 GAAACATCTT TCATTGAAGC CATCTCAAAA GAATTGCACA AGCAGGGGTT
1601 CATCCCTTTG ACATATAATC TTTTGGGCAG AGAGAACCTC GATGAGGAGA
1651 TGTTATACGG ATCTAGAGTC GGTATCATGA TACTTTCAAG TAGTTATGTT
1701 TCTTCTAGAC AGTCCCTGGA TCACCTGGTT GCAGTTATGG AGCATTGGAA
1751 AACAACAGAC CTTGTAATTA TTCCTATATA TTTTAAAGTA AGACTTTCAG
1801 ACATTTGTGG GTTGAAAGGC AGGTTTGAAG CAGCGTTTCT GCAGCTTCAT
1851 ATGTCTCTCC AGGAAGACAG AGTTCAGAAA TGGAAGGCGG CTATGTCTGA
1901 AATAGTGTCC ATCGGTGGAC ATGAATGGAC CAAGGGAAGT CAGTTTATTC
1951 TTGCCGAGGA AGTTGTAAGA AATGCATCCT TAAGGCTATA TCTGAAAAGT
2001 AGCAAGAATC TGCTTGGAAT CTTAGCGTTG TTAAATCACT CCCAGTCTAC
2051 AGACGTGGAA ATTATGGGAA TCTGGGGTAT AGCAGGAATA GGTAAGACAT
2101 CGATTGCAAG AGAAATATTT GAATTACATG CTCCACATTA TGATTTCTGT
2151 TACTTCCTGC AAGACTTTCA TCTAATGTGT CAGATGAAAA GGCCGAGGCA
2201 ATTGCGTGAA GATTTTATCT CAAAATTGTT TGGGGAAGAA AAAGGTCTAG
2251 GTGCTAGTGA TGTAAAGCCA AGTTTCATGA GGGACTGGTT CCATAAAAAA
2301 ACGATTCTTC TCGTTCTTGA TGACGTGAGT AATGCCAGAG ATGCAGAAGC
2351 TGTAATCGGA GGGTTTGGCT GGTTTTCTCA TGGACACAGA ATCATCTTAA
2401 CCTCTAGGAG TAAACAAGTT CTTGTACAGT GTAAGGTTAA AAAGCCATAC
2451 GAGATCCAAA AATTAAGCGA TTTTGAATCG TTTCGTCTCT GCAAACAATA
2501 TTTGGATGGC GAAAATCCGG TCATCTCTGA GCTTATCAGC TGCAGTAGTG
2551 GTATTCCATT GGCTCTCAAA CTTTTAGTTT CCTCTGTATC AAAGCAGTAT
2601 ATAACGAATA TGAAAGACCA TCTCCAAAGC TTGAGGAAAG ATCCTCCTAC
2651 TCAGATTCAA GAAGCATTTC GGAGAAGTTT TGATGGACTA GATGAAAACG
2701 AGAAAAACAT ATTTTTGGAT CTTGCATGTT TTTTCAGGGG GCAGAGCAAA
```

Figure 10 - continued:

```
2751 GATTATGCGG TGCTATTACT TGATGCTTGT GGTTTTTTTA CATATATGGG
2801 AATCTGTGAG CTCATTGACG AGTCACTCAT TAGCCTTGTA GACAACAAGA
2851 TAGAGATGCC TATTCCTTTT CAAGACATGG GCCGAATTAT TGTTCATGAA
2901 GAAGATGAGG ATCCATGTGA ACGTAGCAGA TTGTGGGACT CGAAGGACAT
2951 CGTTGATGTT TTGACAAACA ATTCAGGAAC AGAAGCAATT GAGGGCATCT
3001 TCCTGGATGC GTCTGACTTG ACCTGCGAGC TTAGTCCTAC TGTGTTTGGT
3051 AAGATGTATA ATCTTAGATT GCTGAAGTTC TATTGTTCAA CCTCTGGGAA
3101 CCAGTGCAAG CTTACTCTAC CTCACGGCCT AGACACTTTG CCTGATGAGC
3151 TAAGTCTACT TCACTGGGAG AATTACCCTC TGGTTTACTT GCCTCAGAAA
3201 TTTAATCCTG TGAACCTTGT AGAGTTAAAC ATGCCTTATA GCAACATGGA
3251 GAAGTTGTGG GAAGGAAAGA AAAATCTCGA GAAGCTAAAG AACATCAAAC
3301 TGAGTCACTC CAGAGAATTA ACTGATATCC TGATGTTATC AGAAGCCCTG
3351 AACCTGGAAC ACATTGATCT CGAAGGGTGT ACGAGTCTGA TTGATGTTAG
3401 CATGTCTATT CCTTGTTGTG GAAGCTTGT TTCCTTGAAT ATGAAAGACT
3451 GTTCTCGTTT GCGAAGTCTG CCTTCTATGG TTGATTTAAC AACTCTCAAG
3501 CTTCTTAATT TGTCTGGCTG CTCAGAATTT GAGGATATTC AGGATTTTGC
3551 ACCAAACCTG GAAGAGATAT ATCTAGCTGG GACATCCATT AGAGAGCTTC
3601 CGTTGTCAAT CAGGAATCTC ACTGAACTTG TTACGCTAGA TCTGGAGAAC
3651 TGCGAAAGGC TTCAGGAAAT GCCGAGAACA TGTAATTGGA AACTGAAATT
3701 TTTCCGCAAA AAAAAAAATC CGCCAAACT TTTTTCCGC CAAAACAAAA
3751 AATTCCCGCC AAAAAAAAAA TTCCCGGCAA ATATCTTTTT CATAACAAAT
3801 CTTTTCTCAG CCAAAAAAAT ACTTTTAAAA ATCCTTGTAA ATTTAAAGTA
3851 ATAGAGAGTC TAAGTTTAAA TTAAAGAATT TAATATAAA
```

Figure 11:

```
MTGVLSVLGSTEALVDRLIFSSEAFGIKPEENPFRSQAVTSYLKAARDMT      50
REKECILVFSCHDNLDVDETSFIEAISKELHKQGFIPLTYNLLGRENLDE     100
EMLYGSRVGIMILSSSYVSSRQSLDHLVAVMEHWKTTDLVIIPIYFKVRL     150
SDICGLKGRFEAAFLQLHMSLQEDRVQKWKAAMSEIVSIGGHEWTKGSQF     200
ILAEEVVRNASLRLYLKSSKNLLGILALLNHSQSTDVEIMGIWGIAGIGK     250
TSIAREIFELHAPHYDFCYFLQDFHLMCQMKRPRQLREDFISKLFGEEKG     300
LGASDVKPSFMRDWFHKKTILLVLDDVSNARDAEAVIGGFGWFSHGHRII     350
LTSRSKQVLVQCKVKKPYEIQKLSDFESFRLCKQYLDGENPVISELISCS     400
SGIPLALKLLVSSVSKQYITNMKDHLQSLRKDPPTQIQEAFRRSFDGLDE     450
NEKNIFLDLACFFRGQSKDYAVLLLDACGFFTYMGICELIDESLISLVDN     500
KIEMPIPFQDMGRIIVHEEDEDPCERSRLWDSKDIVDVLTNNSGTEAIEG     550
IFLDASDLTCELSPTVFGKMYNLRLLKFYCSTSGNQCKLTLPHGLDTLPD     600
ELSLLHWENYPLVYLPQKFNPVNLVELNMPYSNMEKLWEGKKNLEKLKNI     650
KLSHSRELTDILMLSEALNLEHIDLEGCTSLIDVSMSIPCCGKLVSLNMK     700
DCSRLRSLPSMVDLTTLKLLNLSGCSEFEDIQDFAPNLEEIYLAGTSIRE     750
LPLSIRNLTELVTLDLENCERLQEMPRTCNWKLKFFRKKKNPAKLFFRQN     800
KKFPPKKKFPANIFFITNLFSAKKILLKILVNLK*
```

Figure 12:

```
   1 TAAACCATTG ATATTTAATT ATTTGTCTTG AAGTTTAAAA TTCATCAATA
  51 ATAACTACTC ATTCTGTTCT TTTTTAATTA ATTTTCTAGA AAAACACACA
 101 TATTAATAAA ACATATAAAA CTGATTATAA ATGTATTAAT TTTTGTGATT
 151 TACAATTTTT TATAATTTTA AACCAATGAT ATTCAATTAT TTGTCTTGAA
 201 ATTTAAAATT CATCAATAAT AACTAATAAA TAGTGCATAA AAAACTTAAA
 251 AAATTAAACA ATATTGTTTT CTAAAAGATC AAGTAATAAG GAACCGAAGG
 301 AGTACTAAAT AGTGCATAGA AACCTAAAAA ATCAACTTTT TTGAAACAAA
 351 TTTTTTTCCT AAAAAATCAA ATAATAAGGA GCAAAGGAG  TATAATCTAA
 401 TCTCTAACCG ATATATAATC TCATTTAACT ATAAAATTTA AATCTTAATC
 451 TTCTTTGATT AACCCAAACC GATATATAAT CTCATTTAAT TACAAAATCT
 501 AAACCTTAAT CTTCTAATTA GAAACTCAAT CCGATATTAA ACCCGTTTAA
 551 TTGTAAAATT TAAATTTTAA CAATACTTTT TAAATTTAAA CTGATATTTA
 601 GTTTTGTTTA ATTGTAAAAT TTAAATCCGT TTATAATTCA GATCGATATT
 651 TAATTATAAA TCTAAACCGA TATTTAACTT TGTTTAATCA TATAATCTAA
 701 TCCTAAAAAA TTCTTATATA AACTCAACCA ATATATCATT TCGTTTTGAT
 751 AGTGGAGTAT ATTTTATAAT TAAATGAATT TTAGTTTTAT TAGCTAGCTG
 801 ATTATGATTG GCTAAAATAG AAAGAGTAAA GAGTGAATAA GAAGGTTCAT
 851 TTTTGGTTTT CAAATTATCC ATCTTTATTT TTTGTCCTGG ATACTGGATA
 901 GGCCTTTATC TTTCATTCTT GGGGTTTCGC ATCTCTTCCA CTAATTTATT
 951 TGAGATGGAA TTCCATTGAG AATATTCGTC TCTTCTTTCT TTCGTTCTCA
1001 ATTCCCATCC CATATTCCCC ATGGCAGCTT CTTTTGCGG  CAGCCGGAGA
1051 TACGATGTTT TCCCGAGCTT CAGTAAGGTA GATGTCCGCA GGTCATTCCT
1101 CGCGCATCTT CTCAAGGAGC TCGACCGCAG ATTAATCAAT ACGTTCACAG
1151 ATCATGGTAT GGAGAGAAAC CTCCCAATCG ACGCTGAACT TTTATCGGCG
1201 ATAGCAGAAT CGAGGATCTC AATAGTCATC TTCTCTAAAA ACTATGCTTC
1251 TTCCACGTGG TGCTTAGATG AATTGGTTGA GATCCACACG TGTTATAAGG
1301 AATTGGCTCA ATAGTGGTT  CCGGTTTTCT TTAACGTACA TCCTTCGCAA
1351 GTTAAAAAAC AGACCGGAGA ATTTGGTAAG GTTTTTGGAA AGACATGCAA
1401 AGGTAAACCA GAGAATCGGA AACTAAGATG GATGCAAGCT CTAGCAGCGG
1451 TAGCAAATAT TGCTGGATAT GATCTTCAGA ACTGGTATTT TCTTTTCCAT
1501 TCCAACCCTA ATATATATAT GTGCCTGTGT TCAATTTTGG GGTGCCTCTT
1551 TAATGACAAA ATTGACTATT GTTATTAGGC CTGATGAAGC TGTCATGATT
1601 GAGATGGTAG CTGACGATGT TCGAAAAAA  CTTTTTAAAT CATCGAATGA
1651 TTTCAGTGAT ATCGTCGGGA TTGAAGCTCA TTTAGAGGCA ATGAGTTCAA
1701 TATTGCGCTT GAAATCTGAG AAAGCTAGAA TGGTCGGGAT TTCGGGGCCT
1751 TCAGGGATTG GTAAGACTAC CATCGCAAAA GCTCTTTTCA GTAAACTCTC
1801 TCCCAATTC  CACCTTCGTG CTTTCGTTAC TTATAAAAGA ACCAACCAGG
1851 ACGACTATGA CATGAAGTTG TGTTGGATAG AAAAATTTCT GTCAGAAATT
1901 CTTGGTCAAA AGGACTTGAA GGTTTTGGAT TTAGGTGCGG TGGAACAAAG
1951 TCTAATGCAC AAGAAAGTTC TTATCATTCT TGACGATGTA GATGATCTTG
2001 AGCTATTAAA GACCTTGGTG GGACAAACTG GATGGTTCGG GTTTGGAAGC
2051 AGAATTGTTT TGATCACTCA GGATAGGCAG CTTCTCAAGG CTCATGATAT
2101 TAACCTCATA TATGAGGTGG CCTTCCCATC TGCCCATCTT GCTCTTGAGA
2151 TTTTCTGCCA ATCTGCTTTT GGGAAAATAT ATCCACCATC TGATTTTAGA
2201 GAACTCTCTG TTGAATTTGC ATATCTTGCC GGCAATCTTC CTTTGGATCT
2251 TAGGGTCTTG GGTTTGGCCA TGAAAGGAAA GCACAGGGAG GAGTGGATAG
2301 AGATGCTGCC TAGGCTCCGA AATGATTTGG ACGGGAAATT TAAGAAAACA
2351 TTGAGAAATT ACCTGCCTGT GATACGGAAG CGCGTTTCCA ATGAAGAAGG
2401 GGGCCGTGAG AAATTGAAAA AGGGAAATAA AAAGTTGGAT TTGGATGAGG
2451 AGTTTCCTGG TGGAGAAATT TACAGTGATG AGATACCTTC GCCAACATCT
2501 AACTGGAAAG ATACAGATGA CTTTGATTCA GGGGACATCA TTCCAATCAT
2551 TGCAGACAAA TCTACTACTA TAATTCCCAA CAGGAGGCAC TCGAACGATG
2601 ACTGGTGTTC TTTCTGTGAG TTCCTCAGAA ACCGTATACC CCCGTTGAAT
2651 CCCTTTAAAT GTAGTGCCAA TGATGTCATT GATTTCTTC  GCACACGGCA
2701 GGTTTTAGGC AGCACTGAGG CTCTCGTTGA CCGCCTCATT TTCAGTAGTG
```

Figure 12 - continued:

```
2751 AGGCATTTGG CATAAAACCT GAGGAAAACC CTTTTCGCAG CCAAGCTGTA
2801 ACATCGTACT TGAAGGCGGC CAGGGATATG ACACGAGAAA AAGAATGCAT
2851 ACTTGTGTTT TCGTGCCACG ACAACCTTGA TGTAGATGAA ACATCTTTCA
2901 TTGAAGCCAT CTCAAAAGAA TTGCACAAGC AGGGGTTCAT CCCTTTGACA
2951 TATAATCTTT TGGGCAGAGA GAACCTCGAT GAGGAGATGT TATACGGATC
3001 TAGAGTCGGT ATCATGATAC TTTCAAGTAG TTATGTTTCT TCTAGACAGT
3051 CCCTGGATCA CCTGGTTGCA GTTATGGAGC ATTGGAAAAC AACAGACCTT
3101 GTAATTATTC CTATATATTT TAAAGTAAGA CTTTCAGACA TTTGTGGGTT
3151 GAAAGGCAGG TTTGAAGCAG CGTTTCTGCA GCTTCATATG TCTCTCCAGG
3201 AAGACAGAGT TCAGAAATGG AAGGCGGCTA TGTCTGAAAT AGTGTCCATC
3251 GGTGGACATG AATGGACCAA GGGGTATATT TACTTATCTT TGTTGTCCCT
3301 TTACTATTCA AAGCTAGTTT ATTAATATTT GGAAGAGTAT TTCTTATTGG
3351 TGTGGTGCTA AATCAGTACT TCCATTTTCT CTGTCCTATT TGCAGAAGTC
3401 AGTTTATTCT TGCCGAGGAA GTTGTAAGAA ATGCATCCTT AAGGCTATAT
3451 CTGAAAAGTA GCAAGAATCT GCTTGGAATC TTAGCGTTGT TAAATCACTC
3501 CCAGTCTACA GACGTGGAAA TTATGGGAAT CTGGGGTATA GCAGGAATAG
3551 GTAAGACATC GATTGCAAGA GAAATATTTG AATTACATGC TCCACATTAT
3601 GATTTCTGTT ACTTCCTGCA AGACTTTCAT CTAATGTGTC AGATGAAAAG
3651 GCCGAGGCAA TTGCGTGAAG ATTTTATCTC AAAATTGTTT GGGGAAGAAA
3701 AAGGTCTAGG TGCTAGTGAT GTAAAGCCAA GTTTCATGAG GGACTGGTTC
3751 CATAAAAAAA CGATTCTTCT CGTTCTTGAT GACGTGAGTA ATGCCAGAGA
3801 TGCAGAAGCT GTAATCGGAG GGTTTGGCTG GTTTTCTCAT GGACACAGAA
3851 TCATCTTAAC CTCTAGGAGT AAACAAGTTC TTGTACAGTG TAAGGTTAAA
3901 AAGCCATACG AGATCCAAAA ATTAAGCGAT TTTGAATCGT TTCGTCTCTG
3951 CAAACAATAT TTGGATGGCG AAAATCCGGT CATCTCTGAG CTTATCAGCT
4001 GCAGTAGTGG TATTCCATTG GCTCTCAAAC TTTTAGTTTC CTCTGTATCA
4051 AAGCAGTATA TAACGAATAT GAAAGACCAT CTCCAAAGCT TGAGGAAAGA
4101 TCCTCCTACT CAGATTCAAG AAGCATTTCG GAGAAGTTTT GATGGACTAG
4151 ATGAAAACGA GAAAACATA TTTTTGGATC TTGCATGTTT TTTCAGGGGG
4201 CAGAGCAAAG ATTATGCGGT GCTATTACTT GATGCTTGTG GTTTTTTTAC
4251 ATATATGGGA ATCTGTGAGC TCATTGACGA GTCACTCATT AGCCTTGTAG
4301 ACAACAAGAT AGAGATGCCT ATTCCTTTTC AAGACATGGG CCGAATTATT
4351 GTTCATGAAG AAGATGAGGA TCCATGTGAA CGTAGCAGAT TGTGGGACTC
4401 GAAGGACATC GTTGATGTTT TGACAAACAA TTCAGTAAGT CGAACTGTGT
4451 TTAGTTCTTT TAACACTTCA GATACTTCGT GCATTCGTGG TTATCCTTTC
4501 TTTAGTTGTA ACAGGTGAGG GTTTCTTACT TATGTGATTG TTTTTGTCAG
4551 GGAACAGAAG CAATTGAGGG CATCTTCCTG GATGCGTCTG ACTTGACCTG
4601 CGAGCTTAGT CCTACTGTGT TTGGTAAGAT GTATAATCTT AGATTGCTGA
4651 AGTTCTATTG TTCAACCTCT GGGAACCAGT GCAAGCTTAC TCTACCTCAC
4701 GGCCTAGACA CTTTGCCTGA TGAGCTAAGT CTACTTCACT GGGAGAATTA
4751 CCCTCTGGTT TACTTGCCTC AGAAATTTAA TCCTGTGAAC CTTGTAGAGT
4801 TAAACATGCC TTATAGCAAC ATGGAGAAGT TGTGGGAAGG AAAGAAAGTA
4851 AGTGTTGACA TTATGGTTTT TAAAGCTGCT TGCATGAATT TATAACCTTG
4901 CATCTGATGA CTAATCTTGG TTATTGATGT TGTAAATAGA ATCTCGAGAA
4951 GCTAAAGAAC ATCAAACTGA GTCACTCCAG AGAATTAACT GATATCCTGA
5001 TGTTATCAGA AGCCCTGAAC CTGGAACACA TTGATCTCGA AGGGTGTACG
5051 AGTCTGATTG ATGTTAGCAT GTCTATTCCT TGTTGTGGGA AGCTTGTTTC
5101 CTTGAATATG AAAGACTGTT CTCGTTTGCG AAGTCTGCCT TCTATGGTTG
5151 ATTTAACAAC TCTCAAGCTT CTTAATTTGT CTGGCTGCTC AGAATTTGAG
5201 GATATTCAGG ATTTTGCACC AAACCTGGAA GAGATATATC TAGCTGGGAC
5251 ATCCATTAGA GAGCTTCCGT TGTCAATCAG GAATCTCACT GAACTTGTTA
5301 CGCTAGATCT GGAGAACTGC GAAAGGCTTC AGGAAATGCC GAGTCTTCCG
5351 GTGAAATAA TCAGGAGAAC CTGAAAAAAC GCAGAAATCA CCTCTCAATC
5401 CCTGTTCTAC CAAGGGATTG TGATGTAATT GTGGTATATT CTCGGACCGT
5451 GTATTCTCTA TCTTATTTCC CAAACGTTTT TGTAGATTAG GCAAGGAAAG
```

Figure 12 - continued:

```
5501 GAAAAATCCT AATTGACACA GATTTGTTAA TAGATTTAGA TGATCATTGT
5551 GTTTTAATAA TATTATTGTT ATTTGTTGTA TTTTAACAGT TCTATAATGA
5601 TAATTGTGAT CTCAAAATCT CGTTTATTAT TAGACTTTGT GTAAATTTGA
5651 TTCTAAAGCA AACTTAGTCT GAATTCTGGT GCATACCTCG GTATTATTTT
5701 GTTTTATTGG AGACGGTGTT AATGTTATCA TGATCCTCAT TGTTTTCTTA
5751 TGATATCAAA CTCCAAATCT GTAACATTAA AAGTTAAGAA ATAGCTAGTT
5801 GTTTAGAAGA CTAAACACAA AAAGTAAAGC ATGAAAAGAA CCATGATTAA
5851 ACAAAGCCAT ATAAATCTAC TTTTCAATAA GTGTTTTAAA AACATGTCTA
5901 GGTAGCCGTT TAGAGCATCT CCATCAGTAG TGAAAAAGTA GGAGATAGAG
5951 TCATAGAGGT ATTTGAGAAA CTTAGACCAT CCACATTGCA TATATTTTTT
6001 GTGTGTCTTT TCATATAAAT ATTATTAATA AAGTATGAAT AGTCTTTTTA
6051 AGACCCATTT ATCAATGTAT CTCAAAATGT CTTCTTTGAG ACCTTTTTGG
6101 AGAGATGTCT TTCATTTAAA GACCCTCATA TTATTTAATA AATTAAATTT
6151 ATGTGGGAAG ACATTTAAAC TGAATGTGCA ATGTGGATGC TCTAAAGCAA
6201 CTGTCTTTCC ATGTGTCTTT ATATTATTGG CCAAAATCTA CTTTTATAAT
6251 TCAAAATTTA AATAAATAAC TTAATTATTA TAAATTGATT AACATAATAT
6301 TGTTGATAAA CCCACACAGT ATAAGACCGA TGGAGATGGT CTTAGGCCCC
6351 GCTTAGACGC GTAGACGACC AAGATTTGTA TAAGTTTTGT TTAACGTTT
6401 TTTCAATTTT TAATTACATA AAGTTTATTT ATAAGTTCTA GCTTCATTGT
6451 TTAATATGAA TTGAAGAAAG TGAGATTTGT AAAATTAACC TTTTTTTACT
6501 ACTTTTTTGC AATAATACCT TTTTATGTTG TCCATTTTTA AAAATACTCA
6551 TTTCCTTGAA TAGAATGACC AAATTACCCT CATCTAATAG GAACATGTAA
6601 TTGGAAACTG AAATTTTTCC GCAAAAAAAA AAATCCCGCC AAACTTTTTT
6651 TCCGCCAAAA CAAAAAATTC CCGCCAAAAA AAAAATTCCC GGCAAATATC
6701 TTTTTCATAA CAAATCTTTT CTCAGCCAAA AAAATACTTT TAAAAATCCT
6751 TGTAAATTTA AAGTAATAGA GAGTCTAAGT TTAAATTAAA GAATTTAATA
6801 TAAATTTAAA CAAAACTTAG ATAAACATTT AAAGTAAACA AAACTTAGAT
6851 AAACTTATAT TTTGAAATTA CAAATATTTA ATTTTACATA TAGTTTTTTT
6901 TCTATATTTA AAAGTTATTC TTTCTTAAAT TATTAAAAAA ATACTGAAAC
6951 TTAAAGAATA TTGAAAATTA AATATACTAA ATAATAATAA AAACTTAATA
7001 TTTATGGTGT ATGAACTAAA ATTAAATATA TGAACTAAAA CTAACTTGGT
7051 ATCCTTTTTA GTTTTGTTAT TTTTAATTTA TTGCATAAGT TTTTAATTAA
7101 ATGAATATTG CTATTTGTTA GTATATATAT TCGTTGTTAC AAATATATCT
7151 ACGTGTTGTC GTAGCTCAGC GGTAGAGCTC ATAAAACCAC GTCGTTTGA
7201 TTTAACAGAA AATTCTAACA AAAAGTTAAC TCCGTTTACA AAAATTTCAC
7251 GGCATGCCCA CAATGGCCCA ATCAACAAAA TTTGACTATT TAATCAAAAA
7301 ATCAAAAAAA AGTTTTATGA TTTAAATGAC ATTTCGAAAG TTCAGATCTT
7351 TTTCATTCCA AATTTAAAAG CTAGCACTTT TTTCGACATT TTTCCTTTCT
7401 AAAATTTGGA TAAAATTGCA ATGCAATTTG TAATATTAAA CATTGTTAAG
7451 TATAAGTATG ACTTTTTATT TATTTGGATC CAGAATCATT TACTTTTTTC
7501 TTATATTATT TTTTGAACAA ATACTTTAAT TTAAGTCGAA GGGAACATTC
7551 ACTTTACATA TTTTTTTTCT TTATGAATTG AGTAAATTAT GTCTGCTTTT
7601 AAGATTAGAA TCACAACATA TACAACAAAA GCATTAGATT TTAATTTATA
7651 TAAACTGATT CAAAAAAAAT CTAAAAATAG GTTCAT
```

Figure 13:

```
                        893                                                         952
NM_118070      (1)   ACTGGATAGGCCTTTATCTTTCATTCTTGGGGTTTCGCATCTCTTCCACTAATTTATTTG
NM_001203843   (1)   ACTGGATAGGCCTTTATCTTTCATTCTTGGGGTTTCGCATCTCTTCCACTAATTTATTTG
HCP4-genomic   (1)   ------------------------------------------------------------
Genome       (893)   ACTGGATAGGCCTTTATCTTTCATTCTTGGGGTTTCGCATCTCTTCCACTAATTTATTTG
                        953                                                        1012
NM_118070     (61)   AGATGGAATTCCATTGAGAATATTCGTCTCTTCTTTCTTTCGTTCTCAATTCCCATCCCA
NM_001203843  (61)   AGATGGAATTCCATTGAGAATATTCGTCTCTTCTTTCTTTCGTTCTCAATTCCCATCCCA
HCP4-genomic   (1)   ------------------------------------------------------------
Genome       (953)   AGATGGAATTCCATTGAGAATATTCGTCTCTTCTTTCTTTCGTTCTCAATTCCCATCCCA
                       1013                                                        1072
NM_118070    (121)   TATTCCCCATGGCAGCTTCTTTTTGCGGCAGCCGGAGATACGATGTTTCCCGAGCTTCA
NM_001203843 (121)   TATTCCCCATGGCAGCTTCTTTTTGCGGCAGCCGGAGATACGATGTTTCCCGAGCTTCA
HCP4-genomic   (1)   --------ATGGCAGCTTCTTTTTGCGGCAGCCGGAGATACGATGTTTCCCGAGCTTCA
Genome      (1013)   TATTCCCCATGGCAGCTTCTTTTTGCGGCAGCCGGAGATACGATGTTTCCCGAGCTTCA
                       1073                                                        1132
NM_118070    (181)   GTAAGGTAGATGTCCGCAGGTCATTCCTCGCGCATCTTCTCAAGGAGCTCGACCGCAGAT
NM_001203843 (181)   GTAAGGTAGATGTCCGCAGGTCATTCCTCGCGCATCTTCTCAAGGAGCTCGACCGCAGAT
HCP4-genomic  (53)   GTAAGGTAGATGTCCGCAGGTCATTCCTCGCGCATCTTCTCAAGGAGCTCGACCGCAGAT
Genome      (1073)   GTAAGGTAGATGTCCGCAGGTCATTCCTCGCGCATCTTCTCAAGGAGCTCGACCGCAGAT
                       1133                                                        1192
NM_118070    (241)   TAATCAATACGTTCACAGATCATGGTATGGAGAGAAACCTCCCAATCGACGCTGAACTTT
NM_001203843 (241)   TAATCAATACGTTCACAGATCATGGTATGGAGAGAAACCTCCCAATCGACGCTGAACTTT
HCP4-genomic (113)   TAATCAATACGTTCACAGATCATGGTATGGAGAGAAACCTCCCAATCGACGCTGAACTTT
Genome      (1133)   TAATCAATACGTTCACAGATCATGGTATGGAGAGAAACCTCCCAATCGACGCTGAACTTT
                       1193                                                        1252
NM_118070    (301)   TATCGGCGATAGCAGAATCGAGGATCTCAATAGTCATCTTCTCTAAAAACTATGCTTCTT
NM_001203843 (301)   TATCGGCGATAGCAGAATCGAGGATCTCAATAGTCATCTTCTCTAAAAACTATGCTTCTT
HCP4-genomic (173)   TATCGGCGATAGCAGAATCGAGGATCTCAATAGTCATCTTCTCTAAAAACTATGCTTCTT
Genome      (1193)   TATCGGCGATAGCAGAATCGAGGATCTCAATAGTCATCTTCTCTAAAAACTATGCTTCTT
                       1253                                                        1312
NM_118070    (361)   CCACGTGGTGCTTAGATGAATTGGTTGAGATCCACACGTGTTATAAGGAATTGGCTCAAA
NM_001203843 (361)   CCACGTGGTGCTTAGATGAATTGGTTGAGATCCACACGTGTTATAAGGAATTGGCTCAAA
HCP4-genomic (233)   CCACGTGGTGCTTAGATGAATTGGTTGAGATCCACACGTGTTATAAGGAATTGGCTCAAA
Genome      (1253)   CCACGTGGTGCTTAGATGAATTGGTTGAGATCCACACGTGTTATAAGGAATTGGCTCAAA
                       1313                                                        1372
NM_118070    (421)   TAGTGGTTCCGGTTTTCTTTAACGTACATCCTTCGCAAGTTAAAAAACAGACCGGAGAAT
NM_001203843 (421)   TAGTGGTTCCGGTTTTCTTTAACGTACATCCTTCGCAAGTTAAAAAACAGACCGGAGAAT
HCP4-genomic (293)   TAGTGGTTCCGGTTTTCTTTAACGTACATCCTTCGCAAGTTAAAAAACAGACCGGAGAAT
Genome      (1313)   TAGTGGTTCCGGTTTTCTTTAACGTACATCCTTCGCAAGTTAAAAAACAGACCGGAGAAT
                       1373                                                        1432
NM_118070    (481)   TTGGTAAGGTTTTTGGAAAGACATGCAAAGGTAAACCAGAGAATCGGAAACTAAGATGGA
NM_001203843 (481)   TTGGTAAGGTTTTTGGAAAGACATGCAAAGGTAAACCAGAGAATCGGAAACTAAGATGGA
HCP4-genomic (353)   TTGGTAAGGTTTTTGGAAAGACATGCAAAGGTAAACCAGAGAATCGGAAACTAAGATGGA
Genome      (1373)   TTGGTAAGGTTTTTGGAAAGACATGCAAAGGTAAACCAGAGAATCGGAAACTAAGATGGA
                       1433                                                        1492
NM_118070    (541)   TGCAAGCTCTAGCAGCGGTAGCAAATATTGCTGGATATGATCTTCAGAACTGG-------
NM_001203843 (541)   TGCAAGCTCTAGCAGCGGTAGCAAATATTGCTGGATATGATCTTCAGAACTGG-------
HCP4-genomic (413)   TGCAAGCTCTAGCAGCGGTAGCAAATATTGCTGGATATGATCTTCAGAACTGGTATTTTC
Genome      (1433)   TGCAAGCTCTAGCAGCGGTAGCAAATATTGCTGGATATGATCTTCAGAACTGGTATTTTC
                       1493                                                        1552
NM_118070    (594)   ------------------------------------------------------------
NM_001203843 (594)   ------------------------------------------------------------
HCP4-genomic (473)   TTTTCCATTCCAACCCTAATATATATATGTGCCTGTGTTCAATTTTGGGGTGCCTCTTTA
Genome      (1493)   TTTTCCATTCCAACCCTAATATATATATGTGCCTGTGTTCAATTTTGGGGTGCCTCTTTA
                       1553                                                        1612
NM_118070    (594)   --------------------------CCTGATGAAGCTGTCATGATTGAGATGGTAGCT
NM_001203843 (594)   --------------------------CCTGATGAAGCTGTCATGATTGAGATGGTAGCT
HCP4-genomic (533)   ATGACAAAATTGACTATTGTTATTAGGCCTGATGAAGCTGTCATGATTGAGATGGTAGCT
Genome      (1553)   ATGACAAAATTGACTATTGTTATTAGGCCTGATGAAGCTGTCATGATTGAGATGGTAGCT
                       1613                                                        1672
NM_118070    (627)   GACGATGTTTCGAAAAAACTTTTTAAATCATCGAATGATTTCAGTGATATCGTCGGGATT
NM_001203843 (627)   GACGATGTTTCGAAAAAACTTTTTAAATCATCGAATGATTTCAGTGATATCGTCGGGATT
HCP4-genomic (593)   GACGATGTTTCGAAAAAACTTTTTAAATCATCGAATGATTTCAGTGATATCGTCGGGATT
Genome      (1613)   GACGATGTTTCGAAAAAACTTTTTAAATCATCGAATGATTTCAGTGATATCGTCGGGATT
                       1673                                                        1732
NM_118070    (687)   GAAGCTCATTTAGAGGCAATGAGTTCAATATTGCGCTTGAAATCTGAGAAAGCTAGAATG
```

Figure 13 - continued:

```
    NM_118070   (687) GAAGCTCATTTAGAGGCAATGAGTTCAATATTGCGCTTGAAATCTGAGAAAGCTAGAATG
 NM_001203843   (687) GAAGCTCATTTAGAGGCAATGAGTTCAATATTGCGCTTGAAATCTGAGAAAGCTAGAATG
  HCP4-genomic  (653) GAAGCTCATTTAGAGGCAATGAGTTCAATATTGCGCTTGAAATCTGAGAAAGCTAGAATG
        Genome (1673) GAAGCTCATTTAGAGGCAATGAGTTCAATATTGCGCTTGAAATCTGAGAAAGCTAGAATG
                     1733                                                         1792
    NM_118070   (747) GTCGGGATTTCGGGGCCTTCAGGGATTGGTAAGACTACCATCGCAAAAGCTCTTTTCAGT
 NM_001203843   (747) GTCGGGATTTCGGGGCCTTCAGGGATTGGTAAGACTACCATCGCAAAAGCTCTTTTCAGT
  HCP4-genomic  (713) GTCGGGATTTCGGGGCCTTCAGGGATTGGTAAGACTACCATCGCAAAAGCTCTTTTCAGT
        Genome (1733) GTCGGGATTTCGGGGCCTTCAGGGATTGGTAAGACTACCATCGCAAAAGCTCTTTTCAGT
                     1793                                                         1852
    NM_118070   (807) AAACTCTCTCCCCAATTCCACCTTCGTGCTTTCGTTACTTATAAAAGAACCAACCAGGAC
 NM_001203843   (807) AAACTCTCTCCCCAATTCCACCTTCGTGCTTTCGTTACTTATAAAAGAACCAACCAGGAC
  HCP4-genomic  (773) AAACTCTCTCCCCAATTCCACCTTCGTGCTTTCGTTACTTATAAAAGAACCAACCAGGAC
        Genome (1793) AAACTCTCTCCCCAATTCCACCTTCGTGCTTTCGTTACTTATAAAAGAACCAACCAGGAC
                     1853                                                         1912
    NM_118070   (867) GACTATGACATGAAGTTGTGTTGGATAGAAAAATTTCTGTCAGAAATTCTTGGTCAAAAG
 NM_001203843   (867) GACTATGACATGAAGTTGTGTTGGATAGAAAAATTTCTGTCAGAAATTCTTGGTCAAAAG
  HCP4-genomic  (833) GACTATGACATGAAGTTGTGTTGGATAGAAAAATTTCTGTCAGAAATTCTTGGTCAAAAG
        Genome (1853) GACTATGACATGAAGTTGTGTTGGATAGAAAAATTTCTGTCAGAAATTCTTGGTCAAAAG
                     1913                                                         1972
    NM_118070   (927) GACTTGAAGGTTTTGGATTTAGGTGCGGTGGAACAAAGTCTAATGCACAAGAAAGTTCTT
 NM_001203843   (927) GACTTGAAGGTTTTGGATTTAG--------------------------------------
  HCP4-genomic  (893) GACTTGAAGGTTTTGGATTTAGGTGCGGTGGAACAAAGTCTAATGCACAAGAAAGTTCTT
        Genome (1913) GACTTGAAGGTTTTGGATTTAGGTGCGGTGGAACAAAGTCTAATGCACAAGAAAGTTCTT
                     1973                                                         2032
    NM_118070   (987) ATCATTCTTGACGATGTAGATGATCTTGAGCTATTAAAGACCTTGGTGGGACAAACTGGA
 NM_001203843   (949) ------------------------------------------------------------
  HCP4-genomic  (953) ATCATTCTTGACGATGTAGATGATCTTGAGCTATTAAAGACCTTGGTGGGACAAACTGGA
        Genome (1973) ATCATTCTTGACGATGTAGATGATCTTGAGCTATTAAAGACCTTGGTGGGACAAACTGGA
                     2033                                                         2092
    NM_118070  (1047) TGGTTCGGGTTTGGAAGCAGAATTGTTGTGATCACTCAGGATAGGCAGCTTCTCAAGGCT
 NM_001203843   (949) ------------------------------------------------------------
  HCP4-genomic (1013) TGGTTCGGGTTTGGAAGCAGAATTGTTGTGATCACTCAGGATAGGCAGCTTCTCAAGGCT
        Genome (2033) TGGTTCGGGTTTGGAAGCAGAATTGTTGTGATCACTCAGGATAGGCAGCTTCTCAAGGCT
                     2093                                                         2152
    NM_118070  (1107) CATGATATTAACCTCATATATGAGGTGGCCTTCCCATCTGCCCATCTTGCTCTTGAGATT
 NM_001203843   (949) ------------------------------------------------------------
  HCP4-genomic (1073) CATGATATTAACCTCATATATGAGGTGGCCTTCCCATCTGCCCATCTTGCTCTTGAGATT
        Genome (2093) CATGATATTAACCTCATATATGAGGTGGCCTTCCCATCTGCCCATCTTGCTCTTGAGATT
                     2153                                                         2212
    NM_118070  (1167) TTCTGCCAATCTGCTTTTGGGAAAATATATCCACCATCTGATTTTAGAGAACTCTCTGTT
 NM_001203843   (949) ----------------------------------------------AGAACTCTCTGTT
  HCP4-genomic (1133) TTCTGCCAATCTGCTTTTGGGAAAATATATCCACCATCTGATTTTAGAGAACTCTCTGTT
        Genome (2153) TTCTGCCAATCTGCTTTTGGGAAAATATATCCACCATCTGATTTTAGAGAACTCTCTGTT
                     2213                                                         2272
    NM_118070  (1227) GAATTTGCATATCTTGCCGGCAATCTTCCTTTGGATCTTAGGGTCTTGGGTTTGGCCATG
 NM_001203843   (962) GAATTTGCATATCTTGCCGGCAATCTTCCTTTGGATCTTAGGGTCTTGGGTTTGGCCATG
  HCP4-genomic (1193) GAATTTGCATATCTTGCCGGCAATCTTCCTTTGGATCTTAGGGTCTTGGGTTTGGCCATG
        Genome (2213) GAATTTGCATATCTTGCCGGCAATCTTCCTTTGGATCTTAGGGTCTTGGGTTTGGCCATG
                     2273                                                         2332
    NM_118070  (1287) AAAGGAAAGCACAGGGAGGAGTGGATAGAGATGCTGCCTAGGCTCCGAAATGATTTGGAC
 NM_001203843  (1022) AAAGGAAAGCACAGGGAGGAGTGGATAGAGATGCTGCCTAGGCTCCGAAATGATTTGGAC
  HCP4-genomic (1253) AAAGGAAAGCACAGGGAGGAGTGGATAGAGATGCTGCCTAGGCTCCGAAATGATTTGGAC
        Genome (2273) AAAGGAAAGCACAGGGAGGAGTGGATAGAGATGCTGCCTAGGCTCCGAAATGATTTGGAC
                     2333                                                         2392
    NM_118070  (1347) GGGAAATTTAAGAAAACATTGAGAAATTACCTGCCTGTGATACGGAAGCGCGTTTCCAAT
 NM_001203843  (1082) GGGAAATTTAAGAAAACATTGAGAAATTACCTGCCTGTGATACGGAAGCGCGTTTCCAAT
  HCP4-genomic (1313) GGGAAATTTAAGAAAACATTGAGAAATTACCTGCCTGTGATACGGAAGCGCGTTTCCAAT
        Genome (2333) GGGAAATTTAAGAAAACATTGAGAAATTACCTGCCTGTGATACGGAAGCGCGTTTCCAAT
                     2393                                                         2452
    NM_118070  (1407) GAAGAAGGGGCCGTGAGAAATTGAAAAGGGAAATAAAAAGTTGGATTTGGATGAGGAG
 NM_001203843  (1142) GAAGAAGGGGCCGTGAGAAATTGAAAAGGGAAATAAAAAGTTGGATTTGGATGAGGAG
  HCP4-genomic (1373) GAAGAAGGGGCCGTGAGAAATTGAAAAGGGAAATAAAAAGTTGGATTTGGATGAGGAG
        Genome (2393) GAAGAAGGGGCCGTGAGAAATTGAAAAGGGAAATAAAAAGTTGGATTTGGATGAGGAG
                     2453                                                         2512
    NM_118070  (1467) TTTCCTGGTGGAGAAATTTACAGTGATGAGATACCTTCGCCAACATCTAACTGGAAAGAT
 NM_001203843  (1202) TTTCCTGGTGGAGAAATTTACAGTGATGAGATACCTTCGCCAACATCTAACTGGAAAGAT
  HCP4-genomic (1433) TTTCCTGGTGGAGAAATTTACAGTGATGAGATACCTTCGCCAACATCTAACTGGAAAGAT
```

Figure 13 - continued:

```
         Genome  (2453) TTTCCTGGTGGAGAAATTTACAGTGATGAGATACCTTCGCCAACATCTAACTGGAAAGAT
                        2513                                                         2572
      NM_118070  (1527) ACAGATGACTTTGATTCAGGGGACATCATTCCAATCATTGCAGACAAATCTACTACTATA
   NM_001203843  (1262) ACAGATGACTTTGATTCAGGGGACATCATTCCAATCATTGCAGACAAATCTACTACTATA
   HCP4-genomic  (1493) ACAGATGACTTTGATTCAGGGGACATCATTCCAATCATTGCAGACAAATCTACTACTATA
         Genome  (2513) ACAGATGACTTTGATTCAGGGGACATCATTCCAATCATTGCAGACAAATCTACTACTATA
                        2573                                                         2632
      NM_118070  (1587) ATTCCCAACAGGAGGCACTCGAACGATGACTGGTGTTCTTTCTGTGAGTTCCTCAGAAAC
   NM_001203843  (1322) ATTCCCAACAGGAGGCACTCGAACGATGACTGGTGTTCTTTCTGT---------------
   HCP4-genomic  (1553) ATTCCCAACAGGAGGCACTCGAACGATGACTGGTGTTCTTTCTGTGAGTTCCTCAGAAAC
         Genome  (2573) ATTCCCAACAGGAGGCACTCGAACGATGACTGGTGTTCTTTCTGTGAGTTCCTCAGAAAC
                        2633                                                         2692
      NM_118070  (1647) CGTATACCCCCGTTGAATCCCTTTAAATGTAGTGCCAATGATGTCATTGATTTCTTCGC
   NM_001203843  (1367) ------------------------------------------------------------
   HCP4-genomic  (1613) CGTATACCCCCGTTGAATCCCTTTAAATGTAGTGCCAATGATGTCATTGATTTCTTCGC
         Genome  (2633) CGTATACCCCCGTTGAATCCCTTTAAATGTAGTGCCAATGATGTCATTGATTTCTTCGC
                        2693                                                         2752
      NM_118070  (1707) ACACGGCAGGTTTTAGGCAGCACTGAGGCTCTCGTTGACCGCCTCATTTTCAGTAGTGAG
   NM_001203843  (1367) -----------TTTAGGCAGCACTGAGGCTCTCGTTGACCGCCTCATTTTCAGTAGTGAG
   HCP4-genomic  (1673) ACACGGCAGGTTTTAGGCAGCACTGAGGCTCTCGTTGACCGCCTCATTTTCAGTAGTGAG
         Genome  (2693) ACACGGCAGGTTTTAGGCAGCACTGAGGCTCTCGTTGACCGCCTCATTTTCAGTAGTGAG
                        2753                                                         2812
      NM_118070  (1767) GCATTTGGCATAAAACCTGAGGAAAAACCCTTTTCGCAGCCAAGCTGTAACATCGTACTTG
   NM_001203843  (1416) GCATTTGGCATAAAACCTGAGGAAAAACCCTTTTCGCAGCCAAGCTGTAACATCGTACTTG
   HCP4-genomic  (1733) GCATTTGGCATAAAACCTGAGGAAAAACCCTTTTCGCAGCCAAGCTGTAACATCGTACTTG
         Genome  (2753) GCATTTGGCATAAAACCTGAGGAAAAACCCTTTTCGCAGCCAAGCTGTAACATCGTACTTG
                        2813                                                         2872
      NM_118070  (1827) AAGGCGGCCAGGGATATGACACGAGAAAAAGAATGCATACTTGTGTTTTCGTGCCACGAC
   NM_001203843  (1476) AAGGCGGCCAGGGATATGACACGAGAAAAAGAATGCATACTTGTGTTTTCGTGCCACGAC
   HCP4-genomic  (1793) AAGGCGGCCAGGGATATGACACGAGAAAAAGAATGCATACTTGTGTTTTCGTGCCACGAC
         Genome  (2813) AAGGCGGCCAGGGATATGACACGAGAAAAAGAATGCATACTTGTGTTTTCGTGCCACGAC
                        2873                                                         2932
      NM_118070  (1887) AACCTTGATGTAGATGAAACATCTTTCATTGAAGCCATCTCAAAAGAATTGCACAAGCAG
   NM_001203843  (1536) AACCTTGATGTAGATGAAACATCTTTCATTGAAGCCATCTCAAAAGAATTGCACAAGCAG
   HCP4-genomic  (1853) AACCTTGATGTAGATGAAACATCTTTCATTGAAGCCATCTCAAAAGAATTGCACAAGCAG
         Genome  (2873) AACCTTGATGTAGATGAAACATCTTTCATTGAAGCCATCTCAAAAGAATTGCACAAGCAG
                        2933                                                         2992
      NM_118070  (1947) GGGTTCATCCCTTTGACATATAATCTTTTGGGCAGAGAGAACCTCGATGAGGAGATGTTA
   NM_001203843  (1596) GGGTTCATCCCTTTGACATATAATCTTTTGGGCAGAGAGAACCTCGATGAGGAGATGTTA
   HCP4-genomic  (1913) GGGTTCATCCCTTTGACATATAATCTTTTGGGCAGAGAGAACCTCGATGAGGAGATGTTA
         Genome  (2933) GGGTTCATCCCTTTGACATATAATCTTTTGGGCAGAGAGAACCTCGATGAGGAGATGTTA
                        2993                                                         3052
      NM_118070  (2007) TACGGATCTAGAGTCGGTATCATGATACTTTCAAGTAGTTATGTTTCTTCTAGACAGTCC
   NM_001203843  (1656) TACGGATCTAGAGTCGGTATCATGATACTTTCAAGTAGTTATGTTTCTTCTAGACAGTCC
   HCP4-genomic  (1973) TACGGATCTAGAGTCGGTATCATGATACTTTCAAGTAGTTATGTTTCTTCTAGACAGTCC
         Genome  (2993) TACGGATCTAGAGTCGGTATCATGATACTTTCAAGTAGTTATGTTTCTTCTAGACAGTCC
                        3053                                                         3112
      NM_118070  (2067) CTGGATCACCTGGTTGCAGTTATGGAGCATTGGAAAACAACAGACCTTGTAATTATTCCT
   NM_001203843  (1716) CTGGATCACCTGGTTGCAGTTATGGAGCATTGGAAAACAACAGACCTTGTAATTATTCCT
   HCP4-genomic  (2033) CTGGATCACCTGGTTGCAGTTATGGAGCATTGGAAAACAACAGACCTTGTAATTATTCCT
         Genome  (3053) CTGGATCACCTGGTTGCAGTTATGGAGCATTGGAAAACAACAGACCTTGTAATTATTCCT
                        3113                                                         3172
      NM_118070  (2127) ATATATTTTAAAGTAAGACTTTCAGACATTTGTGGGTTGAAAGGCAGGTTTGAAGCAGCG
   NM_001203843  (1776) ATATATTTTAAAGTAAGACTTTCAGACATTTGTGGGTTGAAAGGCAGGTTTGAAGCAGCG
   HCP4-genomic  (2093) ATATATTTTAAAGTAAGACTTTCAGACATTTGTGGGTTGAAAGGCAGGTTTGAAGCAGCG
         Genome  (3113) ATATATTTTAAAGTAAGACTTTCAGACATTTGTGGGTTGAAAGGCAGGTTTGAAGCAGCG
                        3173                                                         3232
      NM_118070  (2187) TTTCTGCAGCTTCATATGTCTCTCCAGGAAGACAGAGTTCAGAAATGGAAGGCGGCTATG
   NM_001203843  (1836) TTTCTGCAGCTTCATATGTCTCTCCAGGAAGACAGAGTTCAGAAATGGAAGGCGGCTATG
   HCP4-genomic  (2153) TTTCTGCAGCTTCATATGTCTCTCCAGGAAGACAGAGTTCAGAAATGGAAGGCGGCTATG
         Genome  (3173) TTTCTGCAGCTTCATATGTCTCTCCAGGAAGACAGAGTTCAGAAATGGAAGGCGGCTATG
                        3233                                                         3292
      NM_118070  (2247) TCTGAAATAGTGTCCATCGGTGGACATGAATGGACCAAGGG-------------------
   NM_001203843  (1896) TCTGAAATAGTGTCCATCGGTGGACATGAATGGACCAAGGG-------------------
   HCP4-genomic  (2213) TCTGAAATAGTGTCCATCGGTGGACATGAATGGACCAAGGG-------------------
         Genome  (3233) TCTGAAATAGTGTCCATCGGTGGACATGAATGGACCAAGGGGTATATTTACTTATCTTTG
                        3293                                                         3352
```

Figure 13 - continued:

```
NM_118070      (2288) ----------------------------------------------------------
NM_001203843   (1937) ----------------------------------------------------------
HCP4-genomic   (2254) ----------------------------------------------------------
Genome         (3293) TTGTCCCTTTACTATTCAAAGCTAGTTTATTAATATTTGGAAGAGTATTCTTATTGGTG
                                                                            3353
                                                                                    3412
NM_118070      (2288) ------------------------------------------------AAGTCAGTTTATTCTTG
NM_001203843   (1937) ------------------------------------------------AAGTCAGTTTATTCTTG
HCP4-genomic   (2254) ------------------------------------------------AAGTCAGTTTATTCTTG
Genome         (3353) TGGTGCTAAATCAGTACTTCCATTTTCTCTGTCCTATTTGCAGAAGTCAGTTTATTCTTG
                                                                            3413
                                                                                    3472
NM_118070      (2305) CCGAGGAAGTTGTAAGAAATGCATCCTTAAGGCTATATCTGAAAAGTAGCAAGAATCTGC
NM_001203843   (1954) CCGAGGAAGTTGTAAGAAATGCATCCTTAAGGCTATATCTGAAAAGTAGCAAGAATCTGC
HCP4-genomic   (2271) CCGAGGAAGTTGTAAGAAATGCATCCTTAAGGCTATATCTGAAAAGTAGCAAGAATCTGC
Genome         (3413) CCGAGGAAGTTGTAAGAAATGCATCCTTAAGGCTATATCTGAAAAGTAGCAAGAATCTGC
                                                                            3473
                                                                                    3532
NM_118070      (2365) TTGGAATCTTAGCGTTGTTAAATCACTCCCAGTCTACAGACGTGGAAATTATGGGAATCT
NM_001203843   (2014) TTGGAATCTTAGCGTTGTTAAATCACTCCCAGTCTACAGACGTGGAAATTATGGGAATCT
HCP4-genomic   (2331) TTGGAATCTTAGCGTTGTTAAATCACTCCCAGTCTACAGACGTGGAAATTATGGGAATCT
Genome         (3473) TTGGAATCTTAGCGTTGTTAAATCACTCCCAGTCTACAGACGTGGAAATTATGGGAATCT
                                                                            3533
                                                                                    3592
NM_118070      (2425) GGGGTATAGCAGGAATAGGTAAGACATCGATTGCAAGAGAAATATTTGAATTACATGCTC
NM_001203843   (2074) GGGGTATAGCAGGAATAGGTAAGACATCGATTGCAAGAGAAATATTTGAATTACATGCTC
HCP4-genomic   (2391) GGGGTATAGCAGGAATAGGTAAGACATCGATTGCAAGAGAAATATTTGAATTACATGCTC
Genome         (3533) GGGGTATAGCAGGAATAGGTAAGACATCGATTGCAAGAGAAATATTTGAATTACATGCTC
                                                                            3593
                                                                                    3652
NM_118070      (2485) CACATTATGATTTCTGTTACTTCCTGCAAGACTTTCATCTAATGTGTCAGATGAAAAGGC
NM_001203843   (2134) CACATTATGATTTCTGTTACTTCCTGCAAGACTTTCATCTAATGTGTCAGATGAAAAGGC
HCP4-genomic   (2451) CACATTATGATTTCTGTTACTTCCTGCAAGACTTTCATCTAATGTGTCAGATGAAAAGGC
Genome         (3593) CACATTATGATTTCTGTTACTTCCTGCAAGACTTTCATCTAATGTGTCAGATGAAAAGGC
                                                                            3653
                                                                                    3712
NM_118070      (2545) CGAGGCAATTGCGTGAAGATTTTATCTCAAAATTGTTTGGGGAAGAAAAAGGTCTAGGTG
NM_001203843   (2194) CGAGGCAATTGCGTGAAGATTTTATCTCAAAATTGTTTGGGGAAGAAAAAGGTCTAGGTG
HCP4-genomic   (2511) CGAGGCAATTGCGTGAAGATTTTATCTCAAAATTGTTTGGGGAAGAAAAAGGTCTAGGTG
Genome         (3653) CGAGGCAATTGCGTGAAGATTTTATCTCAAAATTGTTTGGGGAAGAAAAAGGTCTAGGTG
                                                                            3713
                                                                                    3772
NM_118070      (2605) CTAGTGATGTAAAGCCAAGTTTCATGAGGGACTGGTTCCATAAAAAAACGATTCTTCTCG
NM_001203843   (2254) CTAGTGATGTAAAGCCAAGTTTCATGAGGGACTGGTTCCATAAAAAAACGATTCTTCTCG
HCP4-genomic   (2571) CTAGTGATGTAAAGCCAAGTTTCATGAGGGACTGGTTCCATAAAAAAACGATTCTTCTCG
Genome         (3713) CTAGTGATGTAAAGCCAAGTTTCATGAGGGACTGGTTCCATAAAAAAACGATTCTTCTCG
                                                                            3773
                                                                                    3832
NM_118070      (2665) TTCTTGATGACGTGAGTAATGCCAGAGATGCAGAAGCTGTAATCGGAGGGTTTGGCTGGT
NM_001203843   (2314) TTCTTGATGACGTGAGTAATGCCAGAGATGCAGAAGCTGTAATCGGAGGGTTTGGCTGGT
HCP4-genomic   (2631) TTCTTGATGACGTGAGTAATGCCAGAGATGCAGAAGCTGTAATCGGAGGGTTTGGCTGGT
Genome         (3773) TTCTTGATGACGTGAGTAATGCCAGAGATGCAGAAGCTGTAATCGGAGGGTTTGGCTGGT
                                                                            3833
                                                                                    3892
NM_118070      (2725) TTTCTCATGGACACAGAATCATCTTAACCTCTAGGAGTAAACAAGTTCTTGTACAGTGTA
NM_001203843   (2374) TTTCTCATGGACACAGAATCATCTTAACCTCTAGGAGTAAACAAGTTCTTGTACAGTGTA
HCP4-genomic   (2691) TTTCTCATGGACACAGAATCATCTTAACCTCTAGGAGTAAACAAGTTCTTGTACAGTGTA
Genome         (3833) TTTCTCATGGACACAGAATCATCTTAACCTCTAGGAGTAAACAAGTTCTTGTACAGTGTA
                                                                            3893
                                                                                    3952
NM_118070      (2785) AGGTTAAAAAGCCATACGAGATCCAAAAATTAAGCGATTTTGAATCGTTTCGTCTCTGCA
NM_001203843   (2434) AGGTTAAAAAGCCATACGAGATCCAAAAATTAAGCGATTTTGAATCGTTTCGTCTCTGCA
HCP4-genomic   (2751) AGGTTAAAAAGCCATACGAGATCCAAAAATTAAGCGATTTTGAATCGTTTCGTCTCTGCA
Genome         (3893) AGGTTAAAAAGCCATACGAGATCCAAAAATTAAGCGATTTTGAATCGTTTCGTCTCTGCA
                                                                            3953
                                                                                    4012
NM_118070      (2845) AACAATATTTGGATGGCGAAAATCCGGTCATCTCTGAGCTTATCAGCTGCAGTAGTGGTA
NM_001203843   (2494) AACAATATTTGGATGGCGAAAATCCGGTCATCTCTGAGCTTATCAGCTGCAGTAGTGGTA
HCP4-genomic   (2811) AACAATATTTGGATGGCGAAAATCCGGTCATCTCTGAGCTTATCAGCTGCAGTAGTGGTA
Genome         (3953) AACAATATTTGGATGGCGAAAATCCGGTCATCTCTGAGCTTATCAGCTGCAGTAGTGGTA
                                                                            4013
                                                                                    4072
NM_118070      (2905) TTCCATTGGCTCTCAAACTTTTAGTTTCCTCTGTATCAAAGCAGTATATAACGAATATGA
NM_001203843   (2554) TTCCATTGGCTCTCAAACTTTTAGTTTCCTCTGTATCAAAGCAGTATATAACGAATATGA
HCP4-genomic   (2871) TTCCATTGGCTCTCAAACTTTTAGTTTCCTCTGTATCAAAGCAGTATATAACGAATATGA
Genome         (4013) TTCCATTGGCTCTCAAACTTTTAGTTTCCTCTGTATCAAAGCAGTATATAACGAATATGA
                                                                            4073
                                                                                    4132
NM_118070      (2965) AAGACCATCTCCAAAGCTTGAGGAAAGATCCTCCTACTCAGATTCAAGAAGCATTTCGGA
NM_001203843   (2614) AAGACCATCTCCAAAGCTTGAGGAAAGATCCTCCTACTCAGATTCAAGAAGCATTTCGGA
```

Figure 13 - continued:

```
HCP4-genomic  (2931) AAGACCATCTCCAAAGCTTGAGGAAAGATCCTCCTACTCAGATTCAAGAAGCATTTCGGA
Genome        (4073) AAGACCATCTCCAAAGCTTGAGGAAAGATCCTCCTACTCAGATTCAAGAAGCATTTCGGA
                     4133                                                         4192
NM_118070     (3025) GAAGTTTTGATGGACTAGATGAAAACGAGAAAAACATATTTTTGGATCTTGCATGTTTTT
NM_001203843  (2674) GAAGTTTTGATGGACTAGATGAAAACGAGAAAAACATATTTTTGGATCTTGCATGTTTTT
HCP4-genomic  (2991) GAAGTTTTGATGGACTAGATGAAAACGAGAAAAACATATTTTTGGATCTTGCATGTTTTT
Genome        (4133) GAAGTTTTGATGGACTAGATGAAAACGAGAAAAACATATTTTTGGATCTTGCATGTTTTT
                     4193                                                         4252
NM_118070     (3085) TCAGGGGGCAGAGCAAAGATTATGCGGTGCTATTACTTGATGCTTGTGGTTTTTTTACAT
NM_001203843  (2734) TCAGGGGGCAGAGCAAAGATTATGCGGTGCTATTACTTGATGCTTGTGGTTTTTTTACAT
HCP4-genomic  (3051) TCAGGGGGCAGAGCAAAGATTATGCGGTGCTATTACTTGATGCTTGTGGTTTTTTTACAT
Genome        (4193) TCAGGGGGCAGAGCAAAGATTATGCGGTGCTATTACTTGATGCTTGTGGTTTTTTTACAT
                     4253                                                         4312
NM_118070     (3145) ATATGGGAATCTGTGAGCTCATTGACGAGTCACTCATTAGCCTTGTAGACAACAAGATAG
NM_001203843  (2794) ATATGGGAATCTGTGAGCTCATTGACGAGTCACTCATTAGCCTTGTAGACAACAAGATAG
HCP4-genomic  (3111) ATATGGGAATCTGTGAGCTCATTGACGAGTCACTCATTAGCCTTGTAGACAACAAGATAG
Genome        (4253) ATATGGGAATCTGTGAGCTCATTGACGAGTCACTCATTAGCCTTGTAGACAACAAGATAG
                     4313                                                         4372
NM_118070     (3205) AGATGCCTATTCCTTTTCAAGACATGGGCCGAATTATTGTTCATGAAGAAGATGAGGATC
NM_001203843  (2854) AGATGCCTATTCCTTTTCAAGACATGGGCCGAATTATTGTTCATGAAGAAGATGAGGATC
HCP4-genomic  (3171) AGATGCCTATTCCTTTTCAAGACATGGGCCGAATTATTGTTCATGAAGAAGATGAGGATC
Genome        (4313) AGATGCCTATTCCTTTTCAAGACATGGGCCGAATTATTGTTCATGAAGAAGATGAGGATC
                     4373                                                         4432
NM_118070     (3265) CATGTGAACGTAGCAGATTGTGGGACTCGAAGGACATCGTTGATGTTTTGACAAACAATT
NM_001203843  (2914) CATGTGAACGTAGCAGATTGTGGGACTCGAAGGACATCGTTGATGTTTTGACAAACAATT
HCP4-genomic  (3231) CATGTGAACGTAGCAGATTGTGGGACTCGAAGGACATCGTTGATGTTTTGACAAACAATT
Genome        (4373) CATGTGAACGTAGCAGATTGTGGGACTCGAAGGACATCGTTGATGTTTTGACAAACAATT
                     4433                                                         4492
NM_118070     (3325) CAG---------------------------------------------------------
NM_001203843  (2974) CAG---------------------------------------------------------
HCP4-genomic  (3291) CAG---------------------------------------------------------
Genome        (4433) CAGTAAGTCGAACTGTGTTTAGTTCTTTTAACACTTCAGATACTTCGTGCATTCGTGGTT
                     4493                                                         4552
NM_118070     (3328) -----------------------------------------------------------G
NM_001203843  (2977) -----------------------------------------------------------G
HCP4-genomic  (3294) -----------------------------------------------------------G
Genome        (4493) ATCCTTTCTTTAGTTGTAACAGGTGAGGGTTCTTACTTATGTGATTGTTTTGTCAGGG
                     4553                                                         4612
NM_118070     (3329) AACAGAAGCAATTGAGGGCATCTTCCTGGATGCGTCTGACTTGACCTGCGAGCTTAGTCC
NM_001203843  (2978) AACAGAAGCAATTGAGGGCATCTTCCTGGATGCGTCTGACTTGACCTGCGAGCTTAGTCC
HCP4-genomic  (3295) AACAGAAGCAATTGAGGGCATCTTCCTGGATGCGTCTGACTTGACCTGCGAGCTTAGTCC
Genome        (4553) AACAGAAGCAATTGAGGGCATCTTCCTGGATGCGTCTGACTTGACCTGCGAGCTTAGTCC
                     4613                                                         4672
NM_118070     (3389) TACTGTGTTTGGTAAGATGTATAATCTTAGATTGCTGAAGTTCTATTGTTCAACCTCTGG
NM_001203843  (3038) TACTGTGTTTGGTAAGATGTATAATCTTAGATTGCTGAAGTTCTATTGTTCAACCTCTGG
HCP4-genomic  (3355) TACTGTGTTTGGTAAGATGTATAATCTTAGATTGCTGAAGTTCTATTGTTCAACCTCTGG
Genome        (4613) TACTGTGTTTGGTAAGATGTATAATCTTAGATTGCTGAAGTTCTATTGTTCAACCTCTGG
                     4673                                                         4732
NM_118070     (3449) GAACCAGTGCAAGCTTACTCTACCTCACGGCCTAGACACTTTGCCTGATGAGCTAAGTCT
NM_001203843  (3098) GAACCAGTGCAAGCTTACTCTACCTCACGGCCTAGACACTTTGCCTGATGAGCTAAGTCT
HCP4-genomic  (3415) GAACCAGTGCAAGCTTACTCTACCTCACGGCCTAGACACTTTGCCTGATGAGCTAAGTCT
Genome        (4673) GAACCAGTGCAAGCTTACTCTACCTCACGGCCTAGACACTTTGCCTGATGAGCTAAGTCT
                     4733                                                         4792
NM_118070     (3509) ACTTCACTGGGAGAATTACCCTCTGGTTTACTTGCCTCAGAAATTTAATCCTGTGAACCT
NM_001203843  (3158) ACTTCACTGGGAGAATTACCCTCTGGTTTACTTGCCTCAGAAATTTAATCCTGTGAACCT
HCP4-genomic  (3475) ACTTCACTGGGAGAATTACCCTCTGGTTTACTTGCCTCAGAAATTTAATCCTGTGAACCT
Genome        (4733) ACTTCACTGGGAGAATTACCCTCTGGTTTACTTGCCTCAGAAATTTAATCCTGTGAACCT
                     4793                                                         4852
NM_118070     (3569) TGTAGAGTTAAACATGCCTTATAGCAACATGGAGAAGTTGTGGGAAGGAAAGAAA-----
NM_001203843  (3218) TGTAGAGTTAAACATGCCTTATAGCAACATGGAGAAGTTGTGGGAAGGAAAGAAA-----
HCP4-genomic  (3535) TGTAGAGTTAAACATGCCTTATAGCAACATGGAGAAGTTGTGGGAAGGAAAGAAA-----
Genome        (4793) TGTAGAGTTAAACATGCCTTATAGCAACATGGAGAAGTTGTGGGAAGGAAAGAAAGTAAG
                     4853                                                         4912
NM_118070     (3624) ------------------------------------------------------------
NM_001203843  (3273) ------------------------------------------------------------
HCP4-genomic  (3590) ------------------------------------------------------------
Genome        (4853) TGTTGACATTATGGTTTTTAAAGCTGCTTGCATGAATTTATAACCTTGCATCTGATGACT
```

Figure 13 - continued:

```
                             4913                                          4972
   NM_118070   (3624)  ---------------------------AATCTCGAGAAGCTAAAGAACATCAAACTGAGT
NM_001203843   (3273)  ---------------------------AATCTCGAGAAGCTAAAGAACATCAAACTGAGT
 HCP4-genomic  (3590)  ---------------------------AATCTCGAGAAGCTAAAGAACATCAAACTGAGT
       Genome  (4913)  AATCTTGGTTATTGATGTTGTAAATAGAATCTCGAGAAGCTAAAGAACATCAAACTGAGT
                             4973                                          5032
   NM_118070   (3657)  CACTCCAGAGAATTAACTGATATCCTGATGTTATCAGAAGCCCTGAACCTGGAACACATT
NM_001203843   (3306)  CACTCCAGAGAATTAACTGATATCCTGATGTTATCAGAAGCCCTGAACCTGGAACACATT
 HCP4-genomic  (3623)  CACTCCAGAGAATTAACTGATATCCTGATGTTATCAGAAGCCCTGAACCTGGAACACATT
       Genome  (4973)  CACTCCAGAGAATTAACTGATATCCTGATGTTATCAGAAGCCCTGAACCTGGAACACATT
                             5033                                          5092
   NM_118070   (3717)  GATCTCGAAGGGTGTACGAGTCTGATTGATGTTAGCATGTCTATTCCTTGTTGTGGGAAG
NM_001203843   (3366)  GATCTCGAAGGGTGTACGAGTCTGATTGATGTTAGCATGTCTATTCCTTGTTGTGGGAAG
 HCP4-genomic  (3683)  GATCTCGAAGGGTGTACGAGTCTGATTGATGTTAGCATGTCTATTCCTTGTTGTGGGAAG
       Genome  (5033)  GATCTCGAAGGGTGTACGAGTCTGATTGATGTTAGCATGTCTATTCCTTGTTGTGGGAAG
                             5093                                          5152
   NM_118070   (3777)  CTTGTTTCCTTGAATATGAAAGACTGTTCTCGTTTGCGAAGTCTGCCTTCTATGGTTGAT
NM_001203843   (3426)  CTTGTTTCCTTGAATATGAAAGACTGTTCTCGTTTGCGAAGTCTGCCTTCTATGGTTGAT
 HCP4-genomic  (3743)  CTTGTTTCCTTGAATATGAAAGACTGTTCTCGTTTGCGAAGTCTGCCTTCTATGGTTGAT
       Genome  (5093)  CTTGTTTCCTTGAATATGAAAGACTGTTCTCGTTTGCGAAGTCTGCCTTCTATGGTTGAT
                             5153                                          5212
   NM_118070   (3837)  TTAACAACTCTCAAGCTTCTTAATTTGTCTGGCTGCTCAGAATTTGAGGATATTCAGGAT
NM_001203843   (3486)  TTAACAACTCTCAAGCTTCTTAATTTGTCTGGCTGCTCAGAATTTGAGGATATTCAGGAT
 HCP4-genomic  (3803)  TTAACAACTCTCAAGCTTCTTAATTTGTCTGGCTGCTCAGAATTTGAGGATATTCAGGAT
       Genome  (5153)  TTAACAACTCTCAAGCTTCTTAATTTGTCTGGCTGCTCAGAATTTGAGGATATTCAGGAT
                             5213                                          5272
   NM_118070   (3897)  TTTGCACCAAACCTGGAAGAGATATATCTAGCTGGGACATCCATTAGAGAGCTTCCGTTG
NM_001203843   (3546)  TTTGCACCAAACCTGGAAGAGATATATCTAGCTGGGACATCCATTAGAGAGCTTCCGTTG
 HCP4-genomic  (3863)  TTTGCACCAAACCTGGAAGAGATATATCTAGCTGGGACATCCATTAGAGAGCTTCCGTTG
       Genome  (5213)  TTTGCACCAAACCTGGAAGAGATATATCTAGCTGGGACATCCATTAGAGAGCTTCCGTTG
                             5273                                          5332
   NM_118070   (3957)  TCAATCAGGAATCTCACTGAACTTGTTACGCTAGATCTGGAGAACTGCGAAAGGCTTCAG
NM_001203843   (3606)  TCAATCAGGAATCTCACTGAACTTGTTACGCTAGATCTGGAGAACTGCGAAAGGCTTCAG
 HCP4-genomic  (3923)  TCAATCAGGAATCTCACTGAACTTGTTACGCTAGATCTGGAGAACTGCGAAAGACTTCAG
       Genome  (5273)  TCAATCAGGAATCTCACTGAACTTGTTACGCTAGATCTGGAGAACTGCGAAAGGCTTCAG
                             5333                                          5392
   NM_118070   (4017)  GAAATGCCGAGTCTTCCGGTGGAAATAATCAGGAGAACCTGAAAAAACGCAGAAATCACC
NM_001203843   (3666)  GAAATGCCGAG-------------------------------------------------
 HCP4-genomic  (3983)  GAAATGCCGAGTCTTCCGGTGGAAATAATCAGGAGAACCTGA------------------
       Genome  (5333)  GAAATGCCGAGTCTTCCGGTGGAAATAATCAGGAGAACCTGAAAAAACGCAGAAATCACC
                             5393                                          5452
   NM_118070   (4077)  TCTCAATCCCTGTTCTACCAAGGGATTGTGATGTAATTGTGGTATATTCTCGGACCGTGT
NM_001203843   (3677)  ------------------------------------------------------------
 HCP4-genomic  (4025)  ------------------------------------------------------------
       Genome  (5393)  TCTCAATCCCTGTTCTACCAAGGGATTGTGATGTAATTGTGGTATATTCTCGGACCGTGT
                             5453                                          5512
   NM_118070   (4137)  ATTCTCTATCTTATTTCCAAACGTTTTGTAGATTAGGCAAGGAAAGGAAAAATCCTAA
NM_001203843   (3677)  ------------------------------------------------------------
 HCP4-genomic  (4025)  ------------------------------------------------------------
       Genome  (5453)  ATTCTCTATCTTATTTCCAAACGTTTTGTAGATTAGGCAAGGAAAGGAAAAATCCTAA
                             5513                                          5572
   NM_118070   (4197)  TTGACACAGATTTGTAATAGATTTAGATGATCATTGTGTTTAATAATATTATTGTTAT
NM_001203843   (3677)  ------------------------------------------------------------
 HCP4-genomic  (4025)  ------------------------------------------------------------
       Genome  (5513)  TTGACACAGATTTGTAATAGATTTAGATGATCATTGTGTTTAATAATATTATTGTTAT
                             5573                                          5632
   NM_118070   (4257)  TTGTTGTATTTTAACAGTTCTATAATGATAATTGTGATCTCAAAATCTCGTTTATTA---
NM_001203843   (3677)  ------------------------------------------------------------
 HCP4-genomic  (4025)  ------------------------------------------------------------
       Genome  (5573)  TTGTTGTATTTTAACAGTTCTATAATGATAATTGTGATCTCAAAATCTCGTTTATTATTA
                             5633                                          5692
   NM_118070   (4314)  ------------------------------------------------------------
NM_001203843   (3677)  ------------------------------------------------------------
 HCP4-genomic  (4025)  ------------------------------------------------------------
       Genome  (5633)  GACTTTGTGTAAATTTGATTCTAAAGCAAACTTAGTCTGAATTCTGGTGCATACCTCGGT
                             5693                                          5752
   NM_118070   (4314)  ------------------------------------------------------------
```

Figure 13 - continued:

```
NM_001203843  (3677) ------------------------------------------------------------
HCP4-genomic  (4025) ------------------------------------------------------------
      Genome  (5693) ATTATTTTGTTTTATTGGAGACGGTGTTAATGTTATCATGATCCTCATTGTTTTCTTATG
                     5753                                                     5812
   NM_118070  (4314) ------------------------------------------------------------
NM_001203843  (3677) ------------------------------------------------------------
HCP4-genomic  (4025) ------------------------------------------------------------
      Genome  (5753) ATATCAAACTCCAAATCTGTAACATTAAAAGTTAAGAAATAGCTAGTTGTTTAGAAGACT
                     5813                                                     5872
   NM_118070  (4314) ------------------------------------------------------------
NM_001203843  (3677) ------------------------------------------------------------
HCP4-genomic  (4025) ------------------------------------------------------------
      Genome  (5813) AAACACAAAAAGTAAAGCATGAAAAGAACCATGATTAAACAAAGCCATATAAATCTACTT
                     5873                                                     5932
   NM_118070  (4314) ------------------------------------------------------------
NM_001203843  (3677) ------------------------------------------------------------
HCP4-genomic  (4025) ------------------------------------------------------------
      Genome  (5873) TTCAATAAGTGTTTTAAAAACATGTCTAGGTAGCCGTTTAGAGCATCTCCATCAGTAGTG
                     5933                                                     5992
   NM_118070  (4314) ------------------------------------------------------------
NM_001203843  (3677) ------------------------------------------------------------
HCP4-genomic  (4025) ------------------------------------------------------------
      Genome  (5933) AAAAAGTAGGAGATAGAGTCATAGAGGTATTTGAGAAACTTAGACCATCCACATTGCATA
                     5993                                                     6052
   NM_118070  (4314) ------------------------------------------------------------
NM_001203843  (3677) ------------------------------------------------------------
HCP4-genomic  (4025) ------------------------------------------------------------
      Genome  (5993) TATTTTTGTGTGTCTTTTCATATAAATATTATTAATAAAGTATGAATAGTCTTTTTAAG
                     6053                                                     6112
   NM_118070  (4314) ------------------------------------------------------------
NM_001203843  (3677) ------------------------------------------------------------
HCP4-genomic  (4025) ------------------------------------------------------------
      Genome  (6053) ACCCATTTATCAATGTATCTCAAAATGTCTTCTTTGAGACCTTTTTGGAGAGATGTCTTT
                     6113                                                     6172
   NM_118070  (4314) ------------------------------------------------------------
NM_001203843  (3677) ------------------------------------------------------------
HCP4-genomic  (4025) ------------------------------------------------------------
      Genome  (6113) CATTTAAAGACCCTCATATTATTTAATAAATTAAATTTATGTGGGAAGACATTTAAACTG
                     6173                                                     6232
   NM_118070  (4314) ------------------------------------------------------------
NM_001203843  (3677) ------------------------------------------------------------
HCP4-genomic  (4025) ------------------------------------------------------------
      Genome  (6173) AATGTGCAATGTGGATGCTCTAAAGCAACTGTCTTTCCATGTGTCTTTATATTATTGGCC
                     6233                                                     6292
   NM_118070  (4314) ------------------------------------------------------------
NM_001203843  (3677) ------------------------------------------------------------
HCP4-genomic  (4025) ------------------------------------------------------------
      Genome  (6233) AAAATCTACTTTTATAATTCAAAATTTAAATAAATAACTTAATTATTATAAATTGATTAA
                     6293                                                     6352
   NM_118070  (4314) ------------------------------------------------------------
NM_001203843  (3677) ------------------------------------------------------------
HCP4-genomic  (4025) ------------------------------------------------------------
      Genome  (6293) CATAATATTGTTGATAAACCCACACAGTATAAGACCGATGGAGATGGTCTTAGGCCCCGC
                     6353                                                     6412
   NM_118070  (4314) ------------------------------------------------------------
NM_001203843  (3677) ------------------------------------------------------------
HCP4-genomic  (4025) ------------------------------------------------------------
      Genome  (6353) TTAGACGCGTAGACGACCAAGATTTGTATAAGTTTTGTTTTAACGTTTTTTCAATTTTTA
                     6413                                                     6472
   NM_118070  (4314) ------------------------------------------------------------
NM_001203843  (3677) ------------------------------------------------------------
HCP4-genomic  (4025) ------------------------------------------------------------
      Genome  (6413) ATTACATAAAGTTTATTTATAAGTTCTAGCTTCATTGTTTAATATGAATTGAAGAAAGTG
                     6473                                                     6532
   NM_118070  (4314) ------------------------------------------------------------
NM_001203843  (3677) ------------------------------------------------------------
HCP4-genomic  (4025) ------------------------------------------------------------
```

Figure 13 - continued:

```
Genome        (6473)  AGATTTGTAAAATTAACCTTTTTTTACTACTTTTTTGCAATAATACCTTTTTATGTTGTC
                      6533                                                         6592
NM_118070     (4314)  ------------------------------------------------------------
NM_001203843  (3677)  -----------------------------------------------------------A
HCP4-genomic  (4025)  ------------------------------------------------------------
Genome        (6533)  CATTTTTAAAAATACTCATTTCCTTGAATAGAATGACCAAATTACCCTCATCTAATAGGA
                      6593                                                         6652
NM_118070     (4314)  ------------------------------------------------------------
NM_001203843  (3678)  ACATGTAATTGGAAACTGAAATTTTTCGGCAAAAAAAAAATCCGCCAAACTTTTTTTC
HCP4-genomic  (4025)  ------------------------------------------------------------
Genome        (6593)  ACATGTAATTGGAAACTGAAATTTTTCGGCAAAAAAAAAATCCGCCAAACTTTTTTTC
                      6653                                                         6712
NM_118070     (4314)  ------------------------------------------------------------
NM_001203843  (3738)  CGCCAAACAAAAAATTCCCGCCAAAAAAAAAATTCCGGCAAATATCTTTTTCATAACA
HCP4-genomic  (4025)  ------------------------------------------------------------
Genome        (6653)  CGCCAAACAAAAAATTCCCGCCAAAAAAAAAATTCCGGCAAATATCTTTTTCATAACA
                      6713                                                         6772
NM_118070     (4314)  ------------------------------------------------------------
NM_001203843  (3798)  AATCTTTTCTCAGCCAAAAAAATACTTTTAAAAATCCTTGTAAATTTAAAGTAATAGAGA
HCP4-genomic  (4025)  ------------------------------------------------------------
Genome        (6713)  AATCTTTTCTCAGCCAAAAAAATACTTTTAAAAATCCTTGTAAATTTAAAGTAATAGAGA
                      6773              6804
NM_118070     (4314)  ------------------------------
NM_001203843  (3858)  GTCTAAGTTTAAATTAAAGAATTTAATATAAA
HCP4-genomic  (4025)  --------------------------------
Genome        (6773)  GTCTAAGTTTAAATTAAAGAATTTAATATAAA
```

Figure 14:

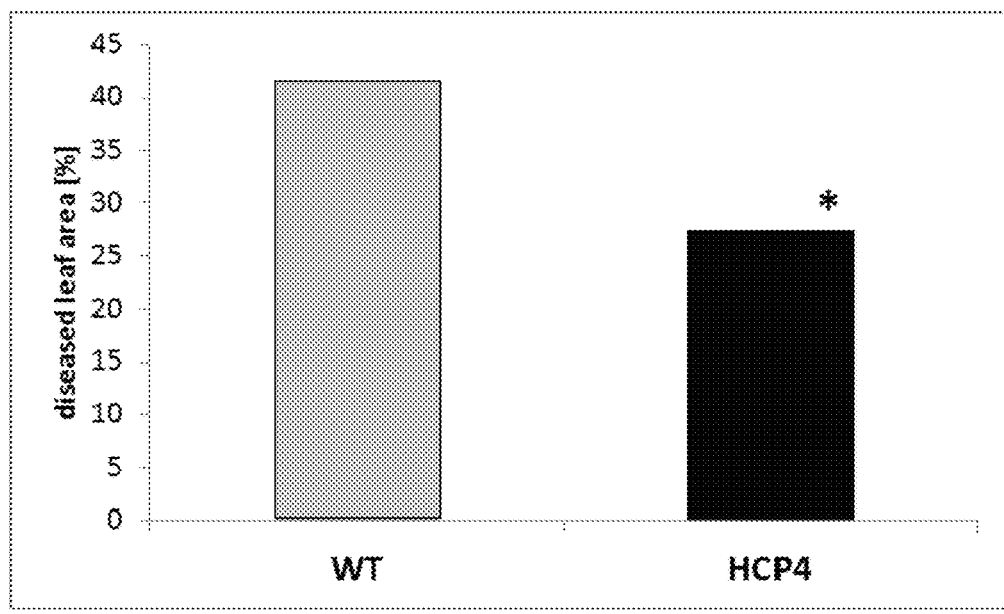

Figure 15:

| SEQ ID NO: | Description of the sequence listing |
|---|---|
| 1 | Nucleotide sequence HCP4 splice variant 1; Arabidopsis thaliana |
| 2 | Amino acid sequence from HCP4; first reading frame of splice variant 1; Arabidopsis thaliana |
| 3 | Amino acid sequence from HCP4; second reading frame of splice variant 1; Arabidopsis thaliana |
| 4 | Nucleotide sequence HCP4 splice variant 2; Arabidopsis thaliana |
| 5 | Amino acid sequence from HCP4; first reading frame of splice variant 2; Arabidopsis thaliana |
| 6 | Nucleotide sequence HCP4 splice variant 3; database accession number NM118070; Arabidopsis thaliana |
| 7 | Amino acid sequence from HCP4; third reading frame of splice variant 3; Arabidopsis thaliana |
| 8 | Nucleotide sequence HCP4 splice variant 4; database accession number NM1203843; Arabidopsis thaliana |
| 9 | Amino acid sequence from HCP4; third reading frame of splice variant 4; Arabidopsis thaliana |
| 10 | Nucleotide sequence HCP4 genomic sequence |
| 11 | Nucleotide sequence HCP4 genomic sequence truncated (as shown in Fig. 13); Arabidopsis thaliana |
| 12 | HCP4 forward primer |
| 13 | HCP4 reverse primer |
| 14 | Nucleotide sequence HCP4; variant of splice variant 1; Arabidopsis thaliana |
| 15 | Nucleotide sequence of HCP4 large exon (small version); Arabidopsis thaliana |
| 16 | Nucleotide sequence of HCP4 large exon (large version); Arabidopsis thaliana |
| 17 | Amino acid sequence of HCP4 large exon (small version); Arabidopsis thaliana |
| 18 | Amino acid sequence of HCP4 large exon (large version); Arabidopsis thaliana |
| 19 | Nucleotide sequence HCP4, variant 1 |
| 20 | Nucleotide sequence HCP4, variant 2 |
| 21 | Nucleotide sequence HCP4, variant 3 |
| 22 | Nucleotide sequence HCP4, variant 4 |
| 23 | Nucleotide sequence HCP4, variant 5 |
| 24 | Nucleotide sequence HCP4, variant 6 |
| 25 | Nucleotide sequence HCP4, variant 7 |

Figure 15 – continued:

| SEQ ID NO: | Description of the sequence listing |
|---|---|
| 25 | Nucleotide sequence HCP4, variant 7 |
| 26 | Nucleotide sequence HCP4, variant 8 |
| 27 | Nucleotide sequence HCP4, variant 9 |
| 28 | Amino acid sequence HCP4, variant 9 |
| 29 | Nucleotide sequence HCP4, variant 10 |
| 30 | Amino acid sequence HCP4, variant 10 |
| 31 | Nucleotide sequence HCP4, variant 11 |
| 32 | Amino acid sequence HCP4, variant 11 |
| 33 | Nucleotide sequence HCP4, variant 12 |
| 34 | Amino acid sequence HCP4, variant 12 |
| 35 | Nucleotide sequence HCP4, variant 13 |
| 36 | Amino acid sequence HCP4, variant 13 |
| 37 | Nucleotide sequence HCP4, variant 14 |
| 38 | Amino acid sequence HCP4, variant 14 |
| 39 | Nucleotide sequence HCP4, variant 15 |
| 40 | Amino acid sequence HCP4, variant 15 |
| 41 | Nucleotide sequence HCP4, variant 16 |
| 42 | Amino acid sequence HCP4, variant 16 |

FUNGAL RESISTANT PLANTS EXPRESSING HCP4

This application is a National Stage application of International Application No. PCT/IB2013/056316, filed Aug. 1, 2013, which claims the benefit of U.S. Provisional Application No. 61/681,155, filed Aug. 9, 2012, the entire contents of which are hereby incorporated herein by reference. This application also claims priority under 35 U.S.C. § 119 to European Patent Application No. 12179842.5, filed Aug. 9, 2012, the entire contents of which are incorporated herein by reference.

REFERENCE TO SEQUENCE LISTING SUBMITTED VIA EFS-WEB

This application was filed electronically via EFS-Web and includes an electronically submitted sequence listing in .txt format. The .txt file contains a sequence listing entitled "Sequence_List.txt" created on Nov. 26, 2014, and is 270, 336 bytes in size. The sequence listing contained in this .txt file is part of the specification and is hereby incorporated by reference herein in its entirety.

SUMMARY OF THE INVENTION

The present invention relates to a method of increasing resistance against fungal pathogens, in particular, pathogens of the order Pucciniales, for example soybean rust, in plants, plant parts, and/or plant cells. This is achieved by increasing the expression and/or activity of an HCP4 protein in a plant, plant part and/or plant cell in comparison to wild type plants, wild type plant parts and/or wild type plant cells.

Furthermore, the invention relates to transgenic plants, plant parts, and/or plant cells having an increased resistance against fungal pathogens, in particular, pathogens of the order Pucciniales, for example soybean rust, and to recombinant expression vectors comprising a sequence that is identical or homologous to a sequence encoding an HCP4 protein.

BACKGROUND OF THE INVENTION

The cultivation of agricultural crop plants serves mainly for the production of foodstuffs for humans and animals. Monocultures in particular, which are the rule nowadays, are highly susceptible to an epidemic-like spreading of diseases. The result is markedly reduced yields. To date, the pathogenic organisms have been controlled mainly by using pesticides. Nowadays, the possibility of directly modifying the genetic disposition of a plant or pathogen is also open to man.

Resistance generally describes the ability of a plant to prevent, or at least curtail the infestation and colonization by a harmful pathogen. Different mechanisms can be discerned in the naturally occurring resistance, with which the plants fend off colonization by phytopathogenis organisms. These specific interactions between the pathogen and the host determine the course of infection (Schopfer and Brennicke (1999) Pflanzenphysiologie, Springer Verlag, Berlin-Heidelberg, Germany).

With regard to the race specific resistance, also called host resistance, a differentiation is made between compatible and incompatible interactions. In the compatible interaction, an interaction occurs between a virulent pathogen and a susceptible plant. The pathogen survives, and may build up reproduction structures, while the host mostly dies off. An incompatible interaction occurs on the other hand when the pathogen infects the plant but is inhibited in its growth before or after weak development of symptoms (mostly by the presence of R genes of the NBS-LRR family, see below). In the latter case, the plant is resistant to the respective pathogen (Schopfer and Brennicke, vide supra). However, this type of resistance is specific for a certain strain or pathogen.

In both compatible and incompatible interactions a defensive and specific reaction of the host to the pathogen occurs. In nature, however, this resistance is often overcome because of the rapid evolutionary development of new virulent races of the pathogens (Neu et al. (2003) American Cytopathol. Society, MPMI 16 No. 7: 626-633).

Most pathogens are plant-species specific. This means that a pathogen can induce a disease in a certain plant species, but not in other plant species (Heath (2002) Can. J. Plant Pathol. 24: 259-264). The resistance against a pathogen in certain plant species is called non-host resistance. The non-host resistance offers strong, broad, and permanent protection from phytopathogens. Genes providing non-host resistance provide the opportunity of a strong, broad and permanent protection against certain diseases in non-host plants. In particular, such a resistance works for different strains of the pathogen.

Fungi are distributed worldwide. Approximately 100 000 different fungal species are known to date. Thereof rusts are of great importance. They can have a complicated development cycle with up to five different spore stages (spermatium, aecidiospore, uredospore, teleutospore and basidiospore).

During the infection of plants by pathogenic fungi, different phases are usually observed. The first phases of the interaction between phytopathogenic fungi and their potential host plants are decisive for the colonization of the plant by the fungus. During the first stage of the infection, the spores become attached to the surface of the plants, germinate, and the fungus penetrates the plant. Fungi may penetrate the plant via existing ports such as stomata, lenticels, hydatodes and wounds, or else they penetrate the plant epidermis directly as the result of the mechanical force and with the aid of cell-wall-digesting enzymes. Specific infection structures are developed for penetration of the plant.

Immediately after recognition of a potential pathogen the plant starts to elicit defense reactions. Mostly the presence of the pathogen is sensed via so called PAMP receptors, a class of trans-membrane receptor like kinases recognizing conserved pathogen associated molecules (e.g. flagellin or chitin). Downstream of the PAMP receptors, the phytohormones salicylic acid (SA), jasmonate (JA) and ethylene (ET) play a critical role in the regulation of the different defense reactions. Depending on the ratio of the different phytohormones, different defense reactions are elicited by the host cell. Generally SA dependent defense is linked with resistance against biotrophic pathogens, whereas JA/ET dependent defense reactions are active against necrotrophic pathogens (and insects).

Another more specific resistance mechanism is based on the presence of so called resistance genes (R-genes). Most R genes belong to the nucleotide-binding site-leucine-rich repeat (NBS-LRR) gene family and function in monitoring the presence of pathogen effector proteins (virulence factors; avirulence factors). After recognizing the pathogen derived proteins a strong defense reaction (mostly accompanied by a programmed cell death) is elicited.

The soybean rust *Phakopsora pachyrhizi* directly penetrates the plant epidermis. After crossing the epidermal cell, the fungus reaches the intercellular space of the mesophyll, where the fungus starts to spread through the leaves. To acquire nutrients the fungus penetrates mesophyll cells and develops haustoria inside the mesophyl cell. During the penetration process the plasmamembrane of the penetrated mesophyll cell stays intact. Therefore the soybean rust fungus establishes a biotrophic interaction with soybean.

The biotrophic phytopathogenic fungi, such as soybean rust and all other rust fungi, depend for their nutrition on the metabolism of living cells of the plants. This type of fungi belong to the group of biotrophic fungi, like other rust fungi, powdery mildew fungi or oomycete pathogens like the genus *Phytophthora* or *Peronospora*. The necrotrophic phytopathogenic fungi depend for their nutrition on dead cells of the plants, e.g. species from the genus *Fusarium, Rhizoctonia* or *Mycospaerella*. Soybean rust has occupied an intermediate position, since it penetrates the epidermis directly, whereupon the penetrated cell becomes necrotic. After the penetration, the fungus changes over to an obligatory-biotrophic lifestyle. The subgroup of the biotrophic fungal pathogens which follows essentially such an infection strategy is heminecrotrohic. In contrast to a heminecrotrophic pathogen, a hemibiotrophic pathogen lives for a short period of time in a biotrophic manner and subsequently starts killing the host cell and/or host organism, i.e., changes for the rest of its life-cycle to a necrotrophic life-style.

Soybean rust has become increasingly important in recent times. The disease may be caused by the biotrophic rusts *Phakopsora pachyrhizi* and *Phakopsora meibomiae*. They belong to the class Basidiomycota, order Uredinales, family Phakopsoraceae. Both rusts infect a wide spectrum of leguminosic host plants. *P. pachyrhizi*, also referred to as Asian rust, is the more aggressive pathogen on soy (*Glycine max*), and is therefore, at least currently, of great importance for agriculture. *P. pachyrhizi* can be found in nearly all tropical and subtropical soy growing regions of the world. *P. pachyrhizi* is capable of infecting 31 species from 17 families of the Leguminosae under natural conditions and is capable of growing on further 60 species under controlled conditions (Sinclair et al. (eds.), Proceedings of the rust workshop (1995), National SoyaResearch Laboratory, Publication No. 1 (1996); Rytter J. L. et al., Plant Dis. 87, 818 (1984)). *P. meibomiae* has been found in the Caribbean Basin and in Puerto Rico, and has not caused substantial damage as yet.

*P. pachyrhizi* can currently be controlled in the field only by means of fungicides. Soy plants with resistance to the entire spectrum of the isolates are not available. When searching for resistant soybean accessions, six dominant R-genes of the NBS-LRR family, named Rpp1-5 and Rpp? (Hyuuga), which mediate resistance of soy to *P. pachyrhizi*, were discovered by screening thousands of soybean varieties. As the R-genes are derived from a host (soybean), the resistance was lost rapidly, as *P. pachyrhizi* develops new virulent races. Therefore there is a strong need to discover R-genes that are derived from non-hosts plants (e.g. *Arabidopsis*) as they are thought to be more durable.

In recent years, fungal diseases, e.g. soybean rust, has gained in importance as pest in agricultural production. There was therefore a demand in the prior art for developing methods to control fungi and to provide fungal resistant plants.

Much research has been performed on the field of powdery and downy mildew infecting the epidermal layer of plants. However, the problem to cope with soybean rust which infects the mesophyll remains unsolved.

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that fungal pathogens, in particular of the order Pucciniales, for example soybean rust, can be controlled by increasing the expression of an HCP4 protein.

The present invention therefore provides a method of increasing resistance against fungal pathogens, preferably against rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more HCP4 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP4 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF SUMMARY OF THE INVENTION

The object of the present invention is inter alia to provide a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust.

Surprisingly, we found that resistance against fungal pathogens, in particular of the order Pucciniales, for example soybean rust, can be enhanced by increasing the expression of a HCP4 protein.

The present invention therefore provides a method of increasing resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust, in transgenic plants, transgenic plant parts, or transgenic plant cells by overexpressing one or more HCP4 nucleic acids.

A further object is to provide transgenic plants resistant against fungal pathogens, preferably rust pathogens (i.e., fungal pathogens of the order Pucciniales), preferably of the family Phakopsoraceae, more preferably against fungal pathogens of the genus *Phakopsora*, most preferably against *Phakopsora pachyrhizi* and *Phakopsora meibomiae*, also known as soybean rust, a method for producing such plants as well as a vector construct useful for the above methods.

Therefore, the present invention also refers to a recombinant vector construct and a transgenic plant, transgenic plant part, or transgenic plant cell comprising an exogenous HCP4 nucleic acid. Furthermore, a method for the production of a transgenic plant, transgenic plant part or transgenic plant cell using the nucleic acid of the present invention is claimed herein. In addition, the use of a nucleic acid or the recombinant vector of the present invention for the transformation of a plant, plant part, or plant cell is claimed herein.

The objects of the present invention, as outlined above, are achieved by the subject-matter of the main claims. Preferred embodiments of the invention are defined by the subject matter of the dependent claims.

BRIEF DESCRIPTION OF THE SEVERAL VIEWS OF THE DRAWINGS

FIG. 1 shows the scoring system used to determine the level of diseased leaf area of wildtype and transgenic soy plants against the rust fungus *P. pachyrhizi* (as described in GODOY, C. V., KOGA, L. J. & CANTERI, M. G. Diagrammatic scale for assessment of soybean rust severity. Fitopatologia Brasileira 31:063-068. 2006).

FIG. 2 shows the schematic illustration of the plant transformation vector harboring the HCP4 cDNA under control of the parsley ubiquitine promoter.

FIG. 3 shows the sequence of a cDNA generated from the HCP4 genomic sequence (as shown in SEQ ID NO: 10) from *Arabidopsis thaliana* having SEQ ID NO:1.

FIG. 4 shows the sequence of an HCP4 protein (SEQ ID NO: 2) encoded by SEQ ID NO: 1 based on the first reading frame.

FIG. 5 shows the sequence of an HCP4 protein (SEQ ID NO: 3) encoded by SEQ ID NO: 1 based on the second reading frame.

FIG. 6 shows the sequence of another cDNA generated from the HCP4 genomic sequence (as shown in SEQ ID NO: 10) from *Arabidopsis thaliana* having SEQ ID NO:4.

FIG. 7 shows the sequence of the a HCP4 protein having SEQ ID NO:5 encoded by SEQ ID NO: 4 based on the first reading frame.

FIG. 8 shows the sequence of another HCP4 cDNA (accession No. NM_118070) generated from the HCP4 genomic sequence (as shown in SEQ ID NO: 10) from *Arabidopsis thaliana* having SEQ ID NO: 6.

FIG. 9 shows the protein sequence encoded by a HCP4 cDNA (NM_118070, SEQ ID NO: 6) having SEQ ID NO: 7 based on the third reading frame of SEQ ID NO: 6.

FIG. 10 shows the sequence of a HCP4 cDNA (accession No: NM_001203843) generated from the HCP4 genomic sequence (as shown in SEQ ID NO: 10) from *Arabidopsis thaliana* having SEQ ID NO: 8.

FIG. 11 shows the protein sequence encoded by a HCP4 cDNA (NM_001203843, SEQ ID NO: 8) having SEQ ID NO: 9 based on the third reading frame of SEQ ID NO: 8.

FIG. 12 shows the sequence of the genomic sequence (having SEQ ID NO: 10) from *Arabidopsis thaliana* around the region which codes for HCP4.

FIG. 13 shows the alignment of the *Arabidopsis* genome sequence (SEQ ID NO: 10), the cDNAs and/or splice variants as shown in SEQ ID NO: 1 (HCP4-genomic), SEQ ID NO: 6 (NM_118070), and SEQ ID NO: 8 (NM_001203843). In FIG. 13 the genome sequence (SEQ ID NO: 10) is truncated at its 3' and 5' end. The truncated genome sequence is shown in SEQ ID NO: 11.

FIG. 14 shows the result of the scoring of 50 transgenic soy plants (derived from 5 independent events) expressing the HCP4 overexpression vector construct. $T_1$ soybean plants expressing HCP4 protein were inoculated with spores of *Phakopsora pachyrhizi*. The evaluation of the diseased leaf area on all leaves was performed 14 days after inoculation. The average of the percentage of the leaf area showing fungal colonies or strong yellowing/browning on all leaves was considered as diseased leaf area. At all 50 soybean $T_1$ plants expressing HCP4 (expression checked by RT-PCR) were evaluated in parallel to non-transgenic control plants. The average of the diseased leaf area is shown in FIG. 14. Increase in expression of HCP4 significantly (*: $p<0.05$) reduces the diseased leaf area in comparison to non-transgenic control plants by 34.1%.

FIG. 15 contains a brief description of the sequences of the sequence listing.

DETAILED DESCRIPTION OF THE INVENTION

The present invention may be understood more readily by reference to the following detailed description of the preferred embodiments of the invention and the examples included herein.

Definitions

Unless otherwise noted, the terms used herein are to be understood according to conventional usage by those of ordinary skill in the relevant art. In addition to the definitions of terms provided herein, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, “a” or “an” can mean one or more, depending upon the context in which it is used. Thus, for example, reference to “a cell” can mean that at least one cell can be utilized. It is to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

"Homologues" of a protein encompass peptides, oligopeptides, polypeptides, proteins and/or enzymes having amino acid substitutions, deletions and/or insertions relative to the unmodified protein in question and having similar functional activity as the unmodified protein from which they are derived.

"Homologues" of a nucleic acid encompass nucleotides and/or polynucleotides having nucleic acid substitutions, deletions and/or insertions relative to the unmodified nucleic acid in question, wherein the protein coded by such nucleic acids has similar or higher functional activity as the unmodified protein coded by the unmodified nucleic acid from which they are derived. In particular, homologues of a nucleic acid may encompass substitutions on the basis of the degenerative amino acid code.

A "deletion" refers to removal of one or more amino acids from a protein or to the removal of one or more nucleic acids from DNA, ssRNA and/or dsRNA.

An "insertion" refers to one or more amino acid residues or nucleic acid residues being introduced into a predetermined site in a protein or the nucleic acid.

A "substitution" refers to replacement of amino acids of the protein with other amino acids having similar properties (such as similar hydrophobicity, hydrophilicity, antigenicity, propensity to form or break α-helical structures or beta-sheet structures).

On the nucleic acid level a substitution refers to a replacement of one or more nucleotides with other nucleotides within a nucleic acid, wherein the protein coded by the modified nucleic acid has a similar function. In particular homologues of a nucleic acid encompass substitutions on the basis of the degenerative amino acid code.

Amino acid substitutions are typically of single residues, but may be clustered depending upon functional constraints placed upon the protein and may range from 1 to 10 amino acids; insertions or deletion will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table 1 below, or Taylor W. R. (1986) The classification of amino acid conservation J Theor Biol., 119:205-18).

TABLE 1

Examples of conserved amino acid substitutions

| Residue | Conservative Substitutions | Residue | Conservative Substitutions |
|---------|----------------------------|---------|----------------------------|
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu, Val | | |

Amino acid substitutions, deletions and/or insertions may readily be made using peptide synthetic techniques well known in the art, such as solid phase peptide synthesis and the like, or by recombinant DNA manipulation.

Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gene in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The terms "encode" or "coding for" is used for the capability of a nucleic acid to contain the information for the amino acid sequence of a protein via the genetic code, i.e., the succession of codons each being a sequence of three nucleotides, which specify which amino acid will be added next during protein synthesis. The terms "encode" or "coding for" therefore includes all possible reading frames of a nucleic acid. Furthermore, the terms "encode" or "coding for" also applies to a nucleic acid, which coding sequence is interrupted by noncoding nucleic acid sequences, which are removed prior translation, e.g., a nucleic acid sequence comprising introns.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, Nucleic Acids Res. 31:3784-3788 (2003)). Domains or motifs may also be identified using routine techniques, such as by sequence alignment.

Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the global (i.e. spanning the complete sequences) alignment of two sequences that maximizes the number of matches and minimizes the number of gaps. The BLAST algorithm (Altschul et al. (1990) J Mol Biol 215: 403-10) calculates percent sequence identity or similarity or homology and performs a statistical analysis of the identity or similarity or homology between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity/homology/identity may also be determined using one of the methods available in the MatGAT software package (Campanella et al., BMC Bioinformatics. 2003 Jul. 10; 4:29.

MatGAT: an application that generates similarity/homology/identity matrices using protein or DNA sequences.). Minor manual editing may be performed to optimise alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (Smith T F, Waterman M S (1981) J. Mol. Biol 147(1); 195-7).

As used herein the terms "fungal-resistance", "resistant to a fungus" and/or "fungal-resistant" mean reducing, preventing, or delaying an infection by fungi. The term "resistance" refers to fungal resistance. Resistance does not imply that the plant necessarily has 100% resistance to infection. In preferred embodiments, enhancing or increasing fungal resistance means that resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant.

As used herein the terms "soybean rust-resistance", "resistant to a soybean rust", "soybean rust-resistant", "rust-resistance", "resistant to a rust", or "rust-resistant" mean reducing or preventing or delaying an infection of a plant, plant part, or plant cell by Phakopsoracea, in particular *Phakopsora pachyrhizi* and *Phakopsora meibomiae*— also known as soybean rust or Asian Soybean Rust (ASR), as compared to a wild type plant, wild type plant part, or wild type plant cell. Resistance does not imply that the plant necessarily has 100% resistance to infection. In preferred embodiments, enhancing or increasing rust resistance means that rust resistance in a resistant plant is greater than 10%, greater than 20%, greater than 30%, greater than 40%, greater than 50%, greater than 60%, greater than 70%, greater than 80%, greater than 90%, or greater than 95% in comparison to a wild type plant that is not resistant to soybean rust. Preferably the wild type plant is a plant of a similar, more preferably identical, genotype as the plant having increased resistance to the soybean rust, but does not comprise an exogenous HCP4 nucleic acid, functional fragments thereof and/or an exogenous nucleic acid capable of hybridizing with an HCP4 nucleic acid.

The level of fungal resistance of a plant can be determined in various ways, e.g. by scoring/measuring the infected leaf area in relation to the overall leaf area. Another possibility to determine the level of resistance is to count the number of soybean rust colonies on the plant or to measure the amount of spores produced by these colonies. Another way to resolve the degree of fungal infestation is to specifically measure the amount of rust DNA by quantitative (q) PCR. Specific probes and primer sequences for most fungal pathogens are available in the literature (Frederick R D, Snyder C L, Peterson G L, et al. 2002 Polymerase chain reaction assays for the detection and discrimination of the rust pathogens *Phakopsora pachyrhizi* and *P. meibomiae*, Phytopathology 92(2) 217-227).

The term "hybridization" as used herein includes "any process by which a strand of nucleic acid molecule joins with a complementary strand through base pairing" (J. Coombs (1994) Dictionary of Biotechnology, Stockton Press, New York). Hybridization and the strength of hybridization (i.e., the strength of the association between the nucleic acid molecules) is impacted by such factors as the degree of complementarity between the nucleic acid molecules, stringency of the conditions involved, the Tm of the formed hybrid, and the G:C ratio within the nucleic acid molecules.

As used herein, the term "Tm" is used in reference to the "melting temperature." The melting temperature is the temperature at which a population of double-stranded nucleic acid molecules becomes half dissociated into single strands. The equation for calculating the Tm of nucleic acid molecules is well known in the art. As indicated by standard references, a simple estimate of the Tm value may be calculated by the equation: $Tm=81.5+0.41(\% G+C)$, when a nucleic acid molecule is in aqueous solution at 1 M NaCl (see e.g., Anderson and Young, Quantitative Filter Hybridization, in Nucleic Acid Hybridization (1985). Other references include more sophisticated computations, which take structural as well as sequence characteristics into account for the calculation of Tm. Stringent conditions, are known to those skilled in the art and can be found in Current Protocols in Molecular Biology, John Wiley & Sons, N.Y. (1989), 6.3.1-6.3.6.

In particular, the term "stringency conditions" refers to conditions, wherein 100 contiguous nucleotides or more, 150 contigous nucleotides or more, 200 contigous nucleotides or more or 250 contiguous nucleotides or more which are a fragment or identical to the complementary nucleic acid molecule (DNA, RNA, ssDNA or ssRNA) hybridizes under conditions equivalent to hybridization in 7% sodium dodecyl sulfate (SDS), 0.5 M NaPO4, 1 mM EDTA at 50° C. with washing in 2×SSC, 0.1% SDS at 50° C. or 65° C., preferably at 65° C., with a specific nucleic acid molecule (DNA; RNA, ssDNA or ss RNA). Preferably, the hybridizing conditions are equivalent to hybridization in 7% sodium dodecyl sulfate (SDS), 0.5 M NaPO4, 1 mM EDTA at 50° C. with washing in 1×SSC, 0.1% SDS at 50° C. or 65° C., preferably 65° C., more preferably the hybridizing conditions are equivalent to hybridization in 7% sodium dodecyl sulfate (SDS), 0.5 M NaPO4, 1 mM EDTA at 50° C. with washing in 0.1×SSC, 0.1% SDS at 50° C. or 65° C., preferably 65° C. Preferably, the complementary nucleotides hybridize with a fragment or the whole HCP4 nucleic acids. Alternatively, preferred hybridization conditions encompass hybridisation at 65° C. in 1×SSC or at 42° C. in 1×SSC and 50% formamide, followed by washing at 65° C. in 0.3×SSC or hybridisation at 50° C. in 4×SSC or at 40° C. in 6×SSC and 50% formamide, followed by washing at 50° C. in 2×SSC. Further preferred hybridization conditions are 0.1% SDS, 0.1 SSD and 65° C.

"Identity" or "homology" or "similarity" between two nucleic acids sequences or amino acid sequences refers in each case over the entire length of the HCP4 nucleic acid sequences or HCP4 amino acid sequences. The terms "identity", "homology" and "similarity" are used herein interchangeably.

Preferably, "percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the region being compared and multiplying the result by 100.

For example the identity may be calculated by means of the Vector NTI Suite 7.1 program of the company Informax (USA) employing the Clustal Method (Higgins D G, Sharp P M. Fast and sensitive multiple sequence alignments on a microcomputer. Comput Appl. Biosci. 1989 April; 5(2):151-1) with the following settings:
Multiple Alignment Parameter:
Gap opening penalty 10
Gap extension penalty 10
Gap separation penalty range 8
Gap separation penalty off
% identity for alignment delay 40
Residue specific gaps off
Hydrophilic residue gap off
Transition weighing 0
Pairwise Alignment Parameter:
FAST algorithm on
K-tuple size 1
Gap penalty 3
Window size 5
Number of best diagonals 5

Alternatively the identity may be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13):3497-500, the web page: http://www.ebi.ac.uk/Tools/clustalw/index.html# and the following settings
DNA Gap Open Penalty 15.0
DNA Gap Extension Penalty 6.66
DNA Matrix Identity
Protein Gap Open Penalty 10.0
Protein Gap Extension Penalty 0.2
Protein matrix Gonnet
Protein/DNA ENDGAP −1
Protein/DNA GAPDIST 4

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

Sequence identity between the nucleic acid or protein useful according to the present invention and the HCP4 nucleic acids or HCP4 proteins may be optimized by sequence comparison and alignment algorithms known in the art (see Gribskov and Devereux, Sequence Analysis Primer, Stockton Press, 1991, and references cited therein) and calculating the percent difference between the nucleotide or protein sequences by, for example, the Smith-Waterman algorithm as implemented in the BESTFIT software program using default parameters (e.g., University of Wisconsin Genetic Computing Group).

The term "plant" is intended to encompass plants at any stage of maturity or development, as well as any tissues or organs (plant parts) taken or derived from any such plant unless otherwise clearly indicated by context. Plant parts include, but are not limited to, plant cells, stems, roots, flowers, ovules, stamens, seeds, leaves, embryos, meristematic regions, callus tissue, anther cultures, gametophytes, sporophytes, pollen, microspores, protoplasts, hairy root cultures, and/or the like. The present invention also includes seeds produced by the plants of the present invention. Preferably, the seeds comprise the exogenous HCP4 nucleic acids. In one embodiment, the seeds can develop into plants with increased resistance to fungal infection as compared to a wild-type variety of the plant seed. As used herein, a "plant cell" includes, but is not limited to, a protoplast, gamete producing cell, and a cell that regenerates into a whole plant. Tissue culture of various tissues of plants and regeneration of plants therefrom is well known in the art and is widely published.

Reference herein to an "endogenous" nucleic acid and/or protein refers to the nucleic acid and/or protein in question as found in a plant in its natural form (i.e., without there being any human intervention).

The term "exogenous" nucleic acid refers to a nucleic acid that has been introduced in a plant by means of genetechnology. An "exogenous" nucleic acid can either not occur in a plant in its natural form, be different from the nucleic acid in question as found in a plant in its natural form, or can be identical to a nucleic acid found in a plant in its natural form, but integrated not within their natural genetic environment. The corresponding meaning of "exogenous" is applied in the context of protein expression. For example, a transgenic plant containing a transgene, i.e., an exogenous nucleic acid, may, when compared to the expression of the endogenous gene, encounter a substantial increase of the expression of the respective gene or protein in total. A transgenic plant according to the present invention includes an exogenous HCP4 nucleic acid integrated at any genetic loci and optionally the plant may also include the endogenous gene within the natural genetic background.

For the purposes of the invention, "recombinant" means with regard to, for example, a nucleic acid sequence, a nucleic acid molecule, an expression cassette or a vector construct comprising any one or more HCP4 nucleic acids, all those constructions brought about by man by genetechnological methods in which either (a) the sequences of the HCP4 nucleic acids or a part thereof, or
(b) genetic control sequence(s) which is operably linked with the HCP4 nucleic acid sequence according to the invention, for example a promoter, or
(c) a) and b)

are not located in their natural genetic environment or have been modified by man by genetechnological methods. The modification may take the form of, for example, a substitution, addition, deletion, inversion or insertion of one or more nucleotide residues. The natural genetic environment is understood as meaning the natural genomic or chromosomal locus in the original plant or the presence in a genomic library or the combination with the natural promoter.

A recombinant nucleic acid, expression cassette or vector construct preferably comprises a natural gene and a natural promoter, a natural gene and a non-natural promoter, a non-natural gene and a natural promoter, or a non-natural gene and a non-natural promoter.

In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp.

A naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is modified by man by non-natural, synthetic ("artificial") methods such as, for example, mutagenic treatment. Suitable methods are described, for example, in U.S. Pat. No. 5,565,350, WO 00/15815 or US200405323. Furthermore, a naturally occurring expression cassette—for example the naturally occurring combination of the natural promoter of the nucleic acid sequences with the corresponding nucleic acid sequence encoding a protein useful in the methods of the present invention, as defined above—becomes a recombinant expression cassette when this expression cassette is not integrated in the natural genetic environment but in a different genetic environment.

The term "isolated nucleic acid" or "isolated protein" refers to a nucleic acid or protein that is not located in its natural environment, in particular its natural cellular environment. Thus, an isolated nucleic acid or isolated protein is essentially separated from other components of its natural environment. However, the skilled person in the art is aware that preparations of an isolated nucleic acid or an isolated protein can display a certain degree of impurity depending on the isolation procedure used. Methods for purifying nucleic acids and proteins are well known in the art. The isolated gene may be isolated from an organism or may be manmade, for example by chemical synthesis. In this regard, a recombinant nucleic acid may also be in an isolated form.

As used herein, the term "transgenic" refers to an organism, e.g., a plant, plant cell, callus, plant tissue, or plant part that exogenously contains the nucleic acid, recombinant construct, vector or expression cassette described herein or a part thereof which is preferably introduced by non-essentially biological processes, preferably by Agrobacteria transformation. The recombinant construct or a part thereof is stably integrated into a chromosome, so that it is passed on to successive generations by clonal propagation, vegetative propagation or sexual propagation. Preferred successive generations are transgenic too. Essentially biological processes may be crossing of plants and/or natural recombination.

A transgenic plant, plants cell or tissue for the purposes of the invention is thus understood as meaning that an exogenous HCP4 nucleic acid, recombinant construct, vector or expression cassette including one or more HCP4 nucleic acids is integrated into the genome by means of genetechnology.

Preferably, constructs or vectors or expression cassettes are not present in the genome of the original plant or are present in the genome of the transgenic plant not at their natural locus of the genome of the original plant.

A "wild type" plant, "wild type" plant part, or "wild type" plant cell means that said plant, plant part, or plant cell does not express exogenous HCP4 nucleic acid or exogenous HCP4 protein.

Natural locus means the location on a specific chromosome, preferably the location between certain genes, more preferably the same sequence background as in the original plant which is transformed.

Preferably, the transgenic plant, plant cell or tissue thereof expresses the HCP4 nucleic acids, HCP4 constructs or HCP4 expression cassettes described herein.

The term "expression" or "gene expression" means the transcription of a specific gene or specific genes or specific genetic vector construct. The term "expression" or "gene expression" in particular means the transcription of a gene or genes or genetic vector construct into structural RNA (rRNA, tRNA), or mRNA with or without subsequent translation of the latter into a protein. The process includes transcription of DNA and processing of the resulting RNA product. The term "expression" or "gene expression" can also include the translation of the mRNA and therewith the synthesis of the encoded protein, i.e., protein expression.

The term "increased expression" or "enhanced expression" or "overexpression" or "increase of content" as used herein means any form of expression that is additional to the original wild-type expression level. For the purposes of this invention, the original wild-type expression level might also be zero (absence of expression).

Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the protein of interest. For example, endogenous promoters may be altered in vivo by mutation, deletion, and/or substitution (see, Kmiec, U.S. Pat. No. 5,565,350; Zarling et al., WO9322443), or isolated promoters may be introduced into a plant cell in the proper orientation and distance from a gene of the present invention so as to control the expression of the gene.

If protein expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region (UTR) and/or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold (Buchman and Berg (1988) Mol. Cell biol. 8: 4395-4405; Callis et al. (1987) Genes Dev 1:1183-1200). Such intron enhancement of gene expression is typically greatest when placed near the 5' end of the transcription unit. Use of the maize introns Adh1-S intron 1, 2, and 6, the Bronze-1 intron are known in the art. For general information see: The Maize Handbook, Chapter 116, Freeling and Walbot, Eds., Springer, N.Y. (1994).

The term "functional fragment" refers to any nucleic acid or protein which comprises merely a part of the fulllength nucleic acid or fulllength protein, respectively, but still provides the same function, e.g., fungal resistance, when expressed or repressed in a plant, respectively. Preferably, the fragment comprises at least 50%, at least 60%, at least 70%, at least 80%, at least 90% at least 95%, at least 98%, at least 99% of the original sequence. Preferably, the functional fragment comprises contiguous nucleic acids or amino acids as in the original nucleic acid or original protein, respectively. In one embodiment the fragment of any of the HCP4 nucleic acids has an identity as defined above over a length of at least 20%, at least 30%, at least 50%, at least 75%, at least 90% of the nucleotides of the respective HCP4 nucleic acid.

The term "splice variant" as used herein encompasses variants of a nucleic acid sequence in which selected introns and/or exons or parts thereof have been excised, replaced, displaced or added, or in which introns have been shortened or lengthened. Thus, a splice variant can have one or more or even all introns removed or added or partially removed or partially added. According to this definition, a cDNA is considered as a splice variant of the respective intron-containing genomic sequence and vice versa. Such splice variants may be found in nature or may be manmade. Methods for predicting and isolating such splice variants are well known in the art (see for example Foissac and Schiex (2005) BMC Bioinformatics 6: 25).

In cases where overexpression of nucleic acid is desired, the term "similar functional activity" or "similar function" means that any homologue and/or fragment provide fungal resistance when expressed in a plant. Preferably similar functional activity means at least 50%, at least 60%, at least 70%, at least 80%, at least 90%, at least 95%, at least 98%, at least 99% or 100% or higher fungal resistance compared with functional activity provided by the exogenous expression of the HCP4 nucleotide sequence as defined by SEQ ID NO: 1 or 14.

The term "increased activity" or "enhanced activity" as used herein means any protein having increased activity and which provides an increased fungal resistance compared with the wildtype plant merely expressing the respective endogenous HCP4 nucleic acid. As far as overexpression is concerned, for the purposes of this invention, the original wild-type expression level might also be zero (absence of expression).

With respect to a vector construct and/or the recombinant nucleic acid molecules, the term "operatively linked" is intended to mean that the nucleic acid to be expressed is linked to the regulatory sequence, including promoters, terminators, enhancers and/or other expression control elements (e.g., polyadenylation signals), in a manner which allows for expression of the nucleic acid (e.g., in a host plant cell when the vector is introduced into the host plant cell). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the vector can depend on such factors as the choice of the host cell to be transformed, the level of expression of nucleic acid desired, and the like.

The term "introduction" or "transformation" as referred to herein encompass the transfer of an exogenous polynucleotide into a host cell, irrespective of the method used for transfer. Plant tissue capable of subsequent clonal propagation, whether by organogenesis or embryogenesis, may be transformed with a vector construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The host genome includes the nucleic acid contained in the nucleus as well as the nucleic acid contained in the plastids, e.g., chloroplasts, and/or mitochondria. The resulting transformed plant cell may then be used to regenerate a transformed plant in a manner known to persons skilled in the art.

The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, or less preferably from any other eukaryotic gene.

DETAILED DESCRIPTION

HCP4 Nucleic Acids

The HCP4 nucleic acid to be overexpressed in order to achieve increased resistance to fungal pathogens, e.g., of the family Phakopsoraceae, for example soybean rust, is preferably a nucleic acid coding for an HCP4 protein, and is preferably as defined by SEQ ID NO: 14, 4, 6, 8, 1, 10, 19-26, 27, 29, 31, 33, 35, 37, 39, or 41, or a fragment, homolog, derivative, orthologue or paralogue thereof, or a splice variant thereof. Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 14, 4, 6, 8, 1, 10, 19-26, 27, 29, 31, 33, 35, 37, 39, or 41, or is a functional fragment thereof, or a splice variant thereof. Most preferred is at least 90% identity, at least 95% identity, more preferred is at least 98% or at least 99% identity with SEQ ID NO: 14, 4, 6, 8, 1, 10, 19-26, 27, 29, 31, 33, 35, 37, 39, or 41.

Preferably, the HCP4 nucleic acid to be overexpressed in order to achieve increased resistance to fungal pathogens, e.g., of the family Phakopsoraceae, for example soybean rust, is preferably a nucleic acid coding for an HCP4 protein, and is preferably as defined by SEQ ID NO: 10, or a fragment, homolog, derivative, orthologue or paralogue thereof, or a splice variant thereof. Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 10 or is a functional fragment thereof, or a splice variant thereof. Most preferred is at least 90% identity, at least 95% identity, more preferred is at least 98% or at least 99% identity with SEQ ID NO: 10.

More preferably, the HCP4 nucleic acid to be overexpressed in order to achieve increased resistance to fungal pathogens, e.g., of the family Phakopsoraceae, for example soybean rust, is preferably a nucleic acid coding for an HCP4 protein, and is preferably as defined by SEQ ID NO: 1, or a fragment, homolog, derivative, orthologue or paralogue thereof, or a splice variant thereof. Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 1 or is a functional fragment thereof, or a splice variant thereof. Most preferred is at least 95% identity, more preferred is at least 98% or at least 99% identity with SEQ ID NO: 1.

More preferably, the HCP4 nucleic acid to be overexpressed in order to achieve increased resistance to fungal pathogens, e.g., of the family Phakopsoraceae, for example soybean rust, is preferably a nucleic acid coding for an HCP4 protein, and is preferably as defined by SEQ ID NO: 14, or a fragment, homolog, derivative, orthologue or paralogue thereof, or a splice variant thereof. Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 14 or is a functional fragment thereof, or a splice variant thereof. Most preferred is at least 95% identity, more preferred is at least 98% or at least 99% identity with SEQ ID NO: 14.

More preferably, the HCP4 nucleic acid to be overexpressed in order to achieve increased resistance to fungal pathogens, e.g., of the family Phakopsoraceae, for example soybean rust, is preferably a nucleic acid coding for an HCP4 protein, and is preferably as defined by SEQ ID NO: 11, or a fragment, homolog, derivative, orthologue or paralogue thereof, or a splice variant thereof. Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 11 or is a functional fragment thereof, or a splice variant thereof. Most preferred is at least 95% identity, more preferred is at least 98% or at least 99% identity with SEQ ID NO: 11.

More preferably, the HCP4 nucleic acid to be overexpressed in order to achieve increased resistance to fungal pathogens, e.g., of the family Phakopsoraceae, for example soybean rust, is preferably a nucleic acid coding for an HCP4 protein, and is preferably as defined by SEQ ID NO: 4, or a fragment, homolog, derivative, orthologue or paralogue thereof, or a splice variant thereof. Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 4 or is a functional fragment thereof, or a splice variant thereof. Most preferred is at least 95% identity, more preferred is at least 98% or at least 99% identity with SEQ ID NO: 4.

SEQ ID NO: 14 corresponds to SEQ ID NO: 1, wherein in SEQ ID NO: 14 certain recognition sites for restriction endonucleases have been removed.

Preferably the HCP4 nucleic acid is an isolated nucleic acid molecule consisting of or comprising a nucleic acid selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15, 16, 14, 1, 4, 6, 8, 10, 11, 19-26, 27, 29, 31, 33, 35, 37, 39, or 41, or a functional fragment, derivative, orthologue, or paralogue thereof, or a splice variant thereof;

(ii) a nucleic acid encoding a HCP4 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17, 18, 2, 3, 5, 7, 9, 28, 30, 32, 34, 36, 38, 40, or 42, or a functional fragment, derivative, orthologue, or paralogue thereof; preferably the HCP4 protein has essentially the same biological activity as an HCP4 protein encoded by SEQ ID NO: 15, 16, 14, 1, 4, 6, 8, 10, 11, 19-26, 27, 29, 31, 33, 35, 37, 39, or 41; preferably the HCP4 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, 9, 28, 30, 32, 34, 36, 38, 40, or 42; preferably the encoded protein confers enhanced fungal resistance relative to control plants; and (iv) a nucleic acid encoding the same HCP4 protein as the HCP4 nucleic acids of (i) to (iii) above, but differing from the HCP4 nucleic acids of (i) to (iii) above due to the degeneracy of the genetic code.

Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 1. Most preferred is at least 95% identity, more preferred is at least 98% or at least 99% identity with SEQ ID NO: 1.

Preferably, the nucleic acid coding for an HCP4 protein of the present invention has at least 60% identity, preferably at least 70% sequence identity, at least 80%, at least 90%, at least 95%, at least 98%, at least 99% sequence identity, or even 100% sequence identity with SEQ ID NO: 14. Most preferred is at least 95% identity, more preferred is at least 98% or at least 99% identity with SEQ ID NO: 14.

Preferably the HCP4 nucleic acid is an isolated nucleic acid molecule consisting of or comprising a nucleic acid selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof;
(ii) a nucleic acid encoding a HCP4 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2 or 3, or a functional fragment, derivative, orthologue, or paralogue thereof; preferably the HCP4 protein has essentially the same biological activity as an HCP4 protein encoded by SEQ ID NO: 1, preferably the HCP4 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and
(iv) a nucleic acid encoding the same HCP4 protein as the HCP4 nucleic acids of (i) to (iii) above, but differing from the HCP4 nucleic acids of (i) to (iii) above due to the degeneracy of the genetic code.

Preferably the HCP4 nucleic acid is an isolated nucleic acid molecule comprising a nucleic acid selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 14, or a functional fragment, derivative, orthologue, or paralogue thereof, or a splice variant thereof;
(ii) a nucleic acid encoding a HCP4 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 3, 5, 7, or 9, or a functional fragment, derivative, orthologue, or paralogue thereof; preferably the HCP4 protein has essentially the same biological activity as an HCP4 protein encoded by SEQ ID NO: 14, preferably the HCP4 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and
(iv) a nucleic acid encoding the same HCP4 protein as the HCP4 nucleic acids of (i) to (iii) above, but differing from the HCP4 nucleic acids of (i) to (iii) above due to the degeneracy of the genetic code.

Percentages of identity of a nucleic acid are indicated with reference to the entire nucleotide region given in a sequence specifically disclosed herein.

Preferably the portion of the HCP4 nucleic acid is about 1000-2000, about 2000-2500, about 2500-3000, about 3000-3500, about 3500-4000, about 4000-4500, about 4500-5000, about 5000-5500, about 5500-6000, about 6000-6500, about 6500-7000, or about 7000-7500 nucleotides, preferably consecutive nucleotides, preferably counted from the 5' or 3' end of the nucleic acid, in length, of the nucleic acid sequences given in SEQ ID NO: 14, 1, 4, 6, 8, 10, 11, 19-26, 27, 29, 31, 33, 35, 37, 39, or 41.

Preferably, the HCP4 nucleic acid comprises at least about 1000, at least about 2000, at least about 3000, at least about 4000, at least about 4500, at least about 5000, at least about 5500, at least about 6000, at least about 6500, at least about 7000, at least about 7100, at least about 7200, at least about 7300, at least about 7400, at least about 7500 or at least about 7600 nucleotides, preferably continuous nucleotides, preferably counted from the 5' or 3' end of the nucleic acid or up to the full length of the nucleic acid sequence set out in SEQ ID NO: 14, 1, 4, 6, 8, 10, 11, 19-26, 27, 29, 31, 33, 35, 37, 39, or 41.

Preferably, the HCP4 nucleic acid comprises at least about 1000, at least about 2000, at least about 3000, at least about 3100, at least about 3200, at least about 3300, at least about 3400, at least about 3500, at least about 3600, at least about 3700, at least about 3800, at least about 3900, or at least about 4000 nucleotides, preferably continuous nucleotides, preferably counted from the 5' or 3' end of the nucleic acid or up to the full length of the nucleic acid sequence set out in SEQ ID NO: 1.

Preferably the portion of the HCP4 nucleic acid is about 1000-1500, about 1500-2000, about 2000-2500, about 2500-3000, about 3000-3200, about 3200-3300, about 3300-3400, about 3400-3500, about 3500-3600, about 3600-3700, about 3700-3800, about 3800-3900, about 3900-4000, or about 4000-4024 nucleotides, preferably consecutive nucleotides, preferably counted from the 5' or 3' end of the nucleic acid, in length, of the nucleic acid sequences given in SEQ ID NO: 1.

Preferably, the HCP4 nucleic acid comprises at least about 1000, at least about 2000, at least about 3000, at least about 3100, at least about 3200, at least about 3300, at least about 3400, at least about 3500, at least about 3600, at least about 3700, at least about 3800, at least about 3900, or at least about 4000 nucleotides, preferably continuous nucleotides, preferably counted from the 5' or 3' end of the nucleic acid or up to the full length of the nucleic acid sequence set out in SEQ ID NO: 14.

Preferably the portion of the HCP4 nucleic acid is about 1000-1500, about 1500-2000, about 2000-2500, about 2500-3000, about 3000-3200, about 3200-3300, about 3300-3400, about 3400-3500, about 3500-3600, about 3600-3700, about 3700-3800, about 3800-3900, about 3900-4000, or about 4000-4024 nucleotides, preferably consecutive nucleotides, preferably counted from the 5' or 3' end of the nucleic acid, in length, of the nucleic acid sequences given in SEQ ID NO: 14.

Preferably, the HCP4 nucleic acid comprises at least about 500, at least about 600, at least about 700, at least about 750, at least about 800, at least about 850, at least about 900, at least about 950, or at least about 1000, preferably continuous nucleotides, preferably counted from the 5' or 3' end of the nucleic acid or up to the full length of the nucleic acid sequence set out in SEQ ID NO: 15 or 16.

Preferably the portion of the HCP4 nucleic acid is about 500-600, about 600-700, about 700-750, about 750-800, about 800-814, about 814-850, about 850-900, about 900-950, about 950-1000, or about 1000-1400 nucleotides, preferably consecutive nucleotides, preferably counted from the 5' or 3' end of the nucleic acid, in length, of the nucleic acid sequences given in SEQ ID NO: 15 or 16.

Preferably, the HCP4 nucleic acid is a HCP4 nucleic acid splice variant. Preferred splice variants are splice variants of a nucleic acid represented by SEQ ID NO: 10. Preferred HCP4 nucleic acids being a splice variant of SEQ ID NO: 10 are shown in FIG. 13.

Preferably, the HCP4 nucleic acid is an isolated nucleic acid molecule comprising a splice variant of SEQ ID NO: 10, wherein the splice variant is selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 14, 1, 4, 6, 8, or a functional fragment, derivative, orthologue, or paralogue thereof;
(ii) a nucleic acid encoding a HCP4 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 3, 5, 7, or 9, or a functional fragment, derivative, orthologue, or paralogue thereof; preferably the HCP4 protein has essentially the same biological activity as an HCP4 protein encoded by SEQ ID NO: 14, 1, 4, 6, 8, or 10; preferably the HCP4 protein confers enhanced fungal resistance relative to control plants;
(iii) a nucleic acid molecule which hybridizes with a complementary sequence of any of the nucleic acid molecules of (i) or (ii) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and
(iv) a nucleic acid encoding the same HCP4 protein as the HCP4 nucleic acids of (i) to (iii) above, but differing from the HCP4 nucleic acids of (i) to (iii) above due to the degeneracy of the genetic code.

Preferred splice variants of SEQ ID NO: 10 consist of or comprise anyone of the nucleotide sequences shown in SEQ ID NO: 14, 1, 4, 6, or 8. Most preferred is the HCP4 nucleic acid splice variant as shown in SEQ ID NO: 1.

Preferably the HCP4 nucleic acid is an isolated nucleic acid molecule comprising a nucleic acid selected from the group consisting of:
(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, or a splice variant thereof;
(ii) a nucleic acid molecule which hybridizes with a complementary sequence of any of the nucleic acid molecules of (i) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and (iii) a nucleic acid encoding the same HCP4 protein as the HCP4 nucleic acids of (i) to (ii) above, but differing from the HCP4 nucleic acids of (i) to (ii) above due to the degeneracy of the genetic code;

wherein the splice variant thereof is selected from the group consisting of:

(i) a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 14, 1, 4, 6, 8, or a functional fragment, derivative, orthologue, or paralogue thereof;

(ii) a nucleic acid encoding a HCP4 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 3, 5, 7, or 9, or a functional fragment, derivative, orthologue, or paralogue thereof; preferably the HCP4 protein has essentially the same biological activity as an HCP4 protein encoded by SEQ ID NO: 14, 1, 4, 6, 8, or 10; preferably the HCP4 protein confers enhanced fungal resistance relative to control plants;

(iii) a nucleic acid molecule which hybridizes with a complementary sequence of any of the nucleic acid molecules of (i) or (ii) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and (iv) a nucleic acid encoding the same HCP4 protein as the HCP4 nucleic acids of (i) to (iii) above, but differing from the HCP4 nucleic acids of (i) to (iii) above due to the degeneracy of the genetic code.

More preferably the HCP4 nucleic acid is an isolated nucleic acid molecule comprising a nucleic acid selected from the group consisting of:

a nucleic acid having in increasing order of preference least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 10, or a splice variant thereof;

wherein the splice variant thereof is selected from the group consisting of:

a nucleic acid having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 14, 1, 4, 6, or 8; preferably SEQ ID NO: 1.

In a preferred embodiment, the HCP4 nucleic acid comprises a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15 or 16, or a functional fragment, derivative, orthologue, or paralogue thereof.

Preferably, the HCP4 nucleic acid comprises a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 16.

In a preferred embodiment, the HCP4 nucleic acid comprises a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 14, 1, 4, 6, 8, or 10, or a functional fragment, derivative, orthologue, or paralogue thereof, wherein the HCP4 nucleic acid comprises a nucleic acid sequence having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15 or 16.

In a preferred embodiment, the HCP4 nucleic acid is a splice variant comprising a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15 or 16, or a functional fragment, derivative, orthologue, or paralogue thereof.

Preferably, the HCP4 nucleic acid comprises an exon sequence comprising a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15 or 16, or a functional fragment, derivative, orthologue, or paralogue thereof.

In a preferred embodiment, the HCP4 nucleic acid comprises a nucleic acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 14, 1, 4, 6, 8, or 10, or a splice variant thereof, wherein the splice variant comprises a nucleic acid sequence, preferably an exon sequence, having in increasing order of preference at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15 or 16.

In a preferred embodiment, the HCP4 nucleic acid encodes a HCP4 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17 or 18, or a functional fragment, derivative, orthologue, or paralogue thereof; preferably the HCP4 protein has essentially the same biological activity as an HCP4 protein encoded by SEQ ID NO: 14, 1, 4, 6, 8, or 10; preferably the HCP4 protein confers enhanced fungal resistance relative to control plants.

In a preferred embodiment, the HCP4 nucleic acid encodes a HCP4 protein having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 2, 3, 5, 7, or 9, or a functional fragment, derivative, orthologue, or paralogue thereof, wherein the HCP4 nucleic acid comprises an nucleic acid sequence, preferably an exon sequence, encoding an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17 or 18, or a functional fragment, derivative, orthologue, or paralogue thereof; preferably the HCP4 protein has essentially the same biological activity as an HCP4 protein encoded by SEQ ID NO: 14, 1, 4, 6, 8, or 10; preferably the HCP4 protein confers enhanced fungal resistance relative to control plants.

The HCP4 nucleic acids described herein are useful in the constructs, methods, plants, harvestable parts and products of the invention.

HCP4 Proteins

The HCP4 protein is preferably defined by SEQ ID NO: 5, 7, 2, 3, 9, 28, 30, 32, 34, 36, 38, 40, or 42, or a fragment, homolog, derivative, orthologue or paralogue thereof. Preferably, the HCP4 protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 14, 4, 6, 8, 1, 10, 11, 19-26, 27, 29, 31, 33, 35, 37, 39, or 41, or a functional fragment thereof. More preferably, the HCP4 protein of the present invention has at least 60%, preferably at least 70% sequence identity, at least 80%, at least 90%, at least 95%, at least 98%, at least 99% sequence identity, or even 100% sequence identity with SEQ ID NO: 5, 7, 2, 3, 9, 28, 30, 32, 34, 36, 38, 40, or 42, or is a functional fragment thereof, an orthologue or a paralogue thereof. Most preferred is at least 90% identity, at least 95% identity, more preferred is at least 98% or at least 99% identity with SEQ ID NO: 5, 7, 2, 3, 9, 28, 30, 32, 34, 36, 38, 40, or 42.

More preferably, the HCP4 protein of the present invention has at least 60%, preferably at least 70% sequence identity, at least 80%, at least 90%, at least 95%, at least 98%, at least 99% sequence identity, or even 100% sequence identity with SEQ ID NO: 2 or is a functional fragment thereof, an orthologue or a paralogue thereof.

More preferably, the HCP4 protein of the present invention has at least 60%, preferably at least 70% sequence identity, at least 80%, at least 90%, at least 95%, at least 98%, at least 99% sequence identity, or even 100% sequence identity with SEQ ID NO: 3 or is a functional fragment thereof, an orthologue or a paralogue thereof.

More preferably, the HCP4 protein of the present invention has at least 60%, preferably at least 70% sequence identity, at least 80%, at least 90%, at least 95%, at least 98%, at least 99% sequence identity, or even 100% sequence identity with SEQ ID NO: 5 or 7, or is a functional fragment thereof, an orthologue or a paralogue thereof.

More preferably, the HCP4 protein of the present invention has at least 60%, preferably at least 70% sequence identity, at least 80%, at least 90%, at least 95%, at least 98%, at least 99% sequence identity, or even 100% sequence identity with SEQ ID NO: 9 or is a functional fragment thereof, an orthologue or a paralogue thereof.

In another embodiment, the HCP4 protein of the present invention comprises an amino acid sequence that has at least 60%, preferably at least 70% sequence identity, at least 80%, at least 90%, at least 95%, at least 98%, at least 99% sequence identity, or even 100% sequence identity with SEQ ID NO: 17 or 18.

More preferably, the HCP4 protein of the present invention has at least 60%, preferably at least 70% sequence identity, at least 80%, at least 90%, at least 95%, at least 98%, at least 99% sequence identity, or even 100% sequence identity with SEQ ID NO: 2, 3, 5, 7 or 9, wherein the HCP4 protein comprises an amino acid sequence having at least 80%, at least 90%, at least 95%, at least 98%, at least 99% sequence identity, or even 100% sequence identity with SEQ ID NO: 17 or 18; or is a functional fragment thereof, an orthologue or a paralogue thereof.

The HCP4 protein is preferably defined by SEQ ID NO: 2, 3, 5, 7, or 9, or a fragment, homolog, derivative, orthologue or paralogue thereof. Preferably, the HCP4 protein of the present invention is encoded by a nucleic acid, which has at least 60% identity, preferably at least 70% sequence identity, at least 80%, at least 90%, at least 95%, at least 98%, at least 99% sequence identity, or even 100% sequence identity with SEQ ID NO: 14 or 1 or a functional fragment thereof. More preferably, the HCP4 protein of the present invention has at least 60%, preferably at least 70% sequence identity, at least 80%, at least 90%, at least 95%, at least 98%, at least 99% sequence identity, or even 100% sequence identity with SEQ ID NO: 2, 3, 5, 7, or 9, or is a functional fragment thereof, an orthologue or a paralogue thereof. Most preferred is at least 95% identity, more preferred is at least 98% or at least 99% identity with SEQ ID NO: 2, 3, 5, 7, or 9.

Preferably, the HCP4 protein is a protein consisting of or comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17, 18, 2, 3, 5, 7, 9, 28, 30, 32, 34, 36, 38, 40, or 42, or a functional fragment, derivative, orthologue, or paralogue thereof; preferably the HCP4 protein has essentially the same biological activity as an HCP4 protein encoded by SEQ ID NO: 14, 1, 4, 6, 8, 10, 11, 19-26, 27, 29, 31, 33, 35, 37, 39, or 41; preferably the HCP4 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15, 16, 14, 1, 4, 6, 8, 10, 11, 19-26, 27, 29, 31, 33, 35, 37, 39, or 41, or a functional fragment, derivative, orthologue, or paralogue thereof, or a splice variant thereof; preferably the HCP4 protein confers enhanced fungal resistance relative to control plants.

Preferably, the HCP4 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17, 18, 2, 3, 5, 7 or 9, or a functional fragment, derivative, orthologue, or paralogue thereof; preferably the HCP4 protein has essentially the same biological activity as an HCP4 protein encoded by SEQ ID NO: 1; preferably the HCP4 protein confers enhanced fungal resistance relative to control plants; or
(ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 1, or a functional fragment, derivative, orthologue, or paralogue thereof, or a splice variant thereof; preferably the HCP4 protein confers enhanced fungal resistance relative to control plants.

Preferably, the HCP4 protein is a protein comprising an amino acid sequence selected from the group consisting of:
(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17, 18, 2, 3, 5, 7, or 9, or a functional fragment, derivative, orthologue, or paralogue thereof; preferably the HCP4 protein has essentially the same biological activity as an HCP4 protein encoded by SEQ ID NO: 14; preferably the HCP4 protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 14, or a functional fragment, derivative, orthologue, or paralogue thereof, or a splice variant thereof; preferably the HCP4 protein confers enhanced fungal resistance relative to control plants.

Preferably, the HCP4 protein is a protein consisting of or comprising an amino acid sequence selected from the group consisting of:

(i) an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17 or 18, or a functional fragment, derivative, orthologue, or paralogue thereof; preferably the HCP4 protein has essentially the same biological activity as an HCP4 protein encoded by SEQ ID NO: 14, 1, 4, 6, 8, or 10; preferably the HCP4 protein confers enhanced fungal resistance relative to control plants; or (ii) an amino acid sequence encoded by a nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15 or 16, or a functional fragment, derivative, orthologue, or paralogue thereof, or a splice variant thereof; preferably the HCP4 protein confers enhanced fungal resistance relative to control plants.

A preferred derivative of a HCP4 protein is a HCP4 protein consisting of or comprising an amino acid sequence selected from the group consisting of:

an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence represented by SEQ ID NO: 17, 18, 2, 3, 5, 7, 9, 28, 30, 32, 34, 36, 38, 40, or 42, wherein the non-identical amino acid residues are conservative amino acid substitutions, preferably as shown in Table 1, of the corresponding amino acid residue of SEQ ID NO: 17, 18, 2, 3, 5, 7, or 9; preferably the HCP4 protein has essentially the same biological activity as SEQ ID NO: 2, 3, 5, 7, or 9 or as a HCP4 protein encoded by SEQ ID NO: 14, 1, 4, 6, 8, 10, 11, 19-26, 27, 29, 31, 33, 35, 37, 39, or 41; preferably the HCP4 protein confers enhanced fungal resistance relative to control plants.

Preferably, the HCP4 protein consists of or comprises an amino acid sequence represented by SEQ ID NO: 17, 18, 2, 3, 5, 7, or 9 with one or more conservative amino acid substitutions, preferably as shown in Table 1, of the corresponding amino acid residues of SEQ ID NO: 2, 3, 5, 7, or 9. Preferably 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100, 105, 110, 115, 120, 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 amino acid residues of SEQ ID NO: 17, 18, 2, 3, 5, 7, or 9 are conservative amino acid substitutions, preferably as shown in Table 1, of the corresponding amino acid residue of SEQ ID NO: 17, 18, 2, 3, 5, 7, or 9.

More preferably, the HCP4 protein consists of or comprises an amino acid sequence having at least 80%, at least 85%, at least 90%, at least 95%, at least 98% or at least 99% sequence identity with an amino acid sequence as represented by SEQ ID NO: 17, 18, 2, 3, 5, 7, or 9, wherein at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 35, at least 40, at least 45, at least 50, at least 55, at least 60, at least 65, at least 70, at least 75, at least 80, at least 85, at least 90, at least 95, at least 100, at least 105, at least 110, at least 115, or at least 120 of the non-identical amino acid residues, or wherein 1-10, 10-20, 20-30, 40-50, 50-60, 60-70, 70-80, 80-90, 90-100, 100-110, 110-120, 120-130, 130-140, 140-150, 150-160, 60-170, 170-180, 180-190, 190-200, 200-210, or 210-220 or even all of the non-identical amino acid residues are conservative amino acid substitutions, preferably as shown in Table 1, of the corresponding amino acid residue of SEQ ID NO: 17, 18, 2, 3, 5, 7, or 9.

Percentages of identity of a polypeptide or protein are indicated with reference to the entire amino acid sequence specifically disclosed herein.

Preferably, the HCP4 protein comprises at least about 500, at least about 600, at least about 700, at least about 800, at least about 900, at least about 1000, at least about 1050, at least about 1100, at least about 1150, at least about 1200, at least about 1250, or at least about 1300, amino acid residues, preferably continuous amino acid residues, preferably counted from the N-terminus or the C-terminus of the amino acid sequence, or up to the full length of the amino acid sequence set out in SEQ ID NO: 2, 3, 5, 7, 9, 28, 30, 32, 34, 36, 38, 40, or 42.

Preferably, the HCP4 polypeptide comprises about 500-600, about 600-700, about 700-800, about 800-900, about 900-1000, about 1050-1100, about 1100-1150, about 1150-1200, about 1250-1300, or about 1300-1309, preferably consecutive amino acids, preferably counted from the N-terminus or C-terminus of the amino acid sequence, or up to the full length of any of the amino acid sequences encoded by the nucleic acid sequences set out in SEQ ID NO: 2, 3, 5, 7, 9, 28, 30, 32, 34, 36, 38, 40, or 42.

Preferably, the HCP4 protein comprises at least about 70, at least about 80, at least about 90, at least about 100, at least about 110, at least about 120, at least about 130, at least about 140, at least about 150, at least about 160, at least about 170, or at least about 180 amino acid residues, preferably continuous amino acid residues, preferably counted from the N-terminus or the C-terminus of the amino acid sequence, or up to the full length of the amino acid sequence set out in SEQ ID NO: 2.

Preferably, the HCP4 polypeptide comprises bout 60-70, about 70-80, about 80-90, about 90-100, about 100-110, about 110-120, about 120-130, about 130-140, about 140-150, about 150-160, about 160-170, about 170-180, or about 180-185, preferably consecutive amino acids, preferably counted from the N-terminus or C-terminus of the amino acid sequence, or up to the full length of any of the amino acid sequences encoded by the nucleic acid sequences set out in SEQ ID NO: 2.

Preferably, the HCP4 protein comprises at least about 500, at least about 600, at least about 700, at least about 800, at least about 900, at least about 950, at least about 1000, at least about 1050, at least about 1100, at least about 1150, at least about 1160, or at least about 1170 amino acid residues, preferably continuous amino acid residues, preferably counted from the N-terminus or the C-terminus of the amino acid sequence, or up to the full length of the amino acid sequence set out in SEQ ID NO: 3.

Preferably, the HCP4 polypeptide comprises about 500-600, about 600-700, about 700-800, about 800-900, about 900-1000, about 1050-1100, about 1100-1150, about 1150-1160, about 1160-1170, about 1170-1180, or about 1180-1194, preferably consecutive amino acids, preferably counted from the N-terminus or C-terminus of the amino acid sequence, or up to the full length of any of the amino acid sequences encoded by the nucleic acid sequences set out in SEQ ID NO: 3.

Preferably, the HCP4 protein comprises at least about 100, at least about 150, at least about 200, at least about 225, at least about 250, at least about 275, at least about 300, at least about 325, or at least about 340 amino acid residues, preferably continuous amino acid residues, preferably counted from the N-terminus or the C-terminus of the amino acid sequence, or up to the full length of the amino acid sequence set out in SEQ ID NO: 17 or 18.

Preferably, the HCP4 polypeptide comprises about 100-150, about 150-200, about 200-225, about 225-250, about 250-271, about 250-275, about 275-300, about 300-325, or about 325-346, preferably consecutive amino acids, preferably counted from the N-terminus or C-terminus of the amino acid sequence, or up to the full length of any of the amino acid sequences encoded by the nucleic acid sequences set out in SEQ ID NO: 17 or 18.

The HCP4 proteins described herein are useful in the constructs, methods, plants, harvestable parts and products of the invention.

Methods for Increasing Fungal Resistance; Methods for Modulating Gene Expression One embodiment of the invention is a method for increasing fungal resistance, preferably resistance to Phakopsoracea, for example soy bean rust, in a plant, plant part, or plant cell by increasing the expression of an HCP4 protein or a functional fragment, orthologue, paralogue or homologue thereof in comparison to wild-type plants, wild-type plant parts or wild-type plant cells.

The present invention also provides a method for increasing resistance to fungal pathogens, in particular a heminecrotrophic pathogen, in particular to rust pathogens (i.e., fungal pathogens of the order Pucciniales), preferably fungal pathogens of the family Phakopsoraceae, preferably against fungal pathogens of the genus *Phakopsora*, most preferably against *Phakopsora pachyrhizi* and *Phakopsora meibomiae*, also known as soy bean rust in plants or plant cells, wherein in comparison to wild type plants, wild type plant parts, or wild type plant cells an HCP4 protein is overexpressed.

The present invention further provides a method for increasing resistance to fungal pathogens of the genus *Phakopsora*, most preferably against *Phakopsora pachyrhizi* and *Phakopsora meibomiae*, also known as soy bean rust in plants or plant cells by overexpression of an HCP4 protein.

In preferred embodiments, the protein amount and/or function of the HCP4 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP4 nucleic acid.

In one embodiment of the invention, the HCP4 protein is encoded by a nucleic acid comprising (i) an exogenous nucleic acid having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 15, 16, 14, 1, 4, 6, 8, 10, 11, 19-26, 27, 29, 31, 33, 35, 37, 39, or 41, a functional fragment thereof, or an orthologue or a paralogue thereof, or a splice variant thereof; or by (ii) an exogenous nucleic acid encoding a protein comprising an amino acid sequence having at least 60% identity, preferably at least 70%, for example at least 75%, more preferably at least 80%, for example at least 85%, even more preferably at least 90%, for example at least 95% or at least 96% or at least 97% or at least 98% most preferably 99% homology with SEQ ID NO: 17, 18, 2, 3, 5, 7, 9, 28, 30, 32, 34, 36, 38, 40, or 42, a functional fragment thereof, an orthologue or a paralogue thereof, preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, 9, 28, 30, 32, 34, 36, 38, 40, or 42; preferably the encoded protein confers enhanced fungal resistance relative to control plants; or by (iv) an exogenous nucleic acid encoding the same HCP4 protein as the nucleic acids of (i) to (iii) above, but differing from the nucleic acids of (i) to (iii) above due to the degeneracy of the genetic code.

In another embodiment of the invention, the HCP4 protein comprises an amino acid sequence
(i) having at least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 17 or 18; or
(ii) encoded by a nucleic acid sequence having least 60%, preferably at least 70%, for example at least 75%, more preferably at least 80%, for example at least 85%, even more preferably at least 90%, for example at least 95% or at least 96% or at least 97% or at least 98% most preferably 99% identity with SEQ ID NO: 15 or 16; preferably the HCP4 protein has essentially the same biological activity as SEQ ID NO: 2, 3, 5, 7, or 9 or as a HCP4 protein encoded by SEQ ID NO: 14, 1, 4, 6, 8, or 10; preferably the encoded protein confers enhanced fungal resistance relative to control plants.

A method for increasing fungal resistance, preferably resistance to Phakopsoracea, for example soy bean rust, in a plant, plant part, or plant cell, by increasing the expression of an HCP4 protein or a functional fragment, orthologue, paralogue or homologue thereof, or a splice variant thereof, wherein the HCP4 protein is encoded by a nucleic acid comprising (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 15, 16, 14, 1, 4, 6, 8, 10, 11, 19-26, 27, 29, 31, 33, 35, 37, 39, or 41, or a functional fragment thereof, an orthologue or a paralogue thereof, or a splice variant thereof;

(ii) an exogenous nucleic acid encoding a protein comprising an amino acid sequence having at least 60%, preferably at least 70% sequence identity, at least 80%, at least 90%, at least 95%, at least 98%, at least 99% sequence identity, or even 100% sequence identity with SEQ ID NO: 17, 18, 2, 3, 5, 7, 9, 28, 30, 32, 34, 36, 38, 40, or 42, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by (iv) an exogenous nucleic acid encoding the same HCP4 protein as the nucleic acids of (i) to (iii) above, but differing from the nucleic acids of (i) to (iii) above due to the degeneracy of the genetic code;

is a further embodiment of the invention.

A method for increasing fungal resistance, preferably resistance to Phakopsoracea, for example soy bean rust, in a plant, plant part, or plant cell, by increasing the expression of an HCP4 protein or a functional fragment, orthologue, paralogue or homologue thereof, or a splice variant thereof, wherein the HCP4 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 1 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2 or 3, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by (iv) an exogenous nucleic acid encoding the same HCP4 protein as the nucleic acids of (i) to (iii) above, but differing from the nucleic acids of (i) to (iii) above due to the degeneracy of the genetic code is a further embodiment of the invention.

A method for increasing fungal resistance, preferably resistance to Phakopsoracea, for example soy bean rust, in a plant, plant part, or plant cell, by increasing the expression of an HCP4 protein or a functional fragment, orthologue, paralogue or homologue thereof, or a splice variant thereof, wherein the HCP4 protein is encoded by (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 14 or a functional fragment thereof, an orthologue or a paralogue thereof, or a splice variant thereof;

(ii) an exogenous nucleic acid encoding a protein having at least 60%, preferably at least 70% sequence identity, at least 80%, at least 90%, at least 95%, at least 98%, at least 99% sequence identity, or even 100% sequence identity with SEQ ID NO: 2, 3, 5, 7, or 9, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by (iv) an exogenous nucleic acid encoding the same HCP4 protein as the nucleic acids of (i) to (iii) above, but differing from the nucleic acids of (i) to (iii) above due to the degeneracy of the genetic code is a further embodiment of the invention.

In a further method of the invention, the method comprises the steps of
(a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 15, 16, 14, 1, 4, 6, 8, 10, 11, 19-26, 27, 29, 31, 33, 35, 37, 39, or 41, or a functional fragment thereof, or an orthologue or a paralogue thereof, or a splice variant thereof;
   (ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 17, 18, 2, 3, 5, 7, 9, 28, 30, 32, 34, 36, 38, 40, or 42, a functional fragment thereof, an orthologue or a paralogue thereof; preferably the encoded protein confers enhanced fungal resistance relative to control plants;
   (iii) a nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or
   (iv) a nucleic acid encoding the same HCP4 polypeptide as the nucleic acids of (i) to (iii) above, but differing from the nucleic acids of (i) to (iii) above due to the degeneracy of the genetic code,
in functional linkage with a promoter;
(b) regenerating the plant from the plant cell; and
(c) expressing said nucleic acid, optionally wherein the nucleic acid which codes for an HCP4 protein is expressed in an amount and for a period sufficient to generate or to increase soybean rust resistance in said plant.

Preferably, the method comprises the steps of
(a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 1, or a functional fragment thereof, or an orthologue or a paralogue thereof, or a splice variant thereof;
   (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 3, 5, 7, or 9, a functional fragment thereof, an orthologue or a paralogue thereof; preferably the encoded protein confers enhanced fungal resistance relative to control plants;
   (iii) a nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or
   (iv) a nucleic acid encoding the same HCP4 polypeptide as the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for an HCP4 protein is expressed in an amount and for a period sufficient to generate or to increase soybean rust resistance in said plant.

Preferably, the method comprises the steps of
(a) stably transforming a plant cell with a recombinant expression cassette comprising
   (i) a nucleic acid having at least 60% identity, preferably at least 70% sequence identity, at least 80%, at least 90%, at least 95%, at least 98%, at least 99% sequence identity, or even 100% sequence identity with SEQ ID NO: 14, or a functional fragment thereof, or an orthologue or a paralogue thereof, or a splice variant thereof;
   (ii) a nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 3, 5, 7, or 9, a functional fragment thereof, an orthologue or a paralogue thereof; preferably the encoded protein confers enhanced fungal resistance relative to control plants;
   (iii) a nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or
   (iv) a nucleic acid encoding the same HCP4 polypeptide as the nucleic acids of (i) to (iii) above, but differing from the nucleic acids of (i) to (iii) above due to the degeneracy of the genetic code, in functional linkage with a promoter;
(b) regenerating the plant from the plant cell; and
(c) expressing said nucleic acid, optionally wherein the nucleic acid which codes for an HCP4 protein is expressed in an amount and for a period sufficient to generate or to increase soybean rust resistance in said plant.

Preferably, the method for increasing fungal resistance, preferably resistance to Phakopsoracea, for example soy bean rust, in a plant, plant part, or plant cell further comprises the step of selecting a transgenic plant expressing
(i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 14, 1, 4, 6, 8, 10, 11, 19-26, 27, 29, 31, 33, 35, 37, 39, or 41, or a functional fragment thereof, or an orthologue or a paralogue thereof, or a splice variant thereof;
(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 3, 5, 7, or 9, a functional fragment thereof, an orthologue or a paralogue thereof; preferably the encoded protein confers enhanced fungal resistance relative to control plants;

(iii) an exogenous nucleic acid capable of hybridizing under stringent conditions a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or (iv) an exogenous nucleic acid encoding the same HCP4 polypeptide as the nucleic acids of (i) to (iii) above, but differing from the nucleic acids of (i) to (iii) above due to the degeneracy of the genetic code.

A preferred embodiment is a method for increasing resistance to soy bean rust in a soy bean plant, soy bean plant part, or soy bean plant cell, by increasing the expression of an HCP4 protein, wherein the HCP4 protein is encoded by a nucleic acid comprising (i) an exogenous nucleic acid having at least 80%, at least 90%, at least 95%, at least 98%, at least 99% sequence identity, or even 100% sequence identity with SEQ ID NO: 15, 16, 14, 1, 4, 6, 8, 10, 11, 19-26, 27, 29, 31, 33, 35, 37, 39, or 41;
(ii) an exogenous nucleic acid encoding a protein comprising an amino acid sequence having at least 80%, at least 90%, at least 95%, at least 98%, at least 99% sequence identity, or even 100% sequence identity with SEQ ID NO: 17, 18, 2, 3, 5, 7, or 9; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by
(iv) an exogenous nucleic acid encoding the same HCP4 protein as the nucleic acids of (i) to (iii) above, but differing from the nucleic acids of (i) to (iii) above due to the degeneracy of the genetic code, wherein increasing the expression of the HCP4 protein is achieved by transforming the soy bean plant, plant part or plant cell with a nucleic acid comprising the nucleic acid set out under item (i) or (ii) or (iii) or (iv).

Also a preferred embodiment is a method for increasing resistance to soy bean rust in a soy bean plant, soy bean plant part, or soy bean plant cell, by increasing the expression of an HCP4 protein, wherein the HCP4 protein is encoded by a nucleic acid comprising
(i) an exogenous nucleic acid having at least 80%, at least 90%, at least 95%, at least 98%, at least 99% sequence identity, or even 100% sequence identity with SEQ ID NO: 15, 16, 14, 1, 4, 6, 8, 10, 11, 19-26, 27, 29, 31, 33, 35, 37, 39, or 41;
(ii) an exogenous nucleic acid encoding a protein comprising an amino acid sequence having at least 80%, at least 90%, at least 95%, at least 98%, at least 99% sequence identity, or even 100% sequence identity with SEQ ID NO: 17, 18, 2, 3, 5, 7, 9, 28, 30, 32, 34, 36, 38, 40, or 42; preferably the encoded protein confers enhanced fungal resistance relative to control plants; or
(iii) an exogenous nucleic acid encoding the same HCP4 protein as the nucleic acids of (i) to (ii) above, but differing from the nucleic acids of (i) to (ii) above due to the degeneracy of the genetic code, wherein increasing the expression of the HCP4 protein is achieved by transforming the soy bean plant, plant part or plant cell with a nucleic acid comprising the nucleic acid set out under item (i) or (ii) or (iii).

The fungal pathogens or fungus-like pathogens (such as, for example, Chromista) can belong to the group comprising Plasmodiophoramycota, Oomycota, Ascomycota, Chytridiomycetes, Zygomycetes, Basidiomycota or Deuteromycetes (Fungi imperfecti). Pathogens which may be mentioned by way of example, but not by limitation, are those detailed in Tables 2 and 3, and the diseases which are associated with them.

TABLE 2

Diseases caused by biotrophic and/or 8/25 heminecrotrophic phytopathogenic fungi

| Disease | Pathogen |
|---|---|
| Leaf rust | *Puccinia recondita* |
| Yellow rust | *P. striiformis* |
| Powdery mildew | *Erysiphe graminis/Blumeria graminis* |
| Rust (common corn) | *Puccinia sorghi* |
| Rust (Southern corn) | *Puccinia polysora* |
| Tobacco leaf spot | *Cercospora nicotianae* |
| Rust (soybean) | *Phakopsora pachyrhizi*, *P. meibomiae* |
| Rust (tropical corn) | *Physopella pallescens*, *P. zeae* = Angiopsora zeae |

TABLE 3

Diseases caused by necrotrophic and/or hemibiotrophic fungi and Oomycetes

| Disease | Pathogen |
|---|---|
| Plume blotch | *Septoria* (*Stagonospora*) *nodorum* |
| Leaf blotch | *Septoria tritici* |
| Ear fusarioses | *Fusarium* spp. |
| Late blight | *Phytophthora infestans* |
| *Anthrocnose* leaf blight | *Colletotrichum graminicola* (teleomorph: *Glomerella graminicola Politis*); *Glomerella tucumanensis* (anamorph: *Glomerella falcatum* Went) |
| *Anthracnose* stalk rot | |
| *Curvularia* leaf spot | *Curvularia clavata*, *C. eragrostidis*, = *C. maculans* (teleomorph: *Cochliobolus eragrostidis*), *Curvularia inaequalis*, *C. intermedia* (teleomorph: *Cochliobolus intermedius*), *Curvularia lunata* (teleomorph: *Cochliobolus lunatus*), *Curvularia pallescens* (teleomorph: *Cochliobolus pallescens*), *Curvularia senegalensis*, *C. tuberculata* (teleomorph: *Cochliobolus tuberculatus*) |

TABLE 3-continued

Diseases caused by necrotrophic and/or hemibiotrophic fungi and Oomycetes

| Disease | Pathogen |
|---|---|
| *Didymella* leaf spot | *Didymella exitalis* |
| *Diplodia* leaf spot or streak | *Stenocarpella macrospora* = *Diplodialeaf macrospora* |
| Brown stripe downy mildew | *Sclerophthora rayssiae* var. *zeae* |
| Crazy top downy mildew | *Sclerophthora macrospora* = *Sclerospora macrospora* |
| Green ear downy mildew (graminicola downy mildew) | *Sclerospora graminicola* |
| Leaf spots, minor | *Alternaria alternata*, *Ascochyta maydis, A. tritici, A. zeicola, Bipolaris victoriae* = *Helminthosporium victoriae* (teleomorph: *Cochliobolus victoriae*), *C. sativus* (anamorph: *Bipolaris sorokiniana* = *H. sorokinianum* = *H. sativum*), *Epicoccum nigrum*, *Exserohilum prolatum* = *Drechslera prolata* (teleomorph: *Setosphaeria prolata*) *Graphium penicillioides*, *Leptosphaeria maydis, Leptothyrium zeae*, *Ophiosphaerella herpotricha*, (anamorph: *Scolecosporiella* sp.), *Paraphaeosphaeria michotii, Phoma* sp., *Septoria zeae, S. zeicola, S. zeina* |
| Northern corn leaf blight (white blast, crown stalk rot, stripe) | *Setosphaeria turcica* (anamorph: *Exserohilum turcicum* = *Helminthosporium turcicum*) |
| Northern corn leaf spot *Helminthosporium* ear rot (race 1) | *Cochliobolus carbonum* (anamorph: *Bipolaris zeicola* = *Helminthosporium carbonum*) |
| *Phaeosphaeria* leaf spot | *Phaeosphaeria maydis* = *Sphaerulina maydis* |
| *Rostratum* leaf spot (*Helminthosporium* leaf disease, ear and stalk rot) | *Setosphaeria rostrata*, (anamorph: *xserohilum rostratum* = *Helminthosporium rostratum*) |
| Java downy mildew | *Peronosclerospora maydis* = *Sclerospora maydis* |
| Philippine downy mildew | *Peronosclerospora philippinensis* = *Sclerospora philippinensis* |
| *Sorghum* downy mildew | *Peronosclerospora sorghi* = *Sclerospora sorghi* |
| Spontaneum downy mildew | *Peronosclerospora spontanea* = *Sclerospora spontanea* |
| Sugarcane downy mildew | *Peronosclerospora sacchari* = *Sclerospora sacchari* |
| *Sclerotium* ear rot (southern blight) | *Sclerotium rolfsii* Saco, (teleomorph: *Athelia rolfsii*) |
| Seed rot-seedling blight | *Bipolaris sorokiniana, B. zeicola* = *Helminthosporium carbonum, Diplodia maydis, Exserohilum pedicillaturn, Exserohilum turcicum* = *Helminthosporium turcicum, Fusarium avenaceum, F. culmorum, F. moniliforme, Gibberella zeae* (anamorph: *F. graminearum*), *Macrophomina phaseolina, Penicillium* spp., *Phomopsis* sp., *Pythium* spp., *Rhizoctonia solani, R. zeae, Sclerotium rolfsii, Spicaria* sp. |
| *Selenophoma* leaf spot | *Selenophoma* sp. |
| Yellow leaf blight | *Ascochyta ischaemi, Phyllosticta maydis* (teleomorph: *Mycosphaerella zeae-maydis*) |
| Zonate leaf spot | *Gloeocercospora sorghi* |

The following are especially preferred:

Plasmodiophoromycota such as *Plasmodiophora brassicae* (clubroot of crucifers), *Spongospora subterranea, Polymyxa graminis,*

Oomycota such as *Bremia lactucae* (downy mildew of lettuce), *Peronospora* (downy mildew) in snapdragon (*P. antirrhini*), onion (*P. destructor*), spinach (*P. effusa*), soybean (*P. manchurica*), tobacco ("blue mold"; *P. tabacina*) alfalfa and clover (*P. trifolium*), *Pseudoperonospora humuli* (downy mildew of hops), *Plasmopara* (downy mildew in grapevines) (*P. viticola*) and sunflower (*P. halstedii*), *Sclerophthora macrospora* (downy mildew in cereals and grasses), *Pythium* (for example damping-off of Beta beet caused by *P. debaryanum*), *Phytophthora infestans* (late blight in potato and in tomato and the like), *Albugo* spec.

Ascomycota such as *Microdochium nivale* (snow mold of rye and wheat), *Fusarium, Fusarium graminearum, Fusarium culmorum* (partial ear sterility mainly in wheat), *Fusarium oxysporum* (*Fusarium* wilt of tomato), *Blumeria graminis* (powdery mildew of barley (f.sp. *hordei*) and wheat (f.sp. *tritici*)), *Erysiphe pisi* (powdery mildew of pea), *Nectria galligena* (*Nectria* canker of fruit trees), *Uncinula necator* (powdery mildew of grapevine), *Pseudopeziza tracheiphila* (red fire disease of grapevine), *Claviceps purpurea* (ergot on, for example, rye and grasses), *Gaeumannomyces graminis* (take-all on wheat, rye and other grasses), *Magnaporthe grisea, Pyrenophora graminea* (leaf stripe of barley), *Pyrenophora teres* (net blotch of barley), *Pyrenophora tritici-repentis* (leaf blight of wheat), *Venturia inaequalis* (apple scab), *Sclerotinia sclerotium* (stalk break, stem rot), *Pseudopeziza medicaginis* (leaf spot of alfalfa, white and red clover).

Basidiomycetes such as *Typhula incarnata* (*typhula* blight on barley, rye, wheat), *Ustilago maydis* (blister smut on maize), *Ustilago nuda* (loose smut on barley), *Ustilago tritici* (loose smut on wheat, spelt), *Ustilago avenae* (loose smut on oats), *Rhizoctonia solani* (rhizoctonia root rot of potato), *Sphacelotheca* spp. (head smut of sorghum), *Melampsora lini* (rust of flax), *Puccinia graminis* (stem rust of wheat, barley, rye, oats), *Puccinia recondita* (leaf rust on wheat), *Puccinia dispersa* (brown rust on rye), *Puccinia hordei* (leaf rust of barley), *Puccinia coronata* (crown rust of oats), *Puccinia striiformis* (yellow rust of wheat, barley, rye and a large number of grasses), *Uromyces appendiculatus* (brown rust of bean), *Sclerotium rolfsii* (root and stem rots of many plants).

Deuteromycetes (Fungi imperfecti) such as *Septoria* (*Stagonospora*) *nodorum* (glume blotch) of wheat (*Septoria tritici*), *Pseudocercosporella herpotrichoides* (eyespot of wheat, barley, rye), *Rynchosporium secalis* (leaf spot on rye and barley), *Alternaria solani* (early blight of potato, tomato), *Phoma betae* (blackleg on Beta beet), *Cercospora beticola* (leaf spot on Beta beet), *Alternaria brassicae* (black spot on oilseed rape, cabbage and other crucifers), *Verticillium dahliae* (verticillium wilt), *Colletotrichum, Colletotrichum lindemuthianum* (bean anthracnose), *Phoma lingam* (blackleg of cabbage and oilseed rape), *Botrytis cinerea* (grey mold of grapevine, strawberry, tomato, hops and the like).

Especially preferred are biotrophic pathogens, e.g., *Phakopsora pachyrhizi* and/or those pathogens which have essentially a similar infection mechanism as *Phakopsora pachyrhizi*, as described herein. Particularly preferred are pathogens from the subclass Pucciniomycetes, preferably from the order Pucciniales, preferably the group Uredinales (rusts), among which in particular the Melompsoraceae. Preferred are Phakopsoraceae, more preferably *Phakopsora*. Especially preferred are *Phakopsora pachyrhizi* and/or *Phakopsora meibomiae*.

Also preferred rust fungi are selected from the group of *Puccinia, Gymnosporangium, Juniperus, Cronartium, Hemlleia,* and *Uromyces, preferably Puccinia sorghi, Gymnosporangium juniperi-virginianae, Juniperus virginiana, Cronartium nbicola, Hemlleia vastatrix, Puccinia graminis, Puccinia coronata, Uromyces phaseoli, Puccinia hemerocallidis, Puccinia persistens* subsp. *Triticina, Puccinia stniformis, Puccinia graminis* causes, and/or *Uromyces appendeculatus*.

HCP4 Expression Constructs and Vector Constructs

A recombinant vector construct comprising:
(a) (i) a nucleic acid having at least 60% identity, preferably at least 70% sequence identity, at least 80%, at least 90%, at least 95%, at least 98%, at least 99% sequence identity, or even 100% sequence identity with SEQ ID NO: 15, 16, 14, 1, 4, 6, 8, 10, 11, 19-26, 27, 29, 31, 33, 35, 37, 39, or 41, or a functional fragment thereof, or an orthologue or a paralogue thereof, or a splice variant thereof;

(ii) a nucleic acid coding for a protein comprising an amino acid sequence having at least 60% identity, preferably at least 70% sequence identity, at least 80%, at least 90%, at least 95%, at least 98%, at least 99% sequence identity, or even 100% sequence identity with SEQ ID NO: 17, 18, 2, 3, 5, 7, 9, 28, 30, 32, 34, 36, 38, 40, or 42, a functional fragment thereof, an orthologue or a paralogue thereof; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or (iv) a nucleic acid encoding the same HCP4 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 15, 16, 14, 1, 4, 6, 8, 10, 11, 19-26, 27, 29, 31, 33, 35, 37, 39, or 41;

(ii) a nucleic acid coding for a protein comprising an amino acid sequence having at least 80%, at least 90%, at least 95%, at least 98%, at least 99% sequence identity, or even 100% sequence identity with SEQ ID NO: 17, 18, 2, 3, 5, 7, 9, 28, 30, 32, 34, 36, 38, 40, or 42; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or (iv) a nucleic acid encoding the same HCP4 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 1;

(ii) a nucleic acid coding for a protein having at least 80%, at least 90%, at least 95%, at least 98%, at least 99% sequence identity, or even 100% sequence identity with SEQ ID NO: 2, 3 or 5; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or (iv) a nucleic acid encoding the same HCP4 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Furthermore, a recombinant vector construct is provided comprising:

(a) (i) a nucleic acid having at least 80%, at least 90%, at least 95%, at least 98%, at least 99% sequence identity, or even 100% sequence identity with SEQ ID NO: 14;

(ii) a nucleic acid coding for a protein having at least 80%, at least 90%, at least 95%, at least 98%, at least 99% sequence identity, or even 100% sequence identity with SEQ ID NO: 2, 3, 5, 7, or 9; preferably the encoded protein confers enhanced fungal resistance relative to control plants;

(iii) a nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or (iv) a nucleic acid encoding the same HCP4 protein as the nucleic acids of (i) to (iii) above, but differing from the nucleic acids of (i) to (iii) above due to the degeneracy of the genetic code, operably linked with (b) a promoter and (c) a transcription termination sequence is a further embodiment of the invention.

Promoters according to the present invention may be constitutive, inducible, in particular pathogen-inducible, developmental stage-preferred, cell type-preferred, tissue-preferred or organ-preferred. Constitutive promoters are active under most conditions. Non-limiting examples of constitutive promoters include the CaMV 19S and 35S promoters (Odell et al., 1985, Nature 313:810-812), the sX CaMV 35S promoter (Kay et al., 1987, Science 236:1299-1302), the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and/or the like.

Preferably, the expression vector of the invention comprises a constitutive promoter, mesophyll-specific promoter, epidermis-specific promoter, root-specific promoter, a pathogen inducible promoter, or a fungal-inducible promoter.

A promoter is inducible, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in its induced state, than in its un-induced state. A promoter is cell-, tissue- or organ-specific, if its activity, measured on the amount of RNA produced under control of the promoter, is at least 30%, at least 40%, at least 50% preferably at least 60%, at least 70%, at least 80%, at least 90% more preferred at least 100%, at least 200%, at least 300% higher in a particular cell-type, tissue or organ, then in other cell-types or tissues of the same plant, preferably the other cell-types or tissues are cell types or tissues of the same plant organ, e.g. a root. In the case of organ specific promoters, the promoter activity has to be compared to the promoter activity in other plant organs, e.g. leaves, stems, flowers or seeds. Preferably, the promoter is a constitutive promoter, mesophyll-specific promoter, or epidermis-specific promoter.

Especially preferred is a promoter from parsley, preferably, the parsley ubiquitine promoter. A preferred terminator is the terminator of the cathepsin D inhibitor gene from *Solanum tuberosum*.

In preferred embodiments, the increase in the protein amount and/or activity of the HCP4 protein takes place in a constitutive or tissue-specific manner. In especially preferred embodiments, an essentially pathogen-induced increase in the protein amount and/or protein activity takes place, for example by recombinant expression of the HCP4 nucleic acid under the control of a fungal-inducible promoter. In particular, the expression of the HCP4 nucleic acid takes place on fungal infected sites, where, however, preferably the expression of the HCP4 nucleic acid remains essentially unchanged in tissues not infected by fungus.

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, leaf-preferred, stigma-preferred, pollen-preferred, anther-preferred, a petal-preferred, sepal-preferred, pedicel-preferred, silique-preferred, stem-preferred, root-preferred promoters and/or the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and/or the like.

Other suitable tissue-preferred or organ-preferred promoters include, but are not limited to, the napin-gene promoter from rapeseed (U.S. Pat. No. 5,608,152), the USP-promoter from *Vicia faba* (Baeumlein et al., 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, Plant Journal, 2(2):233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene, and/or rye secalin gene).

Promoters useful according to the invention include, but are not limited to, are the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, bronze promoters, the Zm13 promoter (U.S. Pat. No. 5,086,169), the maize polygalacturonase promoters (PG) (U.S. Pat. Nos. 5,412,085 and 5,545,546), the SGB6 promoter (U.S. Pat. No. 5,470,359), as well as synthetic or other natural promoters.

Epidermis-specific promoters may be selected from the group consisting of:
WIR5 (=GstA1); acc. X56012; Dudler & Schweizer,
GLP4, acc. AJ310534; Wei Y., Zhang Z., Andersen C. H., Schmelzer E., Gregersen P. L., Collinge D. B., Smedegaard-Petersen V. and Thordal-Christensen H., Plant Molecular Biology 36, 101 (1998),
GLP2a, acc. AJ237942, Schweizer P., Christoffel A. and Dudler R., Plant J. 20, 541 (1999);
Prx7, acc. AJ003141, Kristensen B. K., Ammitzbóll H., Rasmussen S. K. and Nielsen K. A., Molecular Plant Pathology, 2(6), 311 (2001);
GerA, acc. AF250933; Wu S., Druka A., Horvath H., Kleinhofs A., Kannangara G. and von Wettstein D., Plant Phys Biochem 38, 685 (2000);
OsROC1, acc. AP004656
RTBV, acc. AAV62708, AAV62707; Klóti A., Henrich C., Bieri S., He X., Chen G., Burkhardt P. K., Wünn J., Lucca P., Hohn T., Potrykus I. and Fütterer J., PMB 40, 249 (1999);
Chitinase ChtC2-Promoter from potato (Ancillo et al., Planta. 217(4), 566, (2003));
AtProT3 Promoter (Grallath et al., Plant Physiology. 137(1), 117 (2005));
SHN-Promoters from *Arabidopsis* (AP2/EREBP transcription factors involved in cutin and wax production) (Aarón et al., Plant Cell. 16(9), 2463 (2004)); and/or
GSTA1 from wheat (Dudler et al., WP2005306368 and Altpeter et al., Plant Molecular Biology. 57(2), 271 (2005)).

Mesophyll-specific promoters may be selected from the group consisting of:
PPCZm1 (=PEPC); Kausch A. P., Owen T. P., Zachwieja S. J., Flynn A. R. and Sheen J., Plant Mol. Biol. 45, 1 (2001);
OsrbcS, Kyozuka et al., PlaNT Phys 102, 991 (1993); Kyozuka J., McElroy D., Hayakawa T., Xie Y., Wu R. and Shimamoto K., Plant Phys. 102, 991 (1993);
OsPPDK, acc. AC099041;
TaGF-2.8, acc. M63223; Schweizer P., Christoffel A. and Dudler R., Plant J. 20, 541 (1999);
TaFBPase, acc. X53957;
TaWIS1, acc. AF467542; US 200220115849;
HvBIS1, acc. AF467539; US 200220115849;
ZmMIS1, acc. AF467514; US 200220115849;
HvPR1a, acc. X74939; Bryngelsson et al., Mol. Plant Microbe Interacti. 7 (2), 267 (1994);
HvPR1b, acc. X74940; Bryngelsson et al., Mol. Plant Microbe Interact. 7(2), 267 (1994);
HvB1,3gluc; acc. AF479647;
HvPrx8, acc. AJ276227; Kristensen et al., Molecular Plant Pathology, 2(6), 311 (2001); and/or
HvPAL, acc. X97313; Wei Y., Zhang Z., Andersen C. H., Schmelzer E., Gregersen P. L., Collinge D. B., Smedegaard-Petersen V. and Thordal-Christensen H. Plant Molecular Biology 36, 101 (1998).

Constitutive promoters may be selected from the group consisting of
PcUbi promoter from parsley (WO 03/102198)
CaMV 35S promoter: Cauliflower Mosaic Virus 35S promoter (Benfey et al. 1989 EMBO J. 8(8): 2195-2202),
STPT promoter: *Arabidopsis thaliana* Short Triose phosphate translocator promoter (Accession NM_123979)
Act1 promoter: *Oryza sativa* actin 1 gene promoter (McElroy et al. 1990 PLANT CELL 2(2) 163-171 a) and/or
EF1A2 promoter: *Glycine max* translation elongation factor EF1 alpha (US 20090133159).

One type of vector construct is a "plasmid," which refers to a circular double stranded DNA loop into which additional DNA segments can be ligated. Another type of vector is a viral vector, wherein additional DNA segments can be ligated into the viral genome. Certain vector constructs are capable of autonomous replication in a host plant cell into which they are introduced. Other vector constructs are integrated into the genome of a host plant cell upon introduction into the host cell, and thereby are replicated along with the host genome. In particular the vector construct is capable of directing the expression of gene to which the vectors is operatively linked. However, the invention is intended to include such other forms of expression vector constructs, such as viral vectors (e.g., potato virus X, tobacco rattle virus, and/or Gemini virus), which serve equivalent functions.

In preferred embodiments, the increase in the protein quantity or function of the HCP4 protein takes place in a constitutive or tissue-specific manner. In especially preferred embodiments, an essentially pathogen-induced increase in the protein quantity or protein function takes place, for example by exogenous expression of the HCP4 nucleic acid under the control of a fungal-inducible promoter. In particular, the expression of the HCP4 nucleic acid takes place on fungal infected sites, where, however, preferably the expression of the HCP4 nucleic acid sequence remains essentially unchanged in tissues not infected by fungus. In preferred embodiments, the protein amount of an HCP4 protein in the plant is increased by at least 10%, at least 20%, at least 30%, at least 40%, at least 50%, at least 60%, at least 70%, at least 80%, at least 90%, or at least 95% or more in comparison to a wild type plant that is not transformed with the HCP4 nucleic acid.

A preferred embodiment is the use of an expression construct or a vector as described herein for the transformation of a plant, plant part, or plant cell to provide a pathogen resistant plant, plant part, or plant cell. Thus, a preferred embodiment is the use of an expression construct or a vector as described herein for increasing pathogen resistance in a plant, plant part, or plant cell compared to a control plant, plant part, or plant cell.

Transgenic Organisms; Transgenic Plants, Plant Parts, and Plant Cells

A preferred embodiment is a transgenic plant, transgenic plant part, or transgenic plant cell overexpressing an exogenous HCP4 protein. Preferably, the HCP4 protein overexpressed in the plant, plant part or plant cell is encoded by a nucleic acid comprising
(i) an exogenous nucleic acid having at least 60% identity with SEQ ID NO: 15, 16, 14, 1, 4, 6, 8, 10, 11, 19-26, 27, 29, 31, 33, 35, 37, 39, or 41, or a functional fragment, thereof, an orthologue or a paralogue thereof, or a splice variant thereof; or by
(ii) an exogenous nucleic acid encoding a protein comprising an amino acid sequence having at least 60% identity with SEQ ID NO: 17, 18, 2, 3, 5, 7, 9, 28, 30, 32, 34, 36, 38, 40, or 42, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, 9, 28, 30, 32, 34, 36, 38, 40, or 42; preferably the encoded protein confers enhanced fungal resistance relative to control plants; and/or by
(iv) an exogenous nucleic acid encoding the same HCP4 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 14, 1, 4, 6, 8, 10, 11, 19-26, 27, 29, 31, 33, 35, 37, 39, or 41; or comprises an exogenous nucleic acid encoding a protein having at least 80%, at least 90%, at least 95%, at least 98%, at least 99% sequence identity, or even 100% sequence identity with SEQ ID NO: 2, 3, 5, 7, or 9.

A preferred embodiment is a transgenic plant, transgenic plant part, or transgenic plant cell overexpressing an exogenous HCP4 protein. Preferably, the HCP4 protein overexpressed in the plant, plant part or plant cell is encoded by
(i) an exogenous nucleic acid having at least 60% identity with SEQ ID NO: 1 or a functional fragment, thereof, an orthologue or a paralogue thereof, or a splice variant thereof; or by
(ii) an exogenous nucleic acid encoding a protein having at least 60% identity with SEQ ID NO: 2, 3, 5, 7, or 9, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by
(iv) an exogenous nucleic acid encoding the same HCP4 protein as the nucleic acids of (i) to (iii) above, but differing from the nucleic acids of (i) to (iii) above due to the degeneracy of the genetic code.

A preferred embodiment is a transgenic plant, transgenic plant part, or transgenic plant cell overexpressing an exogenous HCP4 protein. Preferably, the HCP4 protein overexpressed in the plant, plant part or plant cell is encoded by
(i) an exogenous nucleic acid having at least 60% identity with SEQ ID NO: 14 or a functional fragment, thereof, an orthologue or a paralogue thereof, or a splice variant thereof; or by (ii) an exogenous nucleic acid encoding a protein having at least 60% identity with SEQ ID NO: 2, 3, 5, 7, or 9, a functional fragment thereof, an orthologue or a paralogue thereof; preferably the encoded protein confers enhanced fungal resistance relative to control plants;
(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by
(iv) an exogenous nucleic acid encoding the same HCP4 protein as the nucleic acids of (i) to (iii) above, but differing from the nucleic acids of (i) to (iii) above due to the degeneracy of the genetic code.

Most preferably, the exogenous nucleic acid has at least 80%, at least 90%, at least 95%, at least 98%, at least 99% sequence identity, or even 100% sequence identity with SEQ ID NO: 1; or comprises an exogenous nucleic acid encoding a protein having at least 80%, at least 90%, at least 95%, at least 98%, at least 99% sequence identity, or even 100% sequence identity with SEQ ID NO: 2, 3, 5, 7, or 9.

Most preferably, the exogenous nucleic acid has at least 80%, at least 90%, at least 95%, at least 98%, at least 99% sequence identity, or even 100% sequence identity with SEQ ID NO: 14; or comprises an exogenous nucleic acid encoding a protein having at least 80%, at least 90%, at least 95%, at least 98%, at least 99% sequence identity, or even 100% sequence identity with SEQ ID NO: 2 or 3.

Most preferably, the exogenous nucleic acid has at least 80%, at least 90%, at least 95%, at least 98%, at least 99% sequence identity, or even 100% sequence identity with SEQ ID NO: 14; or comprises an exogenous nucleic acid encoding a protein having at least 80%, at least 90%, at least 95%, at least 98%, at least 99% sequence identity, or even 100% sequence identity with SEQ ID NO: 5, 7 or 9.

More preferably, the transgenic plant, transgenic plant part, or transgenic plant cell according to the present invention has been obtained by transformation with a recombinant vector described herein.

Suitable methods for transforming or transfecting host cells including plant cells are well known in the art of plant biotechnology. Any method may be used to transform the recombinant expression vector into plant cells to yield the transgenic plants of the invention. General methods for transforming dicotyledonous plants are disclosed, for example, in U.S. Pat. Nos. 4,940,838; 5,464,763, and the like. Methods for transforming specific dicotyledonous plants, for example, cotton, are set forth in U.S. Pat. Nos. 5,004,863; 5,159,135; and 5,846,797. Soy transformation methods are set forth in U.S. Pat. Nos. 4,992,375; 5,416,011; 5,569,834; 5,824,877; 6,384,301 and in EP 0301749B1 may be used. Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants.

Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The genetically modified plant cells can be regenerated via all methods with which the skilled worker is familiar. Suitable methods can be found in the abovementioned publications by S. D. Kung and R. Wu, Potrykus or Hofgen and Willmitzer.

After transformation, plant cells or cell groupings may be selected for the presence of one or more markers which are encoded by plant-expressible genes co-transferred with the gene of interest, following which the transformed material is regenerated into a whole plant.

To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Alternatively, the transformed plants are screened for the presence of a selectable marker such as the ones described above. The transformed plants may also be directly selected by screening for the presence of the HCP4 nucleic acid.

Following DNA transfer and regeneration, putatively transformed plants may also be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques. The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

Preferably, the transgenic plant of the present invention or the plant obtained by the method of the present invention has increased resistance against fungal pathogens, preferably rust pathogens (i.e., fungal pathogens of the order Pucciniales), preferably against fungal pathogens of the family Phakopsoraceae, more preferably against fungal pathogens of the genus *Phakopsora*, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Preferably, the plant, plant part, or plant cell is a plant or derived from a plant selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

In one embodiment of the present invention the plant is selected from the group consisting of beans, soya, pea, clover, kudzu, lucerne, lentils, lupins, vetches, and/or groundnut. Preferably, the plant is a legume, comprising plants of the genus *Phaseolus* (comprising French bean, dwarf bean, climbing bean (*Phaseolus vulgaris*), Lima bean (*Phaseolus lunatus* L.), Tepary bean (*Phaseolus acutifolius* A. Gray), runner bean (*Phaseolus coccineus*)); the genus *Glycine* (comprising *Glycine soja*, soybeans (*Glycine max* (L.) Merill)); pea (*Pisum*) (comprising shelling peas (*Pisum sativum* L. convar. *sativum*), also called smooth or round-seeded peas; marrowfat pea (*Pisum sativum* L. convar. medullare Alef. emend. C. O. Lehm), sugar pea (*Pisum sativum* L. convar. axiphium Alef emend. C. O. Lehm), also called snow pea, edible-podded pea or mangetout, (*Pisum granda sneida* L. convar. sneidulo p. shneiderium)); peanut (*Arachis hypogaea*), clover (*Trifolium* spec.), medick (*Medicago*), kudzu vine (*Pueraria lobata*), common lucerne, alfalfa (*M. sativa* L.), chickpea (*Cicer*), lentils (Lens) (*Lens culinaris* Medik.), lupins (*Lupinus*); vetches (*Vicia*), field bean, broad bean (*Vicia faba*), vetchling (*Lathyrus*) (comprising chickling pea (*Lathyrus sativus*), heath pea (*Lathyrus tuberosus*)); genus *Vigna* (comprising moth bean (*Vigna aconitifolia* (Jacq.) Maréchal), adzuki bean (*Vigna angularis* (Willd.) Ohwi & H. Ohashi), urd bean (*Vigna mungo* (L.) Hepper), mung bean (*Vigna radiata* (L.) R. Wilczek), bambara groundnut (*Vigna subterrane* (L.) Verdc.), rice bean (*Vigna umbellata* (Thunb.) Ohwi & H. Ohashi), *Vigna vexillata* (L.) A. Rich., *Vigna unguiculata* (L.) Walp., in the three subspecies asparagus bean, cowpea, catjang bean)); pigeonpea (*Cajanus cajan* (L.) Millsp.), the genus *Macrotyloma* (comprising geocarpa groundnut (*Macrotyloma geocarpum* (Harms) Maréchal & Baudet), horse bean (*Macrotyloma uniflorum* (Lam.) Verdc.); goa bean (*Psophocarpus tetragonolobus* (L.) DC.), African yam bean (*Sphenostylis*

*stenocarpa* (Hochst. ex A. Rich.) Harms), Egyptian black bean, *dolichos* bean, *lablab* bean (*Lablab purpureus* (L.) Sweet), yam bean (*Pachyrhizus*), guar bean (*Cyamopsis tetragonolobus* (L.) Taub.); and/or the genus *Canavalia* (comprising jack bean (*Canavalia ensiformis* (L.) DC.), sword bean (*Canavalia gladiata* (Jacq.) DC.).

Further preferred is a plant selected from the group consisting of beans, soya, pea, clover, kudzu, lucerne, lentils, lupins, vetches, and groundnut. Most preferably, the plant, plant part, or plant cell is or is derived from soy.

Preferably, the transgenic plant of the present invention or the plant obtained by the method of the present invention is a soybean plant and has increased resistance against fungal pathogens of the order Pucciniales (rust), preferably, of the family Phacopsoraceae, more preferably against fungal pathogens of the genus Phacopsora, most preferably against *Phakopsora pachyrhizi* and *Phakopsora meibomiae*, also known as soybean rust. Preferably, resistance against *Phakopsora pachyrhizi* and/or *Phakopsora meibomiae* is increased.

Methods for the Production of Transgenic Plants

One embodiment according to the present invention provides a method for producing a transgenic plant, a transgenic plant part, or a transgenic plant cell resistant to a fungal pathogen, preferably of the family Phacopsoraceae, for example soybean rust, wherein the recombinant nucleic acid used to generate a transgenic plant comprises a promoter that is functional in the plant cell, operably linked to an HCP4 nucleic acid, which is preferably SEQ ID NO: 1, and a terminator regulatory sequence.

In one embodiment, the present invention refers to a method for the production of a transgenic plant, transgenic plant part, or transgenic plant cell having increased fungal resistance, comprising
(a) introducing a recombinant vector construct according to the present invention into a plant, a plant part or a plant cell and
(b) generating a transgenic plant from the plant, plant part or plant cell.

Preferably, the method for the production of the transgenic plant, transgenic plant part, or transgenic plant cell further comprises the step
(c) expressing the HCP4 protein, preferably encoded by a nucleic acid comprising
   (i) an exogenous nucleic acid having at least 60% identity with SEQ ID NO: 15, 16, 14, 1, 4, 6, 8, 10, 11, 19-26, 27, 29, 31, 33, 35, 37, 39, or 41, a functional fragment thereof, an orthologue or a paralogue thereof, or a splice variant thereof;
   (ii) an exogenous nucleic acid encoding a protein comprising an amino acid sequence having at least 60% identity with SEQ ID NO: 17, 18, 2, 3, 5, 7, 9, 28, 30, 32, 34, 36, 38, 40, or 42, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by
   (iv) an exogenous nucleic acid encoding the same HCP4 protein as the nucleic acids of (i) to (iii) above, but differing from the nucleic acids of (i) to (iii) above due to the degeneracy of the genetic code.

Preferably, said introducing and expressing does not comprise an essentially biological process.

More preferably, the method for the production of the transgenic plant, transgenic plant part, or transgenic plant cell further comprises the step
(c) expressing the HCP4 protein, preferably encoded by
   (i) an exogenous nucleic acid having at least 60% identity with SEQ ID NO: 1, a functional fragment thereof, an orthologue or a paralogue thereof, or a splice variant thereof;
   (ii) an exogenous nucleic acid encoding a protein having at least 60% identity with SEQ ID NO: 2, 3, 5, 7, or 9, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by
   (iv) an exogenous nucleic acid encoding the same HCP4 protein as the nucleic acids of (i) to (iii) above, but differing from the nucleic acids of (i) to (iii) above due to the degeneracy of the genetic code.

More preferably, the method for the production of the transgenic plant, transgenic plant part, or transgenic plant cell further comprises the step
(c) expressing the HCP4 protein, preferably encoded by
   (i) an exogenous nucleic acid having at least 60% identity with SEQ ID NO: 14, a functional fragment thereof, an orthologue or a paralogue thereof, or a splice variant thereof;
   (ii) an exogenous nucleic acid encoding a protein having at least 60% identity with SEQ ID NO: 2, 3, 5, 7, or 9, or a functional fragment thereof, an orthologue or a paralogue thereof; preferably the encoded protein confers enhanced fungal resistance relative to control plants;
   (iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by
   (iv) an exogenous nucleic acid encoding the same HCP4 protein as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell further comprises the step of selecting a transgenic plant expressing (i) an exogenous nucleic acid having at least 60% identity, preferably at least 70% sequence identity, at least 80%, at least 90%, at least 95%, at least 98%, at least 99% sequence identity, or even 100% sequence identity with SEQ ID NO: 14, 1, 4, 6, 8, 10, 11, 19-26, 27, 29, 31, 33, 35, 37, 39, or 41, or a functional fragment thereof, or an orthologue or a paralogue thereof, or a splice variant thereof;

(ii) an exogenous nucleic acid coding for a protein having at least 60% identity, preferably at least 70% sequence identity, at least 80%, at least 90%, at least 95%, at least 98%, at least 99% sequence identity, or even 100% sequence identity with SEQ ID NO: 2, 3, 5, 7, 9, 28, 30, 32, 34, 36, 38, 40, or 42, a functional fragment thereof, an orthologue or a paralogue thereof; preferably the encoded protein confers enhanced fungal resistance relative to control plants;

(iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or (iv) an exogenous nucleic acid encoding the same HCP4 polypeptide as the nucleic acids of (i) to (iii) above, but differing from the nucleic acids of (i) to (iii) above due to the degeneracy of the genetic code.

Preferably, the method for the production of the transgenic plant, transgenic plant part, or transgenic plant cell additionally comprises the step of harvesting the seeds of the transgenic plant and planting the seeds and growing the seeds to plants, wherein the grown plant(s) comprises (i) the exogenous nucleic acid having at least 60% identity with SEQ ID NO: 15, 16, 14, 1, 4, 6, 8, 10, 11, 19-26, 27, 29, 31, 33, 35, 37, 39, or 41, a functional fragment thereof, an orthologue or a paralogue thereof, or a splice variant thereof;

(ii) the exogenous nucleic acid encoding a protein comprising an amino acid sequence having at least 60% identity with SEQ ID NO: 17, 18, 2, 3, 5, 7, 9, 28, 30, 32, 34, 36, 38, 40, or 42, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, 9, 28, 30, 32, 34, 36, 38, 40, or 42; preferably the encoded protein confers enhanced fungal resistance relative to control plants; and/or (iv) the exogenous nucleic acid encoding the same HCP4 protein as the nucleic acids of (i) to (iii) above, but differing from the nucleic acids of (i) to (iii) above due to the degeneracy of the genetic code;

preferably, the step of harvesting the seeds of the transgenic plant and planting the seeds and growing the seeds to plants, wherein the grown plant(s) comprises (i) the exogenous nucleic acid having at least 60% identity with SEQ ID NO: 15, 16, 14, 1, 4, 6, 8, 10, 11, 19-26, 27, 29, 31, 33, 35, 37, 39, or 41, a functional fragment thereof, an orthologue or a paralogue thereof, or a splice variant thereof;

(ii) the exogenous nucleic acid encoding a protein comprising an amino acid sequence having at least 60% identity with SEQ ID NO: 17, 18, 2, 3, 5, 7, 9, 28, 30, 32, 34, 36, 38, 40, or 42, or a functional fragment thereof, an orthologue or a paralogue thereof; preferably the encoded protein confers enhanced fungal resistance relative to control plants;

(iii) the exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID No: 15, 16, 14, 1, 4, 6, 8, 10, 11, 19-26, 27, 29, 31, 33, 35, 37, 39, or 41; preferably the encoded protein confers enhanced fungal resistance relative to control plants; and/or (iv) the exogenous nucleic acid encoding the same HCP4 protein as the nucleic acids of (i) to (iii) above, but differing from the nucleic acids of (i) to (iii) above due to the degeneracy of the genetic code;

is repeated more than one time, preferably, 1, 2, 3, 4, 5, 6, 8, 9, 10, 15, 20, 25, 30, 35, 40, 45, or 50 times.

The transgenic plants may be selected by known methods as described above (e.g., by screening for the presence of one or more markers which are encoded by plant-expressible genes co-transferred with the HCP4 gene or by directly screening for the HCP4 nucleic acid).

Furthermore, the use of the exogenous HCP4 nucleic acid or the recombinant vector construct comprising the HCP4 nucleic acid for the transformation of a plant, plant part, or plant cell to provide a fungal resistant plant, plant part, or plant cell is provided.

Harvestable Parts and Products

Harvestable parts of the transgenic plant according to the present invention are part of the invention. Preferably, the harvestable parts comprise the HCP4 nucleic acid or HCP4 protein. The harvestable parts may be seeds, roots, leaves and/or flowers comprising the HCP4 nucleic acid or HCP4 protein or parts thereof. Preferred parts of soy plants are soy beans comprising the HCP4 nucleic acid or HCP4 protein.

Products derived from a transgenic plant according to the present invention, parts thereof or harvestable parts thereof are part of the invention. A preferred product is meal or oil, preferably, soybean meal or soybean oil. Preferably, the soybean meal and/or oil comprises the HCP4 nucleic acid or HCP4 protein.

Preferably the harvestable parts of the transgenic plant according to the present invention or the products derived from a transgenic plant comprise an exogenous nucleic acid molecule consisting of or comprising a nucleic acid selected from the group consisting of:

(i) an exogenous nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15, 16, 14, 1, 4, 6, 8, 10, 11, 19-26, 27, 29, 31, 33, 35, 37, 39, or 41, or a functional fragment, derivative, orthologue, or paralogue thereof, or a splice variant thereof;

(ii) a exogenous nucleic acid encoding a HCP4 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17, 18, 2, 3, 5, 7, 9, 28, 30, 32, 34, 36, 38, 40, or 42, or a functional fragment, derivative, orthologue, or paralogue thereof; preferably the HCP4 protein has essentially the same biological activity as an HCP4 protein encoded by SEQ ID NO: 15, 16, 14, 1, 4, 6, 8, 10, or 11; preferably the HCP4 protein confers enhanced fungal resistance relative to control plants;

(iii) an exogenous nucleic acid molecule which hybridizes with a complementary sequence of any of the nucleic acid molecules of (i) or (ii) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and (iv) an exogenous nucleic acid encoding the same HCP4 protein as the HCP4 nucleic acids of (i) to (iii) above, but differing from the HCP4 nucleic acids of (i) to (iii) above due to the degeneracy of the genetic code;

or wherein the harvestable part of the transgenic plant or the product derived from the transgenic plant comprises a HCP4 protein encoded by any one of the HCP4 nucleic acids of (i) to (iv).

Methods for Manufacturing a Product

In one embodiment the method for the production of a product comprises a) growing the plants of the invention or obtainable by the methods of invention and b) producing said product from or by the plants of the invention and/or parts, e.g. seeds, of these plants.

In a further embodiment the method comprises the steps a) growing the plants of the invention, b) removing the harvestable parts as defined above from the plants and c) producing said product from or by the harvestable parts of the invention.

Preferably the products obtained by said method comprises an exogenous nucleic acid molecule consisting of or comprising a nucleic acid selected from the group consisting of:

(i) an exogenous nucleic acid having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the nucleic acid sequence represented by SEQ ID NO: 15, 16, 14, 1, 4, 6, 8, 10, 11, 19-26, 27, 29, 31, 33, 35, 37, 39, or 41, or a functional fragment, derivative, orthologue, or paralogue thereof, or a splice variant thereof;

(ii) a exogenous nucleic acid encoding a HCP4 protein comprising an amino acid sequence having in increasing order of preference at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% sequence identity to the amino acid sequence represented by SEQ ID NO: 17, 18, 2, 3, 5, 7, 9, 28, 30, 32, 34, 36, 38, 40, or 42, or a functional fragment, derivative, orthologue, or paralogue thereof; preferably the HCP4 protein has essentially the same biological activity as an HCP4 protein encoded by SEQ ID NO: 15, 16, 14, 1, 4, 6, 8, 10, or 11; preferably the HCP4 protein confers enhanced fungal resistance relative to control plants;

(iii) an exogenous nucleic acid molecule which hybridizes with a complementary sequence of any of the nucleic acid molecules of (i) or (ii) under high stringency hybridization conditions; preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and (iv) an exogenous nucleic acid encoding the same HCP4 protein as the HCP4 nucleic acids of (i) to (iii) above, but differing from the HCP4 nucleic acids of (i) to (iii) above due to the degeneracy of the genetic code;

or wherein the product obtained by said method comprises a HCP4 protein encoded by any one of the HCP4 nucleic acids of (i) to (iv).

The product may be produced at the site where the plant has been grown, the plants and/or parts thereof may be removed from the site where the plants have been grown to produce the product. Typically, the plant is grown, the desired harvestable parts are removed from the plant, if feasible in repeated cycles, and the product made from the harvestable parts of the plant. The step of growing the plant may be performed only once each time the methods of the invention is performed, while allowing repeated times the steps of product production e.g. by repeated removal of harvestable parts of the plants of the invention and if necessary further processing of these parts to arrive at the product. It is also possible that the step of growing the plants of the invention is repeated and plants or harvestable parts are stored until the production of the product is then performed once for the accumulated plants or plant parts. Also, the steps of growing the plants and producing the product may be performed with an overlap in time, even simultaneously to a large extend or sequentially. Generally the plants are grown for some time before the product is produced.

In one embodiment the products produced by said methods of the invention are plant products such as, but not limited to, a foodstuff, feedstuff, a food supplement, feed supplement, fiber, cosmetic and/or pharmaceutical. Foodstuffs are regarded as compositions used for nutrition and/or for supplementing nutrition. Animal feedstuffs and animal feed supplements, in particular, are regarded as foodstuffs.

In another embodiment the inventive methods for the production are used to make agricultural products such as, but not limited to, plant extracts, proteins, amino acids, carbohydrates, fats, oils, polymers, vitamins, and the like.

It is possible that a plant product consists of one or more agricultural products to a large extent.

Methods for Breeding/Methods for Plant Improvement/ Methods Plant Variety Production The transgenic plants of the invention may be crossed with similar transgenic plants or with transgenic plants lacking the nucleic acids of the invention or with non-transgenic plants, using known methods of plant breeding, to prepare seeds. Further, the transgenic plant cells or plants of the present invention may comprise, and/or be crossed to another transgenic plant that comprises one or more exogenous nucleic acids, thus creating a "stack" of transgenes in the plant and/or its progeny. The seed is then planted to obtain a crossed fertile transgenic plant comprising the HCP4 nucleic acid. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the exogenous nucleic acid.

Thus, one embodiment of the present invention is a method for breeding a fungal resistant plant comprising the steps of
(a) crossing a transgenic plant described herein or a plant obtainable by a method described herein with a second plant;
(b) obtaining a seed or seeds resulting from the crossing step described in (a);
(c) planting said seed or seeds and growing the seed or seeds to plants; and
(d) selecting from said plants the plants expressing an HCP4 protein, preferably encoded by a nucleic acid comprising
  (i) an exogenous nucleic acid having at least 60% identity with SEQ ID NO: 15, 16, 14, 1, 4, 6, 8, 10, 11, 19-26, 27, 29, 31, 33, 35, 37, 39, or 41, a functional fragment thereof, an orthologue or a paralogue thereof, or a splice variant thereof;
  (ii) an exogenous nucleic acid encoding a protein comprising an amino acid sequence having at least 60% identity with SEQ ID NO: 17, 18, 2, 3, 5, 7, 9, 28, 30, 32, 34, 36, 38, 40, or 42, or a functional fragment thereof, an orthologue or a paralogue thereof; preferably the encoded protein confers enhanced fungal resistance relative to control plants;
  (iii) an exogenous nucleic acid capable of hybridizing under stringent conditions with a complementary sequence of any of the nucleic acids according to (i) or (ii); preferably encoding a HCP4 protein; preferably wherein the nucleic acid molecule codes for a polypeptide which has essentially identical properties to the polypeptide described in SEQ ID NO: 17, 18, 2, 3, 5, 7, or 9; preferably the encoded protein confers enhanced fungal resistance relative to control plants; and/or by
  (iv) an exogenous nucleic acid encoding the same HCP4 protein as the nucleic acids of (i) to (iii) above, but differing from the nucleic acids of (i) to (iii) above due to the degeneracy of the genetic code.

Another preferred embodiment is a method for plant improvement comprising
(a) obtaining a transgenic plant by any of the methods of the present invention;
(b) combining within one plant cell the genetic material of at least one plant cell of the plant of (a) with the genetic material of at least one cell differing in one or more gene from the plant cells of the plants of (a) or crossing the transgenic plant of (a) with a second plant;
(c) obtaining seed from at least one plant generated from the one plant cell of (b) or the plant of the cross of step (b);
(d) planting said seeds and growing the seeds to plants; and
(e) selecting from said plants, plants expressing the nucleic acid encoding the HCP4 protein; and optionally
(f) producing propagation material from the plants expressing the nucleic acid encoding the HCP4 protein.

The transgenic plants may be selected by known methods as described above (e.g., by screening for the presence of one or more markers which are encoded by plant-expressible genes co-transferred with the HCP4 gene or screening for the HCP4 nucleic acid itself).

According to the present invention, the introduced HCP4 nucleic acid may be maintained in the plant cell stably if it is incorporated into a non-chromosomal autonomous replicon or integrated into the plant chromosomes. Whether present in an extra-chromosomal nonreplicating or replicating vector construct or a vector construct that is integrated into a chromosome, the exogenous HCP4 nucleic acid preferably resides in a plant expression cassette. A plant expression cassette preferably contains regulatory sequences capable of driving gene expression in plant cells that are functional linked so that each sequence can fulfill its function, for example, termination of transcription by polyadenylation signals. Preferred polyadenylation signals are those originating from *Agrobacterium* tumefacient-DNA such as the gene 3 known as octopine synthase of the Ti-plasmid pTiACH5 (Gielen et al, 1984, EMBO J. 3:835) or functional equivalents thereof, but also all other terminators functionally active in plants are suitable. As plant gene expression is very often not limited on transcriptional levels, a plant expression cassette preferably contains other functional linked sequences like translational enhancers such as the overdrive-sequence containing the 5'-untranslated leader sequence from tobacco mosaic virus increasing the polypeptide per RNA ratio (Gallie et al, 1987, Nucl. Acids Research 15:8693-8711). Examples of plant expression vectors include those detailed in: Becker, D. et al, 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

EXAMPLES

The following examples are not intended to limit the scope of the claims to the invention, but are rather intended to be exemplary of certain embodiments. Any variations in the exemplified methods that occur to the skilled artisan are intended to fall within the scope of the present invention.

Example 1: General Methods

The chemical synthesis of oligonucleotides can be affected, for example, in the known fashion using the phosphoamidite method (Voet, Voet, 2nd Edition, Wiley Press New York, pages 896-897). The cloning steps carried out for the purposes of the present invention such as, for example, restriction cleavages, agarose gel electrophoresis, purification of DNA fragments, transfer of nucleic acids to nitrocellulose and nylon membranes, linking DNA fragments, transformation of E. coli cells, bacterial cultures, phage multiplication and sequence analysis of recombinant DNA, are carried out as described by Sambrook et al. Cold Spring Harbor Laboratory Press (1989), ISBN 0-87969-309-6. The sequencing of recombinant DNA molecules is carried out with an MWG-Licor laser fluorescence DNA sequencer following the method of Sanger (Sanger et al., Proc. Natl. Acad. Sci. USA 74, 5463 (1977)).

Example 2: Cloning of Overexpression Vector Constructs cDNA was produced from *Arabidopsis thaliana* (ecotype Col-0) RNA by using the Superscript II cDNA synthesis kit (Invitrogen). All steps of cDNA preparation and purification were performed according as described in the manual.

The HCP4 sequence (SEQ ID NO: 1) was amplified from the cDNA by PCR as described in the protocol of the Phusion hot-start, Pfu Ultra, Pfu Turbo or Herculase DNA polymerase (Stratagene).

The composition for the protocol of the Pfu Ultra, Pfu Turbo or Herculase DNA polymerase was as follows: 1×PCR buffer, 0.2 mM of each dNTP, 100 ng cDNA of *Arabidopsis thaliana* (var Columbia-0), 50 pmol forward primer, 50 pmol reverse primer, 1 u Phusion hot-start, Pfu Ultra, Pfu Turbo or Herculase DNA polymerase.

The amplification cycles were as follows:
1 cycle of 60 seconds at 98° C., followed by 35 cycles of in each case 10 seconds at 98° C., 30 seconds at 55° C. and 120 seconds at 72° C., followed by 1 cycle of 10 minutes at 72° C., then 4° C.

The following primer sequences were used to specifically amplify the HCP4 full-length DNA for cloning purposes:

```
i) foward primer:
                                    (SEQ ID NO: 12)
5'-AAGGTACCATGGCAGCTTCTTTTTGC-3' ii) reverse primer:
                                    (SEQ ID NO: 13)
5'-CCGTCGACTCAGGTTCTCCTGATTAT-3'
```

The primers (as shown in SEQ ID NO: 12 and SEQ ID NO: 13) were designed in a way that an Acc65I restriction site is located in front of the start-ATG and a SalI restriction site downstream of the stop-codon.

The amplified fragments were digested using the restriction enzymes Acc65I and SalI (NEB Biolabs) and ligated in a Acc65I/SalI digested Gateway pENTRY vector (Invitrogen, Life Technologies, Carlsbad, Calif., USA) in a way that the full-length HCP4 fragment is located in sense direction between the attL1 and attL2 recombination sites.

It is also possible to generate all DNA fragments mentioned in this invention by DNA synthesis (Geneart, Regensburg, Germany).

Figure 2:
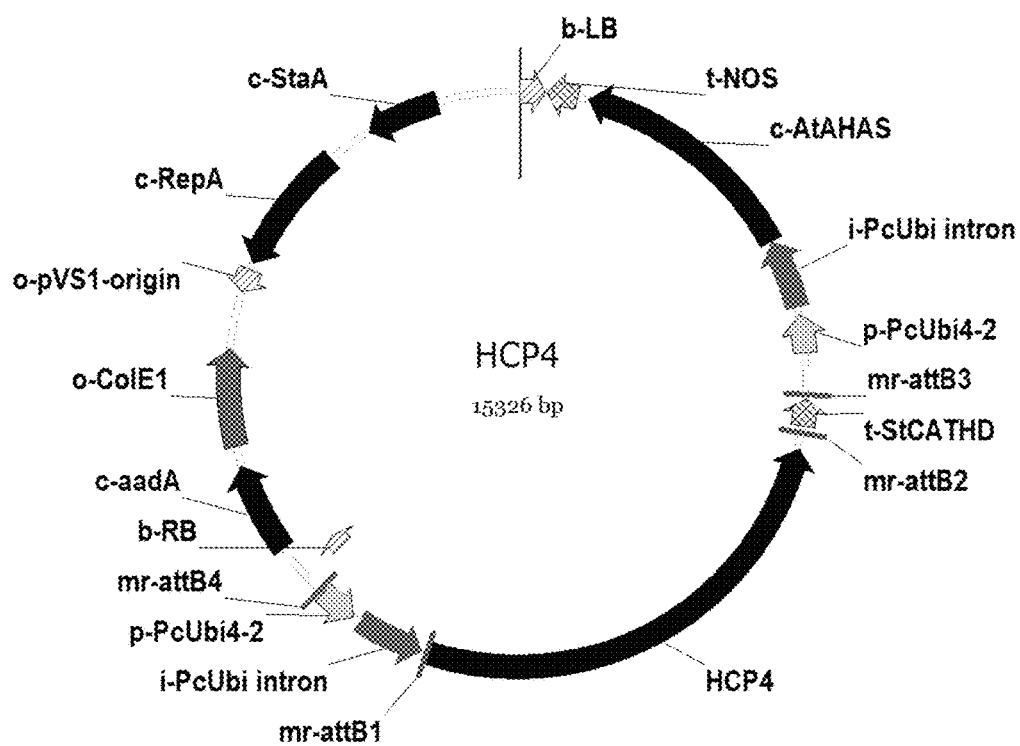

To obtain the binary plant transformation vector, a triple LR reaction (Gateway system, Invitrogen, Life Technologies, Carlsbad, Calif., USA) was performed according to manufacturers protocol by using a pENTRY-A vector containing a parsley ubiquitine promoter, the HCP-4 gene in a pENTRY-B vector and a pENTRY-C vector containing the terminator of the cathepsin D inhibitor gene from *Solanum tuberosum*. As target a binary pDEST vector was used which is composed of: (1) a Spectinomycin/Streptomycin resistance cassette for bacterial selection, (2) a pVS1 origin for replication in Agrobacteria, (3) a pBR322 origin of replication for stable maintenance in *E. coli*, and (4) between the right and left border an AHAS selection under control of a pcUbi-promoter (FIG. 2). The recombination reaction was transformed into *E. coli* (DH5alpha), mini-prepped and screened by specific restriction digestions. A positive clone from each vector construct was sequenced and submitted soy transformation.

Example 3: Soy Transformation

The expression vector constructs (see example 2) were transformed into soy.
3.1 Sterilization and Germination of Soy Seeds Virtually any seed of any soy variety can be employed in the method of the invention. A variety of soybean cultivar (including Jack, Williams 82, Jake, Stoddard and Resnik) is appropriate for soy transformation. Soy seeds were sterilized in a chamber with a chlorine gas produced by adding 3.5 ml 12N HCl drop wise into 100 ml bleach (5.25% sodium hypochlorite) in a desiccator with a tightly fitting lid. After 24 to 48 hours in the chamber, seeds were removed and approximately 18 to 20 seeds were plated on solid GM medium with or without 5 µM 6-benzyl-aminopurine (BAP) in 100 mm Petri dishes. Seedlings without BAP are more elongated and roots develop, especially secondary and lateral root formation. BAP strengthens the seedling by forming a shorter and stockier seedling.

Seven-day-old seedlings grown in the light (>100 µEinstein/m$^2$s) at 25° C. were used for explant material for the three-explant types. At this time, the seed coat was split, and the epicotyl with the unifoliate leaves have grown to, at minimum, the length of the cotyledons. The epicotyl should be at least 0.5 cm to avoid the cotyledonary-node tissue (since soycultivars and seed lots may vary in the developmental time a description of the germination stage is more accurate than a specific germination time).

For inoculation of entire seedlings, see Method A (example 3.3.1 and 3.3.2) or leaf explants, see Method B (example 3.3.3).

For method C (see example 3.3.4), the hypocotyl and one and a half or part of both cotyledons were removed from each seedling. The seedlings were then placed on propagation media for 2 to 4 weeks. The seedlings produce several branched shoots to obtain explants from. The majority of the explants originated from the plantlet growing from the apical bud. These explants were preferably used as target tissue.
3.2—Growth and Preparation of *Agrobacterium* Culture

*Agrobacterium* cultures were prepared by streaking *Agrobacterium* (e.g., *A. tumefaciens* or *A. rhizogenes*) carrying the desired binary vector (e.g. H. Klee. R. Horsch and S. Rogers 1987 *Agrobacterium*-Mediated Plant Transformation and its further Applications to Plant Biology; Annual Review of Plant Physiology Vol. 38: 467-486) onto solid YEP growth medium (YEP media: 10 g yeast extract, 10 g Bacto Peptone, 5 g NaCl, Adjust pH to 7.0, and bring final volume to 1 liter with H2O, for YEP agar plates add 20 g Agar, autoclave) and incubating at 25° C. until colonies appeared (about 2 days). Depending on the selectable marker genes present on the Ti or Ri plasmid, the binary vector, and the bacterial chromosomes, different selection compounds were be used for *A. tumefaciens* and *A. rhizogenes* selection in the YEP solid and liquid media. Various *Agrobacterium* strains can be used for the transformation method.

After approximately two days, a single colony (with a sterile toothpick) was picked and 50 ml of liquid YEP was inoculated with antibiotics and shaken at 175 rpm (25° C.) until an $OD_{600}$ between 0.8-1.0 is reached (approximately 2 d). Working glycerol stocks (15%) for transformation are prepared and one-ml of *Agrobacterium* stock aliquoted into 1.5 ml Eppendorf tubes then stored at −80° C.

The day before explant inoculation, 200 ml of YEP were inoculated with 5 μl to 3 ml of working *Agrobacterium* stock in a 500 ml Erlenmeyer flask. The flask was shaken overnight at 25° C. until the $OD_{600}$ was between 0.8 and 1.0. Before preparing the soy explants, the Agrobacteria were pelleted by centrifugation for 10 min at 5,500×g at 20° C. The pellet was resuspended in liquid CCM to the desired density ($OD_{600}$ 0.5-0.8) and placed at room temperature at least 30 min before use.

3.3—Explant Preparation and Co-Cultivation (Inoculation)

3.3.1 Method A: Explant Preparation on the Day of Transformation.

Seedlings at this time had elongated epicotyls from at least 0.5 cm but generally between 0.5 and 2 cm. Elongated epicotyls up to 4 cm in length had been successfully employed. Explants were then prepared with: i) with or without some roots, ii) with a partial, one or both cotyledons, all preformed leaves were removed including apical meristem, and the node located at the first set of leaves was injured with several cuts using a sharp scalpel.

This cutting at the node not only induced *Agrobacterium* infection but also distributed the axillary meristem cells and damaged pre-formed shoots. After wounding and preparation, the explants were set aside in a Petri dish and subsequently co-cultivated with the liquid CCM/*Agrobacterium* mixture for 30 minutes. The explants were then removed from the liquid medium and plated on top of a sterile filter paper on 15×100 mm Petri plates with solid co-cultivation medium. The wounded target tissues were placed such that they are in direct contact with the medium.

3.3.2 Modified Method A: Epicotyl Explant Preparation

Soyepicotyl segments prepared from 4 to 8 d old seedlings were used as explants for regeneration and transformation. Seeds of soya cv. L00106CN, 93-41131 and Jack were germinated in ⅒ MS salts or a similar composition medium with or without cytokinins for 4 to 8 d. Epicotyl explants were prepared by removing the cotyledonary node and stem node from the stem section. The epicotyl was cut into 2 to 5 segments. Especially preferred are segments attached to the primary or higher node comprising axillary meristematic tissue.

The explants were used for *Agrobacterium* infection. *Agrobacterium* AGL1 harboring a plasmid with the gene of interest (GOI) and the AHAS, bar or dsdA selectable marker gene was cultured in LB medium with appropriate antibiotics overnight, harvested and resuspended in a inoculation medium with acetosyringone. Freshly prepared epicotyl segments were soaked in the *Agrobacterium* suspension for 30 to 60 min and then the explants were blotted dry on sterile filter papers. The inoculated explants were then cultured on a coculture medium with L-cysteine and TTD and other chemicals such as acetosyringone for increasing T-DNA delivery for 2 to 4 d. The infected epicotyl explants were then placed on a shoot induction medium with selection agents such as imazapyr (for AHAS gene), glufosinate (for bar gene), or D-serine (for dsdA gene). The regenerated shoots were subcultured on elongation medium with the selective agent.

For regeneration of transgenic plants the segments were then cultured on a medium with cytokinins such as BAP, TDZ and/or Kinetin for shoot induction. After 4 to 8 weeks, the cultured tissues were transferred to a medium with lower concentration of cytokinin for shoot elongation. Elongated shoots were transferred to a medium with auxin for rooting and plant development. Multiple shoots were regenerated.

Many stable transformed sectors showing strong cDNA expression were recovered. Soy-plants were regenerated from epicotyl explants. Efficient T-DNA delivery and stable transformed sectors were demonstrated.

3.3.3 Method B: Leaf Explants

For the preparation of the leaf explant the cotyledon was removed from the hypocotyl. The cotyledons were separated from one another and the epicotyl is removed. The primary leaves, which consist of the lamina, the petiole, and the stipules, were removed from the epicotyl by carefully cutting at the base of the stipules such that the axillary meristems were included on the explant. To wound the explant as well as to stimulate de novo shoot formation, any preformed shoots were removed and the area between the stipules was cut with a sharp scalpel 3 to 5 times.

The explants are either completely immersed or the wounded petiole end dipped into the *Agrobacterium* suspension immediately after explant preparation. After inoculation, the explants are blotted onto sterile filter paper to remove excess *Agrobacterium* culture and place explants with the wounded side in contact with a round 7 cm Whatman paper overlaying the solid CCM medium (see above). This filter paper prevents *A. tumefaciens* overgrowth on the soy-explants. Wrap five plates with Parafilm™ "M" (American National Can, Chicago, Ill., USA) and incubate for three to five days in the dark or light at 25° C.

3.3.4 Method C: Propagated Axillary Meristem

For the preparation of the propagated axillary meristem explant propagated 3-4 week-old plantlets were used. Axillary meristem explants can be pre-pared from the first to the fourth node. An average of three to four explants could be obtained from each seedling. The explants were prepared from plantlets by cutting 0.5 to 1.0 cm below the axillary node on the internode and removing the petiole and leaf from the explant. The tip where the axillary meristems lie was cut with a scalpel to induce de novo shoot growth and allow access of target cells to the *Agrobacterium*. Therefore, a 0.5 cm explant included the stem and a bud.

Once cut, the explants were immediately placed in the *Agrobacterium* suspension for 20 to 30 minutes. After inoculation, the explants were blotted onto sterile filter paper to remove excess *Agrobacterium* culture then placed almost completely immersed in solid CCM or on top of a round 7 cm filter paper overlaying the solid CCM, depending on the *Agrobacterium* strain. This filter paper prevents *Agrobacterium* overgrowth on the soy-explants. Plates were wrapped with Parafilm™ "M" (American National Can, Chicago, Ill., USA) and incubated for two to three days in the dark at 25° C.

3.4—Shoot Induction

After 3 to 5 days co-cultivation in the dark at 25° C., the explants were rinsed in liquid SIM medium (to remove excess *Agrobacterium*) (SIM, see Olhoft et al 2007 A novel

*Agrobacterium rhizogenes*-mediated transformation method of soy using primary-node explants from seedlings In Vitro Cell. Dev. Biol.—Plant (2007) 43:536-549; to remove excess *Agrobacterium*) or Modwash medium (1×B5 major salts, 1×B5 minor salts, 1× MSIII iron, 3% Sucrose, 1×B5 vitamins, 30 mM MES, 350 mg/L Timentin™ pH 5.6, WO 2005/121345) and blotted dry on sterile filter paper (to prevent damage especially on the lamina) before placing on the solid SIM medium. The approximately 5 explants (Method A) or 10 to 20 (Methods B and C) explants were placed such that the target tissue was in direct contact with the medium. During the first 2 weeks, the explants could be cultured with or without selective medium. Preferably, explants were transferred onto SIM without selection for one week.

For leaf explants (Method B), the explant should be placed into the medium such that it is perpendicular to the surface of the medium with the petiole imbedded into the medium and the lamina out of the medium.

For propagated axillary meristem (Method C), the explant was placed into the medium such that it was parallel to the surface of the medium (basipetal) with the explant partially embedded into the medium.

Wrap plates with Scotch 394 venting tape (3M, St. Paul, Minn., USA) were placed in a growth chamber for two weeks with a temperature averaging 25° C. under 18 h light/6 h dark cycle at 70-100 pE/m²s. The explants remained on the SIM medium with or without selection until de novo shoot growth occurred at the target area (e.g., axillary meristems at the first node above the epicotyl). Transfers to fresh medium can occur during this time. Explants were transferred from the SIM with or without selection to SIM with selection after about one week. At this time, there was considerable de novo shoot development at the base of the petiole of the leaf explants in a variety of SIM (Method B), at the primary node for seedling explants (Method A), and at the axillary nodes of propagated explants (Method C).

Preferably, all shoots formed before transformation were removed up to 2 weeks after co-cultivation to stimulate new growth from the meristems. This helped to reduce chimerism in the primary transformant and increase amplification of transgenic meristematic cells. During this time the explant may or may not be cut into smaller pieces (i.e. detaching the node from the explant by cutting the epicotyl). 3.5—Shoot Elongation After 2 to 4 weeks (or until a mass of shoots was formed) on SIM medium (preferably with selection), the explants were transferred to SEM medium (shoot elongation medium, see Olhoft et al 2007 A novel *Agrobacterium rhizogenes*-mediated transformation method of soy using primary-node explants from seedlings. In Vitro Cell. Dev. Biol. Plant (2007) 43:536-549) that stimulates shoot elongation of the shoot primordia. This medium may or may not contain a selection compound.

After every 2 to 3 weeks, the explants were transferred to fresh SEM medium (preferably containing selection) after carefully removing dead tissue. The explants should hold together and not fragment into pieces and retain somewhat healthy. The explants were continued to be transferred until the explant dies or shoots elongate. Elongated shoots >3 cm were removed and placed into RM medium for about 1 week (Method A and B), or about 2 to 4 weeks depending on the cultivar (Method C) at which time roots began to form. In the case of explants with roots, they were transferred directly into soil. Rooted shoots were transferred to soil and hardened in a growth chamber for 2 to 3 weeks before transferring to the greenhouse. Regenerated plants obtained using this method were fertile and produced on average 500 seeds per plant.

After 5 days of co-cultivation with *Agrobacterium tumefaciens* transient expression of the gene of interest (GOI) was widespread on the seedling axillary meristem explants especially in the regions wounding during explant preparation (Method A). Explants were placed into shoot induction medium without selection to see how the primary-node responds to shoot induction and regeneration. Thus far, greater than 70% of the explants were formed new shoots at this region. Expression of the GOI was stable after 14 days on SIM, implying integration of the T-DNA into the soy genome. In addition, preliminary experiments resulted in the formation of cDNA expressing shoots forming after 3 weeks on SIM.

For Method C, the average regeneration time of a soy plantlet using the propagated axillary meristem protocol was 14 weeks from explant inoculation. Therefore, this method has a quick regeneration time that leads to fertile, healthy soy plants.

Example 4: Pathogen Assay 4.1. Growth of Plants

10 $T_1$ plants per event were potted and grown for 3-4 weeks in the phytochamber (16 h-day-und 8 h-night-Rhythm at a temperature of 16 and 22° C. and a humidity of 75%) till the first 2 trifoliate leaves were fully expanded.

4.2 Inoculation

The plants were inoculated with *P. pachyrhizi*.

In order to obtain appropriate spore material for the inoculation, soybean leaves which had been infected with rust 15-20 days ago, were taken 2-3 days before the inoculation and transferred to agar plates (1% agar in H2O). The leaves were placed with their upper side onto the agar, which allowed the fungus to grow through the tissue and to produce very young spores. For the inoculation solution, the spores were knocked off the leaves and were added to a Tween-H2O solution. The counting of spores was performed under a light microscope by means of a Thoma counting chamber. For the inoculation of the plants, the spore suspension was added into a compressed-air operated spray flask and applied uniformly onto the plants or the leaves until the leaf surface is well moisturized. For macroscopic assays we used a spore density of $1-5 \times 10^5$ spores/ml. For the microscopy, a density of $>5 \times 10^5$ spores/ml is used. The inoculated plants were placed for 24 hours in a greenhouse chamber with an average of 22° C. and >90% of air humidity. The following cultivation was performed in a chamber with an average of 25° C. and 70% of air humidity.

Example 5: Microscopical Screening

For the evaluation of the pathogen development, the inoculated leaves of plants were stained with aniline blue 48 hours after infection.

The aniline blue staining serves for the detection of fluorescent substances. During the defense reactions in host interactions and non-host interactions, substances such as phenols, callose or lignin accumulated or were produced and were incorporated at the cell wall either locally in papillae or in the whole cell (hypersensitive reaction, HR). Complexes were formed in association with aniline blue, which lead e.g. in the case of callose to yellow fluorescence. The leaf material was transferred to falcon tubes or dishes containing destaining solution II (ethanol/acetic acid 6/1)

and was incubated in a water bath at 90° C. for 10-15 minutes. The destaining solution II was removed immediately thereafter, and the leaves were washed 2× with water. For the staining, the leaves were incubated for 1.5-2 hours in staining solution II (0.05% aniline blue=methyl blue, 0.067 M di-potassium hydrogen phosphate) and analyzed by microscopy immediately thereafter.

The different interaction types were evaluated (counted) by microscopy. An Olympus UV microscope BX61 (incident light) and a UV Longpath filter (excitation: 375/15, Beam splitter: 405 LP) are used. After aniline blue staining, the spores appeared blue under UV light. The papillae could be recognized beneath the fungal appressorium by a green/yellow staining. The hypersensitive reaction (HR) was characterized by a whole cell fluorescence.

Example 6: Evaluating the Susceptibility to Soybean Rust

The progression of the soybean rust disease was scored by the estimation of the diseased area (area which was covered by sporulating uredinia) on the backside (abaxial side) of the leaf. Additionally the yellowing of the leaf was taken into account (for scheme see FIG. 1).

At all 50 $T_1$ soybean plants (5 independent events, 10 plants each) expressing HCP4 protein were inoculated with spores of *Phakopsora pachyrhizi* The macroscopic disease symptoms of soy against *P. pachyrhizi* of the inoculated soybean plants were scored 14 days after inoculation.

The average of the percentage of the leaf area showing fungal colonies or strong yellowing/browning on all leaves was considered as diseased leaf area. At all 50 soybean $T_1$ plants expressing HCP4 (expression checked by RT-PCR) were evaluated in parallel to non-transgenic control plants. Non-transgenic soy plants grown in parallel to the transgenic plants were used as control. The average of the diseased leaf area is shown in FIG. 14 for plants exogenously expressing HCP4 compared with wildtype plants. Increase in expression of HCP4 reduces the diseased leaf area in comparison to non-transgenic control plants by 34.1% in average over all events generated. This data clearly indicates that the in-planta expression of the HCP4 expression vector construct lead to a lower disease scoring of transgenic plants compared to non-transgenic controls. So, the expression of HCP4 (as shown in SEQ ID NO: 1) in soybean significantly (*: p<0.01) increases the resistance of soy against soybean rust.

The invention claimed is:

1. A method for increasing fungal resistance against *Phakopsora* in a plant, a plant part, or a plant cell, said method comprising transforming a plant, plant part, or plant cell with an exogenous nucleic acid encoding an HCP4 protein comprising an amino acid sequence having at least 82% identity to SEQ ID NO: 5, wherein the HCP4 protein confers increased resistance against *Phakopsora* thereto in comparison to a wild type plant, wild type plant part or wild type plant cell.

2. The method of claim 1, said method comprising:
   (a) stably transforming a plant cell with an expression cassette comprising
      an exogenous nucleic acid encoding an HCP4 protein comprising an amino acid sequence having at least 82% identity with SEQ ID NO: 5
      in functional linkage with a promoter; and
   (b) regenerating the plant from the plant cell.

3. A recombinant vector construct comprising in operable linkage:
   (a) a nucleic acid encoding an HCP4 protein comprising an amino acid sequence having at least 82% identity to SEQ ID NO: 5;
   (b) a heterologous promoter, and
   (c) a transcription termination sequence.

4. The method of claim 2, wherein the promoter is a constitutive promoter, pathogen-inducible promoter, a mesophyll-specific promoter or an epidermis specific-promoter.

5. A transgenic plant, transgenic plant part, or transgenic plant cell, wherein said plant, plant part or plant cell comprises the recombinant vector construct of claim 3.

6. A method for the production of a transgenic plant, transgenic plant part, or transgenic plant cell having increased fungal resistance, said method comprising:
   (a) introducing the recombinant vector construct of claim 3 into a plant, a plant part, or a plant cell: and
   (b) generating a transgenic plant, transgenic plant part, or transgenic plant cell from the plant, plant part or plant cell, wherein the HCP4 protein confers increased resistance against *Phakopsora* thereto in comparison to a wild type plant, wild type plant part or wild type plant cell.

7. The method of claim 6, further comprising the step of harvesting the seeds of the transgenic plant and planting the seeds and growing the seeds to plants, wherein the grown plants comprise the recombinant vector construct.

8. A harvestable part of the transgenic plant of claim 5, wherein the harvestable part comprises the recombinant vector construct or wherein the harvestable part comprises the exogenous HCP4 protein encoded by the recombinant vector construct.

9. A product derived from the transgenic plant of claim 5, wherein the product comprises the recombinant vector construct or wherein the product comprises the exogenous HCP4 protein encoded by the recombinant vector construct.

10. A method for the production of a product, said method comprising:
    a) growing the transgenic plant of claim 5; and
    b) producing said product from the plant and/or a part thereof;
    wherein the product obtained by said method comprises the recombinant vector construct or wherein the product obtained by said method comprises the exogenous HCP4 protein encoded by the recombinant vector construct.

11. The method of claim 10, wherein the product is produced from the seeds of the plant.

12. The method of claim 10, wherein the product is meal or oil.

13. The method of claim 1, wherein the plant is selected from the group consisting of beans, soya, pea, clover, kudzu, lucerne, lentils, lupins, vetches, groundnut, rice, wheat, barley, *arabidopsis*, lentil, banana, canola, cotton, potatoe, corn, sugar cane, alfalfa, and sugar beet.

14. A method for breeding a fungal resistant plant, said method comprising:
    (a) crossing the transgenic plant of claim 5 with a second plant;
    (b) obtaining seed from the cross of step (a);
    (c) planting said seeds and growing the seeds to plants; and
    (d) selecting from the plants produced in step (c) those plants expressing the HCP4 protein.

15. The recombinant vector construct of claim 3, wherein the promoter is a constitutive promoter, pathogen-inducible promoter, a mesophyll-specific promoter or an epidermis specific-promoter.

16. The harvestable part of claim 8, comprising a transgenic seed of the transgenic plant.

17. The product of claim 9, comprising soybean meal or soy oil.

* * * * *

SEQUENCE LISTING

```
<160> NUMBER OF SEQ ID NOS: 42

<210> SEQ ID NO 1
<211> LENGTH: 4024
<212> TYPE: DNA
<213> ORGANISM: Arabidopsis thaliana
<220> FEATURE:
<221> NAME/KEY: source
<222> LOCATION: 1..4024
<223> OTHER INFORMATION: /organism="Arabidopsis thaliana"
      /mol_type="unassigned DNA"

<400> SEQUENCE: 1
atggcagctt ctttttgcgg cagccggaga tacgatgttt tcccgagctt cagtaaggta     60
gatgtccgca ggtcattcct cgcgcatctt ctcaaggagc tcgaccgcag attaatcaat    120
acgttcacag atcatggtat ggagagaaac ctcccaatcg acgctgaact tttatcggcg    180
atagcagaat cgaggatctc aatagtcatc ttctctaaaa actatgcttc ttccacgtgg    240
tgcttagatg aattggttga gatccacacg tgttataagg aattggctca aatagtggtt    300
ccggttttct ttaacgtaca tccttcgcaa gttaaaaaac agaccggaga atttggtaag    360
gtttttggaa agacatgcaa aggtaaacca gagaatcgga aactaagatg gatgcaagct    420
ctagcagcgg tagcaaatat tgctggatat gatcttcaga actggtattt tcttttccat    480
tccaacccta atatatatat gtgcctgtgt tcaattttgg ggtgcctctt taatgacaaa    540
attgactatt gttattaggc ctgatgaagc tgtcatgatt gagatggtag ctgacgatgt    600
ttcgaaaaaa ctttttaaat catcgaatga tttcagtgat atcgtcggga ttgaagctca    660
tttagaggca atgagttcaa tattgcgctt gaaatctgag aaagctagaa tggtcgggat    720
ttcggggcct tcagggattg gtaagactac catcgcaaaa gctcttttca gtaaactctc    780
tccccaattc caccttcgtg ctttcgttac ttataaaaga accaaccagg acgactatga    840
catgaagttg tgttggatag aaaaatttct gtcagaaatt cttggtcaaa aggacttgaa    900
ggttttggat ttaggtgcgg tggaacaaag tctaatgcac aagaaagttc ttatcattct    960
tgacgatgta gatgatcttg agctattaaa gaccttggtg ggacaaactg gatggttcgg   1020
```

```
gtttggaagc agaattgttg tgatcactca ggataggcag cttctcaagg ctcatgatat    1080
taacctcata tatgaggtgg ccttcccatc tgcccatctt gctcttgaga ttttctgcca    1140
atctgctttt gggaaaatat atccaccatc tgattttaga gaactctctg ttgaatttgc    1200
atatcttgcc ggcaatcttc ctttggatct tagggtcttg ggtttggcca tgaaaggaaa    1260
gcacagggag gagtggatag agatgctgcc taggctccga aatgatttgg acgggaaatt    1320
taagaaaaca ttgagaaatt acctgcctgt gatacgaaag cgcgtttcca atgaagaagg    1380
gggccgtgag aaattgaaaa agggaaataa aaagttggat ttggatgagg agtttcctgg    1440
tggagaaatt tacagtgatg agataccttc gccaacatct aactggaaag atacagatga    1500
ctttgattca ggggacatca ttccaatcat tgcagacaaa tctactacta taattcccaa    1560
caggaggcac tcgaacgatg actggtgttc tttctgtgag ttcctcagaa accgtatacc    1620
cccgttgaat ccctttaaat gtagtgccaa tgatgtcatt gattttcttc gcacacggca    1680
ggttttaggc agcactgagg ctctcgttga ccgcctcatt ttcagtagtg aggcatttgg    1740
cataaaacct gaggaaaacc cttttcgcag ccaagctgta acatcgtact gaaggcggc    1800
cagggatatg acacgagaaa aagaatgcat acttgtgttt tcgtgccacg acaaccttga    1860
tgtagatgaa acatctttca ttgaagccat ctcaaaagaa ttgcacaagc aggggttcat    1920
cccttttgaca tataatcttt tgggcagaga gaacctcgat gaggagatgt tatacgatc     1980
tagagtcggt atcatgatac tttcaagtag ttatgtttct tctagacagt ccctggatca    2040
cctggttgca gttatggagc attggaaaac aacagacctt gtaattattc ctatatattt    2100
taaagtaaga ctttcagaca tttgtgggtt gaaaggcagg tttgaagcag cgtttctgca    2160
gcttcatatg tctctccagg aagacagagt tcagaaatgg aaggcggcta tgtctgaaat    2220
agtgtccatc ggtggacatg aatggaccaa gggaagtcag tttattcttg ccgaggaagt    2280
tgtaagaaat gcatccttaa ggctatatct gaaaagtagc aagaatctgc ttggaatctt    2340
agcgttgtta aatcactccc agtctacaga cgtggaaatt atgggaatct ggggtatagc    2400
aggaataggt aagacatcga ttgcaagaga aatatttgaa ttacatgctc acattatga    2460
tttctgttac ttcctgcaag actttcatct aatgtgtcag atgaaaaggc cgaggcaatt    2520
gcgtgaagat tttatctcaa aattgtttgg ggaagaaaaa ggtctaggtg ctagtgatgt    2580
aaagccaagt ttcatgaggg actggttcca taaaaaacg attcttctcg ttcttgatga    2640
cgtgagtaat gccagagatg cagaagctgt aatcggaggg tttggctggt tttctcatgg    2700
acacagaatc atcttaacct ctaggagtaa acaagttctt gtacagtgta aggttaaaaa    2760
gccatacgag atccaaaaat taagcgattt tgaatcgttt cgtctctgca aacaatattt    2820
ggatggcgaa aatccggtca tctctgagct tatcagctgc agtagtggta ttccattggc    2880
tctcaaactt ttagtttcct ctgtatcaaa gcagtatata acgaatatga aagaccatct    2940
ccaaagcttg aggaaagatc ctcctactca gattcaagaa gcattccgga gaagtttga    3000
tggactagat gaaaacgaga aaaacatatt tttggatctt gcatgttttt tcaggggca    3060
gagcaaagat tatgcggtgc tattacttga tgcttgtggt ttttttacat atatgggaat    3120
ctgtgagctc attgacgagt cactcattag ccttgtagac aacaagatag agatgcctat    3180
tccttttcaa gacatgggcc gaattattgt tcatgaagaa gatgaggatc catgtgaacg    3240
tagcagattg tgggactcga aggacatcgt tgatgttttg acaaacaatt caggaacaga    3300
agcaattgag ggcatcttcc tggatgcgtc tgacttgacc tgcgagctta gtcctactgt    3360
```

```
gtttggtaag atgtataatc ttagattgct gaagttctat tgttcaacct ctgggaacca      3420
gtgcaagctt actctacctc acggcctaga cactttgcct gatgagctaa gtctacttca      3480
ctgggagaat taccctctgg tttacttgcc tcagaaattt aatcctgtga accttgtaga      3540
gttaaacatg ccttatagca acatggagaa gttgtgggaa ggaaagaaaa atctcgagaa      3600
gctaaagaac atcaaactga gtcactccag agaattaact gatatcctga tgttatcaga      3660
agccctgaac ctggaacaca ttgatctcga agggtgtacg agtctgattg atgttagcat      3720
gtctattcct tgttgtggga agcttgtttc cttgaatatg aaagactgtt ctcgtttgcg      3780
aagtctgcct tctatggttg atttaacaac tctcaagctt cttaatttgt ctggctgctc      3840
agaatttgag gatattcagg attttgcacc aaacctggaa gagatatatc tagctgggac      3900
atccattaga gagcttccgt tgtcaatcag gaatctcact gaacttgtta cgctagatct      3960
ggagaactgc gaaagacttc aggaaatgcc gagtcttccg gtggaaataa tcaggagaac      4020
ctga                                                                  4024
```

<210> SEQ ID NO 2
<211> LENGTH: 185
<212> TYPE: PRT
<213> ORGANISM: Arabidopsis thaliana

<400> SEQUENCE: 2

```
Met Ala Ala Ser Phe Cys Gly Ser Arg Arg Tyr Asp Val Phe Pro Ser
1               5                   10                  15

Phe Ser Lys Val Asp Val Arg Arg Ser Phe Leu Ala His Leu Leu Lys
            20                  25                  30

Glu Leu Asp Arg Arg Leu Ile Asn Thr Phe Thr Asp His Gly Met Glu
        35                  40                  45

Arg Asn Leu Pro Ile Asp Ala Glu Leu Leu Ser Ala Ile Ala Glu Ser
    50                  55                  60

Arg Ile Ser Ile Val Ile Phe Ser Lys Asn Tyr Ala Ser Ser Thr Trp
65                  70                  75                  80

Cys Leu Asp Glu Leu Val Glu Ile His Thr Cys Tyr Lys Glu Leu Ala
                85                  90                  95

Gln Ile Val Val Pro Val Phe Phe Asn Val His Pro Ser Gln Val Lys
            100                 105                 110

Lys Gln Thr Gly Glu Phe Gly Lys Val Phe Gly Lys Thr Cys Lys Gly
        115                 120                 125

Lys Pro Glu Asn Arg Lys Leu Arg Trp Met Gln Ala Leu Ala Ala Val
    130                 135                 140

Ala Asn Ile Ala Gly Tyr Asp Leu Gln Asn Trp Tyr Phe Leu Phe His
145                 150                 155                 160

Ser Asn Pro Asn Ile Tyr Met Cys Leu Cys Ser Ile Leu Gly Cys Leu
                165                 170                 175

Phe Asn Asp Lys Ile Asp Tyr Cys Tyr
            180                 185
```

<210> SEQ ID NO 3
<211> LENGTH: 1191
<212> TYPE: PRT
<213> ORGANISM: Arabidopsis thaliana

<400> SEQUENCE: 3

```
Met Ile Phe Arg Thr Gly Ile Phe Phe Ser Ile Pro Thr Leu Ile Tyr
1               5                   10                  15
```

```
Ile Cys Ala Cys Val Gln Phe Trp Gly Ala Ser Leu Met Thr Lys Leu
                20                  25                  30

Thr Ile Val Ile Arg Pro Asp Glu Ala Val Met Ile Glu Met Val Ala
            35                  40                  45

Asp Asp Val Ser Lys Lys Leu Phe Lys Ser Ser Asn Asp Phe Ser Asp
    50                  55                  60

Ile Val Gly Ile Glu Ala His Leu Glu Ala Met Ser Ser Ile Leu Arg
65                  70                  75                  80

Leu Lys Ser Glu Lys Ala Arg Met Val Gly Ile Ser Gly Pro Ser Gly
                85                  90                  95

Ile Gly Lys Thr Thr Ile Ala Lys Ala Leu Phe Ser Lys Leu Ser Pro
                100                 105                 110

Gln Phe His Leu Arg Ala Phe Val Thr Tyr Lys Arg Thr Asn Gln Asp
            115                 120                 125

Asp Tyr Asp Met Lys Leu Cys Trp Ile Glu Lys Phe Leu Ser Glu Ile
    130                 135                 140

Leu Gly Gln Lys Asp Leu Lys Val Leu Asp Leu Gly Ala Val Glu Gln
145                 150                 155                 160

Ser Leu Met His Lys Lys Val Leu Ile Ile Leu Asp Asp Val Asp Asp
                165                 170                 175

Leu Glu Leu Leu Lys Thr Leu Val Gly Gln Thr Gly Trp Phe Gly Phe
                180                 185                 190

Gly Ser Arg Ile Val Val Ile Thr Gln Asp Arg Gln Leu Leu Lys Ala
            195                 200                 205

His Asp Ile Asn Leu Ile Tyr Glu Val Ala Phe Pro Ser Ala His Leu
210                 215                 220

Ala Leu Glu Ile Phe Cys Gln Ser Ala Phe Gly Lys Ile Tyr Pro Pro
225                 230                 235                 240

Ser Asp Phe Arg Glu Leu Ser Val Glu Phe Ala Tyr Leu Ala Gly Asn
                245                 250                 255

Leu Pro Leu Asp Leu Arg Val Leu Gly Leu Ala Met Lys Gly Lys His
                260                 265                 270

Arg Glu Glu Trp Ile Glu Met Leu Pro Arg Leu Arg Asn Asp Leu Asp
            275                 280                 285

Gly Lys Phe Lys Lys Thr Leu Arg Asn Tyr Leu Pro Val Ile Arg Lys
    290                 295                 300

Arg Val Ser Asn Glu Glu Gly Gly Arg Glu Lys Leu Lys Gly Asn
305                 310                 315                 320

Lys Lys Leu Asp Leu Asp Glu Glu Phe Pro Gly Gly Glu Ile Tyr Ser
                325                 330                 335

Asp Glu Ile Pro Ser Pro Thr Ser Asn Trp Lys Asp Thr Asp Asp Phe
            340                 345                 350

Asp Ser Gly Asp Ile Ile Pro Ile Ala Asp Lys Ser Thr Thr Ile
    355                 360                 365

Ile Pro Asn Arg Arg His Ser Asn Asp Asp Trp Cys Ser Phe Cys Glu
370                 375                 380

Phe Leu Arg Asn Arg Ile Pro Pro Leu Asn Pro Phe Lys Cys Ser Ala
385                 390                 395                 400

Asn Asp Val Ile Asp Phe Leu Arg Thr Arg Gln Val Leu Gly Ser Thr
                405                 410                 415

Glu Ala Leu Val Asp Arg Leu Ile Phe Ser Ser Glu Ala Phe Gly Ile
                420                 425                 430

Lys Pro Glu Glu Asn Pro Phe Arg Ser Gln Ala Val Thr Ser Tyr Leu
```

```
                435                 440                 445
Lys Ala Ala Arg Asp Met Thr Arg Glu Lys Glu Cys Ile Leu Val Phe
450                 455                 460

Ser Cys His Asp Asn Leu Asp Val Asp Glu Thr Ser Phe Ile Glu Ala
465                 470                 475                 480

Ile Ser Lys Glu Leu His Lys Gln Gly Phe Ile Pro Leu Thr Tyr Asn
                485                 490                 495

Leu Leu Gly Arg Glu Asn Leu Asp Glu Glu Met Leu Tyr Gly Ser Arg
                500                 505                 510

Val Gly Ile Met Ile Leu Ser Ser Tyr Val Ser Ser Arg Gln Ser
                515                 520                 525

Leu Asp His Leu Val Ala Val Met Glu His Trp Lys Thr Thr Asp Leu
530                 535                 540

Val Ile Ile Pro Ile Tyr Phe Lys Val Arg Leu Ser Asp Ile Cys Gly
545                 550                 555                 560

Leu Lys Gly Arg Phe Glu Ala Ala Phe Leu Gln Leu His Met Ser Leu
                565                 570                 575

Gln Glu Asp Arg Val Gln Lys Trp Lys Ala Ala Met Ser Glu Ile Val
                580                 585                 590

Ser Ile Gly Gly His Glu Trp Thr Lys Gly Ser Gln Phe Ile Leu Ala
                595                 600                 605

Glu Glu Val Val Arg Asn Ala Ser Leu Arg Leu Tyr Leu Lys Ser Ser
                610                 615                 620

Lys Asn Leu Leu Gly Ile Leu Ala Leu Leu Asn His Ser Gln Ser Thr
625                 630                 635                 640

Asp Val Glu Ile Met Gly Ile Trp Gly Ile Ala Gly Ile Gly Lys Thr
                645                 650                 655

Ser Ile Ala Arg Glu Ile Phe Glu Leu His Ala Pro His Tyr Asp Phe
                660                 665                 670

Cys Tyr Phe Leu Gln Asp Phe His Leu Met Cys Gln Met Lys Arg Pro
                675                 680                 685

Arg Gln Leu Arg Glu Asp Phe Ile Ser Lys Leu Phe Gly Glu Glu Lys
                690                 695                 700

Gly Leu Gly Ala Ser Asp Val Lys Pro Ser Phe Met Arg Asp Trp Phe
705                 710                 715                 720

His Lys Lys Thr Ile Leu Leu Val Leu Asp Asp Val Ser Asn Ala Arg
                725                 730                 735

Asp Ala Glu Ala Val Ile Gly Gly Phe Gly Trp Phe Ser His Gly His
                740                 745                 750

Arg Ile Ile Leu Thr Ser Arg Ser Lys Gln Val Leu Gln Cys Lys
                755                 760                 765

Val Lys Lys Pro Tyr Glu Ile Gln Lys Leu Ser Asp Phe Glu Ser Phe
770                 775                 780

Arg Leu Cys Lys Gln Tyr Leu Asp Gly Glu Asn Pro Val Ile Ser Glu
785                 790                 795                 800

Leu Ile Ser Cys Ser Ser Gly Ile Pro Leu Ala Leu Lys Leu Leu Val
                805                 810                 815

Ser Ser Val Ser Lys Gln Tyr Ile Thr Asn Met Lys Asp His Leu Gln
                820                 825                 830

Ser Leu Arg Lys Asp Pro Pro Thr Gln Ile Gln Glu Ala Phe Arg Arg
                835                 840                 845

Ser Phe Asp Gly Leu Asp Glu Asn Glu Lys Asn Ile Phe Leu Asp Leu
850                 855                 860
```

Ala Cys Phe Phe Arg Gly Gln Ser Lys Asp Tyr Ala Val Leu Leu Leu
865                 870                 875                 880

Asp Ala Cys Gly Phe Phe Thr Tyr Met Gly Ile Cys Glu Leu Ile Asp
                885                 890                 895

Glu Ser Leu Ile Ser Leu Val Asp Asn Lys Ile Glu Met Pro Ile Pro
            900                 905                 910

Phe Gln Asp Met Gly Arg Ile Ile Val His Glu Glu Asp Glu Asp Pro
        915                 920                 925

Cys Glu Arg Ser Arg Leu Trp Asp Ser Lys Asp Ile Val Asp Val Leu
    930                 935                 940

Thr Asn Asn Ser Gly Thr Glu Ala Ile Glu Gly Ile Phe Leu Asp Ala
945                 950                 955                 960

Ser Asp Leu Thr Cys Glu Leu Ser Pro Thr Val Phe Gly Lys Met Tyr
                965                 970                 975

Asn Leu Arg Leu Leu Lys Phe Tyr Cys Ser Thr Ser Gly Asn Gln Cys
            980                 985                 990

Lys Leu Thr Leu Pro His Gly Leu Asp Thr Leu Pro Asp Glu Leu Ser
        995                 1000                1005

Leu Leu His Trp Glu Asn Tyr Pro Leu Val Tyr Leu Pro Gln Lys Phe
    1010                1015                1020

Asn Pro Val Asn Leu Val Glu Leu Asn Met Pro Tyr Ser Asn Met Glu
1025                1030                1035                1040

Lys Leu Trp Glu Gly Lys Lys Asn Leu Glu Lys Leu Lys Asn Ile Lys
                1045                1050                1055

Leu Ser His Ser Arg Glu Leu Thr Asp Ile Leu Met Leu Ser Glu Ala
            1060                1065                1070

Leu Asn Leu Glu His Ile Asp Leu Glu Gly Cys Thr Ser Leu Ile Asp
        1075                1080                1085

Val Ser Met Ser Ile Pro Cys Cys Gly Lys Leu Val Ser Leu Asn Met
    1090                1095                1100

Lys Asp Cys Ser Arg Leu Arg Ser Leu Pro Ser Met Val Asp Leu Thr
1105                1110                1115                1120

Thr Leu Lys Leu Leu Asn Leu Ser Gly Cys Ser Glu Phe Glu Asp Ile
                1125                1130                1135

Gln Asp Phe Ala Pro Asn Leu Glu Glu Ile Tyr Leu Ala Gly Thr Ser
            1140                1145                1150

Ile Arg Glu Leu Pro Leu Ser Ile Arg Asn Leu Thr Glu Leu Val Thr
        1155                1160                1165

Leu Asp Leu Glu Asn Cys Glu Arg Leu Gln Glu Met Pro Ser Leu Pro
    1170                1175                1180

Val Glu Ile Ile Arg Arg Thr
1185                1190

<210> SEQ ID NO 4
<211> LENGTH: 3930
<212> TYPE: DNA
<213> ORGANISM: Arabidopsis thaliana
<220> FEATURE:
<221> NAME/KEY: source
<222> LOCATION: 1..3930
<223> OTHER INFORMATION: /organism="Arabidopsis thaliana"
      /mol_type="unassigned DNA"

<400> SEQUENCE: 4
atggcagctt cttttttgcgg cagccggaga tacgatgttt tcccgagctt cagtaaggta      60

| | |
|---|---|
| gatgtccgca ggtcattcct cgcgcatctt ctcaaggagc tcgaccgcag attaatcaat | 120 |
| acgttcacag atcatggtat ggagagaaac ctcccaatcg acgctgaact tttatcggcg | 180 |
| atagcagaat cgaggatctc aatagtcatc ttctctaaaa actatgcttc ttccacgtgg | 240 |
| tgcttagatt aattggttga gatccacacg tgttataagg aattggctca aatagtggtt | 300 |
| ccggttttct ttaacgtaca tccttcgcaa gttaaaaaac agaccggaga atttggtaag | 360 |
| gttttttggaa agacatgcaa aggtaaacca gagaatcgga aactaagatg gatgcaagct | 420 |
| ctagcagcgg tagcaaatat tgctggatat gatcttcaga actggcctga tgaagctgtc | 480 |
| atgattgaga tggtagctga cgatgtttcg aaaaaacttt ttaaatcatc gaatgatttc | 540 |
| agtgatatcg tcgggattga agctcattta gaggcaatga gttcaatatt gcgcttgaaa | 600 |
| tctgagaaag ctagaatggt cgggatttcg gggccttcag ggattggtaa gactaccatc | 660 |
| gcaaaagctc ttttcagtaa actctctccc caattccacc ttcgtgcttt cgttacttat | 720 |
| aaaagaacca accaggacga ctatgacatg aagttgtgtt ggatagaaaa atttctgtca | 780 |
| gaaattcttg gtcaaaagga cttgaaggtt ttggatttag gtgcggtgga acaaagtcta | 840 |
| atgcacaaga aagttcttat cattcttgac gatgtagatg atcttgagct attaaagacc | 900 |
| ttggtgggac aaactggatg gttcgggttt ggaagcagaa ttgttgtgat cactcaggat | 960 |
| aggcagcttc tcaaggctca tgatattaac ctcatatatg aggtggcctt cccatctgcc | 1020 |
| catcttgctc ttgagatttt ctgccaatct gcttttggga aaatatatcc accatctgat | 1080 |
| tttagagaac tctctgttga atttgcatat cttgccggca atcttccttt ggatcttagg | 1140 |
| gtcttgggtt tggccatgaa aggaaagcac agggaggagt ggatagagat gctgcctagg | 1200 |
| ctccgaaatg atttggacgg gaaatttaag aaaacattga gaaattaccct gcctgtgata | 1260 |
| cggaagcgcg tttccaatga agaagggggc cgtgagaaat tgaaaaaggg aaataaaaag | 1320 |
| ttggatttgg atgaggagtt tcctggtgga gaaatttaca gtgatgagat accttcgcca | 1380 |
| acatctaact ggaaagatac agatgacttt gattcagggg acatcattcc aatcattgca | 1440 |
| gacaaatcta ctactataat tcccaacagg aggcactcga acgatgactg gtgttctttc | 1500 |
| tgtgagttcc tcagaaaccg tatacccccg ttgaatccct ttaaatgtag tgccaatgat | 1560 |
| gtcattgatt ttcttcgcac acggcaggtt ttaggcagca ctgaggctct cgttgaccgc | 1620 |
| ctcatttttca gtagtgaggc atttggcata aaacctgagg aaaaccccttt tcgcagccaa | 1680 |
| gctgtaacat cgtacttgaa ggcggccagg gatatgacac gagaaaaaga atgcatactt | 1740 |
| gtgttttcgt gccacgacaa ccttgatgta gatgaaacat cttttcattga agccatctca | 1800 |
| aaagaattgc acaagcaggg gttcatccct ttgacatata atcttttggg cagagagaac | 1860 |
| ctcgatgagg agatgttata cggatctaga gtcggtatca tgatactttc aagtagttat | 1920 |
| gtttcttcta gacagtccct ggatcacctg gttgcagtta tggagcattg gaaaacaaca | 1980 |
| gaccttgtaa ttattcctat atattttaaa gtaagacttt cagacatttg tgggttgaaa | 2040 |
| ggcaggtttg aagcagcgtt tctgcagctt catatgtctc tccaggaaga cagagttcag | 2100 |
| aaatggaagg cggctatgtc tgaaatagtg tccatcggtg acatgaatg gaccaaggga | 2160 |
| agtcagttta ttcttgccga ggaagttgta agaaatgcat ccttaaggct atatctgaaa | 2220 |
| agtagcaaga atctgcttgg aatcttagcg ttgttaaatc actcccagtc tacagacgtg | 2280 |
| gaaattatgg gaatctgggg tatagcagga ataggtaaga catcgattgc aagagaaata | 2340 |
| tttgaattac atgctccaca ttatgatttc tgttacttcc tgcaagactt tcatctaatg | 2400 |
| tgtcagatga aaaggccgag gcaattgcgt gaagatttta tctcaaaatt gtttggggaa | 2460 |

```
gaaaaaggtc taggtgctag tgatgtaaag ccaagtttca tgagggactg gttccataaa    2520
aaaacgattc ttctcgttct tgatgacgtg agtaatgcca gagatgcaga agctgtaatc    2580
ggagggtttg gctggttttc tcatggacac agaatcatct taacctctag gagtaaacaa    2640
gttcttgtac agtgtaaggt taaaaagcca tacgagatcc aaaaattaag cgattttgaa    2700
tcgtttcgtc tctgcaaaca atatttggat ggcgaaaatc cggtcatctc tgagcttatc    2760
agctgcagta gtggtattcc attggctctc aaacttttag tttcctctgt atcaaagcag    2820
tatataacga atatgaaaga ccatctccaa gcttgagga  aagatcctcc tactcagatt    2880
caagaagcat ttcggagaag ttttgatgga ctagatgaaa cgagaaaaa  catattttg    2940 gatcttgcat gttttttcag ggggcagagc aaagattatg cggtgctatt acttgatgct    3000
tgtggttttt ttacatatat gggaatctgt gagctcattg acgagtcact cattagcctt    3060
gtagacaaca agatagagat gcctattcct tttcaagaca tgggccgaat tattgttcat    3120
gaagaagatg aggatccatg tgaacgtagc agattgtggg actcgaagga catcgttgat    3180
gttttgacaa acaattcagg aacagaagca attgagggca tcttcctgga tgcgtctgac    3240
ttgacctgcg agcttagtcc tactgtgttt ggtaagatgt ataatcttag attgctgaag    3300
ttctattgtt caacctctgg gaaccagtgc aagcttactc tacctcacgg cctagacact    3360
ttgcctgatg agctaagtct acttcactgg gagaattacc ctctggttta cttgcctcag    3420
aaatttaatc ctgtgaacct tgtagagtta acatgccttt atagcaacat ggagaagttg    3480
tgggaaggaa agaaaaatct cgagaagcta agaacatca  aactgagtca ctccagagaa    3540
ttaactgata tcctgatgtt atcagaagcc ctgaacctgg aacacattga tctcgaaggg    3600
tgtacgagtc tgattgatgt tagcatgtct attccttgtt gtgggaagct tgtttccttg    3660
aatatgaaag actgttctcg tttgcgaagt ctgccttcta tggttgattt aacaactctc    3720
aagcttctta atttgtctgg ctgctcagaa tttgaggata ttcaggattt tgcaccaaac    3780
ctggaagaga tatatctagc tgggacatcc attagagagc ttccgttgtc aatcaggaat    3840
ctcactgaac ttgttacgct agatctggag aactgcgaaa gacttcagga aatgccgagt    3900
cttccggtgg aaataatcag gagaacctga                                     3930
```

<210> SEQ ID NO 5
<211> LENGTH: 1309
<212> TYPE: PRT
<213> ORGANISM: Arabidopsis thaliana

<400> SEQUENCE: 5

```
Met Ala Ala Ser Phe Cys Gly Ser Arg Arg Tyr Asp Val Phe Pro Ser
1               5                   10                  15

Phe Ser Lys Val Asp Val Arg Arg Ser Phe Leu Ala His Leu Leu Lys
                20                  25                  30

Glu Leu Asp Arg Arg Leu Ile Asn Thr Phe Thr Asp His Gly Met Glu
            35                  40                  45

Arg Asn Leu Pro Ile Asp Ala Glu Leu Leu Ser Ala Ile Ala Glu Ser
        50                  55                  60

Arg Ile Ser Ile Val Ile Phe Ser Lys Asn Tyr Ala Ser Ser Thr Trp
65                  70                  75                  80

Cys Leu Asp Glu Leu Val Glu Ile His Thr Cys Tyr Lys Glu Leu Ala
                85                  90                  95

Gln Ile Val Val Pro Val Phe Phe Asn Val His Pro Ser Gln Val Lys
                100                 105                 110
```

-continued

Lys Gln Thr Gly Glu Phe Gly Lys Val Phe Lys Thr Cys Lys Gly
            115                 120                 125

Lys Pro Glu Asn Arg Lys Leu Arg Trp Met Gln Ala Leu Ala Ala Val
130                 135                 140

Ala Asn Ile Ala Gly Tyr Asp Leu Gln Asn Trp Pro Asp Glu Ala Val
145                 150                 155                 160

Met Ile Glu Met Val Ala Asp Val Ser Lys Lys Leu Phe Lys Ser
            165                 170                 175

Ser Asn Asp Phe Ser Asp Ile Val Gly Ile Glu Ala His Leu Glu Ala
                180                 185                 190

Met Ser Ser Ile Leu Arg Leu Lys Ser Glu Lys Ala Arg Met Val Gly
            195                 200                 205

Ile Ser Gly Pro Ser Gly Ile Gly Lys Thr Thr Ile Ala Lys Ala Leu
210                 215                 220

Phe Ser Lys Leu Ser Pro Gln Phe His Leu Arg Ala Phe Val Thr Tyr
225                 230                 235                 240

Lys Arg Thr Asn Gln Asp Asp Tyr Asp Met Lys Leu Cys Trp Ile Glu
                245                 250                 255

Lys Phe Leu Ser Glu Ile Leu Gly Gln Lys Asp Leu Lys Val Leu Asp
            260                 265                 270

Leu Gly Ala Val Glu Gln Ser Leu Met His Lys Lys Val Leu Ile Ile
            275                 280                 285

Leu Asp Asp Val Asp Asp Leu Glu Leu Leu Lys Thr Leu Val Gly Gln
            290                 295                 300

Thr Gly Trp Phe Gly Phe Gly Ser Arg Ile Val Ile Thr Gln Asp
305                 310                 315                 320

Arg Gln Leu Leu Lys Ala His Asp Ile Asn Leu Ile Tyr Glu Val Ala
                325                 330                 335

Phe Pro Ser Ala His Leu Ala Leu Glu Ile Phe Cys Gln Ser Ala Phe
            340                 345                 350

Gly Lys Ile Tyr Pro Pro Ser Asp Phe Arg Glu Leu Ser Val Glu Phe
            355                 360                 365

Ala Tyr Leu Ala Gly Asn Leu Pro Leu Asp Leu Arg Val Leu Gly Leu
            370                 375                 380

Ala Met Lys Gly Lys His Arg Glu Glu Trp Ile Glu Met Leu Pro Arg
385                 390                 395                 400

Leu Arg Asn Asp Leu Asp Gly Lys Phe Lys Lys Thr Leu Arg Asn Tyr
                405                 410                 415

Leu Pro Val Ile Arg Lys Arg Val Ser Asn Glu Gly Gly Arg Glu
            420                 425                 430

Lys Leu Lys Lys Gly Asn Lys Lys Leu Asp Leu Asp Glu Glu Phe Pro
            435                 440                 445

Gly Gly Glu Ile Tyr Ser Asp Glu Ile Pro Ser Pro Thr Ser Asn Trp
450                 455                 460

Lys Asp Thr Asp Asp Phe Asp Ser Gly Asp Ile Ile Pro Ile Ile Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
            500                 505                 510

Pro Phe Lys Cys Ser Ala Asn Asp Val Ile Asp Phe Leu Arg Thr Arg
            515                 520                 525

```
Gln Val Leu Gly Ser Thr Glu Ala Leu Val Asp Arg Leu Ile Phe Ser
        530                 535                 540

Ser Glu Ala Phe Gly Ile Lys Pro Glu Asn Pro Phe Arg Ser Gln
545                 550                 555                 560

Ala Val Thr Ser Tyr Leu Lys Ala Ala Arg Asp Met Thr Arg Glu Lys
                    565                 570                 575

Glu Cys Ile Leu Val Phe Ser Cys His Asp Asn Leu Asp Val Asp Glu
                580                 585                 590

Thr Ser Phe Ile Glu Ala Ile Ser Lys Glu Leu His Lys Gln Gly Phe
            595                 600                 605

Ile Pro Leu Thr Tyr Asn Leu Leu Gly Arg Glu Asn Leu Asp Glu Glu
610                 615                 620

Met Leu Tyr Gly Ser Arg Val Gly Ile Met Ile Leu Ser Ser Ser Tyr
625                 630                 635                 640

Val Ser Ser Arg Gln Ser Leu Asp His Leu Val Ala Val Met Glu His
                645                 650                 655

Trp Lys Thr Thr Asp Leu Val Ile Ile Pro Ile Tyr Phe Lys Val Arg
                660                 665                 670

Leu Ser Asp Ile Cys Gly Leu Lys Gly Arg Phe Glu Ala Ala Phe Leu
            675                 680                 685

Gln Leu His Met Ser Leu Gln Glu Asp Arg Val Gln Lys Trp Lys Ala
690                 695                 700

Ala Met Ser Glu Ile Val Ser Ile Gly Gly His Glu Trp Thr Lys Gly
705                 710                 715                 720

Ser Gln Phe Ile Leu Ala Glu Glu Val Val Arg Asn Ala Ser Leu Arg
                725                 730                 735

Leu Tyr Leu Lys Ser Ser Lys Asn Leu Leu Gly Ile Leu Ala Leu Leu
            740                 745                 750

Asn His Ser Gln Ser Thr Asp Val Glu Ile Met Gly Ile Trp Gly Ile
            755                 760                 765

Ala Gly Ile Gly Lys Thr Ser Ile Ala Arg Glu Ile Phe Glu Leu His
770                 775                 780

Ala Pro His Tyr Asp Phe Cys Tyr Phe Leu Gln Asp Phe His Leu Met
785                 790                 795                 800

Cys Gln Met Lys Arg Pro Arg Gln Leu Arg Glu Asp Phe Ile Ser Lys
                805                 810                 815

Leu Phe Gly Glu Glu Lys Gly Leu Gly Ala Ser Asp Val Lys Pro Ser
            820                 825                 830

Phe Met Arg Asp Trp Phe His Lys Lys Thr Ile Leu Leu Val Leu Asp
            835                 840                 845

Asp Val Ser Asn Ala Arg Asp Ala Glu Ala Val Ile Gly Gly Phe Gly
850                 855                 860

Trp Phe Ser His Gly His Arg Ile Ile Leu Thr Ser Arg Ser Lys Gln
865                 870                 875                 880

Val Leu Val Gln Cys Lys Val Lys Lys Pro Tyr Glu Ile Gln Lys Leu
                885                 890                 895

Ser Asp Phe Glu Ser Phe Arg Leu Cys Lys Gln Tyr Leu Asp Gly Glu
            900                 905                 910

Asn Pro Val Ile Ser Glu Leu Ile Ser Cys Ser Ser Gly Ile Pro Leu
            915                 920                 925

Ala Leu Lys Leu Leu Val Ser Ser Val Ser Lys Gln Tyr Ile Thr Asn
930                 935                 940

Met Lys Asp His Leu Gln Ser Leu Arg Lys Asp Pro Pro Thr Gln Ile
```

|     |     |     |     |     |     |     |     |     |     |     |     |     |     |     |     |
| --- | --- | --- | --- | --- | --- | --- | --- | --- | --- | --- | --- | --- | --- | --- | --- |
| 945 | | | | | 950 | | | | | 955 | | | | | 960 |

Gln Glu Ala Phe Arg Arg Ser Phe Asp Gly Leu Asp Glu Asn Glu Lys
       965         970         975

Asn Ile Phe Leu Asp Leu Ala Cys Phe Phe Arg Gly Gln Ser Lys Asp
    980          985         990

Tyr Ala Val Leu Leu Asp Ala Cys Gly Phe Phe Thr Tyr Met Gly
    995          1000        1005

Ile Cys Glu Leu Ile Asp Glu Ser Leu Ile Ser Leu Val Asp Asn Lys
   1010         1015         1020

Ile Glu Met Pro Ile Pro Phe Gln Asp Met Gly Arg Ile Ile Val His
1025        1030         1035         1040

Glu Glu Asp Glu Asp Pro Cys Glu Arg Ser Arg Leu Trp Asp Ser Lys
       1045         1050         1055

Asp Ile Val Asp Val Leu Thr Asn Asn Ser Gly Thr Glu Ala Ile Glu
    1060         1065         1070

Gly Ile Phe Leu Asp Ala Ser Asp Leu Thr Cys Glu Leu Ser Pro Thr
     1075         1080         1085

Val Phe Gly Lys Met Tyr Asn Leu Arg Leu Leu Lys Phe Tyr Cys Ser
   1090         1095         1100

Thr Ser Gly Asn Gln Cys Lys Leu Thr Leu Pro His Gly Leu Asp Thr
1105        1110         1115         1120

Leu Pro Asp Glu Leu Ser Leu Leu His Trp Glu Asn Tyr Pro Leu Val
     1125         1130         1135

Tyr Leu Pro Gln Lys Phe Asn Pro Val Asn Leu Val Glu Leu Asn Met
     1140         1145         1150

Pro Tyr Ser Asn Met Glu Lys Leu Trp Glu Gly Lys Lys Asn Leu Glu
     1155         1160         1165

Lys Leu Lys Asn Ile Lys Leu Ser His Ser Arg Glu Leu Thr Asp Ile
   1170         1175         1180

Leu Met Leu Ser Glu Ala Leu Asn Leu Glu His Ile Asp Leu Glu Gly
1185        1190         1195         1200

Cys Thr Ser Leu Ile Asp Val Ser Met Ser Ile Pro Cys Cys Gly Lys
     1205         1210         1215

Leu Val Ser Leu Asn Met Lys Asp Cys Ser Arg Leu Arg Ser Leu Pro
     1220         1225         1230

Ser Met Val Asp Leu Thr Thr Leu Lys Leu Leu Asn Leu Ser Gly Cys
     1235         1240         1245

Ser Glu Phe Glu Asp Ile Gln Asp Phe Ala Pro Asn Leu Glu Glu Ile
     1250         1255         1260

Tyr Leu Ala Gly Thr Ser Ile Arg Glu Leu Pro Leu Ser Ile Arg Asn
1265        1270         1275         1280

Leu Thr Glu Leu Val Thr Leu Asp Leu Glu Asn Cys Glu Arg Leu Gln
     1285         1290         1295

Glu Met Pro Ser Leu Pro Val Glu Ile Ile Arg Arg Thr
       1300         1305

<210> SEQ ID NO 6
<211> LENGTH: 4313
<212> TYPE: DNA
<213> ORGANISM: Arabidopsis thaliana
<220> FEATURE:
<221> NAME/KEY: source
<222> LOCATION: 1..4313
<223> OTHER INFORMATION: /organism="Arabidopsis thaliana"
   /mol_type="unassigned DNA"

<400> SEQUENCE: 6

```
actggatagg cctttatctt tcattcttgg ggtttcgcat ctcttccact aatttatttg        60
agatggaatt ccattgagaa tattcgtctc ttctttcttt cgttctcaat tcccatccca       120
tattccccat ggcagcttct ttttgcggca gccggagata cgatgttttc ccgagcttca       180
gtaaggtaga tgtccgcagg tcattcctcg cgcatcttct caaggagctc gaccgcagat       240
taatcaatac gttcacagat catggtatgg agagaaacct cccaatcgac gctgaacttt       300
tatcggcgat agcagaatcg aggatctcaa tagtcatctt ctctaaaaac tatgcttctt       360
ccacgtggtg cttagatgaa ttggttgaga tccacacgtg ttataaggaa ttggctcaaa       420
tagtggttcc ggttttcttt aacgtacatc cttcgcaagt taaaaaacag accggagaat       480
ttggtaaggt ttttggaaag acatgcaaag gtaaaccaga gaatcggaaa ctaagatgga       540
tgcaagctct agcagcggta gcaaatattg ctggatatga tcttcagaac tggcctgatg       600
aagctgtcat gattgagatg gtagctgacg atgtttcgaa aaactttttt aaatcatcga       660
atgatttcag tgatatcgtc gggattgaag ctcatttaga ggcaatgagt tcaatattgc       720
gcttgaaatc tgagaaagct agaatggtcg ggatttcggg gccttcaggg attggtaaga       780
ctaccatcgc aaaagctctt ttcagtaaac tctctcccca attccacctt cgtgctttcg       840
ttacttataa agaaccaac caggacgact atgacatgaa gttgtgttgg atagaaaaat       900
ttctgtcaga aattcttggt caaaggact tgaaggtttt ggatttaggt gcggtggaac       960
aaagtctaat gcacaagaaa gttcttatca ttcttgacga tgtagatgat cttgagctat      1020
taaagacctt ggtgggacaa actggatggt tcgggtttgg aagcagaatt gttgtgatca      1080
ctcaggatag gcagcttctc aaggctcatg atattaacct catatatgag gtggccttcc      1140
catctgccca tcttgctctt gagattttct gccaatctgc ttttgggaaa atatatccac      1200
catctgattt tagagaactc tctgttgaat ttgcatatct tgccggcaat cttccttttgg      1260
atcttagggt cttgggtttg gccatgaaag gaaagcacag ggaggagtgg atagagatgc      1320
tgcctaggct ccgaaatgat ttggacggga aatttaagaa acattgaga aattacctgc      1380
ctgtgatacg gaagcgcgtt tccaatgaag aaggggggccg tgagaaattg aaaaagggaa      1440
ataaaaagtt ggatttggat gaggagtttc ctggtggaga aatttacagt gatgagatac      1500
cttcgccaac atctaactgg aaagatacag atgactttga ttcagggac atcattccaa      1560
tcattgcaga caaatctact actataattc ccaacaggag gcactcgaac gatgactggt      1620
gttctttctg tgagttcctc agaaaccgta taccccgtt gaatcccttt aaatgtagtg      1680
ccaatgatgt cattgatttt cttcgcacac ggcaggtttt aggcagcact gaggctctcg      1740
ttgaccgcct cattttcagt agtgaggcat ttggcataaa acctgaggaa accccttttc      1800
gcagccaagc tgtaacatcg tacttgaagg cggccaggga tatgacacga gaaaagaat      1860
gcatacttgt gttttcgtgc cacgacaacc ttgatgtaga tgaaacatct ttcattgaag      1920
ccatctcaaa agaattgcac aagcagggt tcatcccttt gacatataat cttttgggca      1980
gagagaacct cgatgaggag atgttatacg gatctagagt cggtatcatg atactttcaa      2040
gtagttatgt ttcttctaga cagtccctgg atcacctggt tgcagttatg gagcattgga      2100
aaacaacaga ccttgtaatt attcctatat attttaaagt aagactttca gacatttgtg      2160
ggttgaaagg caggtttgaa gcagcgtttc tgcagcttca tatgtctctc caggaagaca      2220
gagttcagaa atggaaggcg gctatgtctg aaatagtgtc catcggtgga catgaatgga      2280
ccaagggaag tcagtttatt cttgccgagg aagttgtaag aaatgcatcc ttaaggctat      2340
```

```
atctgaaaag tagcaagaat ctgcttggaa tcttagcgtt gttaaatcac tcccagtcta    2400
cagacgtgga aattatggga atctggggta tagcaggaat aggtaagaca tcgattgcaa    2460
gagaaatatt tgaattacat gctccacatt atgatttctg ttacttcctg caagactttc    2520
atctaatgtg tcagatgaaa aggccgaggc aattgcgtga agattttatc tcaaaattgt    2580
ttggggaaga aaaaggtcta ggtgctagtg atgtaaagcc aagtttcatg agggactggt    2640
tccataaaaa aacgattctt ctcgttcttg atgacgtgag taatgccaga gatgcagaag    2700
ctgtaatcgg agggtttggc tggttttctc atggacacag aatcatctta acctctagga    2760
gtaaacaagt tcttgtacag tgtaaggtta aaaagccata cgagatccaa aaattaagcg    2820
attttgaatc gtttcgtctc tgcaaacaat atttggatgg cgaaaatccg gtcatctctg    2880
agcttatcag ctgcagtagt ggtattccat tggctctcaa acttttagtt tcctctgtat    2940
caaagcagta tataacgaat atgaaagacc atctccaaag cttgaggaaa gatcctccta    3000
ctcagattca agaagcattt cggagaagtt ttgatggact agatgaaaac gagaaaaaca    3060 tattttttgga tcttgcatgt tttttcaggg ggcagagcaa agattatgcg gtgctattac    3120
ttgatgcttg tggttttttt acatatatgg gaatctgtga gctcattgac gagtcactca    3180
ttagccttgt agacaacaag atagagatgc ctattccttt tcaagacatg ggccgaatta    3240
ttgttcatga agaagatgag gatccatgtg aacgtagcag attgtgggac tcgaaggaca    3300
tcgttgatgt tttgacaaac aattcaggaa cagaagcaat tgagggcatc ttcctggatg    3360
cgtctgactt gacctgcgag cttagtccta ctgtgtttgg taagatgtat aatcttagat    3420
tgctgaagtt ctattgttca acctctggga accagtgcaa gcttactcta cctcacggcc    3480
tagacacttt gcctgatgag ctaagtctac ttcactggga gaattaccct ctggtttact    3540
tgcctcagaa atttaatcct gtgaaccttg tagagttaaa catgccttat agcaacatgg    3600
agaagttgtg ggaaggaaag aaaaatctcg agaagctaaa gaacatcaaa ctgagtcact    3660
ccagagaatt aactgatatc ctgatgttat cagaagccct gaacctggaa cacattgatc    3720
tcgaagggtg tacgagtctg attgatgtta gcatgtctat tccttgttgt gggaagcttg    3780
tttccttgaa tatgaaagac tgttctcgtt tgcgaagtct gccttctatg gttgatttaa    3840
caactctcaa gcttcttaat ttgtctggct gctcagaatt tgaggatatt caggattttg    3900
caccaaacct ggaagagata tatctagctg ggacatccat tagagagctt ccgttgtcaa    3960
tcaggaatct cactgaactt gttacgctag atctggagaa ctgcgaaagg cttcaggaaa    4020
tgccgagtct tccggtggaa ataatcagga gaacctgaaa aaacgcagaa atcacctctc    4080
aatccctgtt ctaccaaggg attgtgatgt aattgtggta tattctcgga ccgtgtattc    4140
tctatcttat ttcccaaacg ttttttgtaga ttaggcaagg aaaggaaaaa tcctaattga    4200
cacagatttg ttaatagatt tagatgatca ttgtgttta ataatattat tgttatttgt    4260
tgtattttaa cagttctata atgataattg tgatctcaaa atctcgttta tta           4313
```

<210> SEQ ID NO 7
<211> LENGTH: 1309
<212> TYPE: PRT
<213> ORGANISM: Arabidopsis thaliana

<400> SEQUENCE: 7

```
Met Ala Ala Ser Phe Cys Gly Ser Arg Arg Tyr Asp Val Phe Pro Ser
1               5                   10                  15

Phe Ser Lys Val Asp Val Arg Arg Ser Phe Leu Ala His Leu Leu Lys
```

```
              20                  25                  30
Glu Leu Asp Arg Arg Leu Ile Asn Thr Phe Thr Asp His Gly Met Glu
             35                  40                  45

Arg Asn Leu Pro Ile Asp Ala Glu Leu Leu Ser Ala Ile Ala Glu Ser
 50                  55                  60

Arg Ile Ser Ile Val Ile Phe Ser Lys Asn Tyr Ala Ser Ser Thr Trp
 65                  70                  75                  80

Cys Leu Asp Glu Leu Val Glu Ile His Thr Cys Tyr Lys Glu Leu Ala
                 85                  90                  95

Gln Ile Val Val Pro Val Phe Phe Asn Val His Pro Ser Gln Val Lys
                100                 105                 110

Lys Gln Thr Gly Glu Phe Gly Lys Val Phe Gly Lys Thr Cys Lys Gly
                115                 120                 125

Lys Pro Glu Asn Arg Lys Leu Arg Trp Met Gln Ala Leu Ala Ala Val
                130                 135                 140

Ala Asn Ile Ala Gly Tyr Asp Leu Gln Asn Trp Pro Asp Glu Ala Val
145                 150                 155                 160

Met Ile Glu Met Val Ala Asp Val Ser Lys Lys Leu Phe Lys Ser
                165                 170                 175

Ser Asn Asp Phe Ser Asp Ile Val Gly Ile Glu Ala His Leu Glu Ala
                180                 185                 190

Met Ser Ser Ile Leu Arg Leu Lys Ser Glu Lys Ala Arg Met Val Gly
                195                 200                 205

Ile Ser Gly Pro Ser Gly Ile Gly Lys Thr Thr Ile Ala Lys Ala Leu
                210                 215                 220

Phe Ser Lys Leu Ser Pro Gln Phe His Leu Arg Ala Phe Val Thr Tyr
225                 230                 235                 240

Lys Arg Thr Asn Gln Asp Tyr Asp Met Lys Leu Cys Trp Ile Glu
                245                 250                 255

Lys Phe Leu Ser Glu Ile Leu Gly Gln Lys Asp Leu Lys Val Leu Asp
                260                 265                 270

Leu Gly Ala Val Glu Gln Ser Leu Met His Lys Lys Val Leu Ile Ile
                275                 280                 285

Leu Asp Asp Val Asp Asp Leu Glu Leu Leu Lys Thr Leu Val Gly Gln
                290                 295                 300

Thr Gly Trp Phe Gly Phe Gly Ser Arg Ile Val Val Ile Thr Gln Asp
305                 310                 315                 320

Arg Gln Leu Leu Lys Ala His Asp Ile Asn Leu Ile Tyr Glu Val Ala
                325                 330                 335

Phe Pro Ser Ala His Leu Ala Leu Glu Ile Phe Cys Gln Ser Ala Phe
                340                 345                 350

Gly Lys Ile Tyr Pro Pro Ser Asp Phe Arg Glu Leu Ser Val Glu Phe
                355                 360                 365

Ala Tyr Leu Ala Gly Asn Leu Pro Leu Asp Leu Arg Val Leu Gly Leu
                370                 375                 380

Ala Met Lys Gly Lys His Arg Glu Glu Trp Ile Glu Met Leu Pro Arg
385                 390                 395                 400

Leu Arg Asn Asp Leu Asp Gly Lys Phe Lys Lys Thr Leu Arg Asn Tyr
                405                 410                 415

Leu Pro Val Ile Arg Lys Arg Val Ser Asn Glu Glu Gly Gly Arg Glu
                420                 425                 430

Lys Leu Lys Lys Gly Asn Lys Lys Leu Asp Leu Asp Glu Glu Phe Pro
                435                 440                 445
```

```
Gly Gly Glu Ile Tyr Ser Asp Glu Ile Pro Ser Pro Thr Ser Asn Trp
450                 455                 460

Lys Asp Thr Asp Asp Phe Asp Ser Gly Asp Ile Ile Pro Ile Ile Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
                500                 505                 510

Pro Phe Lys Cys Ser Ala Asn Asp Val Ile Asp Phe Leu Arg Thr Arg
            515                 520                 525

Gln Val Leu Gly Ser Thr Glu Ala Leu Val Asp Arg Leu Ile Phe Ser
        530                 535                 540

Ser Glu Ala Phe Gly Ile Lys Pro Glu Asn Pro Phe Arg Ser Gln
545                 550                 555                 560

Ala Val Thr Ser Tyr Leu Lys Ala Ala Arg Asp Met Thr Arg Glu Lys
                565                 570                 575

Glu Cys Ile Leu Val Phe Ser Cys His Asp Asn Leu Asp Val Asp Glu
                580                 585                 590

Thr Ser Phe Ile Glu Ala Ile Ser Lys Glu Leu His Lys Gln Gly Phe
                595                 600                 605

Ile Pro Leu Thr Tyr Asn Leu Leu Gly Arg Glu Asn Leu Asp Glu Glu
610                 615                 620

Met Leu Tyr Gly Ser Arg Val Gly Ile Met Ile Leu Ser Ser Ser Tyr
625                 630                 635                 640

Val Ser Ser Arg Gln Ser Leu Asp His Leu Val Ala Val Met Glu His
                645                 650                 655

Trp Lys Thr Thr Asp Leu Val Ile Ile Pro Ile Tyr Phe Lys Val Arg
                660                 665                 670

Leu Ser Asp Ile Cys Gly Leu Lys Gly Arg Phe Glu Ala Ala Phe Leu
            675                 680                 685

Gln Leu His Met Ser Leu Gln Glu Asp Arg Val Gln Lys Trp Lys Ala
        690                 695                 700

Ala Met Ser Glu Ile Val Ser Ile Gly His Glu Trp Thr Lys Gly
705                 710                 715                 720

Ser Gln Phe Ile Leu Ala Glu Glu Val Val Arg Asn Ala Ser Leu Arg
                725                 730                 735

Leu Tyr Leu Lys Ser Ser Lys Asn Leu Leu Gly Ile Leu Ala Leu Leu
                740                 745                 750

Asn His Ser Gln Ser Thr Asp Val Glu Ile Met Gly Ile Trp Gly Ile
            755                 760                 765

Ala Gly Ile Gly Lys Thr Ser Ile Ala Arg Glu Ile Phe Glu Leu His
        770                 775                 780

Ala Pro His Tyr Asp Phe Cys Tyr Phe Leu Gln Asp Phe His Leu Met
785                 790                 795                 800

Cys Gln Met Lys Arg Pro Arg Gln Leu Arg Glu Asp Phe Ile Ser Lys
                805                 810                 815

Leu Phe Gly Glu Glu Lys Gly Leu Gly Ala Ser Asp Val Lys Pro Ser
                820                 825                 830

Phe Met Arg Asp Trp Phe His Lys Lys Thr Ile Leu Leu Val Leu Asp
            835                 840                 845

Asp Val Ser Asn Ala Arg Asp Ala Glu Ala Val Ile Gly Gly Phe Gly
        850                 855                 860
```

```
Trp Phe Ser His Gly His Arg Ile Ile Leu Thr Ser Arg Ser Lys Gln
865                 870                 875                 880

Val Leu Val Gln Cys Lys Val Lys Pro Tyr Glu Ile Gln Lys Leu
                885                 890                 895

Ser Asp Phe Glu Ser Phe Arg Leu Cys Lys Gln Tyr Leu Asp Gly Glu
                900                 905                 910

Asn Pro Val Ile Ser Glu Leu Ile Ser Cys Ser Ser Gly Ile Pro Leu
                915                 920                 925

Ala Leu Lys Leu Leu Val Ser Ser Val Ser Lys Gln Tyr Ile Thr Asn
                930                 935                 940

Met Lys Asp His Leu Gln Ser Leu Arg Lys Asp Pro Pro Thr Gln Ile
945                 950                 955                 960

Gln Glu Ala Phe Arg Arg Ser Phe Asp Gly Leu Asp Glu Asn Glu Lys
                965                 970                 975

Asn Ile Phe Leu Asp Leu Ala Cys Phe Phe Arg Gly Gln Ser Lys Asp
                980                 985                 990

Tyr Ala Val Leu Leu Asp Ala Cys Gly Phe Phe Tyr Met Gly
                995                 1000                1005

Ile Cys Glu Leu Ile Asp Glu Ser Leu Ile Ser Leu Val Asp Asn Lys
1010                1015                1020

Ile Glu Met Pro Ile Pro Phe Gln Asp Met Gly Arg Ile Ile Val His
1025                1030                1035                1040

Glu Glu Asp Glu Asp Pro Cys Glu Arg Ser Arg Leu Trp Asp Ser Lys
                1045                1050                1055

Asp Ile Val Asp Val Leu Thr Asn Asn Ser Gly Thr Glu Ala Ile Glu
                1060                1065                1070

Gly Ile Phe Leu Asp Ala Ser Asp Leu Thr Cys Glu Leu Ser Pro Thr
                1075                1080                1085

Val Phe Gly Lys Met Tyr Asn Leu Arg Leu Leu Lys Phe Tyr Cys Ser
                1090                1095                1100

Thr Ser Gly Asn Gln Cys Lys Leu Thr Leu Pro His Gly Leu Asp Thr
1105                1110                1115                1120

Leu Pro Asp Glu Leu Ser Leu Leu His Trp Glu Asn Tyr Pro Leu Val
                1125                1130                1135

Tyr Leu Pro Gln Lys Phe Asn Pro Val Asn Leu Val Glu Leu Asn Met
                1140                1145                1150

Pro Tyr Ser Asn Met Glu Lys Leu Trp Glu Gly Lys Lys Asn Leu Glu
                1155                1160                1165

Lys Leu Lys Asn Ile Lys Leu Ser His Ser Arg Glu Leu Thr Asp Ile
                1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
                1205                1210                1215

Leu Val Ser Leu Asn Met Lys Asp Cys Ser Arg Leu Arg Ser Leu Pro
                1220                1225                1230

Ser Met Val Asp Leu Thr Thr Leu Lys Leu Leu Asn Leu Ser Gly Cys
                1235                1240                1245

Ser Glu Phe Glu Asp Ile Gln Asp Phe Ala Pro Asn Leu Glu Glu Ile
                1250                1255                1260

Tyr Leu Ala Gly Thr Ser Ile Arg Glu Leu Pro Leu Ser Ile Arg Asn
1265                1270                1275                1280

Leu Thr Glu Leu Val Thr Leu Asp Leu Glu Asn Cys Glu Arg Leu Gln
```

Glu Met Pro Ser Leu Pro Val Glu Ile Ile Arg Arg Thr
         1300                  1305

<210> SEQ ID NO 8
<211> LENGTH: 3889
<212> TYPE: DNA
<213> ORGANISM: Arabidopsis thaliana
<220> FEATURE:
<221> NAME/KEY: source
<222> LOCATION: 1..3889
<223> OTHER INFORMATION: /organism="Arabidopsis thaliana"
      /mol_type="unassigned DNA"

<400> SEQUENCE: 8

| | | | | | |
|---|---|---|---|---|---|
| actggatagg | cctttatctt | tcattcttgg | ggtttcgcat | ctcttccact | aatttatttg | 60 |
| agatggaatt | ccattgagaa | tattcgtctc | ttctttcttt | cgttctcaat | tcccatccca | 120 |
| tattccccat | ggcagcttct | ttttgcggca | gccggagata | cgatgttttc | ccgagcttca | 180 |
| gtaaggtaga | tgtccgcagg | tcattcctcg | cgcatcttct | caaggagctc | gaccgcagat | 240 |
| taatcaatac | gttcacagat | catggtatgg | agagaaacct | cccaatcgac | gctgaacttt | 300 |
| tatcggcgat | agcagaatcg | aggatctcaa | tagtcatctt | ctctaaaaac | tatgcttct | 360 |
| ccacgtggtg | cttagatgaa | ttggttgaga | tccacacgtg | ttataaggaa | ttggctcaaa | 420 |
| tagtggttcc | ggttttcttt | aacgtacatc | cttcgcaagt | taaaaaacag | accggagaat | 480 |
| ttggtaaggt | ttttggaaag | acatgcaaag | gtaaaccaga | gaatcggaaa | ctaagatgga | 540 |
| tgcaagctct | agcagcggta | gcaaatattg | ctggatatga | tcttcagaac | tggcctgatg | 600 |
| aagctgtcat | gattgagatg | gtagctgacg | atgtttcgaa | aaacttttt | aaatcatcga | 660 |
| atgatttcag | tgatatcgtc | gggattgaag | ctcatttaga | ggcaatgagt | tcaatattgc | 720 |
| gcttgaaatc | tgagaaagct | agaatggtcg | ggatttcggg | gccttcaggg | attggtaaga | 780 |
| ctaccatcgc | aaaagctctt | ttcagtaaac | tctctcccca | attccacctt | cgtgctttcg | 840 |
| ttacttataa | aagaaccaac | caggacgact | atgacatgaa | gttgtgttgg | atagaaaaat | 900 |
| ttctgtcaga | aattcttggt | caaaaggact | tgaaggtttt | ggatttagag | aactctctgt | 960 |
| tgaatttgca | tatcttgccg | gcaatcttcc | tttggatctt | agggtcttgg | gtttggccat | 1020 |
| gaaaggaaag | cacagggagg | agtggataga | gatgctgcct | aggctccgaa | atgatttgga | 1080 |
| cgggaaattt | aagaaaacat | tgagaaatta | cctgcctgtg | atacggaagc | gcgtttccaa | 1140 |
| tgaagaaggg | ggccgtgaga | aattgaaaaa | gggaaataaa | aagttggatt | tggatgagga | 1200 |
| gtttcctggt | ggagaaattt | acagtgatga | gataccttcg | ccaacatcta | actggaaaga | 1260 |
| tacagatgac | tttgattcag | gggacatcat | tccaatcatt | gcagacaaat | ctactactat | 1320 |
| aattcccaac | aggaggcact | cgaacgatga | ctggtgttct | ttctgtttta | ggcagcactg | 1380 |
| aggctctcgt | tgaccgcctc | attttcagta | gtgaggcatt | tggcataaaa | cctgaggaaa | 1440 |
| acccttttcg | cagccaagct | gtaacatcgt | acttgaaggc | ggccagggat | atgacacgag | 1500 |
| aaaaagaatg | catacttgtg | ttttcgtgcc | acgacaacct | tgatgtagat | gaaacatctt | 1560 |
| tcattgaagc | catctcaaaa | gaattgcaca | agcaggggtt | catcccttg | acatataatc | 1620 |
| ttttgggcag | agagaacctc | gatgaggaga | tgttatacgg | atctagagtc | ggtatcatga | 1680 |
| tactttcaag | tagttatgtt | tcttctagac | agtccctgga | tcacctggtt | gcagttatgg | 1740 |
| agcattggaa | aacaacagac | cttgtaatta | ttcctatata | ttttaaagta | agactttcag | 1800 |
| acatttgtgg | gttgaaaggc | aggtttgaag | cagcgtttct | gcagcttcat | atgtctctcc | 1860 |

```
aggaagacag agttcagaaa tggaaggcgg ctatgtctga aatagtgtcc atcggtggac   1920
atgaatggac caagggaagt cagtttattc ttgccgagga agttgtaaga aatgcatcct   1980
taaggctata tctgaaaagt agcaagaatc tgcttggaat cttagcgttg ttaaatcact   2040
cccagtctac agacgtggaa attatgggaa tctggggtat agcaggaata ggtaagacat   2100
cgattgcaag agaaatattt gaattacatg ctccacatta tgatttctgt tacttcctgc   2160
aagactttca tctaatgtgt cagatgaaaa ggccgaggca attgcgtgaa gattttatct   2220
caaaattgtt tggggaagaa aaaggtctag gtgctagtga tgtaaagcca agtttcatga   2280
gggactggtt ccataaaaaa acgattcttc tcgttcttga tgacgtgagt aatgccagag   2340
atgcagaagc tgtaatcgga gggtttggct ggttttctca tggacacaga atcatcttaa   2400
cctctaggag taaacaagtt cttgtacagt gtaaggttaa aaagccatac gagatccaaa   2460
aattaagcga ttttgaatcg tttcgtctct gcaaacaata tttggatggc gaaaatccgg   2520
tcatctctga gcttatcagc tgcagtagtg gtattccatt ggctctcaaa cttttagttt   2580
cctctgtatc aaagcagtat ataacgaata tgaaagacca tctccaaagc ttgaggaaag   2640
atcctcctac tcagattcaa gaagcatttc ggagaagttt tgatggacta gatgaaaacg   2700
agaaaaacat atttttggat cttgcatgtt tttcagggg gcagagcaaa gattatgcgg   2760
tgctattact tgatgcttgt ggttttttta catatatggg aatctgtgag ctcattgacg   2820
agtcactcat tagccttgta gacaacaaga tagagatgcc tattccttt caagacatgg   2880 gccgaattat tgttcatgaa gaagatgagg atccatgtga acgtagcaga ttgtgggact   2940
cgaaggacat cgttgatgtt ttgacaaaca attcaggaac agaagcaatt gagggcatct   3000
tcctggatgc gtctgacttg acctgcgagc ttagtcctac tgtgtttggt aagatgtata   3060
atcttagatt gctgaagttc tattgttcaa cctctgggaa ccagtgcaag cttactctac   3120
ctcacggcct agacactttg cctgatgagc taagtctact tcactgggag aattaccctc   3180
tggtttactt gcctcagaaa tttaatcctg tgaaccttgt agagttaaac atgccttata   3240
gcaacatgga gaagttgtgg gaaggaaaga aaaatctcga gaagctaaag aacatcaaac   3300
tgagtcactc cagagaatta actgatatcc tgatgttatc agaagccctg aacctggaac   3360
acattgatct cgaagggtgt acgagtctga ttgatgttag catgtctatt ccttgttgtg   3420
ggaagcttgt ttccttgaat atgaaagact gttctcgttt gcgaagtctg ccttctatgg   3480
ttgatttaac aactctcaag cttcttaatt tgtctggctg ctcagaattt gaggatattc   3540
aggattttgc accaaacctg gaagagatat atctagctgg gacatccatt agagagcttc   3600
cgttgtcaat caggaatctc actgaacttg ttacgctaga tctggagaac tgcgaaggc   3660 ttcaggaaat gccgagaaca tgtaattgga aactgaaatt tttccgcaaa aaaaaaaatc   3720
ccgccaaact ttttttccgc caaaacaaaa aattcccgcc aaaaaaaaaa ttcccggcaa   3780
atatcttttt cataacaaat cttttctcag ccaaaaaaat acttttaaaa atccttgtaa   3840
atttaaagta atagagagtc taagtttaaa ttaaagaatt taatataaa            3889
```

<210> SEQ ID NO 9
<211> LENGTH: 834
<212> TYPE: PRT
<213> ORGANISM: Arabidopsis thaliana

<400> SEQUENCE: 9

Met Thr Gly Val Leu Ser Val Leu Gly Ser Thr Glu Ala Leu Val Asp
1               5                   10                  15

```
Arg Leu Ile Phe Ser Ser Glu Ala Phe Gly Ile Lys Pro Glu Glu Asn
             20                  25                  30

Pro Phe Arg Ser Gln Ala Val Thr Ser Tyr Leu Lys Ala Ala Arg Asp
         35                  40                  45

Met Thr Arg Glu Lys Glu Cys Ile Leu Val Phe Ser Cys His Asp Asn
 50                  55                  60

Leu Asp Val Asp Glu Thr Ser Phe Ile Glu Ala Ile Ser Lys Glu Leu
 65                  70                  75                  80

His Lys Gln Gly Phe Ile Pro Leu Thr Tyr Asn Leu Leu Gly Arg Glu
                 85                  90                  95

Asn Leu Asp Glu Glu Met Leu Tyr Gly Ser Arg Val Gly Ile Met Ile
             100                 105                 110

Leu Ser Ser Ser Tyr Val Ser Ser Arg Gln Ser Leu Asp His Leu Val
         115                 120                 125

Ala Val Met Glu His Trp Lys Thr Thr Asp Leu Val Ile Ile Pro Ile
 130                 135                 140

Tyr Phe Lys Val Arg Leu Ser Asp Ile Cys Gly Leu Lys Gly Arg Phe
145                 150                 155                 160

Glu Ala Ala Phe Leu Gln Leu His Met Ser Leu Gln Glu Asp Arg Val
                 165                 170                 175

Gln Lys Trp Lys Ala Ala Met Ser Glu Ile Val Ser Ile Gly Gly His
             180                 185                 190

Glu Trp Thr Lys Gly Ser Gln Phe Ile Leu Ala Glu Glu Val Val Arg
         195                 200                 205

Asn Ala Ser Leu Arg Leu Tyr Leu Lys Ser Ser Lys Asn Leu Leu Gly
210                 215                 220

Ile Leu Ala Leu Leu Asn His Ser Gln Ser Thr Asp Val Glu Ile Met
225                 230                 235                 240

Gly Ile Trp Gly Ile Ala Gly Ile Gly Lys Thr Ser Ile Ala Arg Glu
                 245                 250                 255

Ile Phe Glu Leu His Ala Pro His Tyr Asp Phe Cys Tyr Phe Leu Gln
             260                 265                 270

Asp Phe His Leu Met Cys Gln Met Lys Arg Pro Arg Gln Leu Arg Glu
         275                 280                 285

Asp Phe Ile Ser Lys Leu Phe Gly Glu Glu Lys Gly Leu Gly Ala Ser
290                 295                 300

Asp Val Lys Pro Ser Phe Met Arg Asp Trp Phe His Lys Lys Thr Ile
305                 310                 315                 320

Leu Leu Val Leu Asp Asp Val Ser Asn Ala Arg Asp Ala Glu Ala Val
                 325                 330                 335

Ile Gly Gly Phe Gly Trp Phe Ser His Gly His Arg Ile Ile Leu Thr
             340                 345                 350

Ser Arg Ser Lys Gln Val Leu Val Gln Cys Lys Val Lys Lys Pro Tyr
         355                 360                 365

Glu Ile Gln Lys Leu Ser Asp Phe Glu Ser Phe Arg Leu Cys Lys Gln
370                 375                 380

Tyr Leu Asp Gly Glu Asn Pro Val Ile Ser Glu Leu Ile Ser Cys Ser
385                 390                 395                 400

Ser Gly Ile Pro Leu Ala Leu Lys Leu Leu Val Ser Ser Val Ser Lys
                 405                 410                 415

Gln Tyr Ile Thr Asn Met Lys Asp His Leu Gln Ser Leu Arg Lys Asp
             420                 425                 430
```

```
Pro Pro Thr Gln Ile Gln Glu Ala Phe Arg Arg Ser Phe Asp Gly Leu
        435                 440                 445
Asp Glu Asn Glu Lys Asn Ile Phe Leu Asp Leu Ala Cys Phe Phe Arg
450                 455                 460
Gly Gln Ser Lys Asp Tyr Ala Val Leu Leu Asp Ala Cys Gly Phe
465                 470                 475                 480
Phe Thr Tyr Met Gly Ile Cys Glu Leu Ile Asp Glu Ser Leu Ile Ser
                485                 490                 495
Leu Val Asp Asn Lys Ile Glu Met Pro Ile Pro Phe Gln Asp Met Gly
                500                 505                 510
Arg Ile Ile Val His Glu Glu Asp Pro Cys Glu Arg Ser Arg
                515                 520                 525
Leu Trp Asp Ser Lys Asp Ile Val Asp Val Leu Thr Asn Asn Ser Gly
        530                 535                 540
Thr Glu Ala Ile Glu Gly Ile Phe Leu Asp Ala Ser Asp Leu Thr Cys
545                 550                 555                 560
Glu Leu Ser Pro Thr Val Phe Gly Lys Met Tyr Asn Leu Arg Leu Leu
                565                 570                 575
Lys Phe Tyr Cys Ser Thr Ser Gly Asn Gln Cys Lys Leu Thr Leu Pro
                580                 585                 590
His Gly Leu Asp Thr Leu Pro Asp Glu Leu Ser Leu Leu His Trp Glu
            595                 600                 605
Asn Tyr Pro Leu Val Tyr Leu Pro Gln Lys Phe Asn Pro Val Asn Leu
            610                 615                 620
Val Glu Leu Asn Met Pro Tyr Ser Asn Met Glu Lys Leu Trp Glu Gly
625                 630                 635                 640
Lys Lys Asn Leu Glu Lys Leu Lys Asn Ile Lys Leu Ser His Ser Arg
                645                 650                 655
Glu Leu Thr Asp Ile Leu Met Leu Ser Glu Ala Leu Asn Leu Glu His
                660                 665                 670
Ile Asp Leu Glu Gly Cys Thr Ser Leu Ile Asp Val Ser Met Ser Ile
            675                 680                 685
Pro Cys Cys Gly Lys Leu Val Ser Leu Asn Met Lys Asp Cys Ser Arg
        690                 695                 700
Leu Arg Ser Leu Pro Ser Met Val Asp Leu Thr Thr Leu Lys Leu Leu
705                 710                 715                 720
Asn Leu Ser Gly Cys Ser Glu Phe Glu Asp Ile Gln Asp Phe Ala Pro
                725                 730                 735
Asn Leu Glu Glu Ile Tyr Leu Ala Gly Thr Ser Ile Arg Glu Leu Pro
            740                 745                 750
Leu Ser Ile Arg Asn Leu Thr Glu Leu Val Thr Leu Asp Leu Glu Asn
            755                 760                 765
Cys Glu Arg Leu Gln Glu Met Pro Arg Thr Cys Asn Trp Lys Leu Lys
        770                 775                 780
Phe Phe Arg Lys Lys Lys Asn Pro Ala Lys Leu Phe Arg Gln Asn
785                 790                 795                 800
Lys Lys Phe Pro Pro Lys Lys Lys Phe Pro Ala Asn Ile Phe Ile
                805                 810                 815
Thr Asn Leu Phe Ser Ala Lys Lys Ile Leu Leu Lys Ile Leu Val Asn
                820                 825                 830
Leu Lys

<210> SEQ ID NO 10
```

-continued

```
<211> LENGTH: 7686
<212> TYPE: DNA
<213> ORGANISM: Arabidopsis thaliana
<220> FEATURE:
<221> NAME/KEY: source
<222> LOCATION: 1..7686
<223> OTHER INFORMATION: /organism="Arabidopsis thaliana"
      /mol_type="unassigned DNA"

<400> SEQUENCE: 10
taaaccattg atatttaatt atttgtcttg aagtttaaaa ttcatcaata ataactactc      60
attctgttct tttttaatta attttctaga aaaacacaca tattaataaa acatataaaa     120
ctgattataa atgtattaat ttttgtgatt tacaattttt tataatttta aaccaatgat     180
attcaattat ttgtcttgaa atttaaaatt catcaataat aactaataaa tagtgcataa     240
aaaacttaaa aaattaaaca atattgtttt ctaaagatc aagtaataag gaaccgaagg      300
agtactaaat agtgcataga aacctaaaaa atcaactttt ttgaaacaaa ttttttttcct    360 aaaaaatcaa ataataagga gcaaaaggag tataatctaa tctctaaccg atatataatc     420
tcatttaact ataaaattta aatcttaatc ttctttgatt aacccaaacc gatatataat     480
ctcatttaat tacaaaatct aaaccttaat cttctaatta gaaactcaat ccgatattaa     540
acccgtttaa ttgtaaaatt taaattttaa caatactttt taaatttaaa ctgatatttaa    600 gttttgttta attgtaaaat ttaaatccgt ttataattca gatcgatatt taattataaa     660
tctaaaccga tatttaactt tgtttaatca tataatctaa tcctaaaaaa ttcttatata     720
aactcaacca atatatcatt tcgttttgat agtggagtat attttataat taaatgaatt     780
ttagttttat tagctagctg attatgattg gctaaaatag aaagagtaaa gagtgaataa     840
gaaggttcat ttttggtttt caaattatcc atctttattt tttgtcctgg atactggata     900
ggcctttatc tttcattctt ggggtttcgc atctcttcca ctaatttatt tgagatggaa     960
ttccattgag aatattcgtc tcttctttct ttcgttctca attcccatcc catattcccc    1020
atggcagctt cttttttgcgg cagccggaga tacgatgttt tcccgagctt cagtaaggta    1080
gatgtccgca ggtcattcct cgcgcatctt ctcaaggagc tcgaccgcag attaatcaat    1140
acgttcacag atcatggtat ggagagaaac ctcccaatcg acgctgaact tttatcggcg    1200
atagcagaat cgaggatctc aatagtcatc ttctctaaaa actatgcttc ttccacgtgg    1260
tgcttagatg aattggttga gatccacacg tgttataagg aattggctca aatagtggtt    1320
ccggttttct ttaacgtaca tccttcgcaa gttaaaaaac agaccggaga atttggtaag    1380 gttttttggaa agacatgcaa aggtaaacca gagaatcgga aactaagatg gatgcaagct    1440
ctagcagcgg tagcaaatat tgctggatat gatcttcaga actggtattt tcttttccat    1500
tccaacccta atatatatat gtgcctgtgt tcaattttgg ggtgcctctt taatgacaaa    1560
attgactatt gttattaggc ctgatgaagc tgtcatgatt gagatggtag ctgacgatgt    1620
ttcgaaaaaa cttttttaaat catcgaatga tttcagtgat atcgtcggga ttgaagctca    1680
tttagaggca atgagttcaa tattgcgctt gaaatctgag aaagctagaa tggtcgggat    1740
ttcggggcct tcagggattg gtaagactac catcgcaaaa gctcttttca gtaaactctc    1800
tccccaattc caccttcgtg ctttcgttac ttataaaaga accaaccagg acgactatga    1860
catgaagttg tgttggatag aaaaatttct gtcagaaatt cttggtcaaa aggacttgaa    1920
ggttttggat ttaggtgcgg tggaacaaag tctaatgcac aagaaagttc ttatcattct    1980
tgacgatgta gatgatcttg agctattaaa gaccttggtg ggacaaactg gatggttcgg    2040
```

```
gtttggaagc agaattgttg tgatcactca ggataggcag cttctcaagg ctcatgatat   2100
taacctcata tatgaggtgg ccttcccatc tgcccatctt gctcttgaga ttttctgcca   2160
atctgctttt gggaaaatat atccaccatc tgattttaga gaactctctg ttgaatttgc   2220
atatcttgcc ggcaatcttc ctttggatct tagggtcttg ggtttggcca tgaaaggaaa   2280
gcacagggag gagtggatag agatgctgcc taggctccga aatgatttgg acgggaaatt   2340
taagaaaaca ttgagaaatt acctgcctgt gatacggaag cgcgtttcca atgaagaagg   2400
gggccgtgag aaattgaaaa agggaaataa aaagttggat ttggatgagg agtttcctgg   2460
tggagaaatt tacagtgatg agataccttc gccaacatct aactggaaag atacagatga   2520
ctttgattca ggggacatca ttccaatcat tgcagacaaa tctactacta taattcccaa   2580
caggaggcac tcgaacgatg actggtgttc tttctgtgag ttcctcagaa accgtatacc   2640
cccgttgaat ccctttaaat gtagtgccaa tgatgtcatt gattttcttc gcacacggca   2700
ggttttaggc agcactgagg ctctcgttga ccgcctcatt ttcagtagtg aggcatttgg   2760
cataaaacct gaggaaaacc cttttcgcag ccaagctgta acatcgtact tgaaggcggc   2820
cagggatatg acacgagaaa aagaatgcat acttgtgttt tcgtgccacg acaaccttga   2880
tgtagatgaa acatctttca ttgaagccat ctcaaaagaa ttgcacaagc aggggttcat   2940 cccctttgaca tataatcttt tgggcagaga gaacctcgat gaggagatgt tatacggatc   3000
tagagtcggt atcatgatac tttcaagtag ttatgtttct tctagacagt ccctggatca   3060
cctggttgca gttatggagc attggaaaac aacagacctt gtaattattc ctatatattt   3120
taaagtaaga ctttcagaca tttgtgggtt gaaaggcagg tttgaagcag cgtttctgca   3180
gcttcatatg tctctccagg aagacagagt tcagaaatgg aaggcggcta tgtctgaaat   3240
agtgtccatc ggtggacatg aatggaccaa ggggtatatt tacttatctt tgttgtccct   3300
ttactattca aagctagttt attaatattt ggaagagtat ttcttattgg tgtggtgcta   3360
aatcagtact tccattttct ctgtcctatt tgcagaagtc agtttattct tgccgaggaa   3420
gttgtaagaa atgcatcctt aaggctatat ctgaaaagta gcaagaatct gcttggaatc   3480
ttagcgttgt taaatcactc ccagtctaca gacgtggaaa ttatgggaat ctggggtata   3540
gcaggaatag gtaagacatc gattgcaaga gaaatatttg aattacatgc tccacattat   3600
gatttctgtt acttcctgca agactttcat ctaatgtgtc agatgaaaag gccgaggcaa   3660
ttgcgtgaag attttatctc aaaattgttt ggggaagaaa aaggtctagg tgctagtgat   3720
gtaaagccaa gtttcatgag ggactggttc cataaaaaaa cgattcttct cgttcttgat   3780
gacgtgagta atgccagaga tgcagaagct gtaatcggag ggtttggctg gttttctcat   3840
ggacacagaa tcatcttaac ctctaggagt aaacaagttc ttgtacagtg taaggttaaa   3900
aagccatacg agatccaaaa attaagcgat tttgaatcgt ttcgtctctg caaacaatat   3960
ttggatggcg aaaatccggt catctctgag cttatcagct gcagtagtgg tattccattg   4020
gctctcaaac tttagttttc ctctgtatca aagcagtata taacgaatat gaaagaccat   4080
ctccaaagct tgaggaaaga tcctcctact cagattcaag aagcatttcg gagaagtttt   4140
gatggactag atgaaaacga gaaaaacata ttttggatc ttgcatgttt ttcaggggg   4200 cagagcaaag attatgcggt gctattactt gatgcttgtg gttttttac atatatggga   4260 atctgtgagc tcattgacga gtcactcatt agccttgtag acaacaagat agagatgcct   4320
attccttttc aagacatggg ccgaattatt gttcatgaag aagatgagga tccatgtgaa   4380
cgtagcagat tgtgggactc gaaggacatc gttgatgttt tgacaaacaa ttcagtaagt   4440
```

```
cgaactgtgt ttagttcttt taacacttca gatacttcgt gcattcgtgg ttatcctttc    4500
tttagttgta acaggtgagg gtttcttact tatgtgattg tttttgtcag ggaacagaag    4560
caattgaggg catcttcctg gatgcgtctg acttgacctg cgagcttagt cctactgtgt    4620
ttggtaagat gtataatctt agattgctga agttctattg ttcaacctct gggaaccagt    4680
gcaagcttac tctacctcac ggcctagaca ctttgcctga tgagctaagt ctacttcact    4740
gggagaatta ccctctggtt tacttgcctc agaaatttaa tcctgtgaac cttgtagagt    4800
taaacatgcc ttatagcaac atggagaagt tgtgggaagg aaagaaagta agtgttgaca    4860
ttatggtttt taaagctgct tgcatgaatt ataaccttg catctgatga ctaatcttgg     4920
ttattgatgt tgtaaataga atctcgagaa gctaaagaac atcaaactga gtcactccag    4980
agaattaact gatatcctga tgttatcaga agccctgaac ctggaacaca ttgatctcga    5040
agggtgtacg agtctgattg atgttagcat gtctattcct tgttgtggga agcttgtttc    5100
cttgaatatg aaagactgtt ctcgtttgcg aagtctgcct tctatggttg atttaacaac    5160
tctcaagctt cttaatttgt ctggctgctc agaatttgag gatattcagg attttgcacc    5220
aaacctggaa gagatatatc tagctgggac atccattaga gagcttccgt tgtcaatcag    5280
gaatctcact gaacttgtta cgctagatct ggagaactgc gaaaggcttc aggaaatgcc    5340
gagtcttccg gtggaaataa tcaggagaac ctgaaaaaac gcagaaatca cctctcaatc    5400
cctgttctac caagggattg tgatgtaatt gtggtatatt ctcggaccgt gtattctcta    5460
tcttatttcc caaacgtttt tgtagattag gcaggaaag gaaaaatcct aattgacaca     5520
gatttgttaa tagatttaga tgatcattgt gttttaataa tattattgtt atttgttgta    5580
ttttaacagt tctataatga taattgtgat ctcaaaatct cgtttattat tagactttgt    5640
gtaaatttga ttctaaagca aacttagtct gaattctggt gcatacctcg gtattatttt    5700
gttttattgg agacggtgtt aatgttatca tgatcctcat tgttttctta tgatatcaaa    5760
ctccaaatct gtaacattaa aagttaagaa atagctagtt gtttagaaga ctaaacacaa    5820
aaagtaaagc atgaaaagaa ccatgattaa acaaagccat ataaatctac ttttcaataa    5880
gtgttttaaa aacatgtcta ggtagccgtt tagagcatct ccatcagtag tgaaaaagta    5940
ggagatagag tcatagaggt atttgagaaa cttagaccat ccacattgca tatatttttt    6000
gtgtgtcttt tcatataaat attattaata aagtatgaat agtctttta agacccattt     6060 atcaatgtat ctcaaaatgt cttctttgag accttttgg agagatgtct ttcatttaaa     6120
gaccctcata ttatttaata aattaaattt atgtgggaag acatttaaac tgaatgtgca    6180
atgtggatgc tctaaagcaa ctgtctttcc atgtgtcttt atattattgg ccaaaatcta    6240 ctttttataat tcaaaattta aataaataac ttaattatta taaattgatt aacataatat   6300
tgttgataaa cccacacagt ataagaccga tggagatggt cttaggcccc gcttagacgc    6360
gtagacgacc aagatttgta taagtttgt tttaacgttt tttcaatttt taattacata     6420 aagtttatt ataagttcta gcttcattgt ttaatatgaa ttgaagaaag tgagatttgt     6480
aaaattaacc tttttttact acttttttgc aataatacct tttatgttg tccattttta     6540 aaaatactca tttccttgaa tagaatgacc aaattaccct catctaatag aacatgtaa     6600 ttggaaactg aaattttttcc gcaaaaaaaa aaatcccgcc aaactttttt tccgccaaaa    6660
caaaaaattc ccgccaaaaa aaaaattccc ggcaaatatc tttttcataa caatctttt     6720 ctcagccaaa aaatacttt taaaaatcct tgtaaattta agtaatagaa gagtctaagt     6780
```

-continued

| | |
|---|---|
| ttaaattaaa gaatttaata taaatttaaa caaaacttag ataaacattt aaagtaaaca | 6840 |
| aaacttagat aaacttatat tttgaaatta caaatattta attttacata tagttttttt | 6900 |
| tctatattta aaagttattc tttcttaaat tattaaaaaa atactgaaac ttaaagaata | 6960 |
| ttgaaaatta aatatactaa ataataataa aacttaata tttatggtgt atgaactaaa | 7020 |
| attaaatata tgaactaaaa ctaacttggt atccttttta gttttgttat ttttaattta | 7080 |
| ttgcataagt ttttaattaa atgaatattg ctatttgtta gtatatatat tcgttgttac | 7140 |
| aaatatatct acgtgttgtc gtagctcagc ggtagagctc ataaaaccac gtcgttttga | 7200 |
| tttaacagaa aattctaaca aaaagttaac tccgtttaca aaaatttcac ggcatgccca | 7260 |
| caatggccca atcaacaaaa tttgactatt taatcaaaaa atcaaaaaaa agttttatga | 7320 |
| tttaaatgac atttcgaaag ttcagatctt tttcattcca aatttaaaag ctagcacttt | 7380 |
| tttcgacatt tttcctttct aaaatttgga taaaattgca atgcaatttg taatattaaa | 7440 |
| cattgttaag tataagtatg acttttatt tatttggatc cagaatcatt tactttttc | 7500 |
| ttatattatt ttttgaacaa atactttaat ttaagtcgaa gggaacattc acttacata | 7560 |
| ttttttttct ttatgaattg agtaaattat gtctgctttt aagattagaa tcacaacata | 7620 |
| tacaacaaaa gcattagatt ttaatttata taaactgatt caaaaaaaat ctaaaaatag | 7680 |
| gttcat | 7686 |

<210> SEQ ID NO 11
<211> LENGTH: 5912
<212> TYPE: DNA
<213> ORGANISM: Arabidopsis thaliana
<220> FEATURE:
<221> NAME/KEY: source
<222> LOCATION: 1..5912
<223> OTHER INFORMATION: /organism="Arabidopsis thaliana"
     /mol_type="unassigned DNA"

<400> SEQUENCE: 11

| | |
|---|---|
| actggatagg cctttatctt tcattcttgg ggtttcgcat ctcttccact aatttatttg | 60 |
| agatggaatt ccattgagaa tattcgtctc ttctttcttt cgttctcaat tcccatccca | 120 |
| tattcccat ggcagcttct ttttgcggca gccggagata cgatgttttc ccgagcttca | 180 |
| gtaaggtaga tgtccgcagg tcattcctcg cgcatcttct caaggagctc gaccgcagat | 240 |
| taatcaatac gttcacagat catggtatgg agagaaacct cccaatcgac gctgaacttt | 300 |
| tatcggcgat agcagaatcg aggatctcaa tagtcatctt ctctaaaaac tatgcttctt | 360 |
| ccacgtggtg cttagatgaa ttggttgaga tccacacgtg ttataaggaa ttggctcaaa | 420 |
| tagtggttcc ggttttcttt aacgtacatc cttcgcaagt taaaaaacag accggagaat | 480 |
| ttggtaaggt ttttggaaag acatgcaaag gtaaaccaga gaatcggaaa ctaagatgga | 540 |
| tgcaagctct agcagcggta gcaaatattg ctggatatga tcttcagaac tggtattttc | 600 |
| ttttccattc caaccctaat atatatatgt gcctgtgttc aattttgggg tgcctcttta | 660 |
| atgacaaaat tgactattgt tattaggcct gatgaagctg tcatgattga gatggtagct | 720 |
| gacgatgttt cgaaaaaact ttttaaatca tcgaatgatt tcagtgatat cgtcgggatt | 780 |
| gaagctcatt tagaggcaat gagttcaata ttgcgcttga aatctgagaa agctagaatg | 840 |
| gtcgggattt cggggccttc agggattggt aagactacca tcgcaaaagc tcttttcagt | 900 |
| aaactctctc cccaattcca ccttcgtgct ttcgttactt ataaaagaac caaccaggac | 960 |
| gactatgaca tgaagttgtg ttggatagaa aaatttctgt cagaaattct tggtcaaaag | 1020 |

```
gacttgaagg ttttggattt aggtgcggtg gaacaaagtc taatgcacaa gaaagttctt   1080
atcattcttg acgatgtaga tgatcttgag ctattaaaga ccttggtggg acaaactgga   1140
tggttcgggt ttggaagcag aattgttgtg atcactcagg ataggcagct tctcaaggct   1200
catgatatta acctcatata tgaggtggcc ttcccatctg cccatcttgc tcttgagatt   1260
ttctgccaat ctgcttttgg gaaaatatat ccaccatctg attttagaga actctctgtt   1320
gaatttgcat atcttgccgg caatcttcct ttggatctta gggtcttggg tttggccatg   1380
aaaggaaagc acagggagga gtggatagag atgctgccta ggctccgaaa tgatttggac   1440
gggaaattta agaaaacatt gagaaattac ctgcctgtga tacggaagcg cgtttccaat   1500
gaagaagggg gccgtgagaa attgaaaaag ggaaataaaa agttggattt ggatgaggag   1560
tttcctggtg gagaaattta cagtgatgag ataccttcgc caacatctaa ctggaaagat   1620
acagatgact ttgattcagg ggacatcatt ccaatcattg cagacaaatc tactactata   1680
attcccaaca ggaggcactc gaacgatgac tggtgttctt tctgtgagtt cctcagaaac   1740 cgtataccccc cgttgaatcc ctttaaatgt agtgccaatg atgtcattga tttttcttcgc   1800 acacggcagg ttttaggcag cactgaggct ctcgttgacc gcctcatttt cagtagtgag   1860
gcatttggca taaaacctga ggaaaaccct tttcgcagcc aagctgtaac atcgtacttg   1920
aaggcggcca gggatatgac acgagaaaaa gaatgcatac ttgtgttttc gtgccacgac   1980
aaccttgatg tagatgaaac atctttcatt gaagccatct caaaagaatt gcacaagcag   2040
gggttcatcc ctttgacata taatcttttg ggcagagaga acctcgatga ggagatgtta   2100
tacgatctag agtcggtat catgatactt tcaagtagtt atgtttcttc tagacagtcc   2160
ctggatcacc tggttgcagt tatggagcat tggaaaacaa cagaccttgt aattattcct   2220
atatatttta agtaagact tcagacatt tgtgggttga aaggcaggtt tgaagcagcg   2280
tttctgcagc ttcatatgtc tctccaggaa gacagagttc agaaatggaa ggcggctatg   2340
tctgaaatag tgtccatcgg tggacatgaa tggaccaagg ggtatattta cttatctttg   2400
ttgtcccttt actattcaaa gctagtttat taatatttgg aagagtattt cttattggtg   2460
tggtgctaaa tcagtacttc cattttctct gtcctatttg cagaagtcag tttattcttg   2520
ccgaggaagt tgtaagaaat gcatccttaa ggctatatct gaaaagtagc aagaatctgc   2580
ttggaatctt agcgttgtta aatcactccc agtctacaga cgtggaaatt atgggaatct   2640
ggggtatagc aggaataggt aagacatcga ttgcaagaga aatatttgaa ttacatgctc   2700
cacattatga tttctgttac ttcctgcaag actttcatct aatgtgtcag atgaaaaggc   2760
cgaggcaatt gcgtgaagat tttatctcaa aattgtttgg ggaagaaaaa ggtctaggtg   2820
ctagtgatgt aaagccaagt ttcatgaggg actggttcca taaaaaaacg attcttctcg   2880
ttcttgatga cgtgagtaat gccagagatg cagaagctgt aatcggaggg tttggctggt   2940
tttctcatgg acacagaatc atcttaacct ctaggagtaa acaagttctt gtacagtgta   3000
aggttaaaaa gccatacgag atccaaaaat taagcgattt tgaatcgttt cgtctctgca   3060
aacaatattt ggatggcgaa aatccggtca tctctgagct tatcagctgc agtagtggta   3120
ttccattggc tctcaaactt ttagtttcct ctgtatcaaa gcagtatata acgaatatga   3180
aagaccatct ccaaagcttg aggaaagatc ctcctactca gattcaagaa gcatttcgga   3240
gaagttttga tggactagat gaaaacgaga aaaacatatt tttggatctt gcatgttttt   3300
tcagggggca gagcaaagat tatgcggtgc tattacttga tgcttgtggt tttttacat   3360 atatgggaat ctgtgagctc attgacgagt cactcattag ccttgtagac aacaagatag   3420
```

```
agatgcctat tccttttcaa gacatgggcc gaattattgt tcatgaagaa gatgaggatc   3480
catgtgaacg tagcagattg tgggactcga aggacatcgt tgatgttttg acaaacaatt   3540
cagtaagtcg aactgtgttt agttctttta acacttcaga tacttcgtgc attcgtggtt   3600
atcctttctt tagttgtaac aggtgagggt ttcttactta tgtgattgtt tttgtcaggg   3660
aacagaagca attgagggca tcttcctgga tgcgtctgac ttgacctgcg agcttagtcc   3720
tactgtgttt ggtaagatgt ataatcttag attgctgaag ttctattgtt caacctctgg   3780
gaaccagtgc aagcttactc tacctcacgg cctagacact ttgcctgatg agctaagtct   3840
acttcactgg gagaattacc ctctggttta cttgcctcag aaatttaatc ctgtgaacct   3900
tgtagagtta acatgcctt atagcaacat ggagaagttg tgggaaggaa agaaagtaag   3960
tgttgacatt atggttttta aagctgcttg catgaattta taaccttgca tctgatgact   4020
aatcttggtt attgatgttg taaatagaat ctcgagaagc taaagaacat caaactgagt   4080
cactccagag aattaactga tatcctgatg ttatcagaag ccctgaacct ggaacacatt   4140
gatctcgaag ggtgtacgag tctgattgat gttagcatgt ctattccttg ttgtgggaag   4200
cttgtttcct tgaatatgaa agactgttct cgtttgcgaa gtctgccttc tatggttgat   4260
ttaacaactc tcaagcttct taatttgtct ggctgctcag aatttgagga tattcaggat   4320
tttgcaccaa acctggaaga gatatatcta gctgggacat ccattagaga gcttccgttg   4380
tcaatcagga atctcactga acttgttacg ctagatctgg agaactgcga aaggcttcag   4440
gaaatgccga gtcttccggt ggaaataatc aggagaacct gaaaaaacgc agaaatcacc   4500
tctcaatccc tgttctacca agggattgtg atgtaattgt ggtatattct cggaccgtgt   4560
attctctatc ttatttccca aacgtttttg tagattaggc aaggaaagga aaatcctaa   4620
ttgacacaga tttgttaata gatttagatg atcattgtgt tttaataata ttattgttat   4680
ttgttgtatt ttaacagttc tataatgata attgtgatct caaaatctcg tttattatta   4740
gactttgtgt aaatttgatt ctaaagcaaa cttagtctga attctggtgc ataccctcggt   4800
attattttgt tttattggag acggtgttaa tgttatcatg atcctcattg tttctctatg   4860
atatcaaact ccaaatctgt aacattaaaa gttaagaaat agctagttgt ttagaagact   4920
aaacacaaaa agtaaagcat gaaaagaacc atgattaaac aaagccatat aaatctactt   4980
ttcaataagt gttttaaaaa catgtctagg tagccgttta gagcatctcc atcagtagtg   5040
aaaaagtagg agatagagtc atagaggtat ttgagaaact tagaccatcc acattgcata   5100
tatttttgt gtgtctttc atataaatat tattaataaa gtatgaatag tcttttaag   5160
acccatttat caatgtatct caaaatgtct tctttgagac cttttggag agatgtcttt   5220
catttaaaga ccctcatatt atttaataaa ttaaatttat gtgggaagac atttaaactg   5280
aatgtgcaat gtggatgctc taaagcaact gtctttccat gtgtctttat attattggcc   5340
aaaatctact tttataattc aaaatttaaa taaataactt aattattata aattgattaa   5400
cataatattg ttgataaacc cacacagtat aagaccgatg gagatggtct taggccccgc   5460
ttagacgcgt agacgaccaa gatttgtata agttttgttt taacgttttt tcaattttta   5520
attacataaa gttatttat aagttctagc ttcattgttt aatatgaatt gaagaaagtg   5580
agatttgtaa aattaacctt ttttactac ttttttgcaa taataccttt ttatgttgtc   5640
catttttaaa aatactcatt tccttgaata gaatgaccaa attaccctca tctaatagga   5700
acatgtaatt ggaaactgaa attttccgc aaaaaaaaaa atcccgccaa actttttttc   5760
```

```
cgccaaaaca aaaaattccc gccaaaaaaa aaattcccgg caaatatctt tttcataaca    5820
aatcttttct cagccaaaaa aatactttta aaaatccttg taaatttaaa gtaatagaga    5880
gtctaagttt aaattaaaga atttaatata aa                                 5912
```

```
<210> SEQ ID NO 12
<211> LENGTH: 26
<212> TYPE: DNA
<213> ORGANISM: Artificial sequence
<220> FEATURE:
<221> NAME/KEY: source
<222> LOCATION: 1..26
<223> OTHER INFORMATION: /organism="Artificial sequence"
      /note="HCP4 forward primer"
      /mol_type="unassigned DNA"

<400> SEQUENCE: 12
aaggtaccat ggcagcttct ttttgc                                          26

<210> SEQ ID NO 13
<211> LENGTH: 26
<212> TYPE: DNA
<213> ORGANISM: Artificial sequence
<220> FEATURE:
<221> NAME/KEY: source
<222> LOCATION: 1..26
<223> OTHER INFORMATION: /organism="Artificial sequence"
      /note="HCP4 reverse primer"
      /mol_type="unassigned DNA"

<400> SEQUENCE: 13
ccgtcgactc aggttctcct gattat                                          26

<210> SEQ ID NO 14
<211> LENGTH: 4024
<212> TYPE: DNA
<213> ORGANISM: Arabidopsis thaliana
<220> FEATURE:
<221> NAME/KEY: source
<222> LOCATION: 1..4024
<223> OTHER INFORMATION: /organism="Arabidopsis thaliana"
      /mol_type="unassigned DNA"

<400> SEQUENCE: 14
atggcagctt cttttttgcgg cagccggaga tacgatgttt tcccgagctt cagtaaggta     60
gatgtccgca ggtcattcct cgcgcatctt ctcaaggagc tcgaccgcag attaatcaat    120
acgttcacag atcatggtat ggagagaaac ctcccaatcg acgctgaact tttatcggcg    180
atagcagaat cgaggatctc aatagtcatc ttctctaaaa actatgcttc ttccacgtgg    240
tgcttagatg aattggttga gatccacacg tgttataagg aattggctca aatagtggtt    300 ccggtttttct ttaacgtaca tccttcgcaa gttaaaaaac agaccggaga atttggtaag    360 gttttttggaa agacatgcaa aggtaaacca gagaatcgga aactaagatg gatgcaagct    420
ctagcagcgg tagcaaatat tgctggatat gatcttcaga actggtatttt tcttttccat    480 tccaacccta atatatatat gtgcctgtgt tcaattttgg ggtgcctctt taatgacaaa    540
attgactatt gttattaggc ctgatgaagc tgtcatgatt gagatggtag ctgacgatgt    600
ttcgaaaaaa cttttttaaat catcgaatga tttcagtgat atcgtcggga ttgaagctca    660
tttagaggca atgagttcaa tattgcgctt gaaatctgag aaagctagaa tggtcgggat    720
ttcggggcct tcaggattg gtaagactac tatcgcaaaa gctctttca gtaaactctc     780 tccccaattc caccttcgtg ctttcgttac ttataaaaga accaaccagg acgactatga    840
```

| | |
|---|---|
| catgaagttg tgttggatag aaaaatttct gtcagaaatt cttggtcaaa aggacttgaa | 900 |
| ggttttggat ttaggtgcgg tggaacaaag tctaatgcac aagaaagttc ttatcattct | 960 |
| tgacgatgta gatgatcttg agctattaaa gaccttggtg ggacaaactg gatggttcgg | 1020 |
| gtttggaagc agaattgttg tgatcactca ggataggcag cttctcaagg ctcacgatat | 1080 |
| taacctcata tacgaggtgg ccttcccatc tgcccacctt gctcttgaga ttttctgcca | 1140 |
| atctgctttt gggaaaatat atccaccatc tgattttaga gaactctctg ttgaatttgc | 1200 |
| atatcttgcc ggcaatcttc ctttggatct tagggtcttg ggtttggcga tgaaaggaaa | 1260 |
| gcacagggag gagtggatag agatgctgcc taggctccga aatgatttgg acgggaaatt | 1320 |
| taagaaaaca ttgagaaatt acctgcctgt gatacggaag cgcgtttcca atgaagaagg | 1380 |
| gggccgtgag aaattgaaaa agggaaataa aaagttggat ttggacgagg agtttcctgg | 1440 |
| tggagaaatt tacagtgacg agataccttc gccaacttct aactggaaag atacagatga | 1500 |
| ctttgattca ggggacatca ttccaatcat tgcagacaaa tctactacta taattcccaa | 1560 |
| caggaggcac tcgaacgatg actggtgttc tttctgtgag ttcctcagaa accgtatacc | 1620 |
| cccgttgaat ccctttaaat gtagtgccaa tgatgttatt gattttcttc gcacacggca | 1680 |
| ggttttaggc agcactgagg ctctcgttga ccgccttatt ttcagtagtg aggcatttgg | 1740 |
| tataaaacct gaggaaaacc cttttcgcag ccaagctgta acatcgtact gaaggcggc | 1800 |
| cagggatatg acacgagaaa aagaatgtat acttgtgttt tcgtgccacg caaccttga | 1860 |
| tgtagatgaa acttctttta ttgaagcgat ctcaaaagaa ttgcacaagc aggggtttat | 1920 |
| ccctttgaca tataatcttt tgggcagaga gaacctcgat gaggagatgt tatacggatc | 1980 |
| tagagtcggt ataatgatac tttcaagtag ttatgtttct tctagacagt ccctggatca | 2040 |
| cctggttgca gttatggagc attggaaaac aacagacctt gtaattattc ctatatattt | 2100 |
| taaagtaaga ctttcagaca tttgtgggtt gaaaggcagg tttgaagcag cgtttctgca | 2160 |
| gcttcatatg tctctccagg aagacagagt tcagaaatgg aaggcggcta tgtctgaaat | 2220 |
| agtgtccatc ggtggacacg aatggaccaa gggaagtcag tttattcttg ccgaggaagt | 2280 |
| tgtaagaaat gcatccttaa ggctatatct gaaaagtagc aagaatctgc ttggaatctt | 2340 |
| agcgttgtta aatcactccc agtctacaga cgtggaaatt atgggaatct ggggtatagc | 2400 |
| aggaataggt aagacatcga ttgcaagaga aatatttgaa ttacatgctc cacatattga | 2460 |
| tttctgttac ttcctgcaag actttcatct aatgtgtcag atgaaaaggc cgaggcaatt | 2520 |
| gcgtgaagat tttatctcaa aattgttttg ggaagaaaaa ggtctaggtg ctagtgatgt | 2580 |
| aaagccaagt tttatgaggg actggttcca taaaaaaacg attcttctcg ttcttgatga | 2640 |
| cgtgagtaat gccagagatg cagaagctgt aatcggaggg tttggctggt tttctcacgg | 2700 |
| acacagaatc atcttaacct ctaggagtaa acaagttctt gtacagtgta aggttaaaaa | 2760 |
| gccatacgag atccaaaaat taagcgattt tgaatcgttt cgtctctgca acaatatttt | 2820 |
| ggatggcgaa aatccggtta tctctgagct tatcagctgc agtagtggta ttccattggc | 2880 |
| tctcaaactt ttagtttcct ctgtatcaaa gcagtatata acgaatatga agaccatct | 2940 |
| ccaaagcttg aggaaagatc ctcctactca gattcaagaa gcatttcgga gaagttttga | 3000 |
| tggactagac gaaaacgaga aaaacatatt tttggatctt gcatgttttt tcagggggca | 3060 |
| gagcaaagat tatgcggtgc tattacttga tgcttgtggt tttttttacat atatgggaat | 3120 |
| ctgtgagctc attgacagt cactcattag ccttgtagac aacaagatag agatgcctat | 3180 |
| tcctttttcaa gacatgggcc gaattattgt tcatgaagaa gatgaggatc catgtgaacg | 3240 |

```
tagcagattg tgggactcga aggacatcgt tgatgttttg acaaacaatt caggaacaga      3300
agcaattgag gggatcttcc tggatgcgtc tgacttgacc tgcgagctta gtcctactgt      3360
gtttggtaag atgtataatc ttagattgct gaagttctat tgttcaacct ctgggaacca      3420
gtgcaagctt actctacctc acggcctaga cactttgcct gatgagctaa gtctacttca      3480
ctgggagaat taccctctgg tttacttgcc tcagaaattt aatcctgtga accttgtaga      3540
gttaaacatg ccttatagca acatggagaa gttgtgggaa ggaaagaaaa atctcgagaa      3600
gctaaagaac atcaaactga gtcactccag agaattaact gatatcctga tgttatcaga      3660
agccctgaac ctgaacaca ttgatctcga agggtacg agtctgattg atgttagtat         3720
gtctattcct tgttgtggga agcttgtttc cttgaatatg aaagactgtt ctcgtttgcg      3780
aagtctgcct tctatggttg atttaacaac tctcaagctt cttaatttgt ctggctgctc      3840
agaatttgag gatattcagg attttgcacc aaacctggaa gagatatatc tagctgggac      3900
atccattaga gagcttccgt tgtcaatcag gaatctcact gaacttgtta cgctagatct      3960
ggagaactgc gaaagacttc aggaaatgcc gagtcttccg gtggaaataa tcaggagaac      4020
ctga                                                                  4024
```

<210> SEQ ID NO 15
<211> LENGTH: 814
<212> TYPE: DNA
<213> ORGANISM: Arabidopsis thaliana
<220> FEATURE:
<221> NAME/KEY: source
<222> LOCATION: 1..814
<223> OTHER INFORMATION: /organism="Arabidopsis thaliana"
        /mol_type="unassigned DNA"

<400> SEQUENCE: 15

```
gactttcatc taatgtgtca gatgaaaagg ccgaggcaat tgcgtgaaga ttttatctca       60
aaattgtttg gggaagaaaa aggtctaggt gctagtgatg taaagccaag tttcatgagg      120
gactggttcc ataaaaaaac gattcttctc gttcttgatg acgtgagtaa tgccagagat      180
gcagaagctg taatcggagg gtttggctgg tttttctcatg acacagaat catcttaacc      240 tctaggagta acaagttct tgtacagtgt aaggttaaaa agccatacga gatccaaaaa       300
ttaagcgatt ttgaatcgtt tcgtctctgc aaacaatatt tggatggcga aaatccggtc     360
atctctgagc ttatcagctg cagtagtggt attccattgg ctctcaaact tttagtttcc      420
tctgtatcaa agcagtatat aacgaatatg aagaccatc tccaaagctt gaggaaagat       480
cctcctactc agattcaaga agcatttcgg agaagttttg atggactaga tgaaaacgag     540
aaaaacatat ttttggatct tgcatgtttt tcagggggc agagcaaaga ttatgcggtg     600
ctattacttg atgcttgtgg tttttttaca tatatgggaa tctgtgagct cattgacgag    660
tcactcatta gccttgtaga caacaagata gagatgccta ttccttttca agacatgggc     720
cgaattattg ttcatgaaga agatgaggat ccatgtgaac gtagcagatt gtgggactcg    780
aaggacatcg ttgatgtttt gacaaacaat tcag                                 814
```

<210> SEQ ID NO 16
<211> LENGTH: 1040
<212> TYPE: DNA
<213> ORGANISM: Arabidopsis thaliana
<220> FEATURE:
<221> NAME/KEY: source
<222> LOCATION: 1..1040
<223> OTHER INFORMATION: /organism="Arabidopsis thaliana"

```
        /mol_type="unassigned DNA"

<400> SEQUENCE: 16
aagtcagttt attcttgccg aggaagttgt aagaaatgca tccttaaggc tatatctgaa      60
aagtagcaag aatctgcttg gaatcttagc gttgttaaat cactcccagt ctacagacgt     120
ggaaattatg ggaatctggg gtatagcagg aataggtaag acatcgattg caagagaaat     180
atttgaatta catgctccac attatgattt ctgttacttc ctgcaagact ttcatctaat     240
gtgtcagatg aaaaggccga ggcaattgcg tgaagatttt atctcaaaat gtttgggga      300 agaaaaaggt ctaggtgcta gtgatgtaaa gccaagtttc atgagggact ggttccataa     360
aaaaacgatt cttctcgttc ttgatgacgt gagtaatgcc agagatgcag aagctgtaat     420
cggagggttt ggctggtttt ctcatggaca cagaatcatc ttaacctcta ggagtaaaca     480
agttcttgta cagtgtaagg ttaaaaagcc atacgagatc caaaaattaa gcgattttga     540
atcgtttcgt ctctgcaaac aatatttgga tggcgaaaat ccggtcatct ctgagcttat     600
cagctgcagt agtggtattc cattggctct caaactttta gtttcctctg tatcaaagca     660
gtatataacg aatatgaaag accatctcca aagcttgagg aaagatcctc ctactcagat     720
tcaagaagca tttcggagaa gttttgatgg actagatgaa aacgagaaaa acatattttt     780
ggatcttgca tgttttttca gggggcagag caaagattat gcggtgctat acttgatgc      840 ttgtggtttt tttacatata tgggaatctg tgagctcatt gacgagtcac tcattagcct     900
tgtagacaac aagatagaga tgcctattcc tttcaagac atgggccgaa ttattgttca      960
tgaagaagat gaggatccat gtgaacgtag cagattgtgg gactcgaagg acatcgttga    1020
tgttttgaca aacaattcag                                                1040

<210> SEQ ID NO 17
<211> LENGTH: 271
<212> TYPE: PRT
<213> ORGANISM: Arabidopsis thaliana

<400> SEQUENCE: 17

Asp Phe His Leu Met Cys Gln Met Lys Arg Pro Arg Gln Leu Arg Glu
1               5                   10                  15

Asp Phe Ile Ser Lys Leu Phe Gly Glu Glu Lys Gly Leu Gly Ala Ser
            20                  25                  30

Asp Val Lys Pro Ser Phe Met Arg Asp Trp Phe His Lys Lys Thr Ile
        35                  40                  45

Leu Leu Val Leu Asp Asp Val Ser Asn Ala Arg Asp Ala Glu Ala Val
    50                  55                  60

Ile Gly Gly Phe Gly Trp Phe Ser His Gly His Arg Ile Ile Leu Thr
65                  70                  75                  80

Ser Arg Ser Lys Gln Val Leu Gln Cys Lys Val Lys Lys Pro Tyr
                85                  90                  95

Glu Ile Gln Lys Leu Ser Asp Phe Glu Ser Arg Leu Cys Lys Gln
            100                 105                 110

Tyr Leu Asp Gly Glu Asn Pro Val Ile Ser Glu Leu Ile Ser Cys Ser
        115                 120                 125

Ser Gly Ile Pro Leu Ala Leu Lys Leu Leu Val Ser Ser Val Ser Lys
    130                 135                 140

Gln Tyr Ile Thr Asn Met Lys Asp His Leu Gln Ser Leu Arg Lys Asp
145                 150                 155                 160

Pro Pro Thr Gln Ile Gln Glu Ala Phe Arg Arg Ser Phe Asp Gly Leu
```

165                 170                 175
Asp Glu Asn Glu Lys Asn Ile Phe Leu Asp Leu Ala Cys Phe Phe Arg
            180                 185                 190

Gly Gln Ser Lys Asp Tyr Ala Val Leu Leu Asp Ala Cys Gly Phe
            195                 200                 205

Phe Thr Tyr Met Gly Ile Cys Glu Leu Ile Asp Glu Ser Leu Ile Ser
210                 215                 220

Leu Val Asp Asn Lys Ile Glu Met Pro Ile Pro Phe Gln Asp Met Gly
225                 230                 235                 240

Arg Ile Ile Val His Glu Glu Asp Pro Cys Glu Arg Ser Arg
            245                 250                 255

Leu Trp Asp Ser Lys Asp Ile Val Asp Val Leu Thr Asn Asn Ser
            260                 265                 270

<210> SEQ ID NO 18
<211> LENGTH: 346
<212> TYPE: PRT
<213> ORGANISM: Arabidopsis thaliana

<400> SEQUENCE: 18

Ser Gln Phe Ile Leu Ala Glu Glu Val Val Arg Asn Ala Ser Leu Arg
1               5                   10                  15

Leu Tyr Leu Lys Ser Ser Lys Asn Leu Leu Gly Ile Leu Ala Leu Leu
            20                  25                  30

Asn His Ser Gln Ser Thr Asp Val Glu Ile Met Gly Ile Trp Gly Ile
            35                  40                  45

Ala Gly Ile Gly Lys Thr Ser Ile Ala Arg Glu Ile Phe Glu Leu His
        50                  55                  60

Ala Pro His Tyr Asp Phe Cys Tyr Phe Leu Gln Asp Phe His Leu Met
65                  70                  75                  80

Cys Gln Met Lys Arg Pro Arg Gln Leu Arg Glu Asp Phe Ile Ser Lys
            85                  90                  95

Leu Phe Gly Glu Glu Lys Gly Leu Gly Ala Ser Asp Val Lys Pro Ser
            100                 105                 110

Phe Met Arg Asp Trp Phe His Lys Lys Thr Ile Leu Leu Val Leu Asp
            115                 120                 125

Asp Val Ser Asn Ala Arg Asp Ala Glu Ala Val Ile Gly Gly Phe Gly
            130                 135                 140

Trp Phe Ser His Gly His Arg Ile Ile Leu Thr Ser Arg Ser Lys Gln
145                 150                 155                 160

Val Leu Val Gln Cys Lys Val Lys Pro Tyr Glu Ile Gln Lys Leu
            165                 170                 175

Ser Asp Phe Glu Ser Phe Arg Leu Cys Lys Gln Tyr Leu Asp Gly Glu
            180                 185                 190

Asn Pro Val Ile Ser Glu Leu Ile Ser Cys Ser Gly Ile Pro Leu
            195                 200                 205

Ala Leu Lys Leu Leu Val Ser Val Ser Lys Gln Tyr Ile Thr Asn
            210                 215                 220

Met Lys Asp His Leu Gln Ser Leu Arg Lys Asp Pro Pro Thr Gln Ile
225                 230                 235                 240

Gln Glu Ala Phe Arg Arg Ser Phe Asp Gly Leu Asp Glu Asn Glu Lys
            245                 250                 255

Asn Ile Phe Leu Asp Leu Ala Cys Phe Phe Arg Gly Gln Ser Lys Asp
            260                 265                 270

Tyr Ala Val Leu Leu Asp Ala Cys Gly Phe Phe Thr Tyr Met Gly
                275                 280                 285

Ile Cys Glu Leu Ile Asp Glu Ser Leu Ile Ser Leu Val Asp Asn Lys
    290                 295                 300

Ile Glu Met Pro Ile Pro Phe Gln Asp Met Gly Arg Ile Ile Val His
305                 310                 315                 320

Glu Glu Asp Glu Asp Pro Cys Glu Arg Ser Arg Leu Trp Asp Ser Lys
                325                 330                 335

Asp Ile Val Asp Val Leu Thr Asn Asn Ser
            340                 345

<210> SEQ ID NO 19
<211> LENGTH: 4024
<212> TYPE: DNA
<213> ORGANISM: Artificial Sequence
<220> FEATURE:
<221> NAME/KEY: source
<222> LOCATION: 1..4024
<223> OTHER INFORMATION: /organism="Artificial Sequence"
      /note="Nucleotide sequence HCP4, variant 1"
      /mol_type="unassigned DNA"

<400> SEQUENCE: 19
atggcggcaa gtttctgtgg gagtcgccgc tatgacgtgt tccatcgtt ttccaaagtt      60 gacgttcgtc ggtcctttct agcacactta cttaaagaac tggatcggcg cctcataaac     120
acatttaccg accacggcat ggaacggaac ctacctatag atgccgagct gctgtcagca     180
attgccgagt cacggataag cattgttatt tttagcaaga attacgcgtc gtcaacttgg     240
tgtctggacg agatggtaga aatacatact tgctacaaag atggcgca gattgttgtc       300 cccgtatttt tcaatgtgca ccccagtcag gtaaaaaagc aaactggcga gttcgggaaa     360
gtattcggca aaacttgtaa aggaaagccc gaaaaccgca agctccgatg gatgcaggcc     420
ctcgctgccg ttgccaacat agcagggtac gacttacaaa attggtattt tcttttccat     480
tccaacccta atatatatat gtgcctgtgt tcaattttgg ggtgcctctt taatgacaaa     540
attgactatt gttattaggc ctgatgatca tgccacgact aagacggatc atagagatgc     600
tttgagaaga ccttctaaat tattgagtga ttccaatagt acagaagaga ctgatcatcc     660
tttcgtggga acgaatttaa tatagctcta gagatatagg agtcatgaaa cgggcgggac     720
tttggtgctt ttcgcgactg gtaagattat tacaggaagt catcgttcca atgaacattg     780
agccccatac ctccgtcctg tttccgatat ttgtaaaaaa atcagcccgg taggctgtga     840
cacgaggtcg taatggacag gaagatctca gtacgcaatt cgtggtccaa ggggctcgag     900
ggctttgggt tcaggtgtgg cggcaccaaa tcaaacgctc aggagtcatc atatcacagc     960
tagagatgcc gttagtcgta agcgataaag gatttagggg gtaccaattg gatggtccgt    1020
gtatggaaac aaaactgctg cgaccatagc ggttgagcgg caagccaggg ttccagatat    1080
tagccccaca ttcggggagg tttacctata tgtccgccct gtagttgaga cttcatgcct    1140
atttgtttct gggagaacat ttcgacgatt tagttctgac gcacattatg ctgaatatgt    1200
atcagttgta gacagtcgag cttcgggtcg tgaggcttag gattcggtga cgagcgtaag    1260
gctcaaggtg gtgttgaccg agacgcagcg tgagcaccaa agtgattcgg cagggagata    1320
taagagaata tcgaaaagct gcccgcatgc gacactgagg ctcgctttca gtgacgtcgt    1380
ggcccataag agatagagaa gggtaagtga aaggtaggtt tcggccgcgg cgtgtcatgg    1440
tggcgaaacc ttcaatgacg tgacacgttt gctaattttt agatggagcg ctatcgctga    1500

```
ctatgatttc gaggtcacca ctccaaccac tgtcgccaga tttattatta caactctcag   1560
caagaagctt tagagcgtta gatggtgttt ttcatgtgag tgccacaaaa gccatacacg   1620
cctgtcgagt ctctatgaat gtaatgtcag taatgctact agttcagtag tcatactgcg   1680
ggcttccgtc aacattaagg gtccaggtag cctccgtact tccaataatg aggaatatgg   1740
tacaagacct aaggtaagcc gttctcacaa ccaagctgca atattgtcct tgagggggt    1800
caagggtacg atacgcggaa gcgcatgtac acgtgcgtct ttgttccgag gcagccataa   1860
tgccgttgaa attttttcta ctgatcggac ctgaagcgca tcgctcaggc tggagtatac   1920
ccgttcgata tttaatcatt tggtcaacgc gagccacgct agggtgacgt catcaggata   1980
tgaagcagat acaacgacac gtttaaatga ctgtgctttt tttagaccgt acccggtagt   2040
ccgggctgtt cgtacggtgc gatggagaat aaccgaccgt gcaactactc atacattttc   2100
tgaagcaaaa cctttcgcca catgtgggtc gagcgccaag tgtagtcctc cgtctcagcg   2160
gcaagctacg tgtcgcccgg gcggcaaagc agcgagatgg aaggaggata cgtgtaaaac   2220
tcagttcacc gatggacccg catggatcag ggtaaatccg tttacagctg taggggttca   2280
tgcaaaaagt gtattttaaa agcgattagt gagaaatgac aggagtcggc gtggaacctc   2340
tctgtggtca agagtctgcc ggtgtatagg cgcggtaact acgaaacat gggatacagt    2400
agaaaccgat aggatataga ctgtaaacga acatataaa tcacttgttc tacgttgtga    2460
ttcatgctgt taccagcgcg tttgagttca acgttagtg acgagaaagc ggaagctatc    2520
gcctgacgct tctacctaaa gatagtgtgg ggccgtaagc gatcgcgctg ttgatagtgc   2580
aaggcgaaat tctacgaagg gatggtcccg tagaagaatg actcctccag gtcgtaatga   2640
agggaatgat gtcaacgttg ccgttcctgc aacagacgag tctggatggt gtttagtcga   2700
actcaaaacc atttgaatct ttaggaatga acgtcatcct gcaccgtata ggggtagaag   2760
gcgatccgcg accccaagat caaacgtttc taaattgtgt catccatgca gacgattttc   2820
ggctggcgga agtctggcta cctataagcg taccaaatgc aatgatggta ctctataggt   2880
tcgcagacat tctcattttt gtgcataaag gccgtctaca atgagtacga gcggccctcc   2940
cctaaactag aagagagatc gagttactct gacagccgtt cgatatctga aaaattctag   3000
tggacacggc ggaagcgtga gaagcacata ttcgggagtt gtatgttctt ccagggcgct   3060
gaacagaggc tttgtggggc gataacatag tgtatgtggt ttttctatat ctacggaaac   3120
atgtaggcgc actgaagggt gacacactga ccctgcaggc agcaggaccg ggacgcatac   3180
tcattctcgc gacacggccc taactactgc tcgtgacgcc gttgagggtc gatgtaaact   3240
taacaaatcg tcgggcttga ggggcacagg tagtgcttcg ataagcagtt tagaaatcgc   3300
agtaactgag gagacctacc cggctgtgta tagctggata tgagagccta gtcatattgc   3360
gtgtggtgag acgtgtagag ttagatcgcc gaggtgttga tgtttaatct atgggagcct   3420
gttcaggcct attcgacaag ccgaccccgt catttcgcat aataagcaaa atccacctcc   3480
atggggagc taccatcagg tctgttggca tcggagatct gatcgtgcga accatgccga    3540
gtcaagcacg cgctctgaca gcacggtgag gtagtaggga gaaaggagaa gtcgcgtgag   3600
gcgaaggagc accaaacgga atcgctgcaa aggataaatt gatacccgga cgtcatacgt   3660
tccccggagc caggtaccca ctgatcacgc cgagtttatg aatccgactg atgctagtac   3720
gtgtactcaa tgatgtggga ggcatgcttt ctagagtacg agcgaatgtt tagcttcgca   3780
aaaagtgcgt tttacggata attcaataat tcgcaggcct cgtgattcgt atggatgctt   3840
cgaatctaag gctactccgg gttctgtact aagcccggga gggacatttc atcctgggat   3900
```

-continued

| | |
|---|---|
| attcactgac gcgcctcggt ggtaaaccaa gagagccatt agacgtgcta tgcgcgtagc | 3960 |
| ggggagatgc gcaaaacgtc tggcaacgcg gaatcaagcg ggggcaacaa ccaagaaaat | 4020 |
| ctag | 4024 |

<210> SEQ ID NO 20
<211> LENGTH: 4024
<212> TYPE: DNA
<213> ORGANISM: Artificial Sequence
<220> FEATURE:
<221> NAME/KEY: source
<222> LOCATION: 1..4024
<223> OTHER INFORMATION: /organism="Artificial Sequence"
    /note="Nucleotide sequence HCP4, variant 2"
    /mol_type="unassigned DNA"

<400> SEQUENCE: 20

| | |
|---|---|
| atggcggcat ctttctgtgg gtctcgacgg tatgacgtat ttcccagttt ttctaaagtg | 60 |
| gacgttcgtc gttcctttct agcacacctc ttaaaagaac tcgatcgaag gttaatcaac | 120 |
| acctttaccg accacggaat ggaaagaaat ttgcccatcg atgcagagct cttatcggcc | 180 |
| attgcggaat caaggatttc catcgttatc ttctccaaga attacgcgtc ctcaacctgg | 240 |
| tgcctagatg agatggtcga gatacatact tgctacaaag gatggctca aattgtggtg | 300 |
| ccggtgtttt tcaatgtcca cccgagccag gtaaagaagc aaacgggcga gtttggaaaa | 360 |
| gttttcggca agacctgtaa gggtaagccg gagaatcgta aactcaggtg gatgcaggct | 420 |
| ctggccgctg tagcgaacat cgcgggctat gacctgcaaa attggtattt tcttttccat | 480 |
| tccaaccctc atatatatat gtgcctgtgt tcaattttgg ggtgcctctt taatgacaaa | 540 |
| attgactatt gttattaggc ctgatgatct tgccacgatt aggatggatc ctaacgatgc | 600 |
| ttcgagaaga ccttctgaat aattgagtga ttccagtgat acaggcggga ctgatcaagt | 660 |
| ttccgtggga acgaatttaa catcgctcta gagatatagg agtcctaaaa cggaagggat | 720 |
| tttggagcgt ttcgagactg gtaagattat taccgaaaaa gctctttcca gtagacgtta | 780 |
| agtcccatac cgccgtcttg tttcaggtat ttatgaaaaa atcagcctgg ccggttatag | 840 |
| cacgaggtag ttatggaccg caagatctcc gttcgtaaca gctggagtaa ggggcttgag | 900 |
| gggttcggat tcaggtgtgg tggtacaaaa agtaacgcac aggaatcgtc ctaccacagt | 960 |
| tgacgctgca ggtgatccta agccatcaag gatcttgggg gtacgaactg gatggtgaga | 1020 |
| gtctggaaac aaaactgctg tgaccatagc ggatgagcgg cgtcgcaggg aagtcggtac | 1080 |
| taacctcaca tccgaggtgg gttacctatt tgtcccccat gttcgtgaga ctttatgcct | 1140 |
| atatgtttct gggagaacat tagtactata taattctgaa ggacactatg ctagatctgt | 1200 |
| atttcctgta ggcagtccag tttcggttcg tgaggtttgg gcttcgggga cgagaggaag | 1260 |
| gcccagggag gtgttgaccg cgacgcggcg taggccccga agtaattcgg gcgcgagatc | 1320 |
| tgagagaata tagaaaagtt gccggcatgc gacacagaag cccgctttca gtaacggcgt | 1380 |
| ggaccctagg agattgaaaa ggggaagtga aaagtaggct tcggcagagg ggttagttgg | 1440 |
| tggaggaact tgcaatgacg ggatacgttt gcgaatttct aaatggagcg gtaccgctga | 1500 |
| ttataattca ggggacacca cagcaaccac tgtagacaga tctattatta caatagccag | 1560 |
| caagaggccc tggagcgcta aatggtattt ttcatgtagg tgccacaaaa accctacacg | 1620 |
| ccggtggaga gcttataaat gtaatgtcag tgatgctact aatttagcag ccataccgca | 1680 |
| ggtttccgtc agcattgagg atcccgctga cctccatact tccaatgata aggaatatgg | 1740 |

```
tacaagactt aaggaaagcc gtttagtcaa cctagttgca atattgtgct agagggcggt    1800
caaggatacg atacacgcaa gcgcatgtac acctgtgtat ttgtgcccag acagccatga    1860
tgcagatgaa attttttcta ttgatcagac ttaaagagaa tcgcgcaggc aggtgtatac    1920
cccttcgata tataatcatt cggccagcga gagccccggt aggggacgt cattagaatc     1980
tagtcaaggt acaacgacac ttttaaatga ctttgcttct tctaaaccgt tcccggatcc    2040
ccgggctgta gttacggagc catggagaat aataggccat gcaactatag ttacattttt    2100
taaagcaaga catttcggca catgtgggtt gagcggcaag tctaaagctc agtcagtgcg    2160
gccagttacg tcagtcctgg ccgtcagagt tccgagatgg aaggtggcta cgtttaaaac    2220
tcggttcaca ggtggacgcg tatggaccag ggtaaaagtg tatacagctg cagagggtcc    2280
tgcaaaaagt gtatattaaa agcaataagc gagaaatgac aggagagcgc ctggaacctc    2340
tcagtggtga agagcctccc ggtttacaga cgaggcaatt atggcaacat gggatacagt    2400
cgtaaccggt aggatatcga ctgcaaaaga aatatctgaa tcacctgctc tactctgtaa    2460
ttcatgttgc tgccggctcg actctcatct aacgtaagtg acgagaaagc tgaagccatt    2520
gcgtagagat tctacctaaa gattgtctgg gggcgtaagc gatcgaggtg ttagtgatgc    2580
aaagctaaat tctacgaagg gatggtccca tgaaaaaatg attctagcag gtcctgataa    2640
cgagaatgat gtcagcgttg tcgaagttgc aaccggcgag tatggatggt attcagtcgg    2700
actcaaaacc acctcaatct ctaggaatag actagctcct gcacagtttg aggataaaag    2760
gcgatccggg accccaagat caagaggttc tgaatcgtta gcagtatgca gactatcttc    2820
ggttggagaa agtccggtta cctgtgagcc taccaaatgc agtagtggta ctcaataggc    2880
tctcagacct tcagttttct atgcataaaa gccgtttaca atgaatatga gcgaccctcg    2940
cccaagctag aagagcgatc ctcctatagc gacagtagga gcattagcga aaaattctaa    3000
tggacgagaa ggaagaggga gaagcacata ttcggatctt gtatgttctt ccaaggtgca    3060
gagcagcggc tctgtggagc aatcacgtag tgtatgtggt tcttctacat atatggaaac    3120
atgtgagccc actaaagggt gacccactaa ccatgtagac agcaagaccg agacgcatac    3180
tcgttctctc ggcacggtcc caactactgc agttaacgcc ggtaaggttc gatgtaaact    3240
tgacagatcg tcggcttgga gggtcacaga taatgctttg ataagcaatt taggaataga    3300
tccaactgag gcgacctacc tggatgtgtt tgactagata tgagggcata atcctattgc    3360
gtgtggtaag acgtttagag ttagatcgcc gaggtactga tgttcaatct gtgggagccg    3420
gtccaggcgt attcaacaag tcgtccacgc cactttgcct gataggcgaa aagcacgagc    3480
atggggggaac taccttccgg gctgcttgcc tcagagatat aaagttgcga gccatgccgt    3540
gtaaagcacg ccttatgaca acacggggag gtggtgggac gaaaggagaa gtcgcgagag    3600
gctaaggagc accaaacaga aagcctccag cgaataaatt gatatcccga cgtcattagg    3660
tctcccgagc ctggaacaca ctgatccagg cgggtctatg agtccgacta gtgctaatac    3720
gtttactcca tgatgtggga ggcctgtttt ctggaatacg agcgcatgtt ctcgttcgct    3780
aagtcggcct tttacggctg attcaataat tcacaggctt cctgattcgt atggatgcta    3840
agaatatgag gctactcagg cttctgtacg aagcctggac gcgacatctc atcgtgggat    3900
attcactgaa gggcatccgt agtcaaccaa gagtcacatt gaacgtgcta cgcgcgctct    3960
ggagaactgc gtaaaacatc tgggaacgcg gaatcttctg ggggcaacaa ccaagaaaat    4020
ctga                                                                 4024
```

| | | |
|---|---|---|
| <210> SEQ ID NO 21 | | |
| <211> LENGTH: 4024 | | |
| <212> TYPE: DNA | | |
| <213> ORGANISM: Artificial Sequence | | |
| <220> FEATURE: | | |
| <221> NAME/KEY: source | | |
| <222> LOCATION: 1..4024 | | |
| <223> OTHER INFORMATION: /organism="Artificial Sequence" /note="Nucleotide sequence HCP4, variant 3" /mol_type="unassigned DNA" | | |

<400> SEQUENCE: 21

```
atggcagctt ctttttgcgg aagtcggagg tacgacgtat ttccgtcctt tagtaaagta      60
gacgttaggc gttcgttcct cgcgcatctt ttaaaagaac tagatcgcag actgatcaac     120
acgtttactg accatggtat ggaacgaaat ctaccaattg atgcagagct tctttcagcg     180
attgcggagt ctcgtatttc cattgtcatc ttttctaaaa actatgcgtc atccacatgg     240
tgtcttgacg agatggttga atccatact tgctataaag aaatggcaca gatagtggtt      300
cccgttttct tcaatgtcca tcccagtcag gttaaaaagc aaacgggtga gttcggtaag     360
gttttcggga agacgtgtaa gggaaaaccg gagaatcgaa actaagatg gatgcaggca      420
ctggcagcgg tagcgaatat cgctgggtat gatctgcaaa attggtattt tcttttccat     480
tccaacccta atatatat gtgcctgtgt tcaattttgg ggtgcctctt taatgacaaa       540
attgactatt gttattaggc ctgatgaagc tgccatgact aagacggctc ctagcggtgc     600
tttgagaaga cttttgaat aatagaatga ttccaatagt atcgtcggga ctgaagcagt      660
ttcaggggta acgagttcaa catcgcgctc gagatatgag agagctagaa cggaagagat     720
ttcggtgcct ttagggactg gtaagattat taccgtaaga gttcctttca gtgaaccttg     780
agtcctattc ctccctcatg tttccggtac ctatgaaaaa atcagccggg acgattgtag     840
cacgaggttg tcatggaccg gaaaatatct gtcagaaact cctggagtaa gggcctagag     900
gggtttggct tcaggtgtgg cggaacaaaa tcaaacgcgc aggaatcctc gtaccactca     960
tgacggtgca gatgatcttg agctataaag gatctaggtg ggacgaattg gatggttcgt    1020
gtttggaaac aaaattgctg tgatcattcg gggtaggcgg cgtctcaggg ctcgcgatat    1080
taaccacata ttagggtgg ccttccgata tgtcctccct gtagttgaga ctttctgcct     1140
atctgtttct gggagaacat cagtactatt tagttctaaa gaacgctttg ttaaatttgt    1200
atcagttgtc ggcagagttc cttcggttcg taaggcttgg gcttcgggga tgagaggaag    1260
gcacaaggag gtgttgatcg ggatgcagcc taggctccga agtagtttgg cagggagata    1320
taggaaaata ttgaaaagtt acccgcttgc gacacagaag cgcggtttca gtagagacgg    1380
ggaccgtagg agatagagaa gggaaaatga aaggtaggtt ttggcagggg agtctcgtgg    1440
tggcgtaacc tgcaatgacg tgatacctttt gccaatttt agatggagag atatcggtga    1500
ttataattta gagggcatca ctccaatcac tgcagacaaa tctattatta caattcgcaa    1560
caagaagccc tcgaaagatg aatggtattt tcatgtgag ttcctcaaaa gccttacacc      1620
ccggtggaga gtctttagat gtagtgccaa tgatgttact gattttcttc ccataccgct    1680
ggatttcggc aacactgagg gtcgcgataa cctccctatt tccaatagtg aggaatctgg    1740
tacaagacat gagggaagcc tttctcgcag ccatcttgta atatagtgct tgagggaggc    1800
caaggttacg atacgagaaa gaggatgtat acatgcgtat tgtgcctcg acaaccttga     1860
tgtagatgaa atttttcta ttaatccgac cttaagcgta tagcacaagc cggggtctac     1920
cccttttgata tttgatcttt tggacaacgc gaacctcgat gaggtgatgt tatacgtatc    1980
```

```
taaagtcgat acaacgacac ctttaaatag ctctgctttt tctgaacagt acctggaagc    2040
cctggttgct cctatggcgc gttggagaat aatagaccct gtaactactc ctacattttt    2100
tgaagtaaga cgtttagaca catgtgggta gaacgacagg tgtaaagcag cgttagtgcg    2160
gcttcatacg tgtcaccagg tagacaatct tctgaaatgg agggaggata tgtatgaaac    2220
tccgtgcacc gttggacgcg catggatcaa gggaagagcg tttattcctg ccggggcagt    2280
tgtaaaaagt gcattctcaa agcgatttcg gagaaataac aagagtctgc atggaactta    2340
tctgtcgtga agtcacttcc cgtttataga cgagggaact acggaaatat gggttacagc    2400
cgcaataggt aagatattga ttgtaagcgc aatatctgaa ttacatgttc aaccttgtaa    2460
ttcctgctat tgcctgccag attatcgtct aacgtgtccg acgagaaggc cgaggcaatt    2520
gcatgaagat tctatctcaa gatcgtgtgg ggacgcaagc ggtcgaggtg ttagtagtgc    2580
aaggcaaaat tttacgaggg gatggtcccg taaagaatg actcatctcg ctcttgataa    2640
agagaatgat gccagagatg tagatcatgc aatcggcggg tgtggctggt cttttctcgg    2700
acccaaaatc atctcaatct ctaagaatga acgagctcgt gcaccgtgta gggttagaaa    2760
gctatccgag acccaaaaat caagcgattc taaatagtgt cgagtatgca gactatattt    2820
gggtggcgca agtccgggta cctctaggca tatcagatgc aataatggta ttccattggt    2880
tctcaaactt ttagtttctt gtgtataaaa gcagtgtaca atgagtatga gcggccgtct    2940
cccaagcttg aggagcggtc ctcctatagc gattcgagat ctataagtga gaaattctga    3000
tggacaagaa ggaagaggga gaaacacata tttgggtctt gtatgttctt ccaaggtgct    3060
gagcaaaggt tatgtggagc tataacgtga tgcttgtggt tcttctatat ttatgggaat    3120
ctgtgagctc actgacgagt gactcactag ccatgtaggc agcaggacag agacgcatac    3180
tccttttctc ggcacgggcc gaattattgt tcctgacggc ggtagggcag tatgtgaacc    3240
tagcaaattg tgggactcga gggacatcga taatgttttg ataagcagtt ccggaatcgg    3300
tcgaactgag gggaccctcc gggatgtgta taactcgata tgcgtgcata atcctactgc    3360
gtttggtagg acgtctagtc ttagattgcg gaggttctta tgtttaatct gtgggagcca    3420
gtccaggctt acagcacgtc gcgccctcgg catttcgctt gatgagcaaa atcgaccagt    3480 ctggggagt taccttcggg acttctagca tcagagatat gatcctgtga gccttgtagg    3540
gtcaagcacg cgttatgaca acacggtgag gtagtgggac gcaaggagaa gtctcgcgag    3600
gctaaggagc accagacaga gtcattgcag agaattaatt gatacctga cgtgattcgt    3660 tcgcccgaac cggggactca ttgatctagg cgtgtttatg aatcagacta gtgctagtac    3720
gtctactcca tgttgtggga agcctgcttt ctcgagtacg aaagactgtt cagtttcgcg    3780
aagtctgcgt tttacggcta attcaataat tctcaggcct cataattcgt gtggatgctc    3840
cggatctgag gatattccgg cttctgtacc aaaccagggc gagatatctc ttcctgggac    3900
atccactaac gcgcgtccgt tgtcaatcaa gaatcccact aaacatgtta tgccagatct    3960
ggcgagatgc ggaaaacttc ggggaatgct gaatcgtcgg gaggcaataa ccaagaaaac    4020
ctaa                                                                4024
```

<210> SEQ ID NO 22
<211> LENGTH: 4024
<212> TYPE: DNA
<213> ORGANISM: Artificial Sequence
<220> FEATURE:
<221> NAME/KEY: source
<222> LOCATION: 1..4024
<223> OTHER INFORMATION: /organism="Artificial Sequence"

/note="Nucleotide sequence HCP4, variant 4"
/mol_type="unassigned DNA"

<400> SEQUENCE: 22

| | | | | | |
|---|---|---|---|---|---|
| atggcagcta | gcttctgcgg | ctcacggcga | tatgacgtct | ttccgagttt cagcaaagtg | 60 |
| gacgtccgca | gatcgtttct | ggcgcatctc | ctcaaggaac | tcgaccgccg gctaatcaat | 120 |
| acgttcactg | accacggtat | ggaacgcaat | ttaccaatcg | acgctgaact tctctccgcg | 180 |
| attgccgaat | cgcgtatctc | aatagtaatc | ttttctaaaa | attacgctag ttccacgtgg | 240 |
| tgcttagatg | agttggttga | gatacatacg | tgttataagg | aattggctca aatagttgta | 300 |
| cctgtattct | tcaacgtaca | tccatcgcag | gttaaaaagc | agactggcga gtttgggaag | 360 |
| gttttggta | agacttgtaa | gggaaaacca | gaaaatcgga | agctccgttg gatgcaggct | 420 |
| ctggcagcgg | tagcaaatat | tgccggatat | gaccttcaga | actggtattt tcttttccat | 480 |
| tccaaccta | atatatatat | gtgcctgtgt | tcaattttgg | ggtgcctctt taatgacaaa | 540 |
| attgactatt | gttattaggc | ctgatgatcc | tgccatgatt | aagacggttc ataacgatgt | 600 |
| ttcgagaaaa | ctttctaaat | aatcgaatga | ttccaataat | atcgacgtga ctgaagctca | 660 |
| ttcagaggta | acgaatttaa | tattgcgcta | gaaatctgag | agtcctagaa tggtcgagac | 720 |
| tttggcgcct | ttagggactg | gtgagactac | tatcgcaagt | catcttttca atgaaccttg | 780 |
| agccctattc | ccccttcatg | ttttcgttat | ctttaaaaga | accaaccagg acgactttga | 840 |
| cacgaagtag | tgttggatag | aaaaatcagc | gtcaggaaca | gctggtcaaa gggactcgaa | 900 |
| gggtttggtt | ttcgatgtgg | cggaactaaa | tctaatgcac | aggaaagttc gtaccattcc | 960 |
| tagcgttgta | gatagtcgtg | agctattaaa | gacttaggcg | gcaccaattg gatggttcgc | 1020 |
| gtctggaaac | agaactgctg | cgaccattca | ggttaggcag | cctctcaggg ttcaagatac | 1080 |
| tgaccgcaca | tacggggtgg | cttacccatt | tgtcctcctt | gctcttgaga cttcatgcca | 1140 |
| atctgcttct | gggagaacat | tagtaccata | tgattttaga | gaactctctg ttaaatctgt | 1200 |
| attagctgcc | ggcagtccag | cttttggatct | tagggtcttg | gattcgggga cgaaaggaaa | 1260 |
| gcacaaggag | gtgtggatag | agatgctgcg | tgagctccga | agtaatttgg acgggaaatt | 1320 |
| taagaaaaca | ttgaaaagtt | acctgcctgc | gatactgagg | cacgttttcca gtgaagacga | 1380 |
| gggccataag | aaattgagaa | gggaaaataa | aaagttggtt | ttgggcgagg agtatcctgg | 1440 |
| tggcggaacc | tacaataacg | agataccttt | gccaattttt | gaatgagag atatagatga | 1500 |
| ctgtagttta | ggggtcacca | ttccaaccac | tgtcgccaga | tttattatta taattcccaa | 1560 |
| caggaggcac | tagagcgctg | actggtgttc | ttcctgtagg | tacccagaa accttatacc | 1620 |
| cctgttgaat | ccctgtaaat | gtagtgtcag | tgatgttatt | agttctctag ccataccgca | 1680 |
| ggtttcaggc | agcattgagg | ctctcggtga | ccaccttact | ttcagtgatg aggcatttgg | 1740 |
| tataaaacct | gaggcaagcc | cttttcgcaa | cccagctgca | atattgtatt ggaaggcgga | 1800 |
| cagggctatg | acacgagaaa | acgtatgtac | acttgtgtgt | ttgtcccacg acaaccataa | 1860 |
| tgccgctgaa | attttttta | ctgaagcgac | ctcaagagaa | tcgcccaggc cggggtttac | 1920 |
| ccctttgaca | tataatcttt | cgggcaacga | gaaccgcgat | aaggagatgt tattcggatc | 1980 |
| taaagtcggt | acaatgacac | gttcaagtag | ttgtgcttct | tttagaccgt ccctggaagt | 2040 |
| ccagggtgtt | catatggagc | tatggagaat | aaccgtcctt | gtaattatag ttacatcttt | 2100 |
| tgatccaaga | cttttagaca | tttgtggggtg | gaaaggcaag | tgtaaagcag cgtatctgca | 2160 |
| gctagctacg | tctcaccagg | aagacagagc | agtgagatgg | agggggcta cgtctgaaat | 2220 |

| | |
|---|---|
| agtgtccacc gctggactcg tatggaccag ggaaaatctg tttactcttg tcgaggatcc | 2280 |
| tgcaaaaaat gcatccttaa ggcgatttct gagaagtgac aggagtctgc ttggaatctt | 2340 |
| agcgtggtta aatcactccc agtctaccga cgtggaaatt atgggaacct gggctactcc | 2400 |
| aggaatcgtt aagacatcga ctgtaagaga aatatatgaa ttacttgctc tacattatga | 2460 |
| ttcatgttac ttccagcacg gctatcatcg aatgtatcgg acgaaaaggc cgaggcgatt | 2520 |
| gcgtgacggt tttatctgaa gatcgtatgg gggagaaaaa gatctcggtg ctagtgatgc | 2580 |
| aaggccaaat tttacgaggg gctggtgcca taaaagaacg attcatcccg ttcgtgatga | 2640 |
| cgtgagtgat gccagagatg cagatcttgc aacagaaggg tctggctggt tttctcacga | 2700 |
| acccaaaatc atctaaatct ctaagagtga acaagttcat gtactgtgta aggttaaaaa | 2760 |
| gccatacgag acccgaaaat caagcgcttt tgaatcgttt cgagcctgca acgatctttt | 2820 |
| ggatggcgaa aaagcggtta cctctaagcc tatcaaatgc agtagtggta cagtattggg | 2880 |
| tctcaaacct tctcttttct gtgcatcaag gcagtgtata acgagtatga gaggccatct | 2940 |
| ccaaagcttg aagaaagatc ctcctattca gactcacgaa gtatttcgga gaaattctga | 3000 |
| tggaccaggc gaaaacggga gaaacatatt tttggatctt gtatgttttt ccaaggggcc | 3060 |
| gagcagcgcc tctgtggggc gataacttga tgcatgtggt tcttttacat atatggcaat | 3120 |
| atgtaagctc actagcgagt cacacattag ccttgcagac agcaagatag agatgcttat | 3180 |
| agcttcagtc ggcatgggcc caattattgc tcctaaaggc gataaggatc catgtgaacg | 3240 |
| tagcaaatcg tggggttgga gggccaccgg tgatgcttcg ataaacagtt taggaatcgt | 3300 |
| agcaactgag gagacctacc tggctgcgta tgacttgatc tgcgagcatg atcatactgt | 3360 |
| gtctggtaag atgtgtaatc ttagatagcc gaagttttgt tgtttaacct ctgggaaccg | 3420 |
| gtacaggcat actcgacgtc cagacctcgg cacttcgcgt gatgagctaa atcaacttcg | 3480 |
| atgggagaac taccctctgg tttattggcc tcagagattt aatcttgtga accttgccga | 3540 |
| gttaagcacg ccctatgaca gcatggagag gtggtcggaa ggaaggagaa gagccgagag | 3600 |
| gctaaggaac atcagactga atcactccag agaataaatt gatatcccga tgttattcga | 3660 |
| tccccggagc ctggaacgca ttagagtcgt agggtgtatg agagtgactg atgctgatac | 3720 |
| gtctattcca tgttgtggga ggcatgtttt cttgagtatg agcgtctgtt ttcgttcgca | 3780 |
| aaaagtgcct tctacggttg attcaacaac tctcaggctt cttgatttgt gtggatgttg | 3840 |
| agaatttgag gatactcagg attttgcacg aaacctggac gcgatataag cagctgggat | 3900 |
| atccactagc gtgcttccgt agtcaatcaa gaaagtcact gaacgtgcta tgcccgctct | 3960 |
| ggggagatgc gaaaaacgtc cggaaacgcc gagagcagcg gtggaaacaa ccaagaaaat | 4020 |
| ctga | 4024 |

<210> SEQ ID NO 23
<211> LENGTH: 4024
<212> TYPE: DNA
<213> ORGANISM: Artificial Sequence
<220> FEATURE:
<221> NAME/KEY: source
<222> LOCATION: 1..4024
<223> OTHER INFORMATION: /organism="Artificial Sequence"
    /note="Nucleotide sequence HCP4, variant 5"
    /mol_type="unassigned DNA"

<400> SEQUENCE: 23

| | |
|---|---|
| atggcggcat cttttgcgg atcacggaga tacgacgttt tcccgagctt cagcaaggta | 60 |
| gatgtcagaa ggtcattttt ggcccaccta ctcaaggagc tcgaccgcag actaatcaat | 120 |

```
actttcacag atcacggaat ggaaagaaac ctcccgatag atgcggaact tttatcggcg      180
atagcagagt ccaggatttc catagtcata ttttccaaga actatgcgtc ttcaacctgg      240
tgcttagacg aaatggttga gatccacacg tgctataaag aattgggcca aatcgtggtc      300
cccgttttct tcaatgtaca tccatcgcag gtcaaaaaac agaccggtga atttgggaaa      360
gttttcggaa agacgtgcaa gggtaagcca gaaaaccgga agctaagatg gatgcaagct      420
ctcgcagcgg ttgcaaatat cgcaggatac gatcttcaga actggtattt tcttttccat      480
tccaacccta atatatatat gtgcctgtgt tcaattttgg ggtgcctctt taatgacaaa      540
attgactatt gttattaggc ctgatgaagc tgccatgatt gagacggaag ctgacgatgt      600
tttgagaaaa cttttaaat cattgagtga tttcagtgat atcgtcggga ttgaagctcc      660
ttcagaggca atgagttcaa tattgcccta gaaatctgag aaagctaaaa cggacgggac      720
ttcggggcct tcaggggttg gtaagactat tatcgcaaaa gctcttttcca ataaacactc      780 tccctattc caccttcgtg ctttcgttat ttataaaaga atcagccagg aagactatga      840
catgaggttg tgttggacag aaaaatttct gttagaaata gttggtcaaa aggactggag      900
ggttttggat tccggtgcgg cggaacaaag agtaatgcac aagagtcatc ctatcactct      960
tgacgatgca gatgatcttg agctattaaa gaccttggag ggacaaactg gatggttcgg     1020
gtttggaagc agaattgttg tgatcactcc ggataggcag cttctcaggg cagccgatac     1080
taaccccata tacgaggggg cttgcccata tgccctccat gctcttgaga cttttctgcca     1140 atctgctttt gggaaaacat aagcaccata tgattttaga gaactctctg ctgaatttgc     1200
atttcttgta gacaaagtag ttttggatcg tagggccttg ggttcggcga tgaaaggaaa     1260
gcacagggag gagtggacag agatgctgcc taggcccccta aatgatttgg ccgggaaata     1320
taagaaaaca ttgaaaaatt acccgcctgt gatacggaag cccgtttca atgacgaagg     1380 gggccgtgag aaattgagaa gggggaaataa aaagttggct ttggacgagg agtctcttgg     1440
tggagaaact tgcagtgaag ggatacccttt gccaacttct aaatggaacg atacagatga     1500
ctgtaattta ggggacatca ttccaatcat tgcagacaga tatactacta taattcccaa     1560
caggaggcac tcgaacgata gctggtgttc tttatgtgag ttcctcagaa accctacacc     1620
ccggtggaat ccctttaaat gtaatgtcaa tgatgttact gatttctctcc ccacacggca     1680 ggctttaggc agcattgagg ctcgcgttga ccgcctatt ttcagtaata gggaatttgg     1740
tataagacct agggaaaacc cttttcgcaa ccatcgtgta atatcgtact tgagggtggt     1800 cagggggtatg ataccagaaa aaggatgtat acttgcgtgt tcgtgccccg acagccttga     1860
tgtcggtgaa acttttttcta ctaaagcgat ctcaaaagaa ttgcgcaagc tggggtatat     1920
ccctttgaca tatagtcttt tggtcagaga gaacctcgat aaggcgatgt tatccggatt     1980
tagagtcgct acaacgatac ttttaagtag ttatgttttt tctagacagt ccctggatca     2040
cctggatgca gttacggagc attggaaaac aatcgtcctt gcaactattc atatatattt     2100
taaagtaaaa ctttttagaca catgtgggtt gaaaggcagg tttgaagcag cgtctctgca     2160
gcttcgtatg tctcaccagg aagacaaagt tcagaaatgg aaggaggtta tgtctgaaat     2220
agtgtccatc ggtggacgcg aatggaccaa ggaaagtccg tttattcatg tagaggaagc     2280
tgcaaaaagt gtattcttaa agcgatttct gaaaaatgac aagagagtgc ttggaacctc     2340
agcgttgtta aatcactccc cgtttacaga cgtggaaact atgggaacct gggatactcg     2400
cgcaacaggt aggacatcga ttgcaagaga aatatctgaa ttacatgctc caccctctga     2460
```

|  |  |  |
|---|---|---|
| ttcatgttac ttcctgcaag actttcatct aatgtgtcag atgaaaaggc cgaggcaata | 2520 |
| gcgtgaagat tttatctcaa aattgtttgg ggaagaaaga gatctaggtg ctagtgatgc | 2580 |
| aaagccaagt tctacgaggg gatggtcccg taaaaaaatg attcgtctag atcttgatga | 2640 |
| cgtgagtgat gccaacggtg cagaagctgt aatcggaggg tttggctggt tttcagtcgt | 2700 |
| acacaaaatc atcttaacct ataggagtaa acgagttcct gtacagtgta agggtagaaa | 2760 |
| gccatacgtg atccaaaaat taagcgattt tagatcgtct cgagcatgca acaatatttt | 2820 |
| ggatggcgta aatcaggata tctctgagct tatcaactgc agtgatggta ttcgattggc | 2880 |
| tctcagacat tcagtttctt gtgtatcaaa gcagtgtata atgaatatga gagaccatct | 2940 |
| ccaaaacttg aagaaagatc ctcctactca gattcaagaa gcatatcgga gaagttttga | 3000 |
| tggactcgtc gtaagcgaga aaaacatatt tttggatctt gtatgttttt tcagggggct | 3060 |
| gaacagagac tgtgtggtgc catcacttga tgcttgtggt tcttctatat atacgggaat | 3120 |
| ctgtgagctc actgacgtgt cacacactag ccgtgcagac aacaagatag agacgcttat | 3180 |
| tcctttctta gacatggtcc gaactattgt agttgaagaa gatgaggatc catgtagacg | 3240 |
| tagcagattg ttggactcga aggtcatcgt tgatgcttcg acaagcagtt cagaaataga | 3300 |
| agcaattagg gggatcttcc aggatgtgtc tgactcgaca tgcgtgcatg atcctactgt | 3360 |
| gtttggtaag atgtatagtc ttagattgct gaggtactaa tgttcaacct tgggagcca | 3420 |
| gtccaggctt atagcacctc acggcctagg cactttgcat gatgagccaa gtctacgtca | 3480 |
| atgggcgaat taccctctgg tttacttgcc tctgaaattt aatcttgtga accttgtaga | 3540 |
| gttaaacatg ccctctagca acatggggaa gttgtaggga ggaaagaaaa gtctcgagag | 3600 |
| gctaaggaac accaaactga gtcactccag agaattaatt gatatcctga tgttatcaga | 3660 |
| agccctgaac ctgaacgca ctagtctcga agggtgtacg aatctgactg atgttagtat | 3720 |
| gtctattcct tgttgtggga agcttgtttt cttgaatatg agaggctgtt ctcgtttgcc | 3780 |
| aaatctgcct tctatggatg atttaataac tctcaagcct cttaatttgt ttggctgctc | 3840 |
| agaatttagg gatactcagg attctgtacg aaacccggaa gagacatttc tagttgggac | 3900 |
| atccattaga gagcttccgt cgtcaaccag gaatctcact gaacctgtta cgctagatcc | 3960 |
| ggagaactgc gaaagacttc aggaaacgcg gaatcttccg gtggaaacaa ccaagagaat | 4020 |
| ctga | 4024 |

<210> SEQ ID NO 24
<211> LENGTH: 4024
<212> TYPE: DNA
<213> ORGANISM: Artificial Sequence
<220> FEATURE:
<221> NAME/KEY: source
<222> LOCATION: 1..4024
<223> OTHER INFORMATION: /organism="Artificial Sequence"
    /note="Nucleotide sequence HCP4, variant 6"
    /mol_type="unassigned DNA"

<400> SEQUENCE: 24

|  |  |  |
|---|---|---|
| atggcagctt cttttttgcgg cagccggagg tacgatgtgt tcccaagctt cagtaaagtg | 60 |
| gacgtccgcc gttcttttcct cgcgcacctt ctcaaagagt tagaccgccg ccttatcaat | 120 |
| acgtttaccg accatggaat ggaacgtaac ctgcctatcg atgctgagct tttatcggct | 180 |
| atagcagaga gcaggatctc aatagtaatc ttctccaaga actatgcttc ttctacatgg | 240 |
| tgcctagatg aattggttga aatccatact tgttataagg aaatggctca aatagtggtt | 300 |
| ccggttttct ttaacgtaca ccccttcgca agttaagaaac agaccggcga gtttggtaag | 360 |

```
gttttttggaa agacatgcaa agggaaaccg gagaaccgga aactaagatg gatgcaggca    420
ctagcagcgg tcgcaaatat cgcaggatat gaccttcaga actggtattt tcttttccat    480 tccaaccta atatatatat gtgcctgtgt tcaattttgg ggtgcctctt taatgacaaa     540
attgactatt gttattaggc ctgatgaagc tgtcatgatt gagatggtag ctgacgatgt    600
ttcgaaaaaa cttttttgaat tatcgaatga tttcaatgat accgtcggga ttagagctcc   660
tttagaggca atgagttcaa tattgcgctt gaaatctgag aaagctagaa tggtcgagat    720
ttcggggcct tccgtgattg gtaagattat tatcgcaaat cttcttttca gtaaactctc    780
tccccaattc caccttcgtg ctttcgttac ttataaaaga atcaaccagg acgactttag    840
catgaagttg tgatggatcg aaaaatttct gtcagaaatt cttggtcaaa aggactcgaa    900
ggttttggat ttaggtgcgg tggaacgaaa tccaatgccc aggagagttc ttaccattct    960
tgacgatgca gatgatcttg agctatcaaa gaccttggtg gtacaaactg gatggttaga   1020
gtttggaagc agaattgttg tgatcacagt ggataggcag cttcgcaagg ttcacgttat   1080
taaccacaca tacgaggtgg cttaccaatc tgcccaccct gctcttgaga ctttctgcca   1140
atctgcttct gggaaaatat atcaactatc tgattctaga gaactttgtg ttgaatttgt   1200
atatcttgtc ggcaatcatc ctttggatct tagggtcttg gatttggcga tgaaaggaaa   1260
gcacagggag gagtggatag agatgctgcc taggctccga agtgatttgg acgggagatc   1320
taagaaaata tcgagaagct ccctgcttgt gatacggaag cgcgtttcca atgaagaagg   1380
gggccgtaag aaattgaaaa agggaaataa aaagttgggt ttggccgagg ggtttcctgg   1440
tggagaaatt tacagtgacg agacaccttc gccaactttt aactggagag atacagatga   1500
ctgtgattcc ggggacatca ttccaatcac tgcagacaaa tctattacta taactcccaa   1560
caggaggcac tcgagcgatg actggtgttt tttatgtgag ttcctcagaa accgtatacc   1620
cccgttgaat cccttttaaat gtaatgccaa tgatgttact agttttcttc gcacacggca   1680
ggatttcgcc aacactgagg ctctcgttga ccaccttact tccaatagtg aggcatatgg   1740
tataaaacct agggaaaacc attttcgcaa cccagctgta atatagtact tgaaggcggt   1800
caggggtatg acacgagaaa aagaatgtat acttgtgttt tcgtgccacg acaaccctga   1860
tgtagatgaa atttcttcta ttgaagcgat ctcaagcgta ttgcacaagc aggggtgtac   1920 cccctttgaca tataatcttt tgggcaaaga gaacctcggt agggagatgt tataagaatt   1980
tagagtcggt ataatgatac cttcaagtga ttgtgctttt tctaaaccgt ccctggaagt   2040
cctggttgca gttacggagc cttggaaaac aaccgaccgt gtaattactc ctatatattt   2100
taaagtaaga ctttcagaca tttgtgggtt gaaaggcagg tttgaagcag cgtttctgca   2160
gcttcatacg tctctcccgg aagacagagt agcgaaatgg agggtggcta cgtctgaaat   2220
agtgtccacc gttggacacg aatggatcaa gggaaatcag tttattcttg tcgaggatcc   2280
tgcaagaaat gtattcttaa ggccataagt gaaaagtagc aagaatctgc ttggaatctt   2340
agcgttgtta aatcactccc agtctaccgc cgtggaaatt atggcaacct gggttacagc   2400
aggaacaggt aagacataga ttgcaagaga aatatttgaa taacatgctc cacactatga   2460
tttctgttac ttcctgctcg tcttctcttcg aatgtgtcag atgagaaggc cgaggcaatt   2520
gcatagagat tttatctcaa aatagtgtgg ggaagaaaga ggtctaggtg ttagtgatgt   2580
aaagcaaagt tttatgaggg cctggttcca taaaaaaatg attcttcccg ttcttgatag   2640
cgtgagtaat gccagagatg cagaagctgt aaccggcgcg tttggatggt tttctcacgg   2700
```

```
acacagaatc atttgaacct ctaagaataa acaagttctt gtacagtgta aggctaaaaa    2760
gcaatacgag atccaaaaat taagaggttt tgaatagtat cgtctatgca acaatattc     2820 ggatggcgaa atccggata tctctgagct tatcagatgc agtagtggta ctcaattggc     2880
tctcaaacgt ttagtttcct ttgcatcaaa gcagtatata acgagtacga gagaccatct    2940
cctaagcttg aggaaagatc cagctactct gactcacgca gcatctcgga gaagttttga    3000
tggaccagac gaaagcgaga aaacatata tttggctctt gcatgttttt tcagggtgca     3060
gagcaaagat tatgcggagc tatcacctga tgtttgtggt ttttttatat ctatgggaat    3120
ctgtgagccc attgacgagt gactcattga ccttgtagac aacaagatag agacgcctat    3180
tccttttcaa gacatgggcc aaattattgt tcataacgca gatgaggatc catgtaaact    3240
tagcaaattg tgggactcga aggacatcgt tgatgcttcg acaagcaatt caggaacaga    3300
tcaaattgag gagacttacc tggatgcgtc tgacttgatc tgcgagctta atcatactgc    3360
gtttggtaag atgtataatc ttgaatcgca gaggttctat tgttcaacct gtgggagcct    3420
gtgcaagctt actcaacatc acgtcctaga cacttcgcct gatgagctaa gtctactagt    3480
atgggagagt tacccagtgg gctacttgcc tcagaaattt aatcctgtga accttgtcga    3540
gttaagcatg cctatagca acatggagag gtcgttggac gcaaagagaa atctcgagaa     3600
gctaaagaac atcaaactga atcacttcag aggattaact gatatcctga cgttatcaga    3660
agccctgaac ctggaacgca ttagtctcga agggtttacg aatctgactg atgttagtat    3720
gtgtattctt tgatgtggga agcatgcttc cttgagtatg aaagaatgtt ttcgtttgcg    3780
aaaagtgcat tctacggttg atttaacaac agtcaagctt cttaatttgt ctggctgctc    3840
agaatctagg gctattcagg attttgcacc aagcctggac gcgacatatc tagctgggac    3900
atccattaaa gagcttccgt tgtcaatcag gaatctcatt gaacttgtta cgcaagatct    3960
ggagagctgc gaaagacttc aggaaatgcc gagtcttccg gtggaaataa tcaggagaac    4020
ctga                                                                 4024

<210> SEQ ID NO 25
<211> LENGTH: 4024
<212> TYPE: DNA
<213> ORGANISM: Artificial Sequence
<220> FEATURE:
<221> NAME/KEY: source
<222> LOCATION: 1..4024
<223> OTHER INFORMATION: /organism="Artificial Sequence"
      /note="Nucleotide sequence HCP4, variant 7"
      /mol_type="unassigned DNA"

<400> SEQUENCE: 25
atggcagctt cttttgcgg cagccggaga tacgatgttt tcccgtcttt ctctaaagta     60
gatgtccgca ggtcattcct cgcgcatctt ttgaaggagc tcgaccgcag attaatcaat    120
acgttcaccg atcatggtat ggagagaaac ctccccatcg acgctgagct tttatctgca    180
atagcagaat cgaggatctc aatagtcatc ttctctaaaa actatgcttc ttccacgtgg    240
tgcttagacg aattggtgga gatccacact tgctataagg aattggcaca gatagtcgtt    300
ccggttttct tcaacgtaca tccttcgcaa gtcaaaaaac aaaccggaga atttggtaaa    360 gttttttggaa agacgtgcaa gggtaagcca gaaaaccgga aattgagatg gatgcaagct    420
ctagcagcgg tagcaaacat tgctggttac gatcttcaga actggtatt tcttttccat     480 tccaacccta atatatatat gtgcctgtgt tcaattttgg ggtgcctctt taatgacaaa    540
attgactatt gttattaggc ctgatgaagc tgtcatgatt gagacgggag ctgacgatgt    600
```

```
ttcgaaaaaa cttttaaat catcgaatga tttcagtgat atcgtagaga ttagagctca      660
tttagaggca acgaattcaa tattgcgttg gaaatctgag aaagctagaa tggtcgggat     720
ttcggggcct ttagggattg gtaagattac tatcgcaagt cgtcttcca gtagactctc     780
tccccgattc caccttcgtg cttcgttat ctataaaga accaaccagg acgactatga      840
catgaagttg tgttggatcg taaaatttct gtcagaaatt cttggagtaa aggacttgaa    900
ggtttcggat ttaggtgcgg tggaacaaag tctaatgcac aagaaagttc ttatcattct    960
tgacgatgta gatgatcttg agctataaaa gaccttggtg ggacaaattg gatggtacgg   1020
gtatggaagc aaaattgttg tgaccactca ggttaggcag cttctcaggg ctcacgatat   1080
taacctcata tacgaggtgg ccttccgatc tgcccacctt gctcttgaga ttttctgcca   1140
atctgcttct gggaaaatat atccaccatc tgattttaaa gaactctctg ttgaatttgc   1200
ataagttgcc ggcagtcttc ctttggatcc tagggtcttg ggttcggcga cgaaaggaaa   1260
gcacagggtg gagtggacag agacgctgcc taggctccga aatgattcgg acgggaaatt   1320
tgagagaaca ttgagaaact tcccgcctgt gatacggagg cgcgtttcca atagagaagg   1380
gggccttgag aaattgaaaa agggaagtaa aaagttggat ttggacgcgg agtttcctgg   1440
tggagaaatt tacagtgacg agatacctt gcgaacttt aactggaaag atacagatga    1500
ctttagttta ggggacatca ctccaatcat tgcagacaaa tctactacta taattcccag   1560
caggaggcac ttgagcgctg actggtgttc tttctgtgag ttcctcaaaa gccgtacacc   1620
cccgttgaat cgctttagat gtagtgccaa tgatgttatt gattttcctc gcataccgca   1680
ggttttaggc agcactgagg ctctcgttag ccgccttatt ttcagtagtg agggatctgg   1740
tataaaacct gaggaaaacc cttttcgcaa ccaagctgta acatcgtcct tgaaggcggc   1800
cagggatatg acacgagaaa aagaatgtac acctgtgttt tcgtcccacg acaaccttga   1860
tgtagatgaa acttcttcta ttgaagcgat ctcaaaagaa tagcacaagc gggggtttat   1920
ccctttgaca tataatcttt tgggcagaga gaacctcgat gaggagatgt tataaggatc   1980
tagtcgcggt ataatgatac attcaaatag ttgtgttttt tctagacagt ccctggatca   2040
cctggttgta gttatggagc attggaaaac aacagacctt gtaactattc ctatatattt   2100
taaagtaaga cgttcagaca tttgtgggtc gaaaggcagg tttgatcaag cgtttctgca   2160
gcttcatatg tctctccagg aagacagagt tcagaaatgg aaggcggcta tgtctgaaat   2220
agtgtccatc ggtggacacg aatggaccaa gggaaatcag tttactcttg tcgaggaagt   2280
tgtaagaaat gcatccttaa ggctatatct gaaaagtagc aagaatccgc ttggaatctt   2340
tcggtagtta aatcactccc ggtctacaga cgtggaaatt atgggaatct ggggtatagc   2400
aggaataggt aagacatcga ttgcaagaga aatatttgaa ttacctgctc aacattatga   2460
tttctgttac ttcctgcaag actttcctct aatgtgtcag atgaaaaagc cgaggcgata   2520
gcgtgaagat tttatctcaa aattgttggg ggccgcaaaa ggtctaggtg ctagtgatgt   2580
aaagccaaat tttatgaggg actggttccg taaaaaacg atagctctcg ctcttagtga   2640
cgtgagtaat gccaaagatg cagaagctgt aatcggaggg tatggctggt tttctcacgg   2700
acacagaatc accttaacct gtaggagtaa actagttctt gtacagtgta aggttgaaaa   2760
gccatacgag atccaaaaat taagcgcttt tgaatagttt cgtcgctgca aacaatattt   2820
ggatggcgaa atctggata tctctgagct taccagatgc agtagtggta ttccattggg    2880
tcccaaactt ttagtttcct ctgtatcaaa gcagtatata acgagtatga aagaccatcc   2940
```

-continued

```
ccaaaacttg aggagagaag ctcctactca gactcaagaa gcattagtga gaagttttga    3000
tggactagac gaaaacgaga aaaacatatt tttggatcct gcatgttttt ccaggggggca   3060
gagcaaagat tatgtggtgc gattacttga tgcttgtggt ttttttacat atatgggaac    3120
atgtgagctc attgacgagt cactcattag ccttgtcgtc aacaggatcg agatgcctat    3180
tccttttcaa gacatgggcc gaactattgt tcatgaagaa gatgaggatc catgtgaacg    3240
tagcagattg tgggcctcga agggcaccgt tgatgttttg acaagcaatt caggaacaga    3300
agcaattgag gggatcttcc tgggtgtgtt tgacttgacc tgcgagccta gtcatactgc    3360
gtttggtaag atgtatagtc ttagattgct gaagttctat tgttcaacct ctgggaacca    3420
gtgcaagctt actctacctc acggcctaga cactttgcct gatgagctaa gtctacttca    3480
atgggagaat tacccagcgg tttacttgcc tcagaaatat aatcctgtga accttgtaga    3540
gttaaacatg ccttgtagca acatggagaa gtagtgggaa ggaaagaaaa atctcgagaa    3600
gctaaagaac atcaaactga gtcactccag cgtattaact gatatcctga tgttattaga    3660
agccctgagc ccggaacaca ttaatctcga agggtgtacg agtctgattg atgttagtat    3720
gtctattcct tgttgtggga ggcttgtttc cttgaatatg aaagactgtt ctcctttgcg    3780
aaatctgcct tctatggttg atttaacaac tctcaagctt cttaattcgt ctggctgctc    3840
agaatttgag gctattcagg ttttgcacc aaaccgggaa gagatatatc tagctgggac     3900
atccattaga gagcttccgt tgtcaatcaa gaatctcact gaacttgtta tgctagatct    3960
ggagagctgc gaaagacttc aggaaatgcc gagtcgagcg gtggaaataa tcaggagaac    4020
ctga                                                                 4024
```

<210> SEQ ID NO 26
<211> LENGTH: 4024
<212> TYPE: DNA
<213> ORGANISM: Artificial Sequence
<220> FEATURE:
<221> NAME/KEY: source
<222> LOCATION: 1..4024
<223> OTHER INFORMATION: /organism="Artificial Sequence"
    /note="Nucleotide sequence HCP4, variant 8"
    /mol_type="unassigned DNA"

<400> SEQUENCE: 26

```
atggcagctt cttttttgcgg gagccggaga tacgatgttt tcccgagctt cagtaaggta    60
gatgtacgca ggtcattctt agcgcacctt ctcaaggagc tcgaccgcag attaatcaat   120
acgttcacag accatggtat ggagagaaat cttccaatcg acgctgaact tctgtcggcg   180
atagcagagt cgaggatatc aatcgtcatc ttctctaaaa actatgcttc ttccacgtgg   240
tgtttagatg aattggtcga gattcacacg tgttataagg agttggctca atagtggtt    300
ccggttttct ttaatgtcca tccttcgcaa gttaaaaaac agaccggaga atttggtaag   360
gttttttggaa agacgtgcaa agggaaacca gagaatcgga aactaagatg gatgcaagct   420
ctagcagccg tagcaaacat tgctggatat gatcttcaga actggtattt tcttttccat   480
tccaacccta atatatatat gtgcctgtgt tcaattttgg ggtgcctctt taatgacaaa   540
attgactatt gttattaggc ctgatgaagc tgtcatgatt gagatggtag ctgacgatgt    600
ttcgaaaaaa cttttttaaat catcgaatga tttcagtgat atcgtcggga ttgatcctca   660
tttagaggca atgagttcaa tattgcgctt gaaatctgag aaagctagaa tggtcgggat    720
ttcggggcct tcagggattg gtaagactac tatcgcaaaa gcagctttca gtaaactctc    780
tccccaattc caccttcgtg ctttcgttac ttgtaaaaga accaaccagg acgactatga   840
```

| | | | | |
|---|---|---|---|---|
| catgaagttg | tgttggatag | aaaaatttct | gtcagaaatt | cttggtcaaa | aggacttgaa | 900 |
| ggtttcggat | ttaggtgcgg | tggaacaaag | tctaatgcac | aagaaagttc | ttatcattct | 960 |
| tgacgatgta | gatgatcttg | agctattaaa | gatcttggtg | ggacaaactg | gatggttcgg | 1020 |
| gtttggaagc | agaattgttg | tgatcactca | ggataggcag | cttctcaagg | ctcacgatat | 1080 |
| taacctcata | tacgaggtgg | ccttcccatc | tgcccacctt | gctcttgaga | ctttctgcca | 1140 |
| atctgctttt | gggaaaatat | atccaccatc | taattttaga | gaactctctg | ttgaatttgc | 1200 |
| atatcttgcc | ggcaatcttc | ctttggctct | tagggccttg | ggtttggcga | tgaaaggaaa | 1260 |
| gcacagggag | gagtggatag | agatgctgcc | taggctccga | aatgatttgg | acgggagatt | 1320 |
| taagaaaaca | ttgaaaaatt | acctgcctgc | gacacggaag | cgcgtttcca | atgaagaagg | 1380 |
| gggccgtgag | aaattgaaaa | agggaaataa | aaagttggat | ttggacgagg | agtctcctgg | 1440 |
| tggagaaatt | tacagtgacg | agataccttc | gccaacttct | aactggaaag | ataccgttga | 1500 |
| ctttgattca | ggggacatca | ttccaaccat | tgcagacaaa | tctactacta | taattcccaa | 1560 |
| caggaagcac | tcgaacgatg | actggtgttc | tttctgtgag | ttcctcagaa | accgtatacc | 1620 |
| ccggttgaat | cccttttaaat | gtagtgccaa | tgatgttatt | gattttcttc | gcacacggca | 1680 |
| gggtttaggc | agcattgagg | ctcgcgttga | ccccttatt | ttcagtagtg | aggcatttgg | 1740 |
| tataaaacct | aggggaaacc | cttttcgcag | ccaagctgta | acatagtact | tgaaggcggc | 1800 |
| caagggtatg | acacgagaaa | aagaatgtat | acttgtgttt | tcgtgccacg | acaaccttga | 1860 |
| tgtagatgaa | acttttttta | ttgaagcgat | cttaaaagaa | ttgcacaagc | aggggtttac | 1920 |
| cccttttgaca | tataatcttt | tgggcagaga | gaacctcgat | gaggagatgt | tattcggatc | 1980 |
| tagagtcgtt | ataatgatac | tttcaagtga | ttatgtttct | tctagacagt | ccctggatca | 2040 |
| cctggctgca | gttatggagc | attggaaaac | aacagacctt | gtaattattc | ctatatattc | 2100 |
| taaagtaaga | cttttagaca | tttgtgggtt | gaaaggcagg | tttgaagcag | cgtctctgca | 2160 |
| gctagttatg | tctcaccagg | aagacagagt | tcagaaatgg | aaggcggcta | tgtctgaaat | 2220 |
| agtgtccacc | ggtggacacg | aatggaccag | gggaagtcag | tttattcttg | ccgaggaagt | 2280 |
| tgtaagaaat | gcatccttaa | ggctatatct | gaaaagtagc | aagaatctgc | ttggaatctt | 2340 |
| agcgttgtta | agtcactccc | agtctacaga | cgcggaaatt | atgggaatct | ggggtatagc | 2400 |
| aggaataggt | aagacatcga | ttgcaagaga | aatatttgaa | ttacttgctc | cacactttga | 2460 |
| tttctgttac | ttcctgcaag | actttcatct | aacgtgtcag | atgaaaaagc | cgaggcaatt | 2520 |
| gcctgaagat | tttacctcaa | aattgttttgg | ggaagaaaaa | ggtctaggtg | ctagtgatgc | 2580 |
| aaagccaagt | tttatgaagg | aatggttcca | taaaaaaacg | attcttcccg | ttcgtgatga | 2640 |
| cgtgagtaat | gccagagatg | cagaagctgc | aatcggaggg | tttggctggt | tttctcacgg | 2700 |
| acacagaatc | atcttaacct | ctaggagtag | acaagttctt | gtacagtgta | aggataaaaa | 2760 |
| gccatacgag | atccaaaaat | taagcgattt | tgaatcgttt | cgtctctgca | aacaatattc | 2820 |
| ggatggcgaa | aatccggtta | tctctgagct | tatcaactgc | agtagtggta | tagtattggc | 2880 |
| tctcaaactt | ttagtttcct | ctgtatcaaa | gcagtatata | acgaatatga | aagaccaagt | 2940 |
| ccaaagcttg | aggagaggtc | ctcctactca | gattcaagat | caatttcgga | gaaatttga | 3000 |
| tggactagac | gaaaacgaga | aaaacatatt | tttggatctt | gcatgttttt | ccagggggca | 3060 |
| gagcaaagat | tatgtggtgc | tattacttaa | tgcttgtggt | ttttttacat | atatgggaac | 3120 |
| ctgtgagctc | attgacgagt | cactcattag | ccttgtagac | agcaagatag | agatgcctat | 3180 |

-continued

```
tccttttcaa gacatgggcc gaattattgt tcatgaagaa gatagggatc gatgtgaacg    3240
tagcagatag tgggactcga aggacatcgt tgatgttttg acaaacaatt caggaacaga    3300
agcaattaag gtgatcttcc tggatgcgtc taacttgacc tgcgagctta gtcctactgt    3360
gtttggtaag atgtttaatc ttagattgct gaagttctat tgttcaacct ttgggaacca    3420
gttcaagctt acagcacctc acggcctaga catttcgcct gatgagctaa gtctacttcc    3480
ctgggagaat tacccagcgg tttacttgcc tcagaaattt aatcctgcga accttgcaga    3540
gttaaacacg ccttataaca acatggagaa gttgtgggaa ggaaagaaaa atctcgagaa    3600
gccaaagaac atcaaactga gtcactccag agaattaact gatatcctga tgttatcaga    3660
agccctgagc ctggaacaca ttgatctcga agggtgtacg agtctgattg atgttgatat    3720
gtctattcct tgttgtggga ggcttgtttc cttgaatatg aaagactgtt ttcgtttgcg    3780
aagtctgcct tctatggttg atttaacaac tctcaagctt cttaatttgt ctggctgctc    3840
agaatttgag gatattcagg attttgcacc aaacctggaa gagatatatc tagctgggac    3900
atccactaga gagcttccgt cgtcaatcag gaatctcact gaacttgtta tgcacgtagt    3960
ggagaactgc gaaagacttc aggcaatgcc gagtcttccg gtggaaataa tcaggagaac    4020
ctga                                                                 4024
```

<210> SEQ ID NO 27
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
      /note="Nucleotide sequence HCP4, variant 9"
      /mol_type="unassigned DNA"

<400> SEQUENCE: 27

```
atggccggct gcttcagcgg caccaagaag tacgacgtgt ccccctgctt cagcaagggc      60
gagggcagaa gaagctacgc cgcccacctg atccacgagc tggacagaag actgatccag     120
accttcaccg accacggcat ggagagaaac atgcccatcg acgccgagct gctgagcctg     180
atcggcgagt gcagaatcag catcgtgatc ttcagcagaa actacgccag cagcacctgg     240
tgcatggacg agctggtgga gatccacacc tgcttccacg agctggtgaa catgggcgtg     300
cccggctact accaggtgca cccctgcaac gtgcacaaga acaccgtgga ctacggcaag     360
gtgttcctga gtgcaccaa gggcaagccc gagcagagac acctgagatg gatgcagggc     420
gtggccatgg tggtgcagat cgccggctac gacctgcaga actggcccga cgacgccggc     480
atggccgaga tggtgggcga cgaggtgagc aagaagatct ggaagagcac caacgactac     540
agcgacatcg tgggcatcga ggccaaggcc gagggcatga gctgcatgct gcacgccaga     600
agcgacaagg ccagactggt gatcatcagc ggccccagcg catcggcaa gaccaccctg     660 gccaaggcca tgtacagcaa ggccagcccc cagttcaagc tgagagcctt catgagctgg     720
aagaagaccc agcaggacga gttcgacatc aagctgtgct ggatcgacaa gttcggctgc     780
gacatcctgc tgcagaagga cctgcacgtg ggcgacctgc tggccgtgga caacagcctg     840
atgcacaaga gatgctgggg catcatggac gaggtggacg agatggagct gctgaagacc     900
ctggtggccc agaccctgtt cttcggcttc ggctgccacc tggtggtggc ctgcaacgac     960
agaaacctgg tgaaggccca cgagatcaac atgatgtggg acgtggtgta ccccagcgtg    1020
cacgtggccc tggaggtgtt cagccagtgc gccttcatga gaggctaccc ccccaccgac    1080
```

```
ttcagagagg gcagcatgga cttcgcctac ctggccggcc aggcccccct ggacctgcac    1140
gtgctgggca tcggcatcaa gggcaagcac aaggaggagt gggtggacct gctgcccaga    1200
gtgaagcagg acatcgacgg caagtacaag aagaccatga gaaacttcct gcccggcatc    1260
agaaagcacc tgagcaacga ggagggcgtg cacgagagac tgcaccacgg caaccacaga    1320
ctggacctgg acgaggagta ccccggcggc gagatctact gcgacgacgg ccccctgcccc   1380
agcagccagt ggaaggacac cgaggagttc gactgcatgg agatcatccc cgccatcgcc    1440
gacaagagca ccaccatcat ccccaacaga agacacagca cgacgactg gtgcagcttc     1500
tgcgagttcc tgagaaacag aatccccccc ctgaacccct tcaagtgcag cgccaacgac    1560
gtgatcgact tcctgagaac cagacaggtg ctggtgagct gcgacgccct gatcgacaag    1620
ctgatcttct gcaccgaggg ctacggcgcc accccgacg agcagccctg gagaagcaac     1680
gccgtgacca gcttcctgag aatcgccaga gacggcacca gagagaagga gtgcatcctg    1740
gtgtacagct gccacgagaa cctggacgtg acgagacct gcttcatcga ggccatcagc     1800
aaggacctgc acaagaacgg cttcatcccc gtgagcttca cgtgctgat cagagagcag     1860
ctggacgagg agatgctgtg gggcaccaga gtgatgatcg gcatcctgtg cagcagcttc    1920
ctgagcagca gaaacacccct ggagcacggc gtggccgtga tggagcacta caagacctgc   1980
gacatcgtga tcatccccat ctacttcaag gtgagactga gcgacatcac cggcctgaag    2040
gccaagttcg acgccgcctt catccagctg agaggcagcc tgcaggagga ccacgcccag    2100
aagttcaagg ccgccatgag cgagatcgcc agcatcggcg cccacgactt caccaagggc    2160
acccagtacg ccctggccga ggagatggtg agaaacgcct gctgaagct gtggctgaag     2220
acctgcaaga acctgctggg catcatcggc atcctgaacc actgcaacac caccgaggtg    2280
gagatcgtgg gcatctggct gatcgccgcc atcggcaagt gcagcatggc caaggacatc    2340
ttcgagctga gaccccccca ctacgacttc agctactaca tccaggactg gcacctgatg    2400
agccagatga agagacccag aaacgccaga gaggacttcg ccagccacgc ctacatcgag    2460
gacaagggcc tgggcgccac cgacgtgaag ccctgcttcg ccagagactg gtacagaaag    2520
cacagcggcc tggccgtgct ggaggacatc tgccagctga gagacatcga gctggtgatc    2580
ggcggcttca tgttcttcag ccacatgaag agaatcatcc tgtgcagcag aaccaagcag    2640
ggcgtggtgc agtgcagaat gaagaagccc tacgacatca cagactgag cgagttcgag    2700
tgctggaagc tgagcaagca gttcctggag atcgaccagc ccctgatcag cgagctgatc    2760
agcagcacca ccggcgcccc cctgctgctg aagatggccg tgaccaccgg cagccaccag    2820
tggatcagca acatgcacga gaagctgcag agcatcagaa gaacccccc cacccagatc    2880
caggaggcct tcaagagaac ctacgacgtg ctggacgacc aggacaagaa catcttcctg    2940
gacctggcct gcttcttcag aggccagagc aaggactacg ccgtgctgct gctggacgcc    3000
tgcggcttct tcacctacat gggcatctgc gagctgatcg acgagaccct gatctgcctg    3060
gccgaccaga gaatcgacat gcccatgccc ttcaggaga tgatgagact ggccctgaag     3120
gacgacgagg acgaccctg cgagagaacc cacgcctggg agtgcaagga catcgtggag    3180
ctgggcagca ccagtgcgg caccgaggcc ggcgacctgg tgtggctgga cgtgagcgag    3240
ctgaccagcg agctgtgccc caccgtgttc ggcaagatgt acaacctgca cctgctgaga    3300
tggtactgct gcaccagcgg ccagaactgc aagctgtgcc tgcccaaggg cctggacacc    3360
gtgcccgagg acgtgagcct gctgcactac gagaactacc ccctggtgta cctgcccccag  3420
```

```
aagttcaacc ccgtgaacct ggtggagctg aacatgccct acagcaacat ggagaagctg    3480
tgggagggca agaagaacct ggagaagctg aagaacatca agctgagcca cagcagagag    3540
ctgaccgaca tcctgatgct gagcgaggcc ctgaacctgg agcacatcga cctggagggc    3600
tgcaccagcc tgatcgacgt gagcatgagc atcccctgct gcggcaagct ggtgagcctg    3660
aacatgaagg actgcagcag actgagaagc ctgcccagca tggtggacct gaccaccctg    3720
aagctgctga acctgagcgg ctgcagcgag ttcgaggaca tccaggactt cgccccaac    3780 ctggaggaga tctacctggc cggcaccagc atcagagagc tgcccctgag catcagaaac    3840
ctgaccgagc tggtgaccct ggacctggag aactgcgaga gactgcagga gatgcccagc    3900
ctgcccggcg acatcatcag aagaagc                                       3927
```

<210> SEQ ID NO 28
<211> LENGTH: 1309
<212> TYPE: PRT
<213> ORGANISM: Artificial Sequence
<220> FEATURE:
<223> OTHER INFORMATION: Amino acid sequence HCP4, variant 9

<400> SEQUENCE: 28

```
Met Ala Gly Cys Phe Ser Gly Thr Lys Lys Tyr Asp Val Phe Pro Cys
1               5                   10                  15

Phe Ser Lys Gly Glu Gly Arg Arg Ser Tyr Ala Ala His Leu Ile His
            20                  25                  30

Glu Leu Asp Arg Arg Leu Ile Gln Thr Phe Thr Asp His Gly Met Glu
        35                  40                  45

Arg Asn Met Pro Ile Asp Ala Glu Leu Leu Ser Leu Ile Gly Glu Cys
    50                  55                  60

Arg Ile Ser Ile Val Ile Phe Ser Arg Asn Tyr Ala Ser Ser Thr Trp
65                  70                  75                  80

Cys Met Asp Glu Leu Val Glu Ile His Thr Cys Phe His Glu Leu Val
                85                  90                  95

Asn Met Gly Val Pro Gly Tyr Tyr Gln Val His Pro Cys Asn Val His
            100                 105                 110

Lys Asn Thr Val Asp Tyr Gly Lys Val Phe Leu Lys Cys Thr Lys Gly
        115                 120                 125

Lys Pro Glu Gln Arg His Leu Arg Trp Met Gln Gly Val Ala Met Val
    130                 135                 140

Val Gln Ile Ala Gly Tyr Asp Leu Gln Asn Trp Pro Asp Asp Ala Gly
145                 150                 155                 160

Met Ala Glu Met Val Gly Asp Glu Val Ser Lys Lys Ile Trp Lys Ser
                165                 170                 175

Thr Asn Asp Tyr Ser Asp Ile Val Gly Ile Glu Ala Lys Ala Glu Gly
            180                 185                 190

Met Ser Cys Met Leu His Ala Arg Ser Asp Lys Ala Arg Leu Val Ile
        195                 200                 205

Ile Ser Gly Pro Ser Gly Ile Gly Lys Thr Thr Leu Ala Lys Ala Met
    210                 215                 220

Tyr Ser Lys Ala Ser Pro Gln Phe Lys Leu Arg Ala Phe Met Ser Trp
225                 230                 235                 240

Lys Lys Thr Gln Gln Asp Glu Phe Asp Ile Lys Leu Cys Trp Ile Asp
                245                 250                 255

Lys Phe Gly Cys Asp Ile Leu Gln Lys Asp Leu His Val Gly Asp
            260                 265                 270
```

```
Leu Leu Ala Val Asp Asn Ser Leu Met His Lys Lys Met Leu Gly Ile
            275                 280                 285

Met Asp Glu Val Asp Glu Met Glu Leu Leu Lys Thr Leu Val Ala Gln
        290                 295                 300

Thr Leu Phe Phe Gly Phe Gly Cys His Leu Val Val Ala Cys Asn Asp
305                 310                 315                 320

Arg Asn Leu Val Lys Ala His Glu Ile Asn Met Met Trp Asp Val Val
                325                 330                 335

Tyr Pro Ser Val His Val Ala Leu Glu Val Phe Ser Gln Cys Ala Phe
            340                 345                 350

Met Arg Gly Tyr Pro Pro Thr Asp Phe Arg Glu Gly Ser Met Asp Phe
        355                 360                 365

Ala Tyr Leu Ala Gly Gln Ala Pro Leu Asp Leu His Val Leu Gly Ile
370                 375                 380

Gly Ile Lys Gly Lys His Lys Glu Glu Trp Val Asp Leu Leu Pro Arg
385                 390                 395                 400

Val Lys Gln Asp Ile Asp Gly Lys Tyr Lys Lys Thr Met Arg Asn Phe
                405                 410                 415

Leu Pro Gly Ile Arg Lys His Leu Ser Asn Glu Glu Gly Val His Glu
            420                 425                 430

Arg Leu His His Gly Asn His Arg Leu Asp Leu Asp Glu Glu Tyr Pro
        435                 440                 445

Gly Gly Glu Ile Tyr Cys Asp Asp Gly Pro Cys Pro Ser Ser Gln Trp
450                 455                 460

Lys Asp Thr Glu Glu Phe Asp Cys Met Glu Ile Ile Pro Ala Ile Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
            500                 505                 510

Pro Phe Lys Cys Ser Ala Asn Asp Val Ile Asp Phe Leu Arg Thr Arg
        515                 520                 525

Gln Val Leu Val Ser Cys Asp Ala Leu Ile Asp Lys Leu Ile Phe Cys
530                 535                 540

Thr Glu Gly Tyr Gly Ala His Pro Asp Glu Gln Pro Trp Arg Ser Asn
545                 550                 555                 560

Ala Val Thr Ser Phe Leu Arg Ile Ala Arg Asp Gly Thr Arg Glu Lys
                565                 570                 575

Glu Cys Ile Leu Val Tyr Ser Cys His Glu Asn Leu Asp Val Asp Glu
            580                 585                 590

Thr Cys Phe Ile Glu Ala Ile Ser Lys Asp Leu His Lys Asn Gly Phe
        595                 600                 605

Ile Pro Val Ser Phe Asn Val Leu Ile Arg Glu Gln Leu Asp Glu Glu
610                 615                 620

Met Leu Trp Gly Thr Arg Val Met Ile Gly Ile Leu Cys Ser Ser Phe
625                 630                 635                 640

Leu Ser Ser Arg Asn Thr Leu Glu His Gly Val Ala Val Met Glu His
                645                 650                 655

Tyr Lys Thr Cys Asp Ile Val Ile Pro Ile Tyr Phe Lys Val Arg
            660                 665                 670

Leu Ser Asp Ile Thr Gly Leu Lys Ala Lys Phe Asp Ala Ala Phe Ile
        675                 680                 685

Gln Leu Arg Gly Ser Leu Gln Glu Asp His Ala Gln Lys Phe Lys Ala
```

```
                690             695             700
Ala Met Ser Glu Ile Ala Ser Ile Gly Ala His Asp Phe Thr Lys Gly
705             710             715             720

Thr Gln Tyr Ala Leu Ala Glu Glu Met Val Arg Asn Ala Cys Leu Lys
            725             730             735

Leu Trp Leu Lys Thr Cys Lys Asn Leu Leu Gly Ile Ile Gly Ile Leu
            740             745             750

Asn His Cys Asn Thr Thr Glu Val Glu Ile Val Gly Ile Trp Leu Ile
            755             760             765

Ala Ala Ile Gly Lys Cys Ser Met Ala Lys Asp Ile Phe Glu Leu Arg
            770             775             780

Ala Pro His Tyr Asp Phe Ser Tyr Tyr Ile Gln Asp Trp His Leu Met
785             790             795             800

Ser Gln Met Lys Arg Pro Arg Asn Ala Arg Glu Asp Phe Ala Ser His
            805             810             815

Ala Tyr Ile Glu Asp Lys Gly Leu Gly Ala Thr Asp Val Lys Pro Cys
            820             825             830

Phe Ala Arg Asp Trp Tyr Arg Lys His Ser Gly Leu Ala Val Leu Glu
            835             840             845

Asp Ile Cys Gln Leu Arg Asp Ile Glu Leu Val Ile Gly Gly Phe Met
            850             855             860

Phe Phe Ser His Met Lys Arg Ile Ile Leu Cys Ser Arg Thr Lys Gln
865             870             875             880

Gly Val Val Gln Cys Arg Met Lys Lys Pro Tyr Asp Ile Asn Arg Leu
            885             890             895

Ser Glu Phe Glu Cys Trp Lys Leu Ser Lys Gln Phe Leu Glu Ile Asp
            900             905             910

Gln Pro Leu Ile Ser Glu Leu Ile Ser Ser Thr Gly Ala Pro Leu
            915             920             925

Leu Leu Lys Met Ala Val Thr Thr Gly Ser His Gln Trp Ile Ser Asn
            930             935             940

Met His Glu Lys Leu Gln Ser Ile Arg Arg Asp Pro Pro Thr Gln Ile
945             950             955             960

Gln Glu Ala Phe Lys Arg Thr Tyr Asp Val Leu Asp Asp Gln Asp Lys
            965             970             975

Asn Ile Phe Leu Asp Leu Ala Cys Phe Phe Arg Gly Gln Ser Lys Asp
            980             985             990

Tyr Ala Val Leu Leu Leu Asp Ala Cys Gly Phe Phe Thr Tyr Met Gly
            995             1000            1005

Ile Cys Glu Leu Ile Asp Glu Thr Leu Ile Cys Leu Ala Asp Gln Arg
            1010            1015            1020

Ile Asp Met Pro Met Pro Phe Gln Glu Met Met Arg Leu Ala Leu Lys
1025            1030            1035            1040

Asp Asp Glu Asp Asp Pro Cys Glu Arg Thr His Ala Trp Glu Cys Lys
            1045            1050            1055

Asp Ile Val Glu Leu Gly Ser Asn Gln Cys Gly Thr Glu Ala Gly Asp
            1060            1065            1070

Leu Val Trp Leu Asp Val Ser Glu Leu Thr Ser Glu Leu Cys Pro Thr
            1075            1080            1085

Val Phe Gly Lys Met Tyr Asn Leu His Leu Leu Arg Trp Tyr Cys Cys
            1090            1095            1100

Thr Ser Gly Gln Asn Cys Lys Leu Cys Leu Pro Lys Gly Leu Asp Thr
1105            1110            1115            1120
```

Val Pro Glu Asp Val Ser Leu Leu His Tyr Glu Asn Tyr Pro Leu Val
            1125                1130                1135

Tyr Leu Pro Gln Lys Phe Asn Pro Val Asn Leu Val Glu Leu Asn Met
        1140                1145                1150

Pro Tyr Ser Asn Met Glu Lys Leu Trp Glu Gly Lys Lys Asn Leu Glu
    1155                1160                1165

Lys Leu Lys Asn Ile Lys Leu Ser His Ser Arg Glu Leu Thr Asp Ile
1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
            1205                1210                1215

Leu Val Ser Leu Asn Met Lys Asp Cys Ser Arg Leu Arg Ser Leu Pro
            1220                1225                1230

Ser Met Val Asp Leu Thr Thr Leu Lys Leu Leu Asn Leu Ser Gly Cys
        1235                1240                1245

Ser Glu Phe Glu Asp Ile Gln Asp Phe Ala Pro Asn Leu Glu Glu Ile
    1250                1255                1260

Tyr Leu Ala Gly Thr Ser Ile Arg Glu Leu Pro Leu Ser Ile Arg Asn
1265                1270                1275                1280

Leu Thr Glu Leu Val Thr Leu Asp Leu Glu Asn Cys Glu Arg Leu Gln
            1285                1290                1295

Glu Met Pro Ser Leu Pro Gly Asp Ile Ile Arg Arg Ser
            1300                1305

<210> SEQ ID NO 29
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
      /note="Nucleotide sequence HCP4, variant 10"
      /mol_type="unassigned DNA"

<400> SEQUENCE: 29
atggccgcca gcttctgcgg cagcagaaga tgggagatgt tccccaccta cagcaagggc      60
gacctgagaa agtgcttcct ggccagactg ctgaaggagc tggacaagag actgatcaac     120
accttcaccg agagaggcat ggagagacag ctgcccatcg acgccgagct gctgagcgcc     180
gtggccgaga gcaagggcac cggcgtgatc tggagcaagc agtacgccag cagctgcttc     240
agcctggacg agctggccga gatcaagagc tgctacagag agctggccaa cggcatggtg     300 ccatcttct tccagatgag acccagccag atgagaaagc agaccggcga gttcggcaga     360
gtgttcatgc acaccaccca cggcaagccc gagaacagaa gagtgagatg ggcccagatg     420
ctggccgcca tcgccaacat ggccggctac gacatgcagc agtaccccga cgagctggtg     480
atgatcgaga tggtgggcga cgacatcagc aagagagcct acagaagcag caacgacttc     540
agcgacatcg tgggcatcga ggcccacctg gaggtgatga ccagcgtgct gagactgaag     600
agcgagaagg gcagagccgt gggcatcagc ggccccctgcg catgggcaa gaccagcatc     660 gccaagatcc tgttcaccaa gctgaccccc aacttccacc tgagagcctt cggcacctac     720
cacagaaccc agcaggacga gttcgacatg aagctgtgct ggatcgagag attcatctgc     780
gagatcctgg ccaacagaga cctgaaggtg ctggacatgg ccgccgtgga gcagaccatg     840

```
ggcagaaaga agctgctgct gggcctggac gacgtggagg acctggagct gctgaagacc    900
ctggtgggcc agagcggctg gttcatgtgg ggcagcagaa tcatgggcat caccaacgag    960
caccagctgc tgaaggccaa ggagatcaac ctgatctacg aggccgccta ccccagcggc   1020
aagctggccc tggacgcctt ctgcaacagc ctgttcatca agatgtaccc ccccagcgac   1080
tggcacgaca tcagcgtgga gttcatgtac ctggccctga acctgcccct ggacctgaga   1140
gtgctgggcg gcatgatgaa gggcaagcac agagaggact ggatggacct gctgcccaag   1200
atcagacagg agggcgacgg caagtacaag aagaccctga gaaacttcct gcccgtgatc   1260
agaaagaagg tgagcaacga ggagggcggc agagagaagc tgaagaagat caacaagaag   1320
ctggacctgg acgaggagtt ccccggcgtg gagatctaca gcgacgacat ccccaccccc   1380
accaccaact ggaaggactg cgacgagttc gacagcggcg acatcatgcc catcgccgcc   1440
gacaagagca ccaccatcat ccccaacaga agacacagca cgacgactg gtgcagcttc    1500
tgcgagttcc tgagaaacag aatcccccc ctgaaccct tcaagtgcag cgccaacgac    1560
gtgatcgact tcctgagaac cagacaggtg ctgggcacca ccgacatcct ggtggagaga   1620
ctgatcttca gcagcgacgc ctacggcatc aagcccgagg acaaccccctt cagaagccag   1680
atcgtgtgca cctacctgaa ggccgccaga gacatgacca gagaccacga gagcatcctg   1740
gtgttcacct gccacgacaa catggacgtg gacgagacca gcttcatcga gctgctgagc   1800
aaggacctgc acagaaacgg ctggatcccc ctgacctaca acctgggcgg cagagacaac   1860
ctggacgagg acctgctgta cggcagcaag gtgggcatca tgatcctgtg cagcagctac   1920
gtgagcagca gacagaccgg cgaccacctg gtggccatga tggagaagtt caagaccacc   1980
gagatggtga tcatccccgg ctacttcaag gccagactga gcgacatctg cggcctgcac   2040
atcagattcg acgccatgtt cctgcagatg cacatcagcg tgaacgagga cagagcccag   2100
aagtggaagg gcgtgatgac cgacatcgtg agcggcggcg ccacgactg gacccacgcc    2160
agcaacttca tcggcatgga cgacgtggcc agaaacgcct cgccaagct gtacctgaag    2220
tgcagcaagc agctgctggg cgccctggcc ctggtgaacc acagccagac cacgacgtg    2280
gacctgatgg gcatctgggg cgccgccgcc atcggcaaga gcagcatcat ccacgaggcc   2340
ttcgagctgc acgccccca ctacgacttc tgcttcttcc tgcaggagtt caagatgatg   2400
acccagggca agaccccag acagctgcac gaggacttcg gctgccacct gttcggcgac   2460
gacaagggcc tgggcgcctg cgacggcaga cccagcttca tgagagactg gttccaccac   2520
agaaccatcc tggtggtgct ggaggacgtg accaacgcca gagacgccga gggcgtgatc   2580
ggcggctggg gctggttctg ccacatccac aagatcatcc tgacctgcag aagcaagcag   2640
gtgggcgtgc agtgcaagat gcacaagccc tacgacatca acaagctgag cgacttcgac   2700
agcttcagag gctgcaagaa ctacctggac ggcgagcagc ccgtggtgag cgagctggcc   2760
acctgcagca gcatcatccc catggccgcc aaggccctgg tgtgcagcat cagcaagcag   2820
tacatctgca acatgcacga ccacgtgaac agcgccagaa aggagccccc ctgccagatc   2880
aacgaggcct tcagaagaac cttcgacgcc ctggaggagc aggacagaaa catcttcctg   2940
gacctggcct gcttcttcag aggccagagc aaggactacg ccgtgctgct gctggacgcc   3000
tgcggcttct tcacctacat gggcatctgc gagctgatcg acgagagcct gatctgcatg   3060
gtggagaaca gaatcgaggg ccccatcccc taccaggaca tggtgaagat gggcgccaag   3120
gacgacgagg acgaccccag cgagagaagc agagcctggg acaccacga cggcgtggag    3180
gtgctgacca acaacagcgg caccgaggcc atcgagggca tcttcctgga ggccagcgac   3240
```

```
ctgacctgcg acgtgagccc ctgcgtgtgg ggcaagatgt tccagctgag actggccaag    3300
ttctactgca ccaccaccgg caaccagtgc aaggtgacca tgccccacgg cctggagagc    3360
ctgcccgacg agctgagcgg cgcccacttc gacaactacc ccgtgatgta cggcccccag    3420
aagttcaacc ccgtgaacct ggtggagctg aacatgccct acagcaacat ggagaagctg    3480
tgggagggca agaagaacct ggagaagctg aagaacatca agctgagcca gcagagag    3540
ctgaccgaca tcctgatgct gagcgaggcc ctgaacctgg agcacatcga cctggagggc    3600
tgcaccagcc tgatcgacgt gagcatgagc atcccctgct gcggcaagct ggtgagcctg    3660
aacatgaagg actgcagcag actgagaagc ctgcccagca tggtggacct gaccaccctg    3720
aagctgctga acctgagcgg ctgcagcgag ttcgaggaca tccaggactt cgcccccaac    3780
ctggaggaga tctacctggc cggcaccagc atcagagagc tgcccctgag catcagaaac    3840
ctgaccgagc tggtgaccct ggacctggag aactgcgaga gactgcagga gatgcccagc    3900
ctgcccgtgg agatcatcag aaagacc    3927
```

<210> SEQ ID NO 30
<211> LENGTH: 1309
<212> TYPE: PRT
<213> ORGANISM: Artificial Sequence
<220> FEATURE:
<223> OTHER INFORMATION: Amino acid sequence HCP4, variant 10

<400> SEQUENCE: 30

```
Met Ala Ala Ser Phe Cys Gly Ser Arg Arg Trp Glu Met Phe Pro Thr
1               5                   10                  15

Tyr Ser Lys Gly Asp Leu Arg Lys Cys Phe Leu Ala Arg Leu Leu Lys
            20                  25                  30

Glu Leu Asp Lys Arg Leu Ile Asn Thr Phe Thr Glu Arg Gly Met Glu
        35                  40                  45

Arg Gln Leu Pro Ile Asp Ala Glu Leu Leu Ser Ala Val Ala Glu Ser
    50                  55                  60

Lys Gly Thr Gly Val Ile Trp Ser Lys Gln Tyr Ala Ser Ser Cys Phe
65                  70                  75                  80

Ser Leu Asp Glu Leu Ala Glu Ile Lys Ser Cys Tyr Arg Glu Leu Ala
                85                  90                  95

Asn Gly Met Val Pro Ile Phe Phe Gln Met Arg Pro Ser Gln Met Arg
            100                 105                 110

Lys Gln Thr Gly Glu Phe Gly Arg Val Phe Met His Thr Thr His Gly
        115                 120                 125

Lys Pro Glu Asn Arg Arg Val Arg Trp Ala Gln Met Leu Ala Ala Ile
    130                 135                 140

Ala Asn Met Ala Gly Tyr Asp Met Gln Gln Tyr Pro Asp Glu Leu Val
145                 150                 155                 160

Met Ile Glu Met Val Gly Asp Asp Ile Ser Lys Arg Ala Tyr Arg Ser
                165                 170                 175

Ser Asn Asp Phe Ser Asp Ile Val Gly Ile Glu Ala His Leu Glu Val
            180                 185                 190

Met Thr Ser Val Leu Arg Leu Lys Ser Glu Lys Gly Arg Ala Val Gly
        195                 200                 205

Ile Ser Gly Pro Cys Gly Met Gly Lys Thr Ser Ile Ala Lys Ile Leu
    210                 215                 220

Phe Thr Lys Leu Thr Pro Asn Phe His Leu Arg Ala Phe Gly Thr Tyr
225                 230                 235                 240
```

```
His Arg Thr Gln Gln Asp Glu Phe Asp Met Lys Leu Cys Trp Ile Glu
                245                 250                 255

Arg Phe Ile Cys Glu Ile Leu Ala Asn Arg Asp Leu Lys Val Leu Asp
            260                 265                 270

Met Ala Ala Val Glu Gln Thr Met Gly Arg Lys Lys Leu Leu Leu Gly
        275                 280                 285

Leu Asp Asp Val Glu Asp Leu Glu Leu Leu Lys Thr Leu Val Gly Gln
    290                 295                 300

Ser Gly Trp Phe Met Trp Gly Ser Arg Ile Met Gly Ile Thr Asn Glu
305                 310                 315                 320

His Gln Leu Leu Lys Ala Lys Glu Ile Asn Leu Ile Tyr Glu Ala Ala
                325                 330                 335

Tyr Pro Ser Gly Lys Leu Ala Leu Asp Ala Phe Cys Asn Ser Leu Phe
            340                 345                 350

Ile Lys Met Tyr Pro Pro Ser Asp Trp His Asp Ile Ser Val Glu Phe
        355                 360                 365

Met Tyr Leu Ala Leu Asn Leu Pro Leu Asp Leu Arg Val Leu Gly Gly
    370                 375                 380

Met Met Lys Gly Lys His Arg Glu Asp Trp Met Asp Leu Leu Pro Lys
385                 390                 395                 400

Ile Arg Gln Glu Gly Asp Gly Lys Tyr Lys Lys Thr Leu Arg Asn Phe
                405                 410                 415

Leu Pro Val Ile Arg Lys Val Ser Asn Glu Gly Gly Arg Glu
            420                 425                 430

Lys Leu Lys Lys Ile Asn Lys Lys Leu Asp Leu Asp Glu Glu Phe Pro
        435                 440                 445

Gly Val Glu Ile Tyr Ser Asp Asp Ile Pro Thr Pro Thr Thr Asn Trp
    450                 455                 460

Lys Asp Cys Asp Glu Phe Asp Ser Gly Asp Ile Met Pro Ile Ala Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
            500                 505                 510

Pro Phe Lys Cys Ser Ala Asn Asp Val Ile Asp Phe Leu Arg Thr Arg
        515                 520                 525

Gln Val Leu Gly Thr Thr Asp Ile Leu Val Glu Arg Leu Ile Phe Ser
    530                 535                 540

Ser Asp Ala Tyr Gly Ile Lys Pro Glu Asp Asn Pro Phe Arg Ser Gln
545                 550                 555                 560

Ile Val Cys Thr Tyr Leu Lys Ala Ala Arg Asp Met Thr Arg Asp His
                565                 570                 575

Glu Ser Ile Leu Val Phe Thr Cys His Asp Asn Met Asp Val Asp Glu
            580                 585                 590

Thr Ser Phe Ile Glu Leu Leu Ser Lys Asp Leu His Arg Asn Gly Trp
        595                 600                 605

Ile Pro Leu Thr Tyr Asn Leu Gly Gly Arg Asp Asn Leu Asp Glu Asp
    610                 615                 620

Leu Leu Tyr Gly Ser Lys Val Gly Ile Met Ile Leu Cys Ser Ser Tyr
625                 630                 635                 640

Val Ser Ser Arg Gln Thr Gly Asp His Leu Val Ala Met Met Glu Lys
                645                 650                 655
```

-continued

Phe Lys Thr Thr Glu Met Val Ile Ile Pro Gly Tyr Phe Lys Ala Arg
            660                 665                 670

Leu Ser Asp Ile Cys Gly Leu His Ile Arg Phe Asp Ala Met Phe Leu
        675                 680                 685

Gln Met His Ile Ser Val Asn Glu Asp Arg Ala Gln Lys Trp Lys Gly
    690                 695                 700

Val Met Thr Asp Ile Val Ser Gly Gly His Asp Trp Thr His Ala
705                 710                 715                 720

Ser Asn Phe Ile Gly Met Asp Asp Val Ala Arg Asn Ala Cys Ala Lys
                725                 730                 735

Leu Tyr Leu Lys Cys Ser Lys Gln Leu Leu Gly Ala Leu Ala Leu Val
            740                 745                 750

Asn His Ser Gln Thr Thr Asp Val Asp Leu Met Gly Ile Trp Gly Ala
        755                 760                 765

Ala Ala Ile Gly Lys Ser Ser Ile Ile His Glu Ala Phe Glu Leu His
    770                 775                 780

Ala Pro His Tyr Asp Phe Cys Phe Phe Leu Gln Glu Phe Lys Met Met
785                 790                 795                 800

Thr Gln Gly Lys Arg Pro Arg Gln Leu His Glu Asp Phe Gly Cys His
                805                 810                 815

Leu Phe Gly Asp Asp Lys Gly Leu Gly Ala Cys Asp Gly Arg Pro Ser
            820                 825                 830

Phe Met Arg Asp Trp Phe His His Arg Thr Ile Leu Val Val Leu Glu
        835                 840                 845

Asp Val Thr Asn Ala Arg Asp Ala Glu Gly Val Ile Gly Gly Trp Gly
    850                 855                 860

Trp Phe Cys His Ile His Lys Ile Ile Leu Thr Cys Arg Ser Lys Gln
865                 870                 875                 880

Val Gly Val Gln Cys Lys Met His Lys Pro Tyr Asp Ile Asn Lys Leu
                885                 890                 895

Ser Asp Phe Asp Ser Phe Arg Gly Cys Lys Asn Tyr Leu Asp Gly Glu
            900                 905                 910

Gln Pro Val Val Ser Glu Leu Ala Thr Cys Ser Ser Ile Ile Pro Met
        915                 920                 925

Ala Ala Lys Ala Leu Val Cys Ser Ile Ser Lys Gln Tyr Ile Cys Asn
    930                 935                 940

Met His Asp His Val Asn Ser Ala Arg Lys Glu Pro Pro Cys Gln Ile
945                 950                 955                 960

Asn Glu Ala Phe Arg Arg Thr Phe Asp Ala Leu Glu Glu Gln Asp Arg
                965                 970                 975

Asn Ile Phe Leu Asp Leu Ala Cys Phe Phe Arg Gly Gln Ser Lys Asp
            980                 985                 990

Tyr Ala Val Leu Leu Leu Asp Ala Cys Gly Phe Phe Thr Tyr Met Gly
        995                 1000                1005

Ile Cys Glu Leu Ile Asp Glu Ser Leu Ile Cys Met Val Glu Asn Arg
    1010                1015                1020

Ile Glu Gly Pro Ile Pro Tyr Gln Asp Met Val Lys Met Gly Ala Lys
1025                1030                1035                1040

Asp Asp Glu Asp Asp Pro Ser Glu Arg Ser Arg Ala Trp Asp Thr His
                1045                1050                1055

Asp Gly Val Glu Val Leu Thr Asn Asn Ser Gly Thr Glu Ala Ile Glu
            1060                1065                1070

Gly Ile Phe Leu Glu Ala Ser Asp Leu Thr Cys Asp Val Ser Pro Cys

|  | 1075 |  |  |  | 1080 |  |  |  |  | 1085 |  |
|---|---|---|---|---|---|---|---|---|---|---|---|

Val Trp Gly Lys Met Phe Gln Leu Arg Leu Ala Lys Phe Tyr Cys Thr
    1090                1095                1100

Thr Thr Gly Asn Gln Cys Lys Val Thr Met Pro His Gly Leu Glu Ser
1105               1110             1115                1120

Leu Pro Asp Glu Leu Ser Gly Ala His Phe Asp Asn Tyr Pro Val Met
              1125                1130                1135

Tyr Gly Pro Gln Lys Phe Asn Pro Val Asn Leu Val Glu Leu Asn Met
            1140                1145                1150

Pro Tyr Ser Asn Met Glu Lys Leu Trp Glu Gly Lys Lys Asn Leu Glu
            1155                1160                1165

Lys Leu Lys Asn Ile Lys Leu Ser His Ser Arg Glu Leu Thr Asp Ile
            1170                1175                1180

Leu Met Leu Ser Glu Ala Leu Asn Leu Glu His Ile Asp Leu Glu Gly
1185               1190             1195                1200

Cys Thr Ser Leu Ile Asp Val Ser Met Ser Ile Pro Cys Cys Gly Lys
              1205                1210                1215

Leu Val Ser Leu Asn Met Lys Asp Cys Ser Arg Leu Arg Ser Leu Pro
            1220                1225                1230

Ser Met Val Asp Leu Thr Thr Leu Lys Leu Leu Asn Leu Ser Gly Cys
            1235                1240                1245

Ser Glu Phe Glu Asp Ile Gln Asp Phe Ala Pro Asn Leu Glu Glu Ile
            1250                1255                1260

Tyr Leu Ala Gly Thr Ser Ile Arg Gly Leu Pro Leu Ser Ile Arg Asn
1265               1270             1275                1280

Leu Thr Glu Leu Val Thr Leu Asp Leu Glu Asn Cys Glu Arg Leu Gln
            1285                1290                1295

Glu Met Pro Ser Leu Pro Val Glu Ile Ile Arg Lys Thr
            1300                1305

```
<210> SEQ ID NO 31
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
      /note="Nucleotide sequence HCP4, variant 11"
      /mol_type="unassigned DNA"

<400> SEQUENCE: 31
```

| | | | | | |
|---|---|---|---|---|---|
| atggccgcca | gcttcagcgt | gagccacaga | tacgaggtgt | cccccacctt | cagcaaggtg | 60 |
| gacgtgagaa | gaagcttcgc | cgcccacctg | atcaaggaga | tggacaagag | actgctgcag | 120 |
| accttcaccg | accacggcat | ggagagaaac | ctgcccatcg | acgccgagct | gctgtgcgcc | 180 |
| atcgccgaga | gcagaatgag | catcgtgatc | tggagccaca | actacgccag | cagcaccctg | 240 |
| tgcctggacg | agatcgtgga | cggccacacc | accttcaagg | agctggccca | gatcgtggtg | 300 |
| cccgtgtact | ggaacgtgca | ccccaccaac | atgagaaagc | agtgcggcga | gtacggcaag | 360 |
| gtgttcctga | gacctgcaa | gggcaagccc | gacaacagaa | agctgaagtt | catgcaggcc | 420 |
| ctgctggccg | tggccaacgt | ggccggcttc | gacctgaacc | agtggcccga | cgagatcgtg | 480 |
| atgatcgaga | tggtgatcga | cgaggtgagc | aagcacggct | tcaagagcag | caacgagtac | 540 |
| accgacggcg | tggccggcga | ggcccacatg | acgccatga | ccagcatcct | gagaatgaag | 600 |
| agcgacaagg | ccagaatggt | gggcgtgacc | ggccccagcg | gcatcggcaa | gaccagcatc | 660 |

```
gtgaaggccc tgtacagcaa gctgagcccc cagttccacc tgcacgccta cgtgacctac    720
aagagaacca accaggacga ctacgacatg aagctgagct ggatcgagag attcatcagc    780
gagatcatgg ccagaagga cctgaaggtg ctggacctgg cgccgtgga ccagagcctg    840 gcccacaaga aggtgggcat catcctggac gacgtgagg agggcgagct ggtgaagacc    900
ctggtggtga acaccggctg gttcatcttc atgagcaaga tcgtggtgat caccaacgac    960
agaaacctgc tgaaggccag agacatgaac ctgctgttcg acgtgatgtt ccccagcgcc   1020
cacctggccc tggagatgta cagccagagc gccttcggca agatctaccc cccagcgac   1080 ttcagagagg tgagcgtgga cttcgcctac atcgtgggca acctgcccct ggacctgaga   1140
gtgctggccc tggtgggcaa ggtgaagcac agagaggagt acatcgacat ggtgcccaag   1200
ctgagaaacg acctggaggg caagttcaag aagaccctga aaactacct gcccgtgatc   1260 agaaagagag tgagcaacga ggagggcggc aaggagagaa tcaagcacgg ccagcaccac   1320
ctggacgtgg aggaggagtt ccccatcgcc gaggccttca cgaggagat ccccagcccc   1380 accagcaact ggaaggacac cgacgacttc gacagcggcg acatcatccc catcgtggcc   1440
gacaagagca ccaccatcat ccccaacaga agacacagca cgacgactg gtgcagcttc   1500 tgcgagttcc tgagaaacag aatcccccc ctgaaccccct tcaagtgcag cgccaacgac   1560
gtgatcgact tcctgagaac cagacaggtg ctggtgagct gcgaggccct ggtgacaga   1620 ctgatctaca gcaccgaggc cttcggcatc aagcccgagg agaaccccta cagaagcaac   1680
gccgtgacca gctacctgaa ggccgccaga gacatgacca gagaccacga gaccatcggc   1740
gtgtacagct gccacgacaa cctggacgtg gaggacacca gcttcatcga ggtgatctgc   1800
aaggagctgc acaagcaggg cttcatcccc ctgacctaca acctgctggg cagagagcag   1860
ctggacgagg aggtgctgtt cggcagcaga gtgggcatcg tgggcctgac cagctgctac   1920
gtgagcagca gacagaccct ggaccacatg gtgctggtga tggagcactg gaagaccacc   1980
gacctggtga tcatccccgt gtactggaag gtgagactga gcgacatctg cggcctgaag   2040
ggcagattcg agggcgcctt cctgcagctg agaatgagcc tgcaggagga cagaatgaac   2100
aagtggaaga tcgccatgtg cgagatcgtg tgcatgatcg ccacgactg gaccaagggc   2160 agcaacttcg gcctggccga cgaggccggc agaaacatca gcctgagact gttcctgaag   2220
agcagcaagc agctgctggc catcctgggc ctgctgcagc acagccagag caccgacgtg   2280
gagatcatgg gcatctgggg cgtggccggc atcatgaaga cctgcatcgc ccacgagatc   2340
ttcgacggca acgccccca ctgggacttc agctacttcc tgcaggagtt ccacctgatg   2400
tgcaacatga agagacccag acagctgaag gacgagttcg tgtgcagaat ctacggcgag   2460
gagaagatca tcgcctgag cgacgtgaag ccctgctgga tgagactg gttcaagaag   2520 cacaccatcc tgctggtgct ggacgaggtg agcaacgccc acgaggccga ggccctgatc   2580
ggcgtgttcg gcttcttcag cagaggccac agaatcgccg ccaccagcca cagcagacag   2640
gtgctggtgc agaccaaggt gcacaagccc tacgagatcc agcacctgag cgacttcgag   2700
tgcttcagac tgtgcagaca gtacctggac ggcgagaacc ccgtgctgag cgagctgatc   2760
agctgcagca gcggcatccc cctggccctg aagctgctgg tgagctgcgt gagcaagcag   2820
tacatgacca acatgaagga gcacatgcag agcggccaca aggagccccc cacccaggtg   2880
caggaggcct ggaaaagac cttcgacggc tggaggagc aggacaagaa cggcttcctg   2940
gacctggcct gcttcttcag aggcaacagc aaggactacg ccgtgatcct gctggacgcc   3000
```

-continued

```
accggcttct acacctacat gggcatctgc gacctgatgg acgagagcct gatgagcctg    3060
gtggacaaca aggtggagat gcccggcccc ttccaggaca tcggcagaat catcatccac    3120
gaggaggacg aggacccctg cgagagaagc agactgtggg acagcaagga catcgtggac    3180
ggcctgaccc agaacagcat caccgaggcc atcgagggca tcttcgtgga cgccaccgag    3240
ctgagcagcg agctgagccc cagcgtgttc gtgaagatgt tcaacctgca cctggtgaag    3300
tggtactgca ccagcagcgg caaccagtgc aagctgtgcg ccccccacgg cctggactgc    3360
ctgcccgacg agctgagcgg cctgcactgg gagaactacc ccctgctgta cctgccccag    3420
aagttcaacc ccgtgaacct ggtggagctg aacatgccct acagcaacat ggagaagctg    3480
tgggagggca agaagaacct ggagaagctg aagaacatca agctgagcca cagcagagag    3540
ctgaccgaca tcctgatgct gagcgaggcc ctgaacctgg agcacatcga cctggagggc    3600
tgcaccagcc tgatcgacgt gagcatgagc atcccctgct gcggcaagct ggtgagcctg    3660
aacatgaagg actgcagcag actgagaagc ctgcccagca tggtggacct gaccaccctg    3720
aagctgctga acctgagcgg ctgcagcgag ttcgaggaca tccaggactt cgcccccaac    3780
ctggaggaga tctacctggc cggcaccagc atcagagagc tgcccctgag catcagaaac    3840
ctgaccgagc tggtgaccct ggacctggag aactgcgaga gactgcagga gatgcccagc    3900
ctgcccgtgg agatcatcag acacacc                                        3927
```

<210> SEQ ID NO 32
<211> LENGTH: 1309
<212> TYPE: PRT
<213> ORGANISM: Artificial Sequence
<220> FEATURE:
<223> OTHER INFORMATION: Amino acid sequence HCP4, variant 11

<400> SEQUENCE: 32

```
Met Ala Ala Ser Phe Ser Val Ser His Arg Tyr Glu Val Phe Pro Thr
 1               5                  10                  15

Phe Ser Lys Val Asp Val Arg Arg Ser Phe Ala Ala His Leu Ile Lys
                20                  25                  30

Glu Met Asp Lys Arg Leu Leu Gln Thr Phe Thr Asp His Gly Met Glu
         35                  40                  45

Arg Asn Leu Pro Ile Asp Ala Glu Leu Leu Cys Ala Ile Ala Glu Ser
     50                  55                  60

Arg Met Ser Ile Val Ile Trp Ser His Asn Tyr Ala Ser Ser Thr Trp
 65                  70                  75                  80

Cys Leu Asp Glu Ile Val Asp Gly His Thr Thr Phe Lys Glu Leu Ala
                 85                  90                  95

Gln Ile Val Val Pro Val Tyr Trp Asn Val His Pro Thr Asn Met Arg
            100                 105                 110

Lys Gln Cys Gly Glu Tyr Gly Lys Val Phe Leu Lys Thr Cys Lys Gly
        115                 120                 125

Lys Pro Asp Asn Arg Lys Leu Lys Phe Met Gln Ala Leu Leu Ala Val
    130                 135                 140

Ala Asn Val Ala Gly Phe Asp Leu Asn Gln Trp Pro Asp Glu Ile Val
145                 150                 155                 160

Met Ile Glu Met Val Ile Asp Glu Val Ser Lys His Gly Phe Lys Ser
                165                 170                 175

Ser Asn Glu Tyr Thr Asp Gly Val Ala Gly Glu Ala His Met Asp Ala
            180                 185                 190

Met Thr Ser Ile Leu Arg Met Lys Ser Asp Lys Ala Arg Met Val Gly
```

```
            195                 200                 205
Val Thr Gly Pro Ser Gly Ile Gly Lys Thr Ser Ile Val Lys Ala Leu
210                 215                 220

Tyr Ser Lys Leu Ser Pro Gln Phe His Leu His Ala Tyr Val Thr Tyr
225                 230                 235                 240

Lys Arg Thr Asn Gln Asp Asp Tyr Asp Met Lys Leu Ser Trp Ile Glu
                    245                 250                 255

Arg Phe Ile Ser Glu Ile Met Gly Gln Lys Asp Leu Lys Val Leu Asp
                260                 265                 270

Leu Gly Ala Val Asp Gln Ser Leu Ala His Lys Lys Val Gly Ile Ile
            275                 280                 285

Leu Asp Asp Val Glu Glu Gly Glu Leu Val Lys Thr Leu Val Val Asn
290                 295                 300

Thr Gly Trp Phe Ile Phe Met Ser Lys Ile Val Ile Thr Asn Asp
305                 310                 315                 320

Arg Asn Leu Leu Lys Ala Arg Asp Met Asn Leu Leu Phe Asp Val Met
                325                 330                 335

Phe Pro Ser Ala His Leu Ala Leu Glu Met Tyr Ser Gln Ser Ala Phe
                340                 345                 350

Gly Lys Ile Tyr Pro Pro Ser Asp Phe Arg Glu Val Ser Val Asp Phe
                355                 360                 365

Ala Tyr Ile Val Gly Asn Leu Pro Leu Asp Leu Arg Val Leu Ala Leu
370                 375                 380

Val Gly Lys Val Lys His Arg Glu Glu Tyr Ile Asp Met Val Pro Lys
385                 390                 395                 400

Leu Arg Asn Asp Leu Glu Gly Lys Phe Lys Lys Thr Leu Arg Asn Tyr
                405                 410                 415

Leu Pro Val Ile Arg Lys Arg Val Ser Asn Glu Glu Gly Gly Lys Glu
                420                 425                 430

Arg Ile Lys His Gly Gln His His Leu Asp Val Glu Glu Phe Pro
                435                 440                 445

Ile Gly Glu Ala Phe Ser Glu Glu Ile Pro Ser Pro Thr Ser Asn Trp
450                 455                 460

Lys Asp Thr Asp Asp Phe Asp Ser Gly Asp Ile Ile Pro Ile Val Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
                500                 505                 510

Pro Phe Lys Cys Ser Ala Asn Asp Val Ile Asp Phe Leu Arg Thr Arg
                515                 520                 525

Gln Val Leu Val Ser Cys Glu Ala Leu Val Asp Arg Leu Ile Tyr Ser
                530                 535                 540

Thr Glu Ala Phe Gly Ile Lys Pro Glu Glu Asn Pro Tyr Arg Ser Asn
545                 550                 555                 560

Ala Val Thr Ser Tyr Leu Lys Ala Ala Arg Asp Met Thr Arg Asp His
                565                 570                 575

Glu Thr Ile Gly Val Tyr Ser Cys His Asp Asn Leu Asp Val Glu Asp
                580                 585                 590

Thr Ser Phe Ile Glu Val Ile Cys Lys Glu Leu His Lys Gln Gly Phe
                595                 600                 605

Ile Pro Leu Thr Tyr Asn Leu Leu Gly Arg Glu Gln Leu Asp Glu Glu
                610                 615                 620
```

```
Val Leu Phe Gly Ser Arg Val Gly Ile Val Gly Leu Thr Ser Cys Tyr
625                 630                 635                 640

Val Ser Ser Arg Gln Thr Leu Asp His Met Val Leu Val Met Glu His
            645                 650                 655

Trp Lys Thr Thr Asp Leu Val Ile Ile Pro Val Tyr Trp Lys Val Arg
            660                 665                 670

Leu Ser Asp Ile Cys Gly Leu Lys Gly Arg Phe Glu Gly Ala Phe Leu
            675                 680                 685

Gln Leu Arg Met Ser Leu Gln Glu Asp Arg Met Asn Lys Trp Lys Ile
            690                 695                 700

Ala Met Cys Glu Ile Val Cys Met Ile Gly His Asp Trp Thr Lys Gly
705                 710                 715                 720

Ser Asn Phe Gly Leu Ala Asp Glu Ala Gly Arg Asn Ile Ser Leu Arg
            725                 730                 735

Leu Phe Leu Lys Ser Ser Lys Gln Leu Leu Ala Ile Leu Gly Leu Leu
            740                 745                 750

Gln His Ser Gln Ser Thr Asp Val Glu Ile Met Gly Ile Trp Gly Val
            755                 760                 765

Ala Gly Ile Met Lys Thr Cys Ile Ala His Glu Ile Phe Asp Gly His
770                 775                 780

Ala Pro His Trp Asp Phe Ser Tyr Phe Leu Gln Glu Phe His Leu Met
785                 790                 795                 800

Cys Asn Met Lys Arg Pro Arg Gln Leu Lys Asp Glu Phe Val Cys Arg
            805                 810                 815

Ile Tyr Gly Glu Glu Lys Ile Ile Gly Leu Ser Asp Val Lys Pro Cys
            820                 825                 830

Trp Met Arg Asp Trp Phe Lys Lys His Thr Ile Leu Leu Val Leu Asp
            835                 840                 845

Glu Val Ser Asn Ala His Glu Ala Glu Ala Leu Ile Gly Val Phe Gly
850                 855                 860

Phe Phe Ser Arg Gly His Arg Ile Ala Ala Thr Ser His Ser Arg Gln
865                 870                 875                 880

Val Leu Val Gln Thr Lys Val His Lys Pro Tyr Glu Ile Gln His Leu
            885                 890                 895

Ser Asp Phe Glu Cys Phe Arg Leu Cys Arg Gln Tyr Leu Asp Gly Glu
            900                 905                 910

Asn Pro Val Leu Ser Glu Leu Ile Ser Cys Ser Ser Gly Ile Pro Leu
            915                 920                 925

Ala Leu Lys Leu Leu Val Ser Cys Val Ser Lys Gln Tyr Met Thr Asn
            930                 935                 940

Met Lys Glu His Met Gln Ser Gly His Lys Glu Pro Pro Thr Gln Val
945                 950                 955                 960

Gln Glu Ala Trp Arg Lys Thr Phe Asp Gly Leu Glu Glu Gln Asp Lys
            965                 970                 975

Asn Gly Phe Leu Asp Leu Ala Cys Phe Phe Arg Gly Asn Ser Lys Asp
            980                 985                 990

Tyr Ala Val Ile Leu Leu Asp Ala Thr Gly Phe Tyr Thr Tyr Met Gly
            995                 1000                1005

Ile Cys Asp Leu Met Asp Glu Ser Leu Met Ser Leu Val Asp Asn Lys
            1010                1015                1020

Val Glu Met Pro Gly Pro Phe Gln Asp Ile Gly Arg Ile Ile Ile His
1025                1030                1035                1040
```

-continued

Glu Glu Asp Glu Asp Pro Cys Glu Arg Ser Arg Leu Trp Asp Ser Lys
                1045                1050                1055

Asp Ile Val Asp Gly Leu Thr Gln Asn Ser Ile Thr Glu Ala Ile Glu
        1060                1065                1070

Gly Ile Phe Val Asp Ala Thr Glu Leu Ser Ser Glu Leu Ser Pro Ser
    1075                1080                1085

Val Phe Val Lys Met Phe Asn Leu His Leu Val Lys Trp Tyr Cys Thr
1090                1095                1100

Ser Ser Gly Asn Gln Cys Lys Leu Cys Ala Pro His Gly Leu Asp Cys
1105                1110                1115                1120

Leu Pro Asp Glu Leu Ser Gly Leu His Trp Glu Asn Tyr Pro Leu Leu
                1125                1130                1135

Tyr Leu Pro Gln Lys Phe Asn Pro Val Asn Leu Val Glu Leu Asn Met
        1140                1145                1150

Pro Tyr Ser Asn Met Glu Lys Leu Trp Glu Gly Lys Lys Asn Leu Glu
    1155                1160                1165

Lys Leu Lys Asn Ile Lys Leu Ser His Ser Arg Glu Leu Thr Asp Ile
1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
                1205                1210                1215

Leu Val Ser Leu Asn Met Lys Asp Cys Ser Arg Leu Arg Ser Leu Pro
        1220                1225                1230

Ser Met Val Asp Leu Thr Thr Leu Lys Leu Leu Asn Leu Ser Gly Cys
    1235                1240                1245

Ser Glu Phe Glu Asp Ile Gln Asp Phe Ala Pro Asn Leu Glu Glu Ile
1250                1255                1260

Tyr Leu Ala Gly Thr Ser Ile Arg Glu Leu Pro Leu Ser Ile Arg Asn
1265                1270                1275                1280

Leu Thr Glu Leu Val Thr Leu Asp Leu Glu Asn Cys Glu Arg Leu Gln
                1285                1290                1295

Glu Met Pro Ser Leu Pro Val Glu Ile Ile Arg His Thr
                1300                1305

<210> SEQ ID NO 33
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
      /note="Nucleotide sequence HCP4, variant 12"
      /mol_type="unassigned DNA"

<400> SEQUENCE: 33
atgctggcct gcttctgcgg cagcagaaga tacgacgtgt tccccagctt cagcagagtg      60
gaggtgagac acagcttcct ggcccacctg ctgagagagg ccgacagaag aggcatcaac     120
tgctggtgcg accacggcat ggagaagcag gtgcccatcg acctggagat cctgagcgcc     180
atcgccgaga gcaagggcag catcgtgatc ttcagcaaga actacatgag cagcacctgg     240
tgcctggacg agatcgtgga gatcaagacc tgctggaagg agctggtgaa catcgtggtg     300
cccgtgttct acaacgtgca ccccagccag gtgaagcacc agaccggcga gtggggcaag     360
gtgttcggca agacctgcag aggcaagccc gagaacaaga gactgcactg gatgaacgcc     420

```
ctggtggccg tggtgaacat cgccggcttc gagctgcaga actaccccga cgaggccgtg    480
atgatcgaga tggtggccga ggacgtgagc aagaagctgt ggagaagcag caacgacttc    540
agcgacctgg tgggcatcga ggcccacctg gaggccatga gcaccatcct gagactgaag    600
agcgagaagg ccagaatcgt gggcatcagc ggcccagcg catcggcaa gaccagcatc     660 gccaagctgc tgtacagcaa gctgagcccc aacttccacg gcagaatctt cgtgtgctac    720
aagagaagcc agcaggacga gtacgagatg aagatgtgct ggatcgagaa gttcctgagc    780
gagatcctgg ccagaaggaa cctgaaggcc ctggacctgg gcgccctgga gcagaccctg    840
atgcacagac acgtgctgat catcctggac gacgtggacg acctggagct gctgaagacc    900
ggcgtgggcc agaccggctt cttcggctac gtgaccagaa tcgtggtgat cacccaggac    960
cacaacggcc tgaaggccca cgacatcaac ctgatctggg aggtggcctt ccccagcgcc   1020
cacctgctgc tggagatctt ctgccagagc gccttcggca agatctaccc ccccaccgac   1080
ttcagagagc tgtgcgtgga gtacgcctac ctggccggca acctgccct ggacctgaga    1140 gtgctgggcc tggccgtgaa gggcaagcac agagaggact ggatcgagat gctgcccaga   1200
ctgagaaacg acctggacgg ccacttcaag aagaccctga gaaacttcct gcccgtgatc   1260
agaaagagag tgtgcaacga cgagggcggc agagacaagc tgaagaaggg ccagaagaag   1320
ctggacctgg acgacgagtg gcccggcggc gagatctact gcgacgagat ccccaccccc   1380
acctgccagt ggaaggacac cgacgacttc gacagcggcg acggcatccc catcatcgcc   1440
gacaagagca ccaccatcat ccccaacaga agacacagca cgacgactg gtgcagcttc   1500 tgcgagttcc tgagaaacag aatcccccc ctgaaccct tcaagtgcag cgccaacgac    1560
gtgatcgact tcctgagaac cagacaggtg ctgggcagca ccgaggccct ggccgacaga   1620
ctgatcttct gcagcgaggc cttcggcatc aagcccgagg agaacccctt cagaacccag   1680
gccggcacca gctggctgaa gctggccaga gacatgacca gagagaagga gtgcatcatg   1740
gtgttcagct gccacgagca gctggacgtg gaggagacct gcttcatcga ggccatcagc   1800
aaggagctgc acagacaggg cttcatcccc ctgacctaca acctgctggg cagagagaac   1860
atggacgagg agatgctgta cggcagcaga gtgggcatca tgatcctgtg ctgcagctac   1920
atgaccagca gacagagcct ggagcacctg gtggtggtgg tggagcactt caagaccagc   1980
gagctggtga tcatccccat gtggttcaag gccagactga gcgacatcag cggcctgaag   2040
ggcagattcg acgccgcctt cctgcagctg cacatgagcg cccaggagga gagagtgcag   2100
aagtggaagg ccatgatgag cgagatcgtg tgcatcggcg ccacgagtg gaccaagggc    2160 agccagttca tcctggccga ggacgtggtg agaaacgcct gcctgagact gtacctgaag   2220
agcagcaagc agctgctgat gatcctggcc ggcctgcagc acagccagag cagcgaggtg   2280
gacatcatgg gcatctgggg catcgccggc ccggcaagaa ccagcatcgc cagagagatc   2340
ttcgagctgc acgcccccca ctacgagtac tgctactacc tgaacgactt ccacctgatg   2400
tgccagatga agagacccag aaacatcaga gacgagttca tcagcaagct gtacggcgag   2460
gacaagggcc tgggcgccag cgacgtgaag cccagcttca tgaaggacta cttccacaag   2520
aagaccatcc tggtgggcct ggacgacgtg agcaacgcca gagacgccga ggtgatcatc   2580
ggcggcttcg gctggttcag ccacggccac agaatcatcc tgagcaccag aagcaagcag   2640
gtgggcgtgc agaccaagct gaagaagccc tacgacatcc agaagctgag cgactacgag   2700
agcttcagac tgtgcaagca gtacctggac ggcgacaacc ccgtgatcag cgagctgatc   2760
agctgcacca gcggcatccc cctggccctg aagctgctgg tgagcagcgt gagcaagcag   2820
```

-continued

```
tacatcacca acatgaagga gcacatgcag agcctgagaa aggaccccc cacccagggc    2880 aacgacgcct acagacacag cttcgacctg ctggacgaga cgagaagca gatcttcctg    2940 gacctggcct gcttcttcag aggccagagc aaggactacg ccgtgctgct gctggacgcc    3000
tgcggcttct tcacctacat gggcatctgc gagctgatcg acgagagcct gatcaccctg    3060
gtggaccaga aggtggacgt gcccgtgccc ttccaggaga tggccagaat gatcggccac    3120
gaggaggacg aggaccctg cgagagaagc agagtgtggg acagcaagga catcgtggac    3180
gtgctgaccc agaacagcgg caccgaggcc atcgagggca tcttcctgga gatgagcgac    3240
ctgacctgcg agctgagccc caccgtgtac ggcaagatgt acaacctgag actgctgaag    3300
ttctactgct gcacctgcgg caaccagtgc aagctgaccc tgccccacgt ggtggagacc    3360
ctgcccgacg agctgagcct gctgagatgg gagaactacc ccatggtgtg gatccccag    3420 aagttcaacc ccgtgaacct ggtggagctg aacatgccct acagcaacat ggagaagctg    3480
tgggagggca agaagaacct ggagaagctg aagaacatca agctgagcca cagcagagag    3540
ctgaccgaca tcctgatgct gagcgaggcc ctgaacctgg agcacatcga cctggagggc    3600
tgcaccagcc tgatcgacgt gagcatgagc atcccctgct gcggcaagct ggtgagcctg    3660
aacatgaagg actgcagcag actgagaagc ctgcccagca tggtggacct gaccaccctg    3720
aagctgctga acctgagcgg ctgcagcgag ttcgaggaca tccaggactt cgcccccaac    3780
ctggaggaga tctacctggc cggcaccagc atcagagagc tgcccctgag catcagaaac    3840
ctgaccgagc tggtgaccct ggacctggag aactgcgaga gactgcagga gatgcccagc    3900
ctgcccgtgg agatcatcag acacacc                                       3927
```

<210> SEQ ID NO 34
<211> LENGTH: 1309
<212> TYPE: PRT
<213> ORGANISM: Artificial Sequence
<220> FEATURE:
<223> OTHER INFORMATION: Amino acid sequence HCP4, variant 12

<400> SEQUENCE: 34

```
Met Leu Ala Cys Phe Cys Gly Ser Arg Arg Tyr Asp Val Phe Pro Ser
1               5                   10                  15

Phe Ser Arg Val Glu Val Arg His Ser Phe Leu Ala His Leu Leu Arg
                20                  25                  30

Glu Ala Asp Arg Arg Gly Ile Asn Cys Trp Cys Asp His Gly Met Glu
            35                  40                  45

Lys Gln Val Pro Ile Asp Leu Glu Ile Leu Ser Ala Ile Ala Glu Ser
        50                  55                  60

Lys Gly Ser Ile Val Ile Phe Ser Lys Asn Tyr Met Ser Ser Thr Trp
65                  70                  75                  80

Cys Leu Asp Glu Ile Val Glu Ile Lys Thr Cys Trp Lys Glu Leu Val
                85                  90                  95

Asn Ile Val Val Pro Val Phe Tyr Asn Val His Pro Ser Gln Val Lys
                100                 105                 110

His Gln Thr Gly Glu Trp Gly Lys Val Phe Gly Lys Thr Cys Arg Gly
            115                 120                 125

Lys Pro Glu Asn Lys Arg Leu His Trp Met Asn Ala Leu Val Ala Val
        130                 135                 140

Val Asn Ile Ala Gly Phe Glu Leu Gln Asn Tyr Pro Asp Glu Ala Val
145                 150                 155                 160
```

```
Met Ile Glu Met Val Ala Glu Asp Val Ser Lys Lys Leu Trp Arg Ser
                165                 170                 175

Ser Asn Asp Phe Ser Asp Leu Val Gly Ile Glu Ala His Leu Glu Ala
            180                 185                 190

Met Ser Thr Ile Leu Arg Leu Lys Ser Glu Lys Ala Arg Ile Val Gly
        195                 200                 205

Ile Ser Gly Pro Ser Gly Ile Gly Lys Thr Ser Ile Ala Lys Leu Leu
    210                 215                 220

Tyr Ser Lys Leu Ser Pro Asn Phe His Gly Ile Phe Val Cys Tyr
225                 230                 235                 240

Lys Arg Ser Gln Gln Asp Glu Tyr Glu Met Lys Met Cys Trp Ile Glu
                245                 250                 255

Lys Phe Leu Ser Glu Ile Leu Gly Gln Lys Asp Leu Lys Ala Leu Asp
            260                 265                 270

Leu Gly Ala Leu Glu Gln Thr Leu Met His Arg His Val Leu Ile Ile
        275                 280                 285

Leu Asp Asp Val Asp Asp Leu Glu Leu Leu Lys Thr Gly Val Gly Gln
    290                 295                 300

Thr Gly Phe Phe Gly Tyr Val Thr Arg Ile Val Val Ile Thr Gln Asp
305                 310                 315                 320

His Asn Gly Leu Lys Ala His Asp Ile Asn Leu Ile Trp Glu Val Ala
                325                 330                 335

Phe Pro Ser Ala His Leu Leu Glu Ile Phe Cys Gln Ser Ala Phe
            340                 345                 350

Gly Lys Ile Tyr Pro Pro Thr Asp Phe Arg Glu Leu Cys Val Glu Tyr
        355                 360                 365

Ala Tyr Leu Ala Gly Asn Leu Pro Leu Asp Leu Arg Val Leu Gly Leu
    370                 375                 380

Ala Val Lys Gly Lys His Arg Glu Asp Trp Ile Glu Met Leu Pro Arg
385                 390                 395                 400

Leu Arg Asn Asp Leu Asp Gly His Phe Lys Lys Thr Leu Arg Asn Phe
                405                 410                 415

Leu Pro Val Ile Arg Lys Arg Val Cys Asn Asp Glu Gly Gly Arg Asp
            420                 425                 430

Lys Leu Lys Lys Gly Gln Lys Lys Leu Asp Leu Asp Asp Glu Trp Pro
        435                 440                 445

Gly Gly Glu Ile Tyr Cys Asp Glu Ile Pro Thr Pro Thr Cys Gln Trp
    450                 455                 460

Lys Asp Thr Asp Phe Asp Ser Gly Asp Gly Ile Pro Ile Ile Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
            500                 505                 510

Pro Phe Lys Cys Ser Ala Asn Asp Val Ile Asp Phe Leu Arg Thr Arg
        515                 520                 525

Gln Val Leu Gly Ser Thr Glu Ala Leu Ala Asp Arg Leu Ile Phe Cys
    530                 535                 540

Ser Glu Ala Phe Gly Ile Lys Pro Glu Glu Asn Pro Phe Arg Thr Gln
545                 550                 555                 560

Ala Gly Thr Ser Trp Leu Lys Leu Ala Arg Asp Met Thr Arg Glu Lys
                565                 570                 575

Glu Cys Ile Met Val Phe Ser Cys His Glu Gln Leu Asp Val Glu Glu
```

```
                   580                 585                 590
Thr Cys Phe Ile Glu Ala Ile Ser Lys Glu Leu His Arg Gln Gly Phe
            595                 600                 605
Ile Pro Leu Thr Tyr Asn Leu Leu Gly Arg Glu Asn Met Asp Glu Glu
            610                 615                 620
Met Leu Tyr Gly Ser Arg Val Gly Ile Met Ile Leu Cys Cys Ser Tyr
625                 630                 635                 640
Met Thr Ser Arg Gln Ser Leu Glu His Leu Val Val Val Glu His
            645                 650                 655
Phe Lys Thr Ser Glu Leu Val Ile Ile Pro Met Trp Phe Lys Ala Arg
            660                 665                 670
Leu Ser Asp Ile Ser Gly Leu Lys Gly Arg Phe Asp Ala Ala Phe Leu
            675                 680                 685
Gln Leu His Met Ser Ala Gln Glu Glu Arg Val Gln Lys Trp Lys Ala
            690                 695                 700
Met Met Ser Glu Ile Val Cys Ile Gly Gly His Glu Trp Thr Lys Gly
705                 710                 715                 720
Ser Gln Phe Ile Leu Ala Glu Asp Val Val Arg Asn Ala Cys Leu Arg
            725                 730                 735
Leu Tyr Leu Lys Ser Ser Lys Gln Leu Leu Met Ile Leu Ala Gly Leu
            740                 745                 750
Gln His Ser Gln Ser Ser Glu Val Asp Ile Met Gly Ile Trp Gly Ile
            755                 760                 765
Ala Gly Ala Gly Lys Thr Ser Ile Ala Arg Glu Ile Phe Glu Leu His
            770                 775                 780
Ala Pro His Tyr Glu Tyr Cys Tyr Tyr Leu Asn Asp Phe His Leu Met
785                 790                 795                 800
Cys Gln Met Lys Arg Pro Arg Asn Ile Arg Asp Glu Phe Ile Ser Lys
            805                 810                 815
Leu Tyr Gly Glu Asp Lys Gly Leu Gly Ala Ser Asp Val Lys Pro Ser
            820                 825                 830
Phe Met Lys Asp Tyr Phe His Lys Lys Thr Ile Leu Val Gly Leu Asp
            835                 840                 845
Asp Val Ser Asn Ala Arg Asp Ala Glu Val Ile Ile Gly Gly Phe Gly
            850                 855                 860
Trp Phe Ser His Gly His Arg Ile Ile Leu Ser Thr Arg Ser Lys Gln
865                 870                 875                 880
Val Gly Val Gln Thr Lys Leu Lys Lys Pro Tyr Asp Ile Gln Lys Leu
            885                 890                 895
Ser Asp Tyr Glu Ser Phe Arg Leu Cys Lys Gln Tyr Leu Asp Gly Asp
            900                 905                 910
Asn Pro Val Ile Ser Glu Leu Ile Ser Cys Thr Ser Gly Ile Pro Leu
            915                 920                 925
Ala Leu Lys Leu Leu Val Ser Ser Val Ser Lys Gln Tyr Ile Thr Asn
            930                 935                 940
Met Lys Glu His Met Gln Ser Leu Arg Lys Asp Pro Pro Thr Gln Gly
945                 950                 955                 960
Asn Asp Ala Tyr Arg His Ser Phe Asp Leu Leu Asp Glu Asn Glu Lys
            965                 970                 975
Gln Ile Phe Leu Asp Leu Ala Cys Phe Phe Arg Gly Gln Ser Lys Asp
            980                 985                 990
Tyr Ala Val Leu Leu Leu Asp Ala Cys Gly Phe Phe Thr Tyr Met Gly
            995                 1000                1005
```

-continued

Ile Cys Glu Leu Ile Asp Glu Ser Leu Ile Thr Leu Val Asp Gln Lys
    1010                1015                1020

Val Asp Val Pro Val Pro Phe Gln Glu Met Ala Arg Met Ile Gly His
1025                1030                1035                1040

Glu Glu Asp Glu Asp Pro Cys Glu Arg Ser Arg Val Trp Asp Ser Lys
                1045                1050                1055

Asp Ile Val Asp Val Leu Thr Gln Asn Ser Gly Thr Glu Ala Ile Glu
            1060                1065                1070

Gly Ile Phe Leu Glu Met Ser Asp Leu Thr Cys Glu Leu Ser Pro Thr
        1075                1080                1085

Val Tyr Gly Lys Met Tyr Asn Leu Arg Leu Leu Lys Phe Tyr Cys Cys
    1090                1095                1100

Thr Cys Gly Asn Gln Cys Lys Leu Thr Leu Pro His Val Val Glu Thr
1105                1110                1115                1120

Leu Pro Asp Glu Leu Ser Leu Leu Arg Trp Glu Asn Tyr Pro Met Val
                1125                1130                1135

Trp Ile Pro Gln Lys Phe Asn Pro Val Asn Leu Val Glu Leu Asn Met
            1140                1145                1150

Pro Tyr Ser Asn Met Glu Lys Leu Trp Glu Gly Lys Lys Asn Leu Glu
        1155                1160                1165

Lys Leu Lys Asn Ile Lys Leu Ser His Ser Arg Glu Leu Thr Asp Ile
    1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
                1205                1210                1215

Leu Val Ser Leu Asn Met Lys Asp Cys Ser Arg Leu Arg Ser Leu Pro
            1220                1225                1230

Ser Met Val Asp Leu Thr Thr Leu Lys Leu Leu Asn Leu Ser Gly Cys
        1235                1240                1245

Ser Glu Phe Glu Asp Ile Gln Asp Phe Ala Pro Asn Leu Glu Glu Ile
    1250                1255                1260

Tyr Leu Ala Gly Thr Ser Ile Arg Glu Leu Pro Leu Ser Ile Arg Asn
1265                1270                1275                1280

Leu Thr Glu Leu Val Thr Leu Asp Leu Glu Asn Cys Glu Arg Leu Gln
                1285                1290                1295

Glu Met Pro Ser Leu Pro Val Glu Ile Ile Arg His Thr
            1300                1305

<210> SEQ ID NO 35
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
      /note="Nucleotide sequence HCP4, variant 13"
      /mol_type="unassigned DNA"

<400> SEQUENCE: 35
atggccgcca gcttctgcgg cagccacaga tacgacatgt tccccagctt cagcaaggtg     60
gacgccagaa gaagcttcct ggccagactg ctgaaggagc tggaccacag actgatcaac    120
accttcaccg accacggcat ggagagaaac ctgcccatcg acatggagat cctgagcgcc    180
atcgccgagt gcagaatcag catcgccatc ttcagcaaga actacgccac cagcacctgg    240

```
tgcctggacg agatggtgga gatccacacc tgctacaagg acctggccca gggcgccgtg      300
cccgtgttct tcaacgtgca ccccacccag gtgaagaagc agaccgccga gtacggcaga      360
gtgtacggca gaacctgcaa gggcaagccc gagaacagaa agctgagatg gatgaacctg      420
ctggccgccg tgctgaacat cgccggcttc gacctgcaga actggcccga cgagggcgtg      480
gtgatggaga tggtggccga cgaggtgagc aagaagctgt tcaagagcag caacgacttc      540
agcgacatcg tgatgatcga ggcccacctg gaggtgatga gcagcatcct gagactgcac      600
agcgagaagg ccagaatggt gggcatcagc ggccccagcg gcctgggcaa gaccaccggc      660
gccaaggccc tgttcagcaa gctgagcccc aactaccacc tgagagcctg ggtgacctac      720
aagaagacca accaggacga gtacgacatg aagctgtgct ggatcgagaa gtggctgtgc      780
gagatcggcg ccagaaggca cctgagagtg ctggacctgg cgccgtggca gcagagcctg      840
atgcacaaga aggtgctggg catcctggac gacgtggacg agctggagct gctgaagacc      900
ctgctgggcc agaccggctg gttcggcttc ggcaccagag gcgtggccat cacccaggac      960
agacagctgc tgaaggccca cgacatcaac ctgatctacg agctggcctt ccccagcgcc     1020
cacctggccc tggacatctt ctgccagagc gccttcggca agatctaccc ccccagcgac     1080
ttcagagagc tgagcgtgga gttcgcctac ctggccggca acctgcccct ggaggccaga     1140
gtgctgggca tcgccatgaa gggcaagaag agagaggagt tcatcgagat gctgcccaga     1200
ctgagaaacg acctggacgg caagttcaag aagaccctga gaaactacct gcccgtgatc     1260
agaaagcacg tgagcaacga ggagggcggc agagagaagc tgagaaagat caacaagaag     1320
ctggagctgg acgaggagtt ccccggcgcc gagatctact gcgaggagat ccccagcccc     1380
accagcaact ggaaggacac cgacgacttc gacagcggcg acatcatccc catcatcgcc     1440
gacaagagca ccaccatcat ccccaacaga gacacagca acgacgactg gtgcagcttc     1500
tgcgagttcc tgagaaacag aatccccccc ctgaacccct tcaagtgcag cgccaacgac     1560
gtgatcgact tcctgagaac cagacaggtg ctgggcagca ccgaggccgc cgtggacaga     1620
ctgatcttca gcagcgaggc cttcggcatc aagcccgagg agaacccctt cagaacccag     1680
gccgtgacca gcttcgccaa ggccgccaga gacatgacca gagagaagga gtgcatcctg     1740
gtgttcacct gccacgacaa catggacgtg gacgagacca gcttcggcga ggccatcagc     1800
aaggacctgc acaagcaggg cttcgtgccc ctgacctaca acctgctggg cagagacaac     1860
ctggacgacg acatgctgta cggcagcaga gtgggcatca tgatcctgag cagcagctac     1920
atcagcagca gaaacagcct ggaccacctg gtggccgtga tggagagatg gagaaccacc     1980
gacatggtga tcatccccat gtacttcaag gtgagactga gcgacgtgtg cggcctgaag     2040
ggcagattcg aggccgcctt cctgcagctg cacatgtgcc tgcaggagga cagagtgaac     2100
aagtggaagg ccgccatgag cgagatcgtg agcatcggcg gcaaggagtg gaccaagggc     2160
agccagttca tcctggccga cgacgtggtg agaaacgcca gcctgagact gtacctgaag     2220
agcagcaaga acctgctggg catcctggcc ctgctgaacc acagcagag cagcgacgtg     2280 gaggccatgg gcatgtgggg catcgccggc gtgggcaaga ccagcatcgc cagagagatc     2340
ttcgagctgc acgccccca ctacgacttc tgctacttcc tgcaggactt ccacctgatg     2400
agccagatga gagacccag aaacctgaga gaggacttca tcagcaagct gtacggcgag     2460
gacaaggccc tgctggccag cgacgtgaag cccagcttca tgaaggactg gttccaccac     2520
aagaccatcc tgctggtgct ggacgacgtg agcaacgcca gagacgccga cgccgtgatc     2580
```

-continued

| | |
|---|---|
| ggcggcttcg gctggttcag ccacggccac agaatcatcc tgagcagcaa gagcaagcag | 2640 |
| gtgctggtgc agtgcaaggt gaagaagccc tacgagatcc agaagctgag cgagttcgag | 2700 |
| agctacagac tgtgcaagca gtacctggac ggcgagaacc ccgtgatcag cgagctgatc | 2760 |
| agctgcagca gcggcatccc cctggccctg aaggtgctgc tgagcagcgt gagcaagcag | 2820 |
| tacatcacca acatgaagga cagactgcag agcctgagaa gagaccccccc cagccagatc | 2880 |
| caggaggcct tcagaagaag cttcgacggc ctggacgaga acgagagaaa cggctggctg | 2940 |
| gacctggcct gcttcttcag aggccagagc aaggactacg ccgtgctgct gctggacgcc | 3000 |
| tgcggcttct tcacctacat gggcatctgc gagctgatcg acgagagcct gatctgcctg | 3060 |
| gtggacaaca agatcgagat gcccatgccc tggcaggaca tgggcagaat catcgtgcac | 3120 |
| gaggaggacg aggacccctg cgagcacagc cacctgtacg agagcaagga gatcgtggac | 3180 |
| gtgctgacca acaacagcgg caccgaggcc atcgagggcg ccttcctgga cgcctgcgac | 3240 |
| ctgacctgcg agctgagccc caccgtgttc ggcaagatgt tcaacctgca cctgctgaag | 3300 |
| ttctactgca gctgcagcgg caaccagtgc aagctgaccc tgccccacgg cctggacacc | 3360 |
| ctgcccgacg agggcagcct gctgcactgg gagaactacc ccctggtgta cctgccccag | 3420 |
| aagttcaacc ccgtgaacct ggtggagctg aacatgccct acagcaacat ggagaagctg | 3480 |
| tgggagggca agaagaacct ggagaagctg aagaacatca agctgagcca cagcagagag | 3540 |
| ctgaccgaca tcctgatgct gagcgaggcc ctgaacctgg agcacatcga cctggagggc | 3600 |
| tgcaccagcc tgatcgacgt gagcatgagc atcccctgct gcggcaagct ggtgagcctg | 3660 |
| aacatgaagg actgcagcag actgagaagc ctgcccagca tggtggacct gaccaccctg | 3720 |
| aagctgctga acctgagcgg ctgcagcgag ttcgaggaca tccaggactt cgcccccaac | 3780 |
| ctggaggaga tctacctggc cggcaccagc atcagagagc tgccccctgag catcagaaac | 3840 |
| ctgaccgagc tggtgaccct ggacctggag aactgcgaga gactgcagga gatgcccagc | 3900 |
| ctgcccgtgg agatgatcag aagaacc | 3927 |

<210> SEQ ID NO 36
<211> LENGTH: 1309
<212> TYPE: PRT
<213> ORGANISM: Artificial Sequence
<220> FEATURE:
<223> OTHER INFORMATION: Amino acid sequence HCP4, variant 13

<400> SEQUENCE: 36

```
Met Ala Ala Ser Phe Cys Gly Ser His Arg Tyr Asp Met Phe Pro Ser
1               5                   10                  15

Phe Ser Lys Val Asp Ala Arg Arg Ser Phe Leu Ala Arg Leu Leu Lys
                20                  25                  30

Glu Leu Asp His Arg Leu Ile Asn Thr Phe Thr Asp His Gly Met Glu
            35                  40                  45

Arg Asn Leu Pro Ile Asp Met Glu Ile Leu Ser Ala Ile Ala Glu Cys
        50                  55                  60

Arg Ile Ser Ile Ala Ile Phe Ser Lys Asn Tyr Ala Thr Ser Thr Trp
65                  70                  75                  80

Cys Leu Asp Glu Met Val Glu Ile His Thr Cys Tyr Lys Asp Leu Ala
                85                  90                  95

Gln Gly Ala Val Pro Val Phe Phe Asn Val His Pro Thr Gln Val Lys
            100                 105                 110

Lys Gln Thr Ala Glu Tyr Gly Arg Val Tyr Gly Arg Thr Cys Lys Gly
        115                 120                 125
```

```
Lys Pro Glu Asn Arg Lys Leu Arg Trp Met Asn Leu Leu Ala Ala Val
            130                 135                 140

Leu Asn Ile Ala Gly Phe Asp Leu Gln Asn Trp Pro Asp Glu Gly Val
145                 150                 155                 160

Val Met Glu Met Val Ala Asp Glu Val Ser Lys Lys Leu Phe Lys Ser
                165                 170                 175

Ser Asn Asp Phe Ser Asp Ile Val Met Ile Glu Ala His Leu Glu Val
            180                 185                 190

Met Ser Ser Ile Leu Arg Leu His Ser Glu Lys Ala Arg Met Val Gly
        195                 200                 205

Ile Ser Gly Pro Ser Gly Leu Gly Lys Thr Thr Gly Ala Lys Ala Leu
210                 215                 220

Phe Ser Lys Leu Ser Pro Asn Tyr His Leu Arg Ala Trp Val Thr Tyr
225                 230                 235                 240

Lys Lys Thr Asn Gln Asp Glu Tyr Asp Met Lys Leu Cys Trp Ile Glu
                245                 250                 255

Lys Trp Leu Cys Glu Ile Gly Gly Gln Lys Asp Leu Arg Val Leu Asp
                260                 265                 270

Leu Gly Ala Val Glu Gln Ser Leu Met His Lys Lys Val Leu Gly Ile
            275                 280                 285

Leu Asp Asp Val Asp Glu Leu Glu Leu Leu Lys Thr Leu Leu Gly Gln
290                 295                 300

Thr Gly Trp Phe Gly Phe Gly Thr Arg Gly Val Ala Ile Thr Gln Asp
305                 310                 315                 320

Arg Gln Leu Leu Lys Ala His Asp Ile Asn Leu Ile Tyr Glu Leu Ala
                325                 330                 335

Phe Pro Ser Ala His Leu Ala Leu Asp Ile Phe Cys Gln Ser Ala Phe
                340                 345                 350

Gly Lys Ile Tyr Pro Pro Ser Asp Phe Arg Glu Leu Ser Val Glu Phe
            355                 360                 365

Ala Tyr Leu Ala Gly Asn Leu Pro Leu Glu Ala Arg Val Leu Gly Ile
370                 375                 380

Ala Met Lys Gly Lys Arg Glu Glu Phe Ile Glu Met Leu Pro Arg
385                 390                 395                 400

Leu Arg Asn Asp Leu Asp Gly Lys Phe Lys Lys Thr Leu Arg Asn Tyr
                405                 410                 415

Leu Pro Val Ile Arg Lys His Val Ser Asn Glu Glu Gly Gly Arg Glu
            420                 425                 430

Lys Leu Arg Lys Ile Asn Lys Lys Leu Glu Leu Asp Glu Glu Phe Pro
        435                 440                 445

Gly Ala Glu Ile Tyr Cys Glu Glu Ile Pro Ser Pro Thr Ser Asn Trp
450                 455                 460

Lys Asp Thr Asp Asp Phe Asp Ser Gly Asp Ile Ile Pro Ile Ile Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
            500                 505                 510

Pro Phe Lys Cys Ser Ala Asn Asp Val Ile Asp Phe Leu Arg Thr Arg
        515                 520                 525

Gln Val Leu Gly Ser Thr Glu Ala Ala Val Asp Arg Leu Ile Phe Ser
530                 535                 540
```

```
Ser Glu Ala Phe Gly Ile Lys Pro Glu Glu Asn Pro Phe Arg Thr Gln
545                 550                 555                 560

Ala Val Thr Ser Phe Ala Lys Ala Arg Asp Met Thr Arg Glu Lys
            565                 570                 575

Glu Cys Ile Leu Val Phe Thr Cys His Asp Asn Met Asp Val Asp Glu
                580                 585                 590

Thr Ser Phe Gly Glu Ala Ile Ser Lys Asp Leu His Lys Gln Gly Phe
            595                 600                 605

Val Pro Leu Thr Tyr Asn Leu Leu Gly Arg Asp Asn Leu Asp Asp Asp
            610                 615                 620

Met Leu Tyr Gly Ser Arg Val Gly Ile Met Ile Leu Ser Ser Ser Tyr
625                 630                 635                 640

Ile Ser Ser Arg Asn Ser Leu Asp His Leu Val Ala Val Met Glu Arg
                645                 650                 655

Trp Arg Thr Thr Asp Met Val Ile Ile Pro Met Tyr Phe Lys Val Arg
                660                 665                 670

Leu Ser Asp Val Cys Gly Leu Lys Gly Arg Phe Glu Ala Ala Phe Leu
            675                 680                 685

Gln Leu His Met Cys Leu Gln Glu Asp Arg Val Asn Lys Trp Lys Ala
            690                 695                 700

Ala Met Ser Glu Ile Val Ser Ile Gly Gly Lys Glu Trp Thr Lys Gly
705                 710                 715                 720

Ser Gln Phe Ile Leu Ala Asp Asp Val Val Arg Asn Ala Ser Leu Arg
                725                 730                 735

Leu Tyr Leu Lys Ser Ser Lys Asn Leu Leu Gly Ile Leu Ala Leu Leu
            740                 745                 750

Asn His Ser Gln Ser Ser Asp Val Glu Ala Met Gly Met Trp Gly Ile
            755                 760                 765

Ala Gly Val Gly Lys Thr Ser Ile Ala Arg Glu Ile Phe Glu Leu His
            770                 775                 780

Ala Pro His Tyr Asp Phe Cys Tyr Phe Leu Gln Asp Phe His Leu Met
785                 790                 795                 800

Ser Gln Met Lys Arg Pro Arg Asn Leu Arg Glu Asp Phe Ile Ser Lys
            805                 810                 815

Leu Tyr Gly Glu Asp Lys Ala Leu Leu Ala Ser Asp Val Lys Pro Ser
            820                 825                 830

Phe Met Lys Asp Trp Phe His His Lys Thr Ile Leu Leu Val Leu Asp
            835                 840                 845

Asp Val Ser Asn Ala Arg Asp Ala Asp Ala Val Ile Gly Gly Phe Gly
            850                 855                 860

Trp Phe Ser His Gly His Arg Ile Ile Leu Ser Ser Lys Ser Lys Gln
865                 870                 875                 880

Val Leu Val Gln Cys Lys Val Lys Lys Pro Tyr Glu Ile Gln Lys Leu
            885                 890                 895

Ser Glu Phe Glu Ser Tyr Arg Leu Cys Lys Gln Tyr Leu Asp Gly Glu
            900                 905                 910

Asn Pro Val Ile Ser Glu Leu Ile Ser Cys Ser Ser Gly Ile Pro Leu
            915                 920                 925

Ala Leu Lys Val Leu Ser Ser Val Ser Lys Gln Tyr Ile Thr Asn
            930                 935                 940

Met Lys Asp Arg Leu Gln Ser Leu Arg Arg Asp Pro Pro Ser Gln Ile
945                 950                 955                 960

Gln Glu Ala Phe Arg Arg Ser Phe Asp Gly Leu Asp Glu Asn Glu Arg
```

965                 970                 975

Asn Gly Trp Leu Asp Leu Ala Cys Phe Phe Arg Gly Gln Ser Lys Asp
            980                 985                 990

Tyr Ala Val Leu Leu Leu Asp Ala Cys Gly Phe Phe Thr Tyr Met Gly
        995                1000                1005

Ile Cys Glu Leu Ile Asp Glu Ser Leu Ile Cys Leu Val Asp Asn Lys
   1010                1015                1020

Ile Glu Met Pro Met Pro Trp Gln Asp Met Gly Arg Ile Ile Val His
1025                1030                1035                1040

Glu Glu Asp Glu Asp Pro Cys Glu His Ser His Leu Tyr Glu Ser Lys
            1045                1050                1055

Glu Ile Val Asp Val Leu Thr Asn Asn Ser Gly Thr Glu Ala Ile Glu
        1060                1065                1070

Gly Ala Phe Leu Asp Ala Cys Asp Leu Thr Cys Glu Leu Ser Pro Thr
    1075                1080                1085

Val Phe Gly Lys Met Phe Asn Leu His Leu Leu Lys Phe Tyr Cys Ser
    1090                1095                1100

Cys Ser Gly Asn Gln Cys Lys Leu Thr Leu Pro His Gly Leu Asp Thr
1105                1110                1115                1120

Leu Pro Asp Glu Gly Ser Leu Leu His Trp Glu Asn Tyr Pro Leu Val
            1125                1130                1135

Tyr Leu Pro Gln Lys Phe Asn Pro Val Asn Leu Val Glu Leu Asn Met
        1140                1145                1150

Pro Tyr Ser Asn Met Glu Lys Leu Trp Glu Gly Lys Lys Asn Leu Glu
    1155                1160                1165

Lys Leu Lys Asn Ile Lys Leu Ser His Ser Arg Glu Leu Thr Asp Ile
    1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
            1205                1210                1215

Leu Val Ser Leu Asn Met Lys Asp Cys Ser Arg Leu Arg Ser Leu Pro
        1220                1225                1230

Ser Met Val Asp Leu Thr Thr Leu Lys Leu Leu Asn Leu Ser Gly Cys
    1235                1240                1245

Ser Glu Phe Glu Asp Ile Gln Asp Phe Ala Pro Asn Leu Glu Glu Ile
    1250                1255                1260

Tyr Leu Ala Gly Thr Ser Ile Arg Glu Leu Pro Leu Ser Ile Arg Asn
1265                1270                1275                1280

Leu Thr Glu Leu Val Thr Leu Asp Leu Glu Asn Cys Glu Arg Leu Gln
            1285                1290                1295

Glu Met Pro Ser Leu Pro Val Glu Met Ile Arg Arg Thr
        1300                1305

<210> SEQ ID NO 37
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
      /note="Nucleotide sequence HCP4, variant 14"
      /mol_type="unassigned DNA"

<400> SEQUENCE: 37

```
atggccgcca gcttctgcct gagcaagaga tacgacgtgt cccccagctt cagcaagctg     60
gacgtgagaa gaagcttcct ggcccacctg ctgaaggagc tggacagaag actgatcaac    120
accttcaccg accacggcgt ggagagaaac ctgcccatcg acgccgagct gctgagcgcc    180
atcgccgaca gcagaatcag catcatcatc ttcagcaaga actacgccag cagcaccctg    240
agcctggacg agctgctgga gatccacacc tgctacaagg agctggccca gatcgtggtg    300
cccgtgttct tcaacgtgca ccccagccag gtgagaaagc agaccggcga gtggggcaag    360
ggcttcggca agacctgcaa gggcaagccc gagaacagaa agctgagatg gatgcaggcc    420
ctggccgccg tggccaacat cgccctgtac gacctgaaca actggcccga cgaggccgtg    480
atgatcgaga tggtggccga cgacgtgtgc aagaagctgt tcaagagcag caacgacttc    540
agcgacatcg tgggcatcga ggcccacctg gaggccatga gcagcatcct gagactgaag    600
agcgagaagg ccagaatggt gggcatcagc ggccccagcg gcatcctgaa gaccaccatc    660
gccaaggccc tgttcagcaa gctgagcccc cagttcagag tgagagcctg ggtgtgctac    720
agaagaaccc agcaggacga ctacgacatg aagctgtgct ggatcgagaa gttcctgagc    780
gagatcgccg ccagaaggga cctgaaggtg ctggacatcg cgccgtgga gcagagcctg    840
atgcacagaa aggtgctgat cgccctggac gacgtggacg agctggacct gctgaagacc    900
ctggtgggcc agaccggctg gttcggcttc ggcagcagaa tcgtggtgat cacccaggac    960
agacagctgt gaaggcccca cgacatcaac ctgatctacg aggtggcctt ccccagcgcc   1020
cacctggccc tggagatctt ctgccagagc gccttcggca agatctaccc ccccagcgac   1080
ttcagagagc tgaccctgga gttcgcctac ctggccgcca acctgcccct ggacctgaga   1140
gtgggcggcc tgatcatgca cggcaagcac aaggacgagt ggatcgagat gctgcccaga   1200
ctgagaaacg acctggacgg caagttcaag cacacctga aaactacct gcccgtggtg    1260
aagaagagag tgagcaacga ggagatcggc agagagaagc tgaagaaggg caacaagaag   1320
ctggacctgg acgaggagtt ccccggcggc gagatctaca gcgacgaggt gcccagcccc   1380
accagcaact ggaaggacac cgacgacttc gacagcggcg acatcatccc catcatcgcc   1440
gacaagagca ccaccatcat ccccaacaga gacacagca acgacgactg gtgcagcttc   1500
tgcgagttcc tgagaaacag aatccccccc ctgaacccct tcaagtgcag cgccaacgac   1560
gtgatcgact tcctgagaac cagacaggtg ctgggcagca ccgaggccgc cgtggacaag   1620
ctgatcttca gcagcgaggc cttcggcatc aagcccgagg agaaccccctt cagaagccag   1680
gccgtgacca gctacctgaa ggccgccaga gacatgacca gagagaagga ctgcatcctg   1740
gtgttcagct gccacgacaa cctggacgtg gacgagacct gcttcatcga ggccatcagc   1800
aaggagctgc acaagaacgg cttcatcccc ctgacctaca acctgatggg cagagagcag   1860
ggcgacgagg acatgctgta cggcagcaga gtgggcatca tgatcctgtg cagcagctac   1920
gtgagcagca gacagagcct ggaccacctg gtggccgtga tggagcactg gcacaccacc   1980
gacctggtga tcatccccat ctactggaag gtgagactga cgacatctg cggcctgaag   2040
ggcagattcg aggccgcctg gctgcaggcc cacatgagcc tgcaggagga cagagtgcag   2100
aagtggaagg ccgccatgag cgagatcgtg agcatcggcg ccacgagta caccaagggc   2160
agccagttca tcctggccga ggaggtgggc agacaggcca gcctgagact gtacgccaag   2220
agcagcaaga acctgatcgg catgctggcc ctgctgcagc actgccagag ctgcgacgtg   2280
gacatcatgg gcatctgggg catcgccgcc atcggcaaga ccagcatcat cagagagatc   2340
ttcgaggtgc acgcccccca ctacgacttc tgctacttcc tgcaggactt ccacgtgatg   2400
```

```
tgccagatga agcaccccag acagctgaga gaggacttca tcagcaagct gttcggcgag    2460
gagaagggcc tgggcgccag cgacgtgaag cccagcttca tgagagactg gttccacaag    2520
aagaccggcc tgggcgtgct ggacgacgtg agcaacgcca gagacgccga ggccgtgatc    2580
ggcggcttcg gctggttcag ccacggccac agaatcatcc tgaccagcag aagcaagcag    2640
gtgctggtgc agtgcaaggt gaagcacccc ttcgagatcc agaagctgag cgacttcgag    2700
agcttcagac tgtgcaagca gtacctggag ggcgagcagc ccggcatcag cgaggccatc    2760
agctgcagca gcggcatccc cctggccctg aagctgctgg tgagcaccgt gagcaagcag    2820
tacgccacca acgtgaagga ccacctgcag agcctgagaa aggaccccCC cacccagatc    2880
caggacgcct acagaagaag cttcgacggc ctggacgaca cgagaagaa cgccttcatc    2940 gagctggcct gcttcttcag aggccagagc aaggactacg ccgtgctggg cgccgacgcc    3000
tgcatcttct tcacctacat gggcatctgc gagctgatcg acgagagcct gatcagcatc    3060
gtggacaaca agatcgagat gcccatcccc ttccaggaca tgggcagaat catcgtgcac    3120
gaggaggacg aggaccctg cgagagaagc agactgtggg acagcaagga catcgtggac    3180
gtgctgacca caacagcgg caccgaggcc atcgagggca tcttcctgga cgccagcgac    3240
gtgacctgcg agctgagccc caccgtgttc ggcaagctgt acaacctgaa gctgctgaga    3300
ttctactgca gcaccagcgc caaccagtgc aagctgaccg cccccagagg cctggacacc    3360
ctgcccgacg acgtgagcct gctgcacttc gagcagtacc ccctggtgta cctgccccag    3420
aagttcaacc ccgtgaacct ggtggagctg aacatgccct acagcaacat ggagaagctg    3480
tgggagggca agaagaacct ggagaagctg aagaacatca agctgagcca cagcagagag    3540
ctgaccgaca tcctgatgct gagcgaggcc ctgaacctgg agcacatcga cctggagggc    3600
tgcaccagcc tgatcgacgt gagcatgagc atccctgct gcggcaagct ggtgagcctg    3660
aacatgaagg actgcagcag actgagaagc ctgcccagca tggtggacct gaccaccctg    3720
aagctgctga acctgagcgg ctgcagcgag ttcgaggaca tccaggactt cgcccccaac    3780
ctggaggaga tctacctggc cggcaccagc atcagagagc tgcccctgag catcagaaac    3840
ctgaccgagc tggtgacccc tggacctggag aactgcgaga gactgcagga gatgcccagc    3900
ctgcccgtgg agatcatcag aagaacc                                        3927
```

<210> SEQ ID NO 38
<211> LENGTH: 1309
<212> TYPE: PRT
<213> ORGANISM: Artificial Sequence
<220> FEATURE:
<223> OTHER INFORMATION: Amino acid sequence HCP4, variant 14

<400> SEQUENCE: 38

```
Met Ala Ala Ser Phe Cys Leu Ser Lys Arg Tyr Asp Val Phe Pro Ser
1               5                   10                  15

Phe Ser Lys Leu Asp Val Arg Arg Ser Phe Leu Ala His Leu Leu Lys
            20                  25                  30

Glu Leu Asp Arg Arg Leu Ile Asn Thr Phe Thr Asp His Gly Val Glu
        35                  40                  45

Arg Asn Leu Pro Ile Asp Ala Glu Leu Leu Ser Ala Ile Ala Asp Ser
    50                  55                  60

Arg Ile Ser Ile Ile Ile Phe Ser Lys Asn Tyr Ala Ser Ser Thr Trp
65                  70                  75                  80

Ser Leu Asp Glu Leu Leu Glu Ile His Thr Cys Tyr Lys Glu Leu Ala
```

-continued

```
                 85                  90                  95
Gln Ile Val Val Pro Val Phe Phe Asn Val His Pro Ser Gln Val Arg
            100                 105                 110

Lys Gln Thr Gly Glu Trp Gly Lys Gly Phe Gly Lys Thr Cys Lys Gly
            115                 120                 125

Lys Pro Glu Asn Arg Lys Leu Arg Trp Met Gln Ala Leu Ala Ala Val
            130                 135                 140

Ala Asn Ile Ala Leu Tyr Asp Leu Asn Asn Trp Pro Asp Glu Ala Val
145                 150                 155                 160

Met Ile Glu Met Val Ala Asp Asp Val Cys Lys Lys Leu Phe Lys Ser
                165                 170                 175

Ser Asn Asp Phe Ser Asp Ile Val Gly Ile Glu Ala His Leu Glu Ala
            180                 185                 190

Met Ser Ser Ile Leu Arg Leu Lys Ser Glu Lys Ala Arg Met Val Gly
            195                 200                 205

Ile Ser Gly Pro Ser Gly Ile Leu Lys Thr Thr Ile Ala Lys Ala Leu
            210                 215                 220

Phe Ser Lys Leu Ser Pro Gln Phe Arg Val Arg Ala Trp Val Cys Tyr
225                 230                 235                 240

Arg Arg Thr Gln Gln Asp Asp Tyr Asp Met Lys Leu Cys Trp Ile Glu
                245                 250                 255

Lys Phe Leu Ser Glu Ile Ala Gly Gln Lys Asp Leu Lys Val Leu Asp
            260                 265                 270

Ile Gly Ala Val Glu Gln Ser Leu Met His Arg Lys Val Leu Ile Ala
            275                 280                 285

Leu Asp Asp Val Asp Glu Leu Asp Leu Leu Lys Thr Leu Val Gly Gln
            290                 295                 300

Thr Gly Trp Phe Gly Phe Gly Ser Arg Ile Val Val Ile Thr Gln Asp
305                 310                 315                 320

Arg Gln Leu Val Lys Ala His Asp Ile Asn Leu Ile Tyr Glu Val Ala
                325                 330                 335

Phe Pro Ser Ala His Leu Ala Leu Glu Ile Phe Cys Gln Ser Ala Phe
            340                 345                 350

Gly Lys Ile Tyr Pro Pro Ser Asp Phe Arg Glu Leu Thr Leu Glu Phe
            355                 360                 365

Ala Tyr Leu Ala Ala Asn Leu Pro Leu Asp Leu Arg Val Gly Gly Leu
            370                 375                 380

Ile Met His Gly Lys His Lys Asp Glu Trp Ile Glu Met Leu Pro Arg
385                 390                 395                 400

Leu Arg Asn Asp Leu Asp Gly Lys Phe Lys His Thr Leu Arg Asn Tyr
                405                 410                 415

Leu Pro Val Val Lys Lys Arg Val Ser Asn Glu Ile Gly Arg Glu
            420                 425                 430

Lys Leu Lys Lys Gly Asn Lys Lys Leu Asp Leu Asp Glu Glu Phe Pro
            435                 440                 445

Gly Gly Glu Ile Tyr Ser Asp Glu Val Pro Ser Pro Thr Ser Asn Trp
            450                 455                 460

Lys Asp Thr Asp Asp Phe Asp Ser Gly Asp Ile Pro Ile Ile Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
            500                 505                 510
```

```
Pro Phe Lys Cys Ser Ala Asn Asp Val Ile Asp Phe Leu Arg Thr Arg
        515                 520                 525

Gln Val Leu Gly Ser Thr Glu Ala Val Asp Lys Leu Ile Phe Ser
530             535                 540

Ser Glu Ala Phe Gly Ile Lys Pro Glu Asn Pro Phe Arg Ser Gln
545                 550                 555                 560

Ala Val Thr Ser Tyr Leu Lys Ala Ala Arg Asp Met Thr Arg Glu Lys
            565                 570                 575

Asp Cys Ile Leu Val Phe Ser Cys His Asp Asn Leu Asp Val Asp Glu
                580                 585                 590

Thr Cys Phe Ile Glu Ala Ile Ser Lys Glu Leu His Lys Asn Gly Phe
            595                 600                 605

Ile Pro Leu Thr Tyr Asn Leu Met Gly Arg Glu Gln Gly Asp Glu Asp
        610                 615                 620

Met Leu Tyr Gly Ser Arg Val Gly Ile Met Ile Leu Cys Ser Ser Tyr
625                 630                 635                 640

Val Ser Ser Arg Gln Ser Leu Asp His Leu Val Ala Val Met Glu His
                645                 650                 655

Trp His Thr Thr Asp Leu Val Ile Ile Pro Ile Tyr Trp Lys Val Arg
            660                 665                 670

Leu Ser Asp Ile Cys Gly Leu Lys Gly Arg Phe Glu Ala Ala Trp Leu
        675                 680                 685

Gln Ala His Met Ser Leu Gln Glu Asp Arg Val Gln Lys Trp Lys Ala
690                 695                 700

Ala Met Ser Glu Ile Val Ser Ile Gly Gly His Glu Tyr Thr Lys Gly
705                 710                 715                 720

Ser Gln Phe Ile Leu Ala Glu Glu Val Gly Arg Gln Ala Ser Leu Arg
            725                 730                 735

Leu Tyr Ala Lys Ser Ser Lys Asn Leu Ile Gly Met Leu Ala Leu Leu
        740                 745                 750

Gln His Cys Gln Ser Cys Asp Val Asp Ile Met Gly Ile Trp Gly Ile
    755                 760                 765

Ala Ala Ile Gly Lys Thr Ser Ile Ile Arg Glu Ile Phe Glu Val His
        770                 775                 780

Ala Pro His Tyr Asp Phe Cys Tyr Phe Leu Gln Asp Phe His Val Met
785                 790                 795                 800

Cys Gln Met Lys His Pro Arg Gln Leu Arg Glu Asp Phe Ile Ser Lys
                805                 810                 815

Leu Phe Gly Glu Lys Gly Leu Gly Ala Ser Asp Val Lys Pro Ser
            820                 825                 830

Phe Met Arg Asp Trp Phe His Lys Lys Thr Gly Leu Gly Val Leu Asp
            835                 840                 845

Asp Val Ser Asn Ala Arg Asp Ala Glu Ala Val Ile Gly Gly Phe Gly
850                 855                 860

Trp Phe Ser His Gly His Arg Ile Ile Leu Thr Ser Arg Ser Lys Gln
865                 870                 875                 880

Val Leu Val Gln Cys Lys Val Lys His Pro Phe Glu Ile Gln Lys Leu
                885                 890                 895

Ser Asp Phe Glu Ser Phe Arg Leu Cys Lys Gln Tyr Leu Glu Gly Glu
                900                 905                 910

Gln Pro Gly Ile Ser Glu Ala Ile Ser Cys Ser Ser Gly Ile Pro Leu
            915                 920                 925
```

Ala Leu Lys Leu Leu Val Ser Thr Val Ser Lys Gln Tyr Ala Thr Asn
930                 935                 940

Val Lys Asp His Leu Gln Ser Leu Arg Lys Asp Pro Thr Gln Ile
945                 950                 955                 960

Gln Asp Ala Tyr Arg Arg Ser Phe Asp Gly Leu Asp Asn Glu Lys
            965                 970                 975

Asn Ala Phe Ile Glu Leu Ala Cys Phe Phe Arg Gly Gln Ser Lys Asp
            980                 985                 990

Tyr Ala Val Leu Gly Ala Asp Ala Cys Ile Phe Phe Thr Tyr Met Gly
            995                 1000                1005

Ile Cys Glu Leu Ile Asp Glu Ser Leu Ile Ser Ile Val Asp Asn Lys
1010                1015                1020

Ile Glu Met Pro Ile Pro Phe Gln Asp Met Gly Arg Ile Ile Val His
1025                1030                1035                1040

Glu Glu Asp Glu Asp Pro Cys Glu Arg Ser Arg Leu Trp Asp Ser Lys
                1045                1050                1055

Asp Ile Val Asp Val Leu Thr Asn Asn Ser Gly Thr Glu Ala Ile Glu
                1060                1065                1070

Gly Ile Phe Leu Asp Ala Ser Asp Val Thr Cys Glu Leu Ser Pro Thr
                1075                1080                1085

Val Phe Gly Lys Leu Tyr Asn Leu Lys Leu Leu Arg Phe Tyr Cys Ser
1090                1095                1100

Thr Ser Ala Asn Gln Cys Lys Leu Thr Ala Pro Arg Gly Leu Asp Thr
1105                1110                1115                1120

Leu Pro Asp Asp Val Ser Leu Leu His Phe Glu Gln Tyr Pro Leu Val
                1125                1130                1135

Tyr Leu Pro Gln Lys Phe Asn Pro Val Asn Leu Val Glu Leu Asn Met
                1140                1145                1150

Pro Tyr Ser Asn Met Glu Lys Leu Trp Glu Gly Lys Lys Asn Leu Glu
                1155                1160                1165

Lys Leu Lys Asn Ile Lys Leu Ser His Ser Arg Glu Leu Thr Asp Ile
    1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
                1205                1210                1215

Leu Val Ser Leu Asn Met Lys Asp Cys Ser Arg Leu Arg Ser Leu Pro
                1220                1225                1230

Ser Met Val Asp Leu Thr Thr Leu Lys Leu Leu Asn Leu Ser Gly Cys
    1235                1240                1245

Ser Glu Phe Glu Asp Ile Gln Asp Phe Ala Pro Asn Leu Glu Glu Ile
    1250                1255                1260

Tyr Leu Ala Gly Thr Ser Ile Arg Glu Leu Pro Leu Ser Ile Arg Asn
1265                1270                1275                1280

Leu Thr Glu Leu Val Thr Leu Asp Leu Glu Asn Cys Glu Arg Leu Gln
                1285                1290                1295

Glu Met Pro Ser Leu Pro Val Glu Ile Ile Arg Arg Thr
                1300                1305

<210> SEQ ID NO 39
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
/note="Nucleotide sequence HCP4, variant 15"
/mol_type="unassigned DNA"

<400> SEQUENCE: 39

| | | | | | |
|---|---|---|---|---|---|
| atggccgcca | gcttctgcgg | cagcagaaga | tacgacgtgt | tccccagctt cagcaaggtg | 60 |
| gacgtgagaa | gaagcttcct | ggcccacctg | ctgaaggagc | tggagagaag actgatcaac | 120 |
| tgcttcaccg | accacggcat | ggagagaaac | ctgcccatcg | aggccgagct gctgagcgcc | 180 |
| atcgccgagt | gcagaatcag | catcgtgatc | ttcagcaaga | actacgccac cagcacctgg | 240 |
| accctggaca | gctggtggag | gatccacacc | tgctacaagg | agctggccca gatcgtgatg | 300 |
| cccgtgttct | tcaacatgca | ccccagccag | gtgaagaagc | agaccggcga gttcggccac | 360 |
| gtgttcggca | agacctgcaa | gggcaagccc | gagaacagaa | agctgcactg gatgcaggcc | 420 |
| ctggccgccg | gcgccaacat | cgccggctac | gagctgcaga | ctggcccga cgaggccgtg | 480 |
| atgatcgaga | tggccgccga | cgacgtgagc | aagaagctgt | ggaagagcag caacgacttc | 540 |
| agcgacatcg | tgggcatcga | ggcccacctg | gaggccatga | gcagcatgct gcacctgaag | 600 |
| agcgagaagg | ccagaatggt | gggcatctgc | ggccccagcg | catcggcaa gaccaccatc | 660 |
| gccaaggccc | tgtggagcaa | gctgagcccc | cagttccacc | tgagagcctt cgtgacctac | 720 |
| aagagaacca | ccaggacga | ctacgacatg | aagctgtgct | ggatcgagaa gttcctgagc | 780 |
| gagatcctgg | ccagaaggga | cctgaaggtg | ctggacctgg | gcgccgtgga gcagagcctg | 840 |
| atgcacaaga | gagtgctgat | catcctggac | gacggcgacg | acctggagct gctgaagacc | 900 |
| ctggtgggcc | agaccctgtg | gttcgcctgg | ggcagcagaa | tcgtggtgat cacccaggac | 960 |
| agacagctgc | tgaaggccca | cgacatcaac | ctgatctggg | aggtggcctt ccccagcgcc | 1020 |
| cacctggccc | tggagatctt | ctgccagagc | gccttcggca | agatctaccc ccccagcgac | 1080 |
| ttcagagagc | tgagcgtgga | gttcatctac | ctggccggca | acctgcccct ggacctgaga | 1140 |
| gtgctgggcc | tggccatgaa | gatgaagcac | agagaggagt | ggatcgagat gctgcccaga | 1200 |
| ctgagaaacg | acctggacgg | cagattcaag | aagaccctga | gaaactacct gcccgtgatc | 1260 |
| agaaagagag | gcagcaacga | cgagggcggc | agagagaagc | tgaagcacgg caacaagaag | 1320 |
| ctggacctgg | acgaggagtt | ccccggcggc | gagatctaca | gcgacgagat ccccagcccc | 1380 |
| accagcaact | ggaaggacac | cgacgactac | gacagcggcg | acatcatccc catcatcgcc | 1440 |
| gacaagagca | ccaccatcat | ccccaacaga | agacacagca | cgacgactg gtgcagcttc | 1500 |
| tgcgagttcc | tgagaaacag | aatcccccc | ctgaacccct | tcaagtgcag cgccaacgac | 1560 |
| gtgatcgact | tcctgagaac | cagacaggtg | ctgggcagca | ccgaggccct ggtggacaga | 1620 |
| ctggtgttca | gcagcgaggc | cttcggcatc | aagcccgagg | agcagccctt cagaagccag | 1680 |
| gccgtgacca | gctacctgaa | ggccgccaga | gacatgacca | gagagaagga gtgcatcctg | 1740 |
| gtgttcagct | gccacgacaa | cctggacgtg | gacgagacca | gcttcatcga ggccatcagc | 1800 |
| aaggagctgc | acaagcaggg | cttcatcccc | ctgacctaca | cctgctggg cagagagaac | 1860 |
| ctggacgagg | agatgctgta | catcagcaga | gtgggcatca | tgatcctgag cagcagctac | 1920 |
| gtgtgcagca | gacagagcct | ggacagactg | gtggccgtga | tggagcactg gaagaccacc | 1980 |
| gacctggtga | tcatccccat | ctacttcaag | gtgagactga | gcgacatctg cggcctgaag | 2040 |
| ggcagattcg | aggccgcctt | cctgcagctg | cacatgagcc | tgcaggagga cagagtgcag | 2100 |
| aagtggaagg | tggccatgag | cgagatcgtg | agcatcggcg | ccacgagtg gaccaaggtg | 2160 |

```
agccagttcg tgctggccga ggagctggtg agaaacgcca gcctgagaat gtacctgaag   2220
agcagcaaga acctggccgg catcctggcc ctgctgaacc acagccagag caccgacgtg   2280
gagatcatgg gcatctgggg catcgccggc atcggcaagt gcagcatcgc cagagagatc   2340
tgggagctgc acgcccccca ctacgacttc tgctacttcc tgcaggactt ccacctgatg   2400
tgccagatga agcaccccag acagctgaga gaggacttca tcagcaagct gttcggcgag   2460
gagaagggcc tgggcgccag cgacgtgaag cccagcttca tgagagactg gttccacaag   2520
aagaccatcc tgctggtgct ggacgacggc agcaacgcca gagacgccga gggcgtgatc   2580
ggcgtgttcg gctggtggag ccacggccac agaatcatcc tgaccagcag aagcaagaac   2640
gtgctggtga actgcaaggt gaagcacccc tacgagatcc agaagctgag cgacttcgag   2700
agcttcagac tgtgcaagca gtacctggac ggcgagaacc ccgtgctgag cgagctgatc   2760
agctgcagca gcggcatccc cctggccctg agactgctgg tgagcagcgt gagcaagcag   2820
tacatctgca acatgaagga ccacctgcag agcctgagaa aggaccccc cacccagatc   2880
caggaggcct tcagaagaag ctacgacggc ctggacgaga cgagaagaa catcttcctg   2940
gacctggcct gcttcttcag aggccagagc aaggactacg ccgtgctgct gctggacgcc   3000
tgcggcttct tcacctacat gggcatctgc gagctggccg acgagagcct gatcagcctg   3060
gtggacaaca agatcgagat gcccatcccc ttccaggaca tgggcagaat catcgtgcac   3120
gaggaggacg aggaccctg cgagagaagc agactgtggg acagcaagga catcgtggac   3180
gtgctgacca caacagcgg caccgaggcc atcgagggca tcttcctgga cgccagcgac   3240
ctgaccaccg agctgagccc caccgtgttc ggcaagatgt ggaacctgag aggcctgaag   3300
ttctactgca gcaccagcgg caaccagtgc aagctgaccc tgccccacgg catggacacc   3360
ctgcccgacg agctgagcct gctgagattc gagaactacc ccctggtgta cctgccccag   3420
aagttcaacc ccgtgaacct ggtggagctg aacatgccct acagcaacat ggagaagctg   3480
tgggagggca agaagaacct ggagaagctg aagaacatca gctgagcca cagcagagag   3540
ctgaccgaca tcctgatgct gagcgaggcc ctgaacctgg agcacatcga cctggagggc   3600
tgcaccagcc tgatcgacgt gagcatgagc atccccctgct gcggcaagct ggtgagcctg   3660
aacatgaagg actgcagcag actgagaagc ctgcccagca tggtggacct gaccacctg   3720
aagctgctga acctgagcgg ctgcagcgag ttcgaggaca tccaggactt cgcccccaac   3780
ctggaggaga tctacctggc cggcaccagc atcagagagc tgcccctgag catcagaaac   3840
ctgaccgagc tggtgaccct ggacctggag aactgcgaga gactgcagga gatgcccagc   3900
ctgcccgtgg agatcatcag aagaacc                                       3927
```

<210> SEQ ID NO 40
<211> LENGTH: 1309
<212> TYPE: PRT
<213> ORGANISM: Artificial Sequence
<220> FEATURE:
<223> OTHER INFORMATION: Amion acid sequence HCP4, variant 15

<400> SEQUENCE: 40

Met Ala Ala Ser Phe Cys Gly Ser Arg Arg Tyr Asp Val Phe Pro Ser
1               5                   10                  15

Phe Ser Lys Val Asp Val Arg Arg Ser Phe Leu Ala His Leu Leu Lys
            20                  25                  30

Glu Leu Glu Arg Arg Leu Ile Asn Cys Phe Thr Asp His Gly Met Glu
        35                  40                  45

-continued

```
Arg Asn Leu Pro Ile Glu Ala Glu Leu Leu Ser Ala Ile Ala Glu Cys
 50                  55                  60
Arg Ile Ser Ile Val Ile Phe Ser Lys Asn Tyr Ala Thr Ser Thr Trp
 65                  70                  75                  80
Thr Leu Asp Glu Leu Val Glu Ile His Thr Cys Tyr Lys Glu Leu Ala
                 85                  90                  95
Gln Ile Val Met Pro Val Phe Phe Asn Met His Pro Ser Gln Val Lys
                100                 105                 110
Lys Gln Thr Gly Glu Phe Gly His Val Phe Gly Lys Thr Cys Lys Gly
                115                 120                 125
Lys Pro Glu Asn Arg Lys Leu His Trp Met Gln Ala Leu Ala Ala Gly
            130                 135                 140
Ala Asn Ile Ala Gly Tyr Glu Leu Gln Asn Trp Pro Asp Glu Ala Val
145                 150                 155                 160
Met Ile Glu Met Ala Ala Asp Val Ser Lys Lys Leu Trp Lys Ser
                165                 170                 175
Ser Asn Asp Phe Ser Asp Ile Val Gly Ile Glu Ala His Leu Glu Ala
            180                 185                 190
Met Ser Ser Met Leu His Leu Lys Ser Glu Lys Ala Arg Met Val Gly
            195                 200                 205
Ile Cys Gly Pro Ser Gly Ile Gly Lys Thr Thr Ile Ala Lys Ala Leu
210                 215                 220
Trp Ser Lys Leu Ser Pro Gln Phe His Leu Arg Ala Phe Val Thr Tyr
225                 230                 235                 240
Lys Arg Thr Asn Gln Asp Asp Tyr Asp Met Lys Leu Cys Trp Ile Glu
                245                 250                 255
Lys Phe Leu Ser Glu Ile Leu Gly Gln Lys Asp Leu Lys Val Leu Asp
            260                 265                 270
Leu Gly Ala Val Glu Gln Ser Leu Met His Lys Arg Val Leu Ile Ile
            275                 280                 285
Leu Asp Asp Gly Asp Leu Glu Leu Leu Lys Thr Leu Val Gly Gln
290                 295                 300
Thr Leu Trp Phe Ala Trp Gly Ser Arg Ile Val Val Ile Thr Gln Asp
305                 310                 315                 320
Arg Gln Leu Leu Lys Ala His Asp Ile Asn Leu Ile Trp Glu Val Ala
            325                 330                 335
Phe Pro Ser Ala His Leu Ala Leu Glu Ile Phe Cys Gln Ser Ala Phe
            340                 345                 350
Gly Lys Ile Tyr Pro Pro Ser Asp Phe Arg Glu Leu Ser Val Glu Phe
            355                 360                 365
Ile Tyr Leu Ala Gly Asn Leu Pro Leu Asp Leu Arg Val Leu Gly Leu
            370                 375                 380
Ala Met Lys Met Lys His Arg Glu Glu Trp Ile Glu Met Leu Pro Arg
385                 390                 395                 400
Leu Arg Asn Asp Leu Asp Gly Arg Phe Lys Thr Leu Arg Asn Tyr
            405                 410                 415
Leu Pro Val Ile Arg Lys Arg Gly Ser Asn Asp Glu Gly Arg Glu
            420                 425                 430
Lys Leu Lys His Gly Asn Lys Lys Leu Asp Leu Asp Glu Phe Pro
            435                 440                 445
Gly Gly Glu Ile Tyr Ser Asp Glu Ile Pro Ser Pro Thr Ser Asn Trp
450                 455                 460
Lys Asp Thr Asp Asp Tyr Asp Ser Gly Asp Ile Ile Pro Ile Ile Ala
```

-continued

```
            465                 470                 475                 480
        Asp Lys Ser Thr Thr Ile Ile Pro Asn Arg Arg His Ser Asn Asp Asp
                        485                 490                 495

Trp Cys Ser Phe Cys Glu Phe Leu Arg Asn Arg Ile Pro Pro Leu Asn
                        500                 505                 510

Pro Phe Lys Cys Ser Ala Asn Asp Val Ile Asp Phe Leu Arg Thr Arg
                        515                 520                 525

Gln Val Leu Gly Ser Thr Glu Ala Leu Val Asp Arg Leu Val Phe Ser
                530                 535                 540

Ser Glu Ala Phe Gly Ile Lys Pro Glu Glu Gln Pro Phe Arg Ser Gln
        545                 550                 555                 560

Ala Val Thr Ser Tyr Leu Lys Ala Ala Arg Asp Met Thr Arg Glu Lys
                        565                 570                 575

Glu Cys Ile Leu Val Phe Ser Cys His Asp Asn Leu Asp Val Asp Glu
                        580                 585                 590

Thr Ser Phe Ile Glu Ala Ile Ser Lys Glu Leu His Lys Gln Gly Phe
                        595                 600                 605

Ile Pro Leu Thr Tyr Asn Leu Leu Gly Arg Glu Asn Leu Asp Glu Glu
                610                 615                 620

Met Leu Tyr Ile Ser Arg Val Gly Ile Met Ile Leu Ser Ser Ser Tyr
        625                 630                 635                 640

Val Cys Ser Arg Gln Ser Leu Asp Arg Leu Val Ala Val Met Glu His
                        645                 650                 655

Trp Lys Thr Thr Asp Leu Val Ile Ile Pro Ile Tyr Phe Lys Val Arg
                        660                 665                 670

Leu Ser Asp Ile Cys Gly Leu Lys Gly Arg Phe Glu Ala Ala Phe Leu
                        675                 680                 685

Gln Leu His Met Ser Leu Gln Glu Asp Arg Val Gln Lys Trp Lys Val
                690                 695                 700

Ala Met Ser Glu Ile Val Ser Ile Gly Gly His Glu Trp Thr Lys Val
        705                 710                 715                 720

Ser Gln Phe Val Leu Ala Glu Glu Leu Val Arg Asn Ala Ser Leu Arg
                        725                 730                 735

Met Tyr Leu Lys Ser Ser Lys Asn Leu Ala Gly Ile Leu Ala Leu Leu
                        740                 745                 750

Asn His Ser Gln Ser Thr Asp Val Glu Ile Met Gly Ile Trp Gly Ile
                        755                 760                 765

Ala Gly Ile Gly Lys Cys Ser Ile Ala Arg Glu Ile Trp Glu Leu His
                770                 775                 780

Ala Pro His Tyr Asp Phe Cys Tyr Phe Leu Gln Asp Phe His Leu Met
        785                 790                 795                 800

Cys Gln Met Lys His Pro Arg Gln Leu Arg Glu Asp Phe Ile Ser Lys
                        805                 810                 815

Leu Phe Gly Glu Glu Lys Gly Leu Gly Ala Ser Asp Val Lys Pro Ser
                        820                 825                 830

Phe Met Arg Asp Trp Phe His Lys Lys Thr Ile Leu Leu Val Leu Asp
                        835                 840                 845

Asp Gly Ser Asn Ala Arg Asp Ala Glu Gly Val Ile Gly Val Phe Gly
                850                 855                 860

Trp Trp Ser His Gly His Arg Ile Ile Leu Thr Ser Arg Ser Lys Asn
        865                 870                 875                 880

Val Leu Val Asn Cys Lys Val Lys His Pro Tyr Glu Ile Gln Lys Leu
                        885                 890                 895
```

```
Ser Asp Phe Glu Ser Phe Arg Leu Cys Lys Gln Tyr Leu Asp Gly Glu
            900                 905                 910

Asn Pro Val Leu Ser Glu Leu Ile Ser Cys Ser Ser Gly Ile Pro Leu
            915                 920                 925

Ala Leu Arg Leu Leu Val Ser Ser Val Ser Lys Gln Tyr Ile Cys Asn
            930                 935                 940

Met Lys Asp His Leu Gln Ser Leu Arg Lys Asp Pro Pro Thr Gln Ile
945                 950                 955                 960

Gln Glu Ala Phe Arg Arg Ser Tyr Asp Gly Leu Asp Glu Asn Glu Lys
                965                 970                 975

Asn Ile Phe Leu Asp Leu Ala Cys Phe Phe Arg Gly Ser Lys Asp
            980                 985                 990

Tyr Ala Val Leu Leu Leu Asp Ala Cys Gly Phe Phe Thr Tyr Met Gly
            995                 1000                1005

Ile Cys Glu Leu Ala Asp Glu Ser Leu Ile Ser Leu Val Asp Asn Lys
            1010                1015                1020

Ile Glu Met Pro Ile Pro Phe Gln Asp Met Gly Arg Ile Ile Val His
1025                1030                1035                1040

Glu Glu Asp Glu Asp Pro Cys Glu Arg Ser Arg Leu Trp Asp Ser Lys
                1045                1050                1055

Asp Ile Val Asp Val Leu Thr Asn Asn Ser Gly Thr Glu Ala Ile Glu
            1060                1065                1070

Gly Ile Phe Leu Asp Ala Ser Asp Leu Thr Thr Glu Leu Ser Pro Thr
            1075                1080                1085

Val Phe Gly Lys Met Trp Asn Leu Arg Gly Leu Lys Phe Tyr Cys Ser
            1090                1095                1100

Thr Ser Gly Asn Gln Cys Lys Leu Thr Leu Pro His Gly Met Asp Thr
1105                1110                1115                1120

Leu Pro Asp Glu Leu Ser Leu Leu Arg Phe Glu Asn Tyr Pro Leu Val
                1125                1130                1135

Tyr Leu Pro Gln Lys Phe Asn Pro Val Asn Leu Val Glu Leu Asn Met
            1140                1145                1150

Pro Tyr Ser Asn Met Glu Lys Leu Trp Glu Gly Lys Lys Asn Leu Glu
            1155                1160                1165

Lys Leu Lys Asn Ile Lys Leu Ser His Ser Arg Glu Leu Thr Asp Ile
            1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
            1205                1210                1215

Leu Val Ser Leu Asn Met Lys Asp Cys Ser Arg Leu Arg Ser Leu Pro
            1220                1225                1230

Ser Met Val Asp Leu Thr Thr Leu Lys Leu Leu Asn Leu Ser Gly Cys
            1235                1240                1245

Ser Glu Phe Glu Asp Ile Gln Asp Phe Ala Pro Asn Leu Glu Glu Ile
            1250                1255                1260

Tyr Leu Ala Gly Thr Ser Ile Arg Glu Leu Pro Leu Ser Ile Arg Asn
1265                1270                1275                1280

Leu Thr Glu Leu Val Thr Leu Asp Leu Glu Asn Cys Glu Arg Leu Gln
                1285                1290                1295

Glu Met Pro Ser Leu Pro Val Glu Ile Ile Arg Arg Thr
            1300                1305
```

<210> SEQ ID NO 41
<211> LENGTH: 3927
<212> TYPE: DNA
<213> ORGANISM: Artificial Sequence
<220> FEATURE:
<221> NAME/KEY: source
<222> LOCATION: 1..3927
<223> OTHER INFORMATION: /organism="Artificial Sequence"
    /note="Nucleotide sequence HCP4, variant 16"
    /mol_type="unassigned DNA"

<400> SEQUENCE: 41

| | | | | | |
|---|---|---|---|---|---|
| atggccgcca | gcttctgcgg | cagcagaaga | tacgacgtgt | tccccagctt | cagcaaggtg | 60 |
| gacgtgagaa | agagcttcct | ggcccacctg | atcaaggagc | tggacagaag | actgatcaac | 120 |
| accttcaccg | accacggcat | ggagagaaac | ctgcccatcg | acgccgagct | gctgagcgcc | 180 |
| atcgccgaga | gcagaatcag | catcgtgatc | ttcagcaaga | actacgccac | caccacctac | 240 |
| tgcctggacg | agctggtgga | gatccacacc | tgctacaagg | agctggccca | gatggtggtg | 300 |
| cccgtgttct | ggaacgtgca | ccccagccag | gtgaagaagc | agaccggcga | cttcggcaag | 360 |
| gtgttcggca | agaccaccaa | gggcaagccc | gagaacagaa | agctgagatg | gatgcaggcc | 420 |
| ctggccgccg | tggccaacat | cgccggctgg | gacctgcaga | actggcccga | cgaggccgtg | 480 |
| atgatcgaga | tggtggccga | cgacgtgagc | aagaagctgt | tcaagagcag | caacgacttc | 540 |
| agcgacatcg | tgggcatcga | ggtgcacctg | gaggccatga | gcagcatcct | gagactgaag | 600 |
| tgcgagaagg | ccagaatggt | gggcatcagc | ggcccagcg | gcatcggcaa | gaccaccatc | 660 |
| gccaaggccc | tgttcagcaa | gctgaccccc | cagtggcacg | tgagagcctt | cgtgacctac | 720 |
| aagagaacca | ccaggacga | ctacgacatg | aagctgtgct | ggatcgagaa | gtacctgagc | 780 |
| gagatcctgg | ccagaagga | cctgaaggtg | ctggacctgc | tggccgtgga | gcagagcctg | 840 |
| atgcacaaga | aggtgctgat | catcctggac | gacatcgacg | agctggagct | gctgaagacc | 900 |
| ctggtgggcc | agaccggctg | gttcggcttc | ggcagcagaa | tcgtggtgat | cacccaggac | 960 |
| agacagctgc | tgaaggccca | cgacatcaac | ctgatctacg | aggtggcctg | gcccagcgcc | 1020 |
| cacctggccc | tggagatctt | ctgccagagc | gccttcggca | agatctaccc | cccagcgac | 1080 |
| ttcagagagc | tgagcgtgga | gttcgcctac | atggccggca | acctgccct | ggacctgaga | 1140 |
| gtgctgggcc | tggccatgca | cggcaagcac | agagaggagt | ggatcgagat | gctgcccaga | 1200 |
| ctgagaaacg | acctggacgg | caagttcaag | aagaccctga | gaaactacct | gcccgtgatc | 1260 |
| agaaagagag | tgagcaacga | ggagggcggc | agagagaagc | tgaagaaggg | caacaagaag | 1320 |
| ctggacctgg | acgacgagtt | ccccggcggc | gagatctaca | gcgacgagat | ccccaccccc | 1380 |
| accagcaact | ggaaggacac | cgacgacttc | gacagcggcg | acatcatccc | catcatcgcc | 1440 |
| gacaagagca | ccaccatcat | ccccaacaga | agacacagca | cgacgactg | gtgcagcttc | 1500 |
| tgcgagttcc | tgagaaacag | aatccccccc | ctgaacccct | tcaagtgcag | cgccaacgac | 1560 |
| gtgatcgact | tcctgagaac | cagacaggtg | ctgggcagca | ccgaggccct | ggtggacaga | 1620 |
| ctgatcttca | gcagcgaggc | cttcggcatg | aagcccgacg | agaacccctt | cagaagccag | 1680 |
| gccgtgacca | gctacctgaa | ggccgccaga | gacatgacca | gagagaagga | gtgcatcctg | 1740 |
| gtgttcagct | gccacgacca | gctggacgtg | gacgagacca | gcttcatcga | ggccatcagc | 1800 |
| aaggagctgc | acaagcaggg | cttcatcccc | ctgacctaca | acctgctggg | cagagagaac | 1860 |
| ctggacgagg | agatgctgta | cggcagcaga | gtgggcatca | tgatcctgag | cagcagctac | 1920 |
| gtgagcacca | gacagagcct | ggaccacctg | gtggtggtga | tggagcactg | gaagaccacc | 1980 |

```
gacctggtga tcatccccat ctacttcaag gtgagactga gcgacatctg cggcctgaag    2040
ggcagattcg aggccgcctt cctgcagctg cacatgagcc tgcaggagga cagagtgcag    2100
aagtggaagg ccgccatgag cgagatcgtg agcatcggcg ccacgagtg gaccaagggc     2160 agccagttca tcctggccga ggaggtggtg agaaacgcca gcctgagact gtacctgaag    2220
agcagcaaga acctgctggg catcctggcc ctgctgaacc acagccagag caccgacgtg    2280
gagatcatgg gcatctgggg catcgccggc atcggcaaga ccagcatcgc caaggagatc    2340
ttcgagctgc acgccccca ctacgacttc tgctacttcc tgcaggactt ccacctgatg     2400
tgccagatga gagacccag acagctgaga ggacttca tcagcaagct gtacggcgag       2460
gagaagggcc tgggcgccag cgacgtgaag cccagcttca tgagagactg gttccacaag    2520
aagaccatcc tgctggtgct ggacgacgtg agcaacgcca gagacgccga ggccgtgatc    2580
ggcggcttcg gctggttcag ccacggccac agaatcatcc tgaccagcag aagcaagcag    2640
gtgctggtgc agagcaaggt gaagaagccc tacgagatcc agaagctgag cgacttcgag    2700
agcttcagac tgtgcaagca gtacctggac ggcgagaacc ccgtgatcag cgagctgctg    2760
agctgcagca gcggcatccc cctggccctg aagctgctgg tgagcagcgt gagcaagcag    2820
tacatcacca acatgaagga ccacctgcag agcctgagaa aggaccccc cacccagatc     2880 caggaggcct tcagaagaag cttcgacggc tggacgaga cgagaagaa catcttcctg      2940 gacctggcct gcttcttcag aggccagagc aaggactacg ccgtgctgct gctggacgcc    3000
tgcggcttct tcacctacat gggcatctgc gagctgatcg acgagagcct gatcagcctg    3060
gtggacaaca aggccgagat gcccatcccc ttccaggaca tgggcagaat catcgtgcac    3120
gaggaggacg aggagccctg cgagagaagc agactgtggg acagcaagga catcatcgac    3180
gtgctgacca acaacagcgg caccgaggcc atcgacggca tcttcctgga cgccagcgac    3240
ctgacctgcg agctgagccc caccgtgttc ggcaaggcct acaacctgag actgctgaag    3300
ttctactgca gcaccagcgg caaccagacc aagctgaccc tgccccacgg cctggacacc    3360
ctgcccgacg agctgagcct gatgcactgg gagaactacc ccctggtgta cctgccccag    3420
aagttcaacc ccgtgaacct ggtggagctg aacatgccct acagcaacat ggagaagctg    3480
tgggagggca agaagaacct ggagaagctg aagaacatca gctgagcca cagcagagag     3540 ctgaccgaca tcctgatgct gagcgaggcc ctgaacctgg agcacatcga cctggagggc    3600
tgcaccagcc tgatcgacgt gagcatgagc atcccctgct gcggcaagct ggtgagcctg    3660
aacatgaagg actgcagcag actgagaagc ctgcccagca tggtggacct gaccaccctg    3720
aagctgctga acctgagcgg ctgcagcgag ttcgaggaca tccaggactt cgcccccaac    3780
ctggaggaga tctacctggc cggcaccagc atcagagagt gcccctgag catcagaaac     3840 ctgaccgagc tggtgaccct ggacctggag aactgcgaga gactgcagga gatgcccagc    3900
ctgcccgtgg agatcatcag aagaacc                                         3927
```

<210> SEQ ID NO 42
<211> LENGTH: 1309
<212> TYPE: PRT
<213> ORGANISM: Artificial Sequence
<220> FEATURE:
<223> OTHER INFORMATION: Amino acid sequence HCP4, variant 16

<400> SEQUENCE: 42

```
Met Ala Ala Ser Phe Cys Gly Ser Arg Arg Tyr Asp Val Phe Pro Ser
1               5                   10                  15
```

```
Phe Ser Lys Val Asp Val Arg Lys Ser Phe Leu Ala His Leu Ile Lys
            20                  25                  30

Glu Leu Asp Arg Arg Leu Ile Asn Thr Phe Thr Asp His Gly Met Glu
        35                  40                  45

Arg Asn Leu Pro Ile Asp Ala Glu Leu Leu Ser Ala Ile Ala Glu Ser
    50                  55                  60

Arg Ile Ser Ile Val Ile Phe Ser Lys Asn Tyr Ala Thr Thr Thr Tyr
65                  70                  75                  80

Cys Leu Asp Glu Leu Val Glu Ile His Thr Cys Tyr Lys Glu Leu Ala
                85                  90                  95

Gln Met Val Val Pro Val Phe Trp Asn Val His Pro Ser Gln Val Lys
            100                 105                 110

Lys Gln Thr Gly Asp Phe Gly Lys Val Phe Gly Lys Thr Thr Lys Gly
        115                 120                 125

Lys Pro Glu Asn Arg Lys Leu Arg Trp Met Gln Ala Leu Ala Ala Val
130                 135                 140

Ala Asn Ile Ala Gly Trp Asp Leu Gln Asn Trp Pro Asp Glu Ala Val
145                 150                 155                 160

Met Ile Glu Met Val Ala Asp Asp Val Ser Lys Lys Leu Phe Lys Ser
                165                 170                 175

Ser Asn Asp Phe Ser Asp Ile Val Gly Ile Glu Val His Leu Glu Ala
            180                 185                 190

Met Ser Ser Ile Leu Arg Leu Lys Cys Glu Lys Ala Arg Met Val Gly
        195                 200                 205

Ile Ser Gly Pro Ser Gly Ile Gly Lys Thr Thr Ile Ala Lys Ala Leu
    210                 215                 220

Phe Ser Lys Leu Thr Pro Gln Trp His Val Arg Ala Phe Val Thr Tyr
225                 230                 235                 240

Lys Arg Thr Asn Gln Asp Asp Tyr Asp Met Lys Leu Cys Trp Ile Glu
                245                 250                 255

Lys Tyr Leu Ser Glu Ile Leu Gly Gln Lys Asp Leu Lys Val Leu Asp
            260                 265                 270

Leu Leu Ala Val Glu Gln Ser Leu Met His Lys Lys Val Leu Ile Ile
        275                 280                 285

Leu Asp Asp Ile Asp Glu Leu Glu Leu Leu Lys Thr Leu Val Gly Gln
    290                 295                 300

Thr Gly Trp Phe Gly Phe Gly Ser Arg Ile Val Val Ile Thr Gln Asp
305                 310                 315                 320

Arg Gln Leu Leu Lys Ala His Asp Ile Asn Leu Ile Tyr Glu Val Ala
                325                 330                 335

Trp Pro Ser Ala His Leu Ala Leu Glu Ile Phe Cys Gln Ser Ala Phe
            340                 345                 350

Gly Lys Ile Tyr Pro Pro Ser Asp Phe Arg Glu Leu Ser Val Glu Phe
        355                 360                 365

Ala Tyr Met Ala Gly Asn Leu Pro Leu Asp Leu Arg Val Leu Gly Leu
    370                 375                 380

Ala Met His Gly Lys His Arg Glu Glu Trp Ile Glu Met Leu Pro Arg
385                 390                 395                 400

Leu Arg Asn Asp Leu Asp Gly Lys Phe Lys Lys Thr Leu Arg Asn Tyr
                405                 410                 415

Leu Pro Val Ile Arg Lys Arg Val Ser Asn Glu Glu Gly Gly Arg Glu
            420                 425                 430
```

```
Lys Leu Lys Lys Gly Asn Lys Lys Leu Asp Leu Asp Asp Glu Phe Pro
            435                 440                 445

Gly Gly Glu Ile Tyr Ser Asp Glu Ile Pro Thr Pro Thr Ser Asn Trp
450                 455                 460

Lys Asp Thr Asp Asp Phe Asp Ser Gly Asp Ile Ile Pro Ile Ile Ala
465                 470                 475                 480

Asp Lys Ser Thr Thr Ile Ile Pro Asn Arg Arg His Ser Asn Asp Asp
                485                 490                 495

Trp Cys Ser Phe Cys Glu Phe Leu Arg Asn Arg Ile Pro Pro Leu Asn
                500                 505                 510

Pro Phe Lys Cys Ser Ala Asn Asp Val Ile Asp Phe Leu Arg Thr Arg
            515                 520                 525

Gln Val Leu Gly Ser Thr Glu Ala Leu Val Asp Arg Leu Ile Phe Ser
        530                 535                 540

Ser Glu Ala Phe Gly Met Lys Pro Asp Glu Asn Pro Phe Arg Ser Gln
545                 550                 555                 560

Ala Val Thr Ser Tyr Leu Lys Ala Arg Asp Met Thr Arg Glu Lys
                565                 570                 575

Glu Cys Ile Leu Val Phe Ser Cys His Asp Gln Leu Asp Val Asp Glu
            580                 585                 590

Thr Ser Phe Ile Glu Ala Ile Ser Lys Glu Leu His Lys Gln Gly Phe
        595                 600                 605

Ile Pro Leu Thr Tyr Asn Leu Leu Gly Arg Glu Asn Leu Asp Glu Glu
    610                 615                 620

Met Leu Tyr Gly Ser Arg Val Gly Ile Met Ile Leu Ser Ser Ser Tyr
625                 630                 635                 640

Val Ser Thr Arg Gln Ser Leu Asp His Leu Val Val Met Glu His
                645                 650                 655

Trp Lys Thr Thr Asp Leu Val Ile Ile Pro Ile Tyr Phe Lys Val Arg
                660                 665                 670

Leu Ser Asp Ile Cys Gly Leu Lys Gly Arg Phe Glu Ala Ala Phe Leu
            675                 680                 685

Gln Leu His Met Ser Leu Gln Glu Asp Arg Val Gln Lys Trp Lys Ala
        690                 695                 700

Ala Met Ser Glu Ile Val Ser Ile Gly Gly His Glu Trp Thr Lys Gly
705                 710                 715                 720

Ser Gln Phe Ile Leu Ala Glu Glu Val Val Arg Asn Ala Ser Leu Arg
                725                 730                 735

Leu Tyr Leu Lys Ser Ser Lys Asn Leu Leu Gly Ile Leu Ala Leu Leu
            740                 745                 750

Asn His Ser Gln Ser Thr Asp Val Glu Ile Met Gly Ile Trp Gly Ile
        755                 760                 765

Ala Gly Ile Gly Lys Thr Ser Ile Ala Lys Glu Ile Phe Glu Leu His
    770                 775                 780

Ala Pro His Tyr Asp Phe Cys Tyr Phe Leu Gln Asp Phe His Leu Met
785                 790                 795                 800

Cys Gln Met Lys Arg Pro Arg Gln Leu Arg Glu Asp Phe Ile Ser Lys
                805                 810                 815

Leu Tyr Gly Glu Glu Lys Gly Leu Gly Ala Ser Asp Val Lys Pro Ser
            820                 825                 830

Phe Met Arg Asp Trp Phe His Lys Lys Thr Ile Leu Leu Val Leu Asp
        835                 840                 845

Asp Val Ser Asn Ala Arg Asp Ala Glu Ala Val Ile Gly Gly Phe Gly
```

```
            850                 855                 860
Trp Phe Ser His Gly His Arg Ile Ile Leu Thr Ser Arg Ser Lys Gln
865                 870                 875                 880

Val Leu Val Gln Ser Lys Val Lys Pro Tyr Glu Ile Gln Lys Leu
                885                 890                 895

Ser Asp Phe Glu Ser Phe Arg Leu Cys Lys Gln Tyr Leu Asp Gly Glu
                900                 905                 910

Asn Pro Val Ile Ser Glu Leu Leu Ser Cys Ser Ser Gly Ile Pro Leu
                915                 920                 925

Ala Leu Lys Leu Leu Val Ser Ser Val Ser Lys Gln Tyr Ile Thr Asn
            930                 935                 940

Met Lys Asp His Leu Gln Ser Leu Arg Lys Asp Pro Pro Thr Gln Ile
945                 950                 955                 960

Gln Glu Ala Phe Arg Arg Ser Phe Asp Gly Leu Asp Glu Asn Glu Lys
                965                 970                 975

Asn Ile Phe Leu Asp Leu Ala Cys Phe Phe Arg Gly Gln Ser Lys Asp
                980                 985                 990

Tyr Ala Val Leu Leu Leu Asp Ala Cys Gly Phe Phe Thr Tyr Met Gly
                995                1000                1005

Ile Cys Glu Leu Ile Asp Glu Ser Leu Ile Ser Leu Val Asp Asn Lys
            1010                1015                1020

Ala Glu Met Pro Ile Pro Phe Gln Asp Met Gly Arg Ile Ile Val His
1025                1030                1035                1040

Glu Glu Asp Glu Glu Pro Cys Glu Arg Ser Arg Leu Trp Asp Ser Lys
                1045                1050                1055

Asp Ile Ile Asp Val Leu Thr Asn Asn Ser Gly Thr Glu Ala Ile Asp
                1060                1065                1070

Gly Ile Phe Leu Asp Ala Ser Asp Leu Thr Cys Glu Leu Ser Pro Thr
                1075                1080                1085

Val Phe Gly Lys Ala Tyr Asn Leu Arg Leu Leu Lys Phe Tyr Cys Ser
            1090                1095                1100

Thr Ser Gly Asn Gln Thr Lys Leu Thr Leu Pro His Gly Leu Asp Thr
1105                1110                1115                1120

Leu Pro Asp Glu Leu Ser Leu Met His Trp Glu Asn Tyr Pro Leu Val
                1125                1130                1135

Tyr Leu Pro Gln Lys Phe Asn Pro Val Asn Leu Val Glu Leu Asn Met
                1140                1145                1150

Pro Tyr Ser Asn Met Glu Lys Leu Trp Glu Gly Lys Lys Asn Leu Glu
                1155                1160                1165

Lys Leu Lys Asn Ile Lys Leu Ser His Ser Arg Glu Leu Thr Asp Ile
            1170                1175                1180

Leu Met Leu Ser Glu Ala Leu Asn Leu Glu His Ile Asp Leu Glu Gly
1185                1190                1195                1200

Cys Thr Ser Leu Ile Asp Val Ser Met Ser Ile Pro Cys Cys Gly Lys
                1205                1210                1215

Leu Val Ser Leu Asn Met Lys Asp Cys Ser Arg Leu Arg Ser Leu Pro
                1220                1225                1230

Ser Met Val Asp Leu Thr Thr Leu Lys Leu Leu Asn Leu Ser Gly Cys
                1235                1240                1245

Ser Glu Phe Glu Asp Ile Gln Asp Phe Ala Pro Asn Leu Glu Glu Ile
                1250                1255                1260

Tyr Leu Ala Gly Thr Ser Ile Arg Glu Leu Pro Leu Ser Ile Arg Asn
1265                1270                1275                1280
```

```
Leu Thr Glu Leu Val Thr Leu Asp Leu Glu Asn Cys Glu Arg Leu Gln
            1285                1290                1295

Glu Met Pro Ser Leu Pro Val Glu Ile Ile Arg Arg Thr
            1300                1305
```